(12) United States Patent
Heiser et al.

(10) Patent No.: US 9,512,115 B2
(45) Date of Patent: Dec. 6, 2016

(54) INHIBITORS

(71) Applicant: PROBIODRUG AG, Halle/Saale (DE)

(72) Inventors: Ulrich Heiser, Halle/Saale (DE);
Mirko Buchholz, Halle/Saale (DE);
Robert Sommer, Magdeburg (DE);
Antje Meyer, Halle/Saale (DE);
Hans-Ulrich Demuth, Halle/Saale (DE)

(73) Assignee: PROBIODRUG AG, Halle (Saale) (DE)

( * ) Notice: Subject to any disclaimer, the term of this patent is extended or adjusted under 35 U.S.C. 154(b) by 0 days.

(21) Appl. No.: 14/775,785

(22) PCT Filed: Mar. 14, 2014

(86) PCT No.: PCT/EP2014/055106
§ 371 (c)(1),
(2) Date: Sep. 14, 2015

(87) PCT Pub. No.: WO2014/140279
PCT Pub. Date: Sep. 18, 2014

(65) Prior Publication Data
US 2016/0031869 A1    Feb. 4, 2016

Related U.S. Application Data

(60) Provisional application No. 61/790,604, filed on Mar. 15, 2013.

(51) Int. Cl.
| C07D 413/14 | (2006.01) |
| A61K 45/06 | (2006.01) |
| A61K 31/422 | (2006.01) |
| C07D 413/04 | (2006.01) |

(52) U.S. Cl.
CPC ............ *C07D 413/14* (2013.01); *A61K 31/422* (2013.01); *A61K 45/06* (2013.01); *C07D 413/04* (2013.01)

(58) Field of Classification Search
None
See application file for complete search history.

(56) References Cited

FOREIGN PATENT DOCUMENTS

| WO | WO 2010/026212 A1 | 3/2010 |
| WO | WO 2011/029920 A1 | 3/2011 |
| WO | WO 2012/123562 A1 | 9/2012 |
| WO | WO 2012/163773 A1 | 12/2012 |

OTHER PUBLICATIONS

International Search Report and Written Opinion dated May 22, 2014 in corresponding International Application No. PCT/EP2014/055106, 7 pages.

*Primary Examiner* — Brian J Davis
(74) *Attorney, Agent, or Firm* — Dentons US LLP

(57) ABSTRACT

The invention relates to a compound of formula (I) or a pharmaceutically acceptable salt, solvate or polymorph thereof, including all tautomers and stereoisomers thereof, wherein $R^1$, $R^2$, $R^3$, $R^4$ and $R^5$ are as defined herein, as inhibitors of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

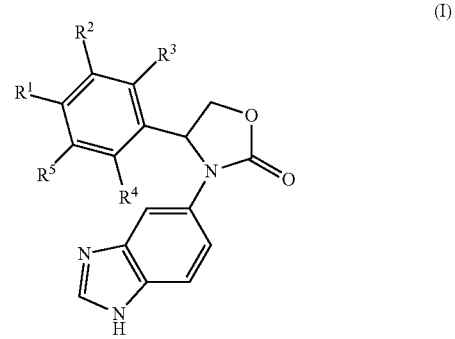

22 Claims, No Drawings

INHIBITORS

CROSS REFERENCE TO RELATED APPLICATIONS

The present application claims the benefit of priority to PCT International Application No. PCT/EP2014/055106 filed 14 Mar. 2014, which claims the benefit of priority to U.S. Application Ser. No. 61/790,604 filed 15 Mar. 2013; each of which is incorporated herein by reference in its entirety.

INCORPORATION-BY-REFERENCE OF SEQUENCE LISTING

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The invention relates to novel halogenated oxazolidinone derivatives with improved pharmacokinetic properties as inhibitors of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

Inhibitors of QC are described in WO 2004/098625, WO 2004/098591, WO 2005/039548, WO 2005/075436, WO 2008/055945, WO 2008/055947, WO 2008/055950, WO2008/065141, WO 2008/110523, WO 2008/128981, WO 2008/128982, WO 2008/128983, WO 2008/128984, WO 2008/128985, WO 2008/128986, WO 2008/128987, WO 2010/026212, WO 2011/029920, WO 2011/107530, WO 2011/110613, WO 2011/131748 and WO 2012/123563, wherein WO 2011/029920 discloses inter alia oxazolidinone derivatives as inhibitors of glutaminyl cyclase.

EP 02 011 349.4 discloses polynucleotides encoding insect glutaminyl cyclase, as well as polypeptides encoded thereby and their use in methods of screening for agents that reduce glutaminyl cyclase activity. Such agents are useful as pesticides.

DEFINITIONS

The terms "$k_i$" or "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DP IV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "PEP-inhibitor" or "prolyl endopeptidase inhibitor" is generally known to a person skilled in the art and means enzyme inhibitors, which inhibit the catalytic activity of prolyl endopeptidase (PEP, prolyl oligopeptidase, POP).

"PEP-activity" is defined as the catalytic activity of an endoprotease that is capable to hydrolyze post proline bonds in peptides or proteins where the proline is in amino acid position 3 or higher counted from the N-terminus of a peptide or protein substrate.

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC. Examples of QC-like enzymes are the glutaminyl-peptide cyclotransferase-like proteins (QPCTLs) from human (GenBank NM_017659), mouse (GenBank BC058181), *Macaca fascicularis* (GenBank AB168255), *Macaca mulatta* (GenBank XM_001110995), *Canis familiaris* (GenBank XM_541552), *Rattus norvegicus* (GenBank XM_001066591), *Mus musculus* (GenBank BC058181) and *Bos taurus* (GenBank BT026254).

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

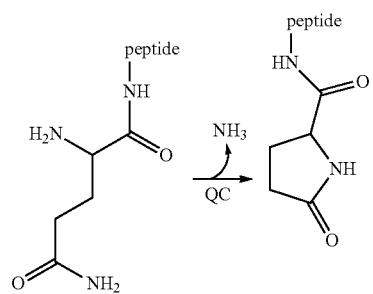

Scheme 2: Cyclization of L-homoglutamine by QC

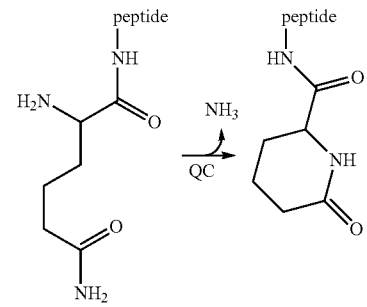

The term "EC" as used herein comprises the activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

Scheme 3: N-terminal cyclization of uncharged glutamyl peptides by QC (EC)

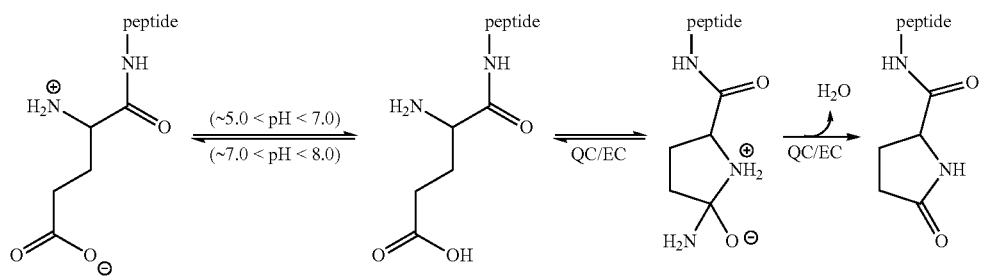

The term "QC-inhibitor" "glutaminyl cyclase inhibitor" is generally known to a person skilled in the art and means enzyme inhibitors, which inhibit the catalytic activity of glutaminyl cyclase (QC) or its glutamyl cyclase (EC) activity.

Potency of QC Inhibition

In light of the correlation with QC inhibition, in preferred embodiments, the subject method and medical use utilize an agent with an $IC_{50}$ for QC inhibition of 10 µM or less, more preferably of 1 µM or less, even more preferably of 0.1 µM or less or 0.01 µM or less, or most preferably 0.001 µM or less. Indeed, inhibitors with $K_i$ values in the lower micromolar, preferably the nanomolar and even more preferably the picomolar range are contemplated. Thus, while the active agents are described herein, for convenience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 500 g/mole or less, 400 g/mole or less, preferably of 350 g/mole or less, and even more preferably of 300 g/mole or less and even of 250 g/mole or less.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

Throughout the description and the claims the expression "alkyl", unless specifically limited, denotes a $C_{1-12}$ alkyl group, suitably a $C_{1-8}$ alkyl group, e.g. $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$, fluoroethyl, fluoropropyl, fluorobutyl, difluoroethyl, difluoropropyl and difluorobutyl.

The expression "alkylene" denotes a chain of formula $-(CH_2)_n-$ wherein n is an integer e.g. 2-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six, e.g. five.

The expression "heterocyclyl", unless specifically limited, denotes a $C_{3-10}$ heterocyclyl group (i.e. 3 to 10 ring carbon atoms), more suitably a $C_{3-8}$ heterocyclyl group, e.g. a $C_{3-6}$ heterocyclyl group. A most suitable number of ring carbon atoms is three to six, e.g. five. Unless specifically limited, one or more (e.g. 1, 2 or 3) carbon atoms in the heterocyclyl ring are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The term "halogen" or "halo" comprises fluorine (F), chlorine (Cl) and bromine (Br).

When benzimidazolyl is shown as benzimidazol-5-yl, which is represented as:

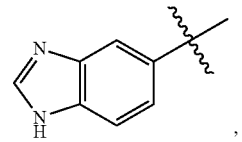 [SMILES: *c1ccc2[nH]cnc2c1]

, the person skilled in the art will appreciate that benzimidazol-6-yl, which is represented as:

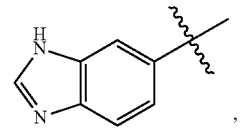 [SMILES: *c1ccc2nc[nH]c2c1]

, is an equivalent structure. As employed herein, the two forms of benzimidazolyl are covered by the term "benzimidazol-5-yl".

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

A protecting group or protective group is introduced into a molecule by chemical modification of a functional group in order to obtain chemoselectivity in a subsequent chemical reaction. Protecting groups are e.g. alcohol protecting groups, amine protecting groups, carbonyl protecting groups, carboxylic acid protecting groups and phosphate protecting groups.

Examples for alcohol protecting groups are acetyl (Ac), benzoyl (Bz), benzyl (Bn, Bnl) β-methoxyethoxymethyl ether (MEM), mimethoxytrityl [bis-(4-methoxyphenyl)phenylmethyl, DMT], methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), trityl (triphenylmethyl, Tr), silyl ethers (such as trimethylsilyl ether (TMS), tert-butyldimethylsilyl ether (TBDMS), tert-butyldimethylsilyloxymethyl ether (TOM), and triisopropylsilyl ether (TIPS)); methyl ethers and ethoxyethyl ethers (EE).

Suitable amine protecting groups are selected from carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), p-methoxybenzyl (PMB), 3,4-dimethoxybenzyl (DMPM), p-methoxyphenyl (PMP), tosyl (Ts), and other sulfonamides (Nosyl & Nps).

Suitable carbonyl protecting groups are selected from acetals and ketals, acylals and dithianes.

Suitable carboxylic acid protecting groups are selected from methyl esters, benzyl esters, tert-butyl esters, silyl esters, orthoesters, and oxazoline.

Examples for phosphate protecting groups are 2-cyanoethyl and methyl (Me)

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as *acacia*, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

SUMMARY OF THE INVENTION

Inhibitors of glutaminyl cyclase are known in the art. WO 2011/029920 discloses inter alia inhibitors of glutaminyl cyclase which comprise a oxazolidinone moiety. However, for use in medicine, i.e. the prevention and therapy of diseases, there is a need for further compounds, which have improved pharmacokinetic properties in order to reduce dosing levels and thereby reducing unwanted side effects and preventing adverse events after administration to a subject. In particular, for the treatment or prevention of diseases of the central nervous system (CNS), for example neurodegenerative diseases such as Mild Cognitive Impairment, Alzheimer's disease, neurodegeneration in Downs Syndrome or Familial Alzheimer's Diseases, there is a need for new compounds, which show increased levels and increased half lifes in the CNS, e.g. in the brain and CSF.

Thus, it was the problem of the present invention to provide new compounds with improved pharmacokinetic properties, in particular for the treatment of CNS related diseases.

This problem was solved by the present invention by provision of compounds of formula (I).

According to the invention there is provided a compound of formula (I):

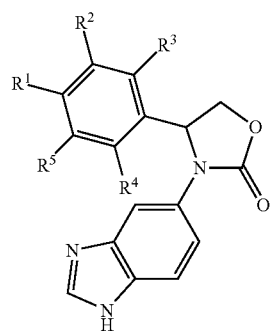

Formula I or a pharmaceutically acceptable salt, solvate or polymorph thereof, including all tautomers and stereoisomers thereof, wherein:

$R^1$ represents alkyl, —O-alkyl, heterocyclyl or cycloalkyl;

$R^2$ and $R^3$ independently represent hydrogen, halogen or CN;

$R^4$ and $R^5$ independently represent hydrogen or halogen; wherein at least one of $R^2$, $R^3$, $R^4$ and $R^5$ is halogen or CN;

and wherein the above alkyl, —O-alkyl, heterocyclyl or cycloalkyl groups are substituted by one or more halogen.

DETAILED DESCRIPTION OF THE INVENTION

Surprisingly, it was found by the inventors that the fluorination of compounds, which comprise an oxazolidinone residue, result in inhibitors of glutaminyl cyclase, which have multiple advantages compared to glutaminyl cyclase inhibitors existing in the prior art. Due to the fluorination, the inhibitor constants, such as the Ki value of the compounds is markedly improved, preferably reduced several fold, more preferably reduced between about 10 fold and about 100 fold compared to the oxazolidinone compounds of the prior art.

More surprisingly, due to the fluorination, the compounds of the present invention show a markedly prolonged half life in brain and CSF as well as improved brain levels (shown by improved AUC values), an improved blood brain barrier permeation steady-state distribution ratio of the compounds between brain tissue and plasma shown by improved (log BB values).

Particularly advantageous compounds according to the present invention have been obtained, when both are fluorinated: (i) the phenyl ring, i.e. at least one of $R^2$, $R^3$, $R^4$ and $R^5$ is fluorine, and (ii) the substituent at position $R^1$.

In one particular embodiment of the invention, there is provided a compound of formula (I):

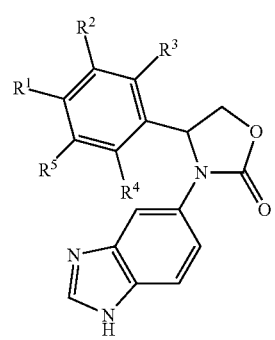

Formula I or a pharmaceutically acceptable salt, solvate or polymorph thereof, including all tautomers and stereoisomers thereof, wherein:

$R^1$ represents alkyl, —O-alkyl, heterocyclyl or cycloalkyl;

$R^2$ and $R^3$ independently represent hydrogen, fluorine or CN;

$R^4$ and $R^5$ independently represent hydrogen or fluorine; wherein at least one of $R^2$, $R^3$, $R^4$ and $R^5$ is fluorine or CN;

and wherein the above alkyl, —O-alkyl, heterocyclyl or cycloalkyl groups are substituted by one or more fluorine.

When alkyl, cycloalkyl and heterocyclyl are substituted, they are typically substituted by 1 or 2 substituents (e.g. 2 substituents). Typically the substituents are both halogen. More typically, the halogen substituents are fluorine.

When phenyl is substituted, it is typically substituted by 1, 2 or 3 (e.g. 1 or 2) halogen substituents. More typically, the halogen substituents are fluorine.

When $R^1$ represents alkyl, examples include $C_1$-$C_{12}$ straight chain or branched alkyl groups. A suitable alkyl is a $C_{1-8}$ alkyl, more suitably a $C_{2-6}$ alkyl, most suitably a $C_{3-4}$ alkyl. Aforementioned alkyl groups are substituted by one or more halogen substituents, typically by 1 or 2 halogen substituents. Most suitably, the halogen substituents are fluorine.

When $R^1$ represents —O-alkyl, examples include —O—$C_{1-8}$ straight chain or branched —O-alkyl groups. A suitable —O-alkyl is a —O—$C_{1-12}$ alkyl, more suitably a —O—$C_{2-8}$ alkyl, most suitably a —O—$C_{3-4}$ alkyl. Aforementioned O-alkyl groups are substituted by one or more halogen substituents, typically by 1 or 2 halogen substituents. Most suitably, the halogen substituents are fluorine.

When $R^1$ represents heterocyclyl, examples include monocyclic (e.g. 5 and 6 membered) and bicyclic (e.g. 9 and 10 membered, particularly 9 membered) heterocyclyl rings, especially rings containing nitrogen atoms (e.g. 1 or 2 nitrogen atoms). Suitably, the heterocyclyl is a 5 and 6 membered heterocyclic ring, most suitably a 5-membered heterocyclic ring. Examples of heterocyclyl rings include pyrrolidine, tetrahydrofuran, tetrahydrothiophene, pyrazolidine, imidazolidine, dioxolane, thiazolidine, and isoxazolidine. Aforementioned heterocyclyl groups are substituted by one or more halogen substituents typically by 1 or 2 halogen substituents. Most suitably, the halogen substituents are fluorine.

When $R^1$ represents cycloalkyl, examples include a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six, e.g. five or six. Aforementioned cycloalkyl groups are substituted by one or more halogen substituents typically by 1 or 2 halogen substituents. Most suitably, the halogen substituents are fluorine.

When $R^1$ is —O-alkyl, $R^1$ preferably represents —O—$C_{2-6}$ alkyl substituted by one or more halogen, such as fluorine.
  More suitably, $R^1$ represents —O—$C_{3-4}$ alkyl, substituted by one or more halogen, such as fluorine.
  Preferably, $R^1$ represents difluoropropoxy or difluorobutoxy.
  Most preferably, $R^1$ represents 2,2-difluoropropoxy, 3,3-difluoropropoxy or 3,3-difluorobutoxy.

When $R^1$ is heterocyclyl, $R^1$ preferably represents pyrrolidinyl substituted by one or more halogen, such as fluorine.
  More preferably, $R^1$ is difluoropyrrolidinyl.
  Most preferably, $R^1$ is 3,3-difluoropyrrolidin-1-yl.

When $R^1$ is cycloalkyl, $R^1$ preferably represents cyclohexyl substituted by one or more halogen, such as fluorine.
  More preferably, $R^1$ is difluorocyclohexyl.
  Most preferably, $R^1$ is 4,4-difluorocyclohexyl.

When $R^1$ is alkyl, $R^1$ preferably represents $C_{2-4}$ alkyl substituted by one or more halogen, such as fluorine.
  Preferably, $R^1$ represents $C_{3-4}$ alkyl substituted by one or more halogen, such as fluorine.
  More preferably, $R^1$ is difluorobutyl.
  Most preferably, $R^1$ is 3,3-difluorobutyl.

Especially preferred according to the present invention are compounds of formula (I), wherein $R^1$ is —O-alkyl.

Further preferred according to the present invention are compounds, in which the phenyl ring in the compound of formula (I) is substituted by at least one halogen or CN, i.e. at least one of $R^2$, $R^3$, $R^4$ and $R^5$ is halogen or CN.

In one embodiment, $R^2$ and $R^5$ are halogen such as fluorine, and $R^3$ and $R^4$ are hydrogen.

In a further embodiment, $R^2$ is halogen such as fluorine, and $R^3$, $R^4$ and $R^5$ are hydrogen.

In a further embodiment, $R^3$ and $R^4$ are halogen such as fluoro, and $R^2$ and $R^5$ are hydrogen.

In another embodiment, $R^3$ is halogen such as fluoro, and $R^2$, $R^4$ and $R^5$ are hydrogen.

In yet another embodiment, $R^2$ and $R^3$ are halogen, such as fluoro, and $R^4$ and $R^5$ are hydrogen.

In a further embodiment, $R^2$ is CN and $R^3$, $R^4$ and $R^5$ are hydrogen.

In another embodiment, $R^3$ is CN and $R^2$, $R^4$ and $R^5$ are hydrogen.

Preferred according to the present invention are compounds of formula (I), wherein at least one of $R^2$, $R^3$, $R^4$ and $R^5$ is halogen. More preferably, at least one of $R^2$, $R^3$, $R^4$ and $R^5$ is fluorine.

Even preferably, $R^3$ is fluorine and $R^2$, $R^4$ and $R^5$ are hydrogen; or $R^2$ and $R^3$ are fluorine and $R^4$ and $R^5$ are hydrogen.

Most preferably, $R^1$ is 2,2-difluoropropoxy, $R^3$ is fluorine, and $R^2$, $R^4$ and $R^5$ are hydrogen; or
$R^1$ is 3,3-difluoropropoxy, $R^2$ and $R^3$ are fluorine and $R^4$ and $R^5$ are hydrogen.

Processes

According to a further aspect of the invention there is provided a process for preparing a compound of formula (I) which comprises:

(a) preparing a compound of formula (I) from a compound of formula (II):

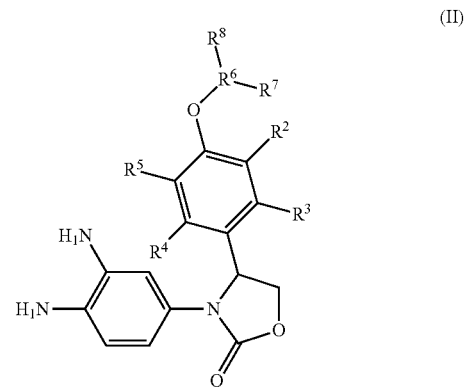

wherein
$R^2$, $R^3$, $R^4$ and $R^5$ and are as defined above for compounds of formula (I); $R^6$ is alkyl and $R^7$ and $R^8$ are halogen, such as fluorine.

The process typically involves reacting a compound of formula (II) with formamidine acetate in the presence of a suitable solvent such as acetonitrile. A non-limiting example of the methodology of process (a) is described in Method K herein.

(b) preparing a compound of formula (I) from a compound of formula (III):

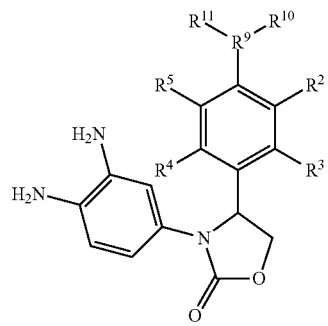

(III)

wherein
$R^2$, $R^3$, $R^4$ and $R^5$ and are as defined above for compounds of formula (I) and $R^9$ is cycloalkyl or heterocyclyl and $R^{10}$ and $R^{11}$ are halogen, such as fluorine.

Process (b) typically involves reacting a compound of formula (III) with formamidine acetate in the presence of a suitable solvent such as acetonitrile. A non-limiting example of the methodology of process (b) is described in Methods R and U herein.

(c) preparing a compound of formula (I) from a compound of formula (IV):

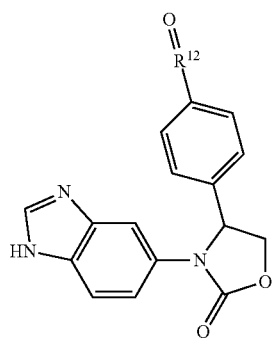

(IV)

wherein $R^{12}$ is cycloalkyl. Process (c) typically comprises reaction of a compound of formula (IV) with a suitable reagent, such as diethylaminosulfur triflouride, which may be employed in the presence of a suitable solvent such as dichloromethane. A non-limiting example of the methodology of process (c) is described in Method V herein.

(d) preparing a compound of formula (I) from a compound of formula (V):

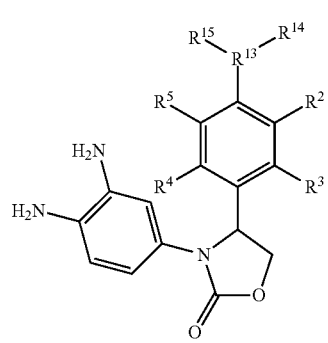

(V)

wherein $R^1$, $R^2$ and $R^4$ are as defined above for compounds of formula (I), $R^{13}$ is alkyl and $R^{14}$ and $R^{15}$ are halogen such as fluorine.

The process typically involves reacting a compound of formula (V) with formamidine acetate in the presence a suitable solvent, such as acetonitrile. A non-limiting example of the methodology of process (d) is described in Method AA herein.

Compounds of formula (I) and intermediate compounds may also be prepared using techniques analogous to those known to a skilled person, or described herein.

Novel intermediates are claimed as an aspect of the present invention.

Therapeutic Uses

Physiological substrates of QC (EC) in mammals are, e.g. amyloid beta-peptides (3-40), (3-42), (11-40 and (11-42), ABri, ADan, Gastrin, Neurotensin, FPP, CCL 2, CCL 7, CCL 8, CCL 16, CCL 18, Fractalkine, Orexin A, [Gln$^3$]-glucagon(3-29), [Gln$^5$]-substance P(5-11) and the peptide QYNAD. For further details see table 1. The compounds and/or combinations according to the present invention and pharmaceutical compositions comprising at least one inhibitor of QC (EC) are useful for the treatment of conditions that can be treated by modulation of QC activity.

TABLE 1

Amino acid sequences of physiological active peptides with an N-terminal glutamine residue, which are prone to be cyclized to final pGlu

| Peptide | Amino acid sequence | Function |
|---|---|---|
| Abeta(1-42) | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(1-40) | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |

TABLE 1 -continued

Amino acid sequences of physiological active peptides with an N-terminal glutamine residue, which are prone to be cyclized to final pGlu

| Peptide | Amino acid sequence | Function |
| --- | --- | --- |
| Abeta(3-42) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(3-40) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| Abeta(11-42) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(11-40) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| ABri | EASNCFA IRHFENKFAV ETLIC SRTVKKNIIEEN | Pyroglutamated form plays a role in Familial British Dementia |
| ADan | EASNCFA IRHFENKFAV ETLIC FNLFLNSQEKHY | Pyroglutamated form plays a role in Familial Danish Dementia |
| Gastrin 17 Swiss-Prot: P01350 | QGPWL EEEEEAYGWM DF (amide) | Gastrin stimulates the stomach mucosa to produce and secrete pancreas to secrete its hydrochloric acid and the digestive enzymes. It also stimulates smooth muscle contraction and increases blood circulation and water secretion in the stomach and intestine. |
| Neurotensin Swiss-Prot: P30990 | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH Swiss-Prot: P20396 | QHP amide | TRH functions as a regulator of the biosynthesis of TSH in the anterior pituitary gland and as a neurotransmitter/neuromodulator in the central and peripheral nervous systems. |
| GnRH Swiss-Prot: P01148 | QHWSYGL RP(G) amide | Stimulates the secretion of gonadotropins; it stimulates the secretion of both luteinizing and follicle-stimulating hormones. |

TABLE 1-continued

Amino acid sequences of physiological active peptides with an N-terminal glutamine residue, which are prone to be cyclized to final pGlu

| Peptide | Amino acid sequence | Function |
| --- | --- | --- |
| CCL16 (small inducible cytokine A16) Swiss-Prot: 015467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8) Swiss-Prot: P80075 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |
| CCL2 (MCP-1, small inducible cytokine A2) Swiss-Prot: P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducible cytokine A18) Swiss-Prot: P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin) Swiss-Prot: P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium binds to CX3CR1. |

TABLE 1 -continued

Amino acid sequences of physiological active peptides with an N-terminal glutamine residue, which are prone to be cyclized to final pGlu

| Peptide | Amino acid sequence | Function |
| --- | --- | --- |
| CCL7 (small inducible cytokine A7) Swiss-Prot: P80098 | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) Swiss-Prot 043612 | QPLPDCCRQK TCSCRLYELL HGAGNHAAGI LTL | Neuropeptide that plays a significant role in the regulation of food intake and sleep-wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P | RPK PQQFFGLM | Belongs to the tachykinins. Tachykinins are active peptides which excite neurons, evoke behavioral responses, are potent vasodilators and secretagogues, and contract (directly or indirectly) many smooth muscles. |
| QYNAD | Gln-Tyr-Asn-Ala-Asp | Acts on voltage-gated sodium channels. |

Glutamate is found in positions 3, 11 and 22 of the amyloid β-peptide. Among them the mutation from glutamic acid (E) to glutamine (Q) in position 22 (corresponding to amyloid precursor protein APP 693, Swissprot P05067) has been described as the so called Dutch type cerebroarterial amyloidosis mutation.

The β-amyloid peptides with a pyroglutamic acid residue in position 3, 11 and/or 22 have been described to be more cytotoxic and hydrophobic than the amyloid β-peptides 1-40(42/43) (Saido T. C. 2000 Medical Hypotheses 54(3): 427-429).

The multiple N-terminal variations, e.g. Abeta(3-40), Abeta(3-42), Abeta(11-40) and Abeta (11-42) can be generated by the β-secretase enzyme β-site amyloid precursor protein-cleaving enzyme (BACE) at different sites (Huse J. T. et al. 2002 J. Biol. Chem. 277 (18): 16278-16284), and/or by aminopeptidase or dipeptidylaminopeptidase processing from the full length peptides Abeta(1-40) and Abeta(1-42). In all cases, cyclization of the then N-terminal occurring glutamic acid residue is catalyzed by QC.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on", others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

CCL2 (MCP-1), CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertention, liver fibrosis, liver cirrhosis, nephrosclerosis, ventricular remodeling, heart failure, arteriopathy after organ transplantations and failure of vein grafts.

A number of studies have underlined in particular the crucial role of MCP-1 for the development of atherosclerosis (Gu, L., et al., (1998) *Mol. Cell* 2, 275-281; Gosling, J., et al., (1999) *J Clin. Invest* 103, 773-778); rheumatoid arthritis (Gong, J. H., et al., (1997) *J Exp. Med* 186, 131-137; Ogata, H., et al., (1997) *J Pathol.* 182, 106-114); pancreatitis (Bhatia, M., et al., (2005) *Am. J Physiol Gastrointest. Liver Physiol* 288, G1259-G1265); Alzheimer's disease (Yamamoto, M., et al., (2005) *Am. J Pathol.* 166, 1475-1485); lung fibrosis (Inoshima, I., et al., (2004) *Am. J Physiol Lung Cell Mol. Physiol* 286, L1038-L1044); renal fibrosis (Wada, T., et al., (2004) *J Am. Soc. Nephrol.* 15, 940-948), and graft rejection (Saiura, A., et al., (2004) *Arterioscler. Thromb. Vasc. Biol.* 24, 1886-1890). Furthermore, MCP-1 might also play a role in gestosis (Katabuchi, H., et al., (2003) *Med Electron Microsc.* 36, 253-262), as a paracrine factor in tumor development (Ohta, M., et al., (2003) *Int. J Oncol.* 22, 773-778; Li, S., et al., (2005) *J Exp. Med* 202, 617-624), neuropathic pain (White, F. A., et al., (2005) *Proc. Natl. Acad. Sci. U.S.A*) and AIDS (Park, I. W., Wang, J. F., and Groopman, J. E. (2001) *Blood* 97, 352-358; Coll, B., et al., (2006) *Cytokine* 34, 51-55).

MCP-1 levels are increased in CSF of AD patients and patients showing mild cognitive impairment (MCI) (Galimberti, D., et al., (2006) *Arch. Neurol.* 63, 538-543). Furthermore, MCP-1 shows an increased level in serum of patients with MCI and early AD (Clerici, F., et al., (2006) *Neurobiol. Aging* 27, 1763-1768).

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, *J Pept Res* 57(6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

Recently, increased levels of the pentapeptide QYNAD were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD), especially its efficacy to interact with and block sodium channels resulting in the promotion of axonal dysfunction, which are involved in inflammatory autoimmune diseases of the central nervous system. But recently, it could be demonstrated that not QYNAD, but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore, QYNAD is a substrate of the enzyme glutaminyl cyclase (QC, EC 2.3.2.5), which is also present in the brain of mammals, especially in human brain. Glutaminyl cyclase catalyzes effectively the formation of pEYNAD from its precursor QYNAD.

Accordingly, the present invention provides the use of the compounds of formula (I) for the preparation of a medicament for the prevention or alleviation or treatment of a disease selected from the group consisting of mild cognitive impairment, Alzheimer's disease, Familial British Dementia, Familial Danish Dementia, neurodegeneration in Down Syndrome, Huntington's disease, Kennedy's disease, ulcer disease, duodenal cancer with or w/o *Helicobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, rheumatoid arthritis, atherosclerosis, pancreatitis, restenosis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barré syndrome and chronic inflammatory demyelinizing polyradiculoneuropathy.

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC (EC) activity in combination with other agents, especially for the treatment of neuronal diseases, atherosclerosis and multiple sclerosis.

The present invention also provides a method of treatment of the aforementioned diseases comprising the administration of a therapeutically active amount of at least one compound of formula (I) to a mammal, preferably a human.

Most preferably, said method and corresponding uses are for the treatment of a disease selected from the group consisting of mild cognitive impairment, Alzheimer's disease, Familial British Dementia, Familial Danish Dementia, neurodegeneration in Down Syndrome, Parkinson's disease and Chorea Huntington, comprising the administration of a therapeutically active amount of at least one compound of formula (I) to a mammal, preferably a human.

Even preferably, the present invention provides a method of treatment and corresponding uses for the treatment of rheumatoid arthritis, atherosclerosis, pancreatitis and restenosis.

Pharmaceutical Combinations

In a preferred embodiment, the present invention provides a composition, preferably a pharmaceutical composition, comprising at least one QC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

Most preferably, said QC inhibitor is a compound of formula (I) of the present invention.

More specifically, the aforementioned other agent is selected from the group consisting of beta-amyloid antibodies, vaccines, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, preferably inhibitors of dipeptidyl peptidases, most preferably DP IV inhibitors; inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Furthermore, the other agent may be, for example, an anti-anxiety drug or antidepressant selected from the group consisting of
  (a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene,
  (b) Selective serotonin re-uptake inhibitors (SSRI's), e.g. citalopram, fluoxetine, fluvoxamine, escitalopram, sertraline, paroxetine,
  (c) Tricyclic antidepressants, e.g. amitryptiline, clomipramine, desipramine, doxepin, imipramine
  (d) Monoamine oxidase (MAO) inhibitors,
  (e) Azapirones, e.g. buspirone, tandopsirone,
  (f) Serotonin-norepinephrine reuptake inhibitors (SNRI's), e.g. venlafaxine, duloxetine,
  (g) Mirtazapine,
  (h) Norepinephrine reuptake inhibitors (NRI's), e.g. reboxetine,
  (i) Bupropione,
  (j) Nefazodone,
  (k) beta-blockers,
  (l) NPY-receptor ligands: NPY agonists or antagonists.

In a further embodiment, the other agent may be, for example, an anti-multiple sclerosis drug selected from the group consisting of
  a) dihydroorotate dehydrogenase inhibitors, e.g. SC-12267, teriflunomide, MNA-715, HMR-1279 (syn. to HMR-1715, MNA-279),
  b) autoimmune suppressant, e.g. laquinimod,
  c) paclitaxel,
  d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-IL-12-antibody,
  e) peptide nucleic acid (PNA) preparations, e.g. reticulose,
  f) interferon alpha, e.g. Alfaferone, human alpha interferon (syn. to Omniferon, Alpha Leukoferon),
  g) interferon beta, e.g. Frone, interferon beta-1a like Avonex, Betron (Rebif), interferon beta analogs, interferon beta-transferrin fusion protein, recombinant interferon beta-1b like Betaseron, h) interferon tau,
i) peptides, e.g. AT-008, AnergiX.MS, Immunokine (alpha-Immunokine-NNSO3), cyclic peptides like ZD-7349,
j) therapeutic enzymes, e.g. soluble CD8 (sCD8),
k) multiple sclerosis-specific autoantigen-encoding plasmid and cytokine-encoding plasmid, e.g. BHT-3009;
l) inhibitor of TNF-alpha, e.g. BLX-1002, thalidomide, SH-636,
m) TNF antagonists, e.g. solimastat, lenercept (syn. to RO-45-2081, Tenef use), onercept (sTNFR1), CC-1069,
n) TNF alpha, e.g. etanercept (syn. to Enbrel, TNR-001)
o) CD28 antagonists, e.g. abatacept,
p) Lck tyrosine kinase inhibitors,
q) cathepsin K inhibitors,
r) analogs of the neuron-targeting membrane transporter protein taurine and the plant-derived calpain inhibitor leupeptin, e.g. Neurodur,
s) chemokine receptor-1 (CCR1) antagonist, e.g. BX-471,
t) CCR2 antagonists,
u) AMPA receptor antagonists, e.g. ER-167288-01 and ER-099487, E-2007, talampanel,
v) potassium channel blockers, e.g. fampridine,
w) tosyl-proline-phenylalanine small-molecule antagonists of the VLA-4/VCAM interaction, e.g. TBC-3342,
x) cell adhesion molecule inhibitors, e.g. TBC-772,
y) antisense oligonucleotides, e.g. EN-101,
z) antagonists of free immunoglobulin light chain (IgLC) binding to mast cell receptors, e.g. F-991,
aa) apoptosis inducing antigens, e.g. Apogen MS,
bb) alpha-2 adrenoceptor agonist, e.g. tizanidine (syn. to Zanaflex, Ternelin, Sirdalvo, Sirdalud, Mionidine),
cc) copolymer of L-tyrosine, L-lysine, L-glutamic acid and L-alanine, e.g. glatiramer acetate (syn. to Copaxone, COP-1, copolymer-1),
dd) topoisomerase II modulators, e.g. mitoxantrone hydrochloride,
ee) adenosine deaminase inhibitor, e.g. cladribine (syn. to Leustatin, Mylinax, RWJ-26251),
ff) interleukin-10, e.g. ilodecakin (syn. to Tenovil, Sch-52000, CSIF),
gg) interleukin-12 antagonists, e.g. lisofylline (syn. to CT-1501R, LSF, lysofylline),
hh) Ethanaminum, e.g. SRI-62-834 (syn. to CRC-8605, NSC-614383),
ii) immunomodulators, e.g. SAIK-MS, PNU-156804, alpha-fetoprotein peptide (i), IPDS,
jj) retinoid receptor agonists, e.g. adapalene (syn. to Differin, CD-271),
kk) TGF-beta, e.g. GDF-1 (growth and differentiation factor 1),
ii) TGF-beta-2, e.g. BetaKine,
mm) MMP inhibitors, e.g. glycomed,
nn) phosphodiesterase 4 (PDE4) inhibitors, e.g. RPR-122818,
oo) purine nucleoside phosphorylase inhibitors, e.g. 9-(3-pyridylmethyl)-9-deazaguanine, peldesine (syn. to BCX-34, TO-200),
mm) alpha-4/beta-1 integrin antagonists, e.g. ISIS-104278,
qq) antisense alpha4 integrin (CD49d), e.g. ISIS-17044, ISIS-27104,
rr) cytokine-inducing agents, e.g. nucleosides, ICN-17261,
ss) cytokine inhibitors,
tt) heat shock protein vaccines, e.g. HSPPC-96,
uu) neuregulin growth factors, e.g. GGF-2 (syn. to neuregulin, glial growth factor 2),
vv) cathepsin S-inhibitors,
ww) bropirimine analogs, e.g. PNU-56169, PNU-63693,
xx) Monocyte chemoattractant protein-1 inhibitors, e.g. benzimidazoles like MCP-1 inhibitors, LKS-1456, PD-064036, PD-064126, PD-084486, PD-172084, PD-172386.

Further, the present invention provides pharmaceutical compositions e.g. for parenteral, enteral or oral administration, comprising at least one QC inhibitor, optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one QC inhibitor and at least one of the other agents or the sequential administration thereof.

Co-administration includes administration of a formulation, which comprises at least one QC inhibitor and at least one of the other agents or the essentially simultaneous administration of separate formulations of each agent.

Beta-amyloid antibodies and compositions containing the same are described, e.g. in WO/2009/065054, WO/2009/056490, WO/2009/053696, WO/2009/033743, WO/2007/113172, WO/2007/022416, WO 2006/137354, WO 2006/118959, WO 2006/103116, WO 2006/095041, WO 2006/081171, WO 2006/066233, WO 2006/066171, WO 2006/066089, WO 2006/066049, WO 2006/055178, WO 2006/046644, WO 2006/039470, WO 2006/036291, WO 2006/026408, WO 2006/016644, WO 2006/014638, WO 2006/014478, WO 2006/008661, WO 2005/123775, WO 2005/120571, WO 2005/105998, WO 2005/081872, WO 2005/080435, WO 2005/028511, WO 2005/025616, WO 2005/025516, WO 2005/023858, WO 2005/018424, WO 2005/011599, WO 2005/000193, WO 2004/108895, WO 2004/098631, WO 2004/080419, WO 2004/071408, WO 2004/069182, WO 2004/067561, WO 2004/044204, WO 2004/032868, WO 2004/031400, WO 2004/029630, WO 2004/029629, WO 2004/024770, WO 2004/024090, WO 2003/104437, WO 2003/089460, WO 2003/086310, WO 2003/077858, WO 2003/074081, WO 2003/070760, WO 2003/063760, WO 2003/055514, WO 2003/051374, WO 2003/048204, WO 2003/045128, WO 2003/040183, WO 2003/039467, WO 2003/016466, WO 2003/015691, WO 2003/014162, WO 2003/012141, WO 2002/088307, WO 2002/088306, WO 2002/074240, WO 2002/046237, WO 2002/046222, WO 2002/041842, WO 2001/062801, WO 2001/012598, WO 2000/077178, WO 2000/072880, WO 2000/063250, WO 1999/060024, WO 1999/027944, WO 1998/044955, WO 1996/025435, WO 1994/017197, WO 1990/014840, WO 1990/012871, WO 1990/012870, WO 1989/006242.

The beta-amyloid antibodies may be selected from, for example, polyclonal, monoclonal, chimenic or humanized antibodies. Furthermore, said antibodies may be useful to develop active and passive immune therapies, i.e. vaccines and monoclonal antibodies.

Suitable examples of beta-amyloid antibodies are ACU-5A5, huC091 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.

Especially preferred are antibodies, which recognize the N-terminus of the Aβ peptide. A suitable antibody, which recognizes the Aβ-N-Terminus is, for example Acl-24 (AC Immune SA).

Monoclonal antibodies against beta-amyloid peptide are disclosed in WO 2007/068412, WO/2008/156621 and WO/2010/012004. Respective chimeric and humanized antibodies are disclosed in WO 2008/011348 and WO/2008/060364. Vaccine composition for treating an amyloid-associated disease is disclosed in WO/2002/096937, WO/2005/014041, WO 2007/068411, WO/2007/097251, WO/2009/029272, WO/2009/054537, WO/2009/090650 WO/2009/095857, WO/2010/016912, WO/2010/011947, WO/2010/011999, WO/2010/044464.

Suitable vaccines for treating an amyloid-associated disease are, e.g. Affitopes AD-01 and AD-02 (GlaxoSmithKline), ACC-01 and ACC-02 (Elan/Wyeth), CAD-106 (Novartis/Cytos Biotechnology), Suitable cysteine protease inhibitors are inhibitors of cathepsin B. Inhibitors of cathepsin B and compositions containing such inhibitors are described, e.g. in WO/2008/077109, WO/2007/038772, WO 2006/060473, WO 2006/042103, WO 2006/039807, WO 2006/021413, WO 2006/021409, WO 2005/097103, WO 2005/007199, WO2004/084830, WO 2004/078908, WO 2004/026851, WO 2002/094881, WO 2002/027418, WO 2002/021509, WO 1998/046559, WO 1996/021655.

Examples of suitable PIMT enhancers are 10-aminoaliphatyl-dibenz[b,f]oxepines described in WO 98/15647 and WO 03/057204, respectively. Further useful according to the present invention are modulators of PIMT activity described in WO 2004/039773.

Inhibitors of beta secretase and compositions containing such inhibitors are described, e.g. in WO/2010/094242, WO/2010/058333, WO/2010/021680, WO/2009/108550, WO/2009/042694, WO/2008/054698, WO/2007/051333, WO/2007/021793, WO/2007/019080, WO/2007/019078, WO/2007/011810, WO03/059346, WO2006/099352, WO2006/078576, WO2006/060109, WO2006/057983, WO2006/057945, WO2006/055434, WO2006/044497, WO2006/034296, WO2006/034277, WO2006/029850, WO2006/026204, WO2006/014944, WO2006/014762, WO2006/002004, U.S. Pat. No. 7,109,217, WO2005/113484, WO2005/103043, WO2005/103020, WO2005/065195, WO2005/051914, WO2005/044830, WO2005/032471, WO2005/018545, WO2005/004803, WO2005/004802, WO2004/062625, WO2004/043916, WO2004/013098, WO03/099202, WO03/043987, WO03/039454, U.S. Pat. No. 6,562,783, WO02/098849 and WO02/096897.

Suitable examples of beta secretase inhibitors for the purpose of the present invention are WY-25105 (Wyeth); Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312, PNU-38773, PNU-90530 (Elan/Pfizer); KMI-370, KMI-358, kmi-008 (Kyoto University); OM-99-2, OM-003 (Athenagen Inc.); AZ-12304146 (AstraZeneca/Astex); GW-840736X (GlaxoSmithKline plc.), DNP-004089 (De Novo Pharmaceuticals Ltd.) and CT-21166 (CoMentis Inc.).

Inhibitors of gamma secretase and compositions containing such inhibitors are described, e.g. in WO/2010/090954, WO/2009/011851, WO/2009/008980, WO/2008/147800, WO/2007/084595, WO2005/008250, WO/2006/004880, U.S. Pat. No. 7,122,675, U.S. Pat. No. 7,030,239, U.S. Pat. No. 6,992,081, U.S. Pat. No. 6,982,264, WO2005/097768, WO2005/028440, WO2004/101562, U.S. Pat. No. 6,756,511, U.S. Pat. No. 6,683,091, WO03/066592, WO03/014075, WO03/013527, WO02/36555, WO01/53255, U.S. Pat. No. 7,109,217, U.S. Pat. No. 7,101,895, U.S. Pat. No. 7,049,296, U.S. Pat. No. 7,034,182, U.S. Pat. No. 6,984,626, WO2005/040126, WO2005/030731, WO2005/014553, U.S. Pat. No. 6,890,956, EP 1334085, EP 1263774, WO2004/101538, WO2004/00958, WO2004/089911, WO2004/073630, WO2004/069826, WO2004/039370, WO2004/031139, WO2004/031137, U.S. Pat. No. 6,713,276, U.S. Pat. No. 6,686,449, WO03/091278, U.S. Pat. No. 6,649,196, U.S. Pat. No. 6,448,229, WO01/77144 and WO01/66564.

Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897, BMS-433796 (Bristol-Myers Squibb Co.); E-2012 (Eisai Co. Ltd.); EHT-0206, EHT-206 (ExonHit Therapeutics SA); NGX-555 (TorreyPines Therapeutics Inc.) and Semagacestat (Eli Lilly).

DP IV-inhibitors and compositions containing such inhibitors are described, e.g. in U.S. Pat. No. 6,011,155; U.S. Pat. No. 6,107,317; U.S. Pat. No. 6,110,949; U.S. Pat. No. 6,124,305; U.S. Pat. No. 6,172,081; WO99/61431, WO99/67278, WO99/67279, DE19834591, WO97/40832, WO95/15309, WO98/19998, WO00/07617, WO99/38501, WO99/46272, WO99/38501, WO01/68603, WO01/40180, WO01/81337, WO01/81304, WO01/55105, WO02/02560, WO01/34594, WO02/38541, WO02/083128, WO03/072556, WO03/002593, WO03/000250, WO03/000180, WO03/000181, EP1258476, WO03/002553, WO03/002531, WO03/002530, WO03/004496, WO03/004498, WO03/024942, WO03/024965, WO03/033524, WO03/035057, WO03/035067, WO03/037327, WO03/040174, WO03/045977, WO03/055881, WO03/057144, WO03/057666, WO03/068748, WO03/068757, WO03/082817, WO03/101449, WO03/101958, WO03/104229, WO03/74500, WO2004/007446, WO2004/007468, WO2004/018467, WO2004/018468, WO2004/018469, WO2004/026822, WO2004/032836, WO2004/033455, WO2004/037169, WO2004/041795, WO2004/043940, WO2004/048352, WO2004/050022, WO2004/052850, WO2004/058266, WO2004/064778, WO2004/069162, WO2004/071454, WO2004/076433, WO2004/076434, WO2004/087053, WO2004/089362, WO2004/099185, WO2004/103276, WO2004/103993, WO2004/108730, WO2004/110436, WO2004/111041, WO2004/112701, WO2005/000846, WO2005/000848, WO2005/011581, WO2005/016911, WO2005/023762, WO2005/025554, WO2005/026148, WO2005/030751, WO2005/033106, WO2005/037828, WO2005/040095, WO2005/044195, WO2005/047297, WO2005/051950, WO2005/056003, WO2005/056013, WO2005/058849, WO2005/075426, WO2005/082348, WO2005/085246, WO2005/087235, WO2005/095339, WO2005/095343, WO2005/095381, WO2005/108382, WO2005/113510, WO2005/116014, WO2005/116029, WO2005/118555, WO2005/120494, WO2005/121089, WO2005/121131, WO2005/123685, WO2006/995613, WO2006/009886; WO2006/013104; WO2006/017292; WO2006/019965; WO2006/020017; WO2006/023750;

WO2006/039325; WO2006/041976; WO2006/047248; WO2006/058064; WO2006/058628; WO2006/066747; WO2006/066770 and WO2006/068978.

Suitable DP IV-inhibitors for the purpose of the present invention are for example Sitagliptin, des-fluoro-sitagliptin (Merck & Co. Inc.); vildagliptin, DPP-728, SDZ-272-070 (Novartis); ABT-279, ABT-341 (Abbott Laboratories); denagliptin, TA-6666 (GlaxoSmithKline plc.); SYR-322 (Takeda San Diego Inc.); talabostat (Point Therapeutics Inc.); Ro-0730699, R-1499, R-1438 (Roche Holding AG); FE-999011 (Ferring Pharmaceuticals); TS-021 (Taisho Pharmaceutical Co. Ltd.); GRC-8200 (Glenmark Pharmaceuticals Ltd.); ALS-2-0426 (Alantos Pharmaceuticals Holding Inc.); ARI-2243 (Arisaph Pharmaceuticals Inc.); SSR-162369 (Sanofi-Synthelabo); MP-513 (Mitsubishi Pharma Corp.); DP-893, CP-867534-01 (Pfizer Inc.); TSL-225, TMC-2A (Tanabe Seiyaku Co. Ltd.); PHX-1149 (Phenomenix Corp.); saxagliptin (Bristol-Myers Squibb Co.); PSN-9301 ((OSI) Prosidion), S-40755 (Servier); KRP-104 (ActivX Biosciences Inc.); sulphostin (Zaidan Hojin); KR-62436 (Korea Research Institute of Chemical Technology); P32/98 (Probiodrug AG); BI-A, BI-B (Boehringer Ingelheim Corp.); SK-0403 (Sanwa Kagaku Kenkyusho Co. Ltd.); and NNC-72-2138 (Novo Nordisk A/S).

Other Preferred DP IV-Inhibitors are
(i) dipeptide-like compounds, disclosed in WO 99/61431, e.g. N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof;
(ii) peptide structures, disclosed in WO 03/002593, e.g. tripeptides;
(iii) peptidylketones, disclosed in WO 03/033524;
(vi) substituted aminoketones, disclosed in WO 03/040174;
(v) topically active DP IV-inhibitors, disclosed in WO 01/14318;
(vi) prodrugs of DP IV-inhibitors, disclosed in WO 99/67278 and WO 99/67279; and
(v) glutaminyl based DP IV-inhibitors, disclosed in WO 03/072556 and WO 2004/099134.

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.), RQ-00000009 (RaQualia Pharma Inc).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); Tramiprosate (Neurochem); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.), i-1176 and SEN-1329 (Senexis Ltd.), AGT-160 (ArmaGen Technologies), Davunetide (Allon Therapeutics), ELND-005 (Elan Corp/Transition Therapeutics) and nilvadipine (Archer Pharmaceuticals).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, CI-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); tipelukast, ibudilast (Kyorin Pharmaceutical), CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuroid SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.). A preferred PDE-4-inhibitor is Rolipram.

MAO inhibitors and compositions containing such inhibitors are described, e.g. in WO2006/091988, WO2005/007614, WO2004/089351, WO01/26656, WO01/12176, WO99/57120, WO99/57119, WO99/13878, WO98/40102, WO98/01157, WO96/20946, WO94/07890 and WO92/21333.

Suitable MAO-inhibitors for the purpose of the present invention are for example Linezolid (Pharmacia Corp.); RWJ-416457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Wellcome Co.); CX-157 (Krenitsky Pharmaceuticals Inc.); desoxypeganine (HF Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer), NW-1048 (Newron Pharmaceuticals SpA.), EVT-302 (Evotec).

Suitable histamine H3 antagonists for the purpose of the present invention are, e.g. ABT-239, ABT-834 (Abbott Laboratories); 3874-H1 (Aventis Pharma); UCL-2173 (Berlin Free University), UCL-1470 (BioProjet, Societe Civile de Recherche); DWP-302 (Daewoong Pharmaceutical Co Ltd); GSK-189254A, GSK-207040A (GlaxoSmithKline Inc.); cipralisant, GT-2203 (Gliatech Inc.); Ciproxifan (INSERM), 1S,2S-2-(2-Aminoethyl)-1-(1H-imidazol-4-yl)cyclopropane (Hokkaido University); JNJ-17216498, JNJ-5207852 (Johnson & Johnson); NNC-0038-0000-1049 (Novo Nordisk A/S); and Sch-79687 (Schering-Plough).

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 95/15310, WO 93/00361, EP 0556482, JP 06234693, JP 01068396, EP 0709373, U.S. Pat. No. 5,965,556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat.

No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5,506,256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757,083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 91/18877, JP 04009367, JP 04235162, U.S. Pat. No. 5,407,950, WO 95/01352, JP 01250370, JP 02207070, U.S. Pat. No. 5,221,752, EP 0468339, JP 04211648, WO 99/46272, WO 2006/058720 and PCT/EP2006/061428.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd.); ONO-1603 (Ono Pharmaceutical Co Ltd); JTP-4819 (Japan Tobacco Inc.) and S-17092 (Servier).

Other suitable compounds that can be used according to the present invention in combination with QC-inhibitors are NPY, an NPY mimetic or an NPY agonist or antagonist or a ligand of the NPY receptors.

Preferred according to the present invention are antagonists of the NPY receptors.

Suitable ligands or antagonists of the NPY receptors are 3a, 4,5,9b-tetrahydro-1 h-benz[e]indol-2-ylamine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420; WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds, which may include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)—N2-(diphenylacetyl)-(R)—N-[1-(4-hydroxy-phenyl) ethyl]arginine amide (Example 4 of international patent application WO 99/15498).

M1 receptor agonists and compositions containing such inhibitors are described, e.g. in WO2004/087158, WO91/10664.

Suitable M1 receptor antagonists for the purpose of the present invention are for example CDD-0102 (Cognitive Pharmaceuticals); Cevimeline (i) (Snow Brand Milk Products Co. Ltd.); NGX-267 (TorreyPines Therapeutics); sabcomeline (GlaxoSmithKline); alvameline (H Lundbeck A/S); LY-593093 (Eli Lilly & Co.); VRTX-3 (Vertex Pharmaceuticals Inc.); WAY-132983 (Wyeth), CI-1017/(PD-151832) (Pfizer Inc.) and MCD-386 (Mitridion Inc.).

Acetylcholinesterase inhibitors and compositions containing such inhibitors are described, e.g. in WO2006/071274, WO2006/070394, WO2006/040688, WO2005/092009, WO2005/079789, WO2005/039580, WO2005/027975, WO2004/084884, WO2004/037234, WO2004/032929, WO03/101458, WO03/091220, WO03/082820, WO03/020289, WO02/32412, WO01/85145, WO01/78728, WO01/66096, WO00/02549, WO01/00215, WO00/15205, WO00/23057, WO00/33840, WO00/30446, WO00/23057, WO00/15205, WO00/09483, WO00/07600, WO00/02549, WO99/47131, WO99/07359, WO98/30243, WO97/38993, WO97/13754, WO94/29255, WO94/20476, WO94/19356, WO93/03034 and WO92/19238.

Suitable acetylcholinesterase inhibitors for the purpose of the present invention are for example Donepezil (Eisai Co. Ltd.); rivastigmine (Novartis AG); (−)-phenserine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Warner-Lambert Co.); metrifonate (Bayer Corp.), INM-176 (Whanln), huperzine A (Neuro-Hitech/Xel Pharmaceutical), mimopezil (Debiopharm) and Dimebon (Medivation/Pfizer).

NMDA receptor antagonists and compositions containing such inhibitors are described, e.g. in WO2006/094674, WO2006/058236, WO2006/058059, WO2006/010965, WO2005/000216, WO2005/102390, WO2005/079779, WO2005/079756, WO2005/072705, WO2005/070429, WO2005/055996, WO2005/035522, WO2005/009421, WO2005/000216, WO2004/092189, WO2004/039371, WO2004/028522, WO2004/009062, WO03/010159, WO02/072542, WO02/34718, WO01/98262, WO01/94321, WO01/92204, WO01/81295, WO01/32640, WO01/10833, WO01/10831, WO00/56711, WO00/29023, WO00/00197, WO99/53922, WO99/48891, WO99/45963, WO99/01416, WO99/07413, WO99/01416, WO98/50075, WO98/50044, WO98/10757, WO98/05337, WO97/32873, WO97/23216, WO97/23215, WO97/23214, WO96/14318, WO96/08485, WO95/31986, WO95/26352, WO95/26350, WO95/26349, WO95/26342, WO95/12594, WO95/02602, WO95/02601, WO94/20109, WO94/13641, WO94/09016 and WO93/25534.

Suitable NMDA receptor antagonists for the purpose of the present invention are for example Memantine (Merz & Co. GmbH); topiramate (Johnson & Johnson); AVP-923

(Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); EpiCept NP-1 (Dalhousie University); indantadol (V-3381; CNP-3381) (Vernalis); perzinfotel (EAA-090, WAY-126090, EAA-129) (Wyeth); RGH-896 (Gedeon Richter Ltd.); traxoprodil (CP-101606), besonprodil (PD-196860, CI-1041) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-CI-kynurenine (4-CI-KYN)), 7-chloro-kynurenic acid (7-CI-KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N-2-(adamantly)-hexamethylen-imine) (RAMS); Lancicemine (AR-R-15896) (AstraZeneca); EVT-102, Ro-25-6981 and Ro-63-1908 (Hoffmann-La Roche AG/Evotec), neramexane (Merz).

Furthermore, the present invention relates to combination therapies useful for the treatment of atherosclerosis, restenosis or arthritis, administering a QC inhibitor in combination with another therapeutic agent selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors providing beneficial or synergistic therapeutic effects over each monotherapy component alone.

Angiotensin II receptor blockers are understood to be those active agents that bind to the AT1-receptor subtype of angiotensin II receptor but do not result in activation of the receptor. As a consequence of the blockade of the AT1 receptor, these antagonists can, e.g. be employed as antihypertensive agents.

Suitable angiotensin II receptor blockers which may be employed in the combination of the present invention include $AT_1$ receptor antagonists having differing structural features, preferred are those with non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-4177 of the formula

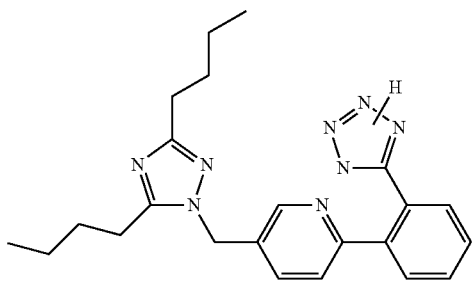

and the compound with the designation the compound ZD-8731 of the formula

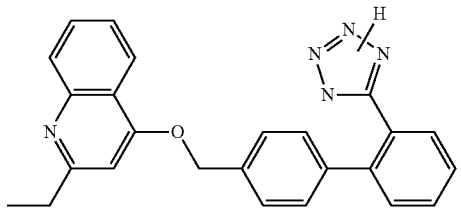

or, in each case, a pharmaceutically acceptable salt thereof.

Preferred AT1-receptor antagonists are those agents that have been approved and reached the market, most preferred is valsartan, or a pharmaceutically acceptable salt thereof.

The interruption of the enzymatic degradation of angiotensin to angiotensin II with ACE inhibitors is a successful variant for the regulation of blood pressure and thus also makes available a therapeutic method for the treatment of hypertension.

A suitable ACE inhibitor to be employed in the combination of the present invention is, e.g. a compound selected from the group consisting alacepril, benazepril, benazeprilat; captopril, ceronapril, cilazapril, delapril, enalapril, enaprilat, fosinopril, imidapril, lisinopril, moveltopril, perindopril, quinapril, ramipril, spirapril, temocapril and trandolapril, or in each case, a pharmaceutically acceptable salt thereof.

Preferred ACE inhibitors are those agents that have been marketed, most preferred are benazepril and enalapril.

A diuretic is, for example, a thiazide derivative selected from the group consisting of chlorothiazide, hydrochlorothiazide, methylclothiazide, and chlorothalidon. The most preferred diuretic is hydrochlorothiazide. A diuretic furthermore comprises a potassium sparing diuretic such as amiloride or triameterine, or a pharmaceutically acceptable salt thereof.

The class of CCBs essentially comprises dihydropyridines (DHPs) and non-DHPs, such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

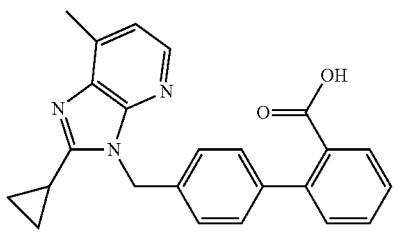

the compound with the designation SC-52458 of the following formula

Preferred CCBs comprise amlodipine, diltiazem, isradipine, nicardipine, nifedipine, nimodipine, nisoldipine, nitrendipine and verapamil or, e.g. dependent on the specific CCB, a pharmaceutically acceptable salt thereof. Especially preferred as DHP is amlodipine or a pharmaceutically acceptable salt thereof, especially the besylate. An especially preferred representative of non-DHPs is verapamil or a pharmaceutically acceptable salt, especially the hydrochloride, thereof.

Beta-blockers suitable for use in the present invention include beta-adrenergic blocking agents (beta-blockers), which compete with epinephrine for beta-adrenergic receptors and interfere with the action of epinephrine. Preferably, the beta-blockers are selective for the beta-adrenergic receptor as compared to the alpha-adrenergic receptors, and so do not have a significant alpha-blocking effect. Suitable beta-blockers include compounds selected from acebutolol, atenolol, betaxolol, bisoprolol, carteolol, carvedilol, esmolol, labetalol, metoprolol, nadolol, oxprenolol, penbutolol, pindolol, propranolol, sotalol and timolol. Where the beta-blocker is an acid or base or otherwise capable of forming pharmaceutically acceptable salts or prodrugs, these forms are considered to be encompassed herein, and it is understood that the compounds may be administered in free form or in the form of a pharmaceutically acceptable salt or a prodrug, such as a physiologically hydrolyzable and acceptable ester. For example, metoprolol is suitably administered as its tartrate salt, propranolol is suitably administered as the hydrochloride salt, and so forth.

Platelet aggregation inhibitors include PLAVIX® (clopidogrel bisulfate), PLETAL® (cilostazol) and aspirin.

Cholesterol absorption modulators include ZETIA® (ezetimibe) and KT6-971 (Kotobuki Pharmaceutical Co. Japan).

HMG-Co-A reductase inhibitors (also called beta-hydroxy-beta-methylglutaryl-co-enzyme-A reductase inhibitors or statins) are understood to be those active agents which may be used to lower lipid levels including cholesterol in blood.

The class of HMG-Co-A reductase inhibitors comprises compounds having differing structural features. For example, mention may be made of the compounds, which are selected from the group consisting of atorvastatin, cerivastatin, fluvastatin, lovastatin, pitavastatin, pravastatin, rosuvastatin and simvastatin, or in each case, a pharmaceutically acceptable salt thereof.

Preferred HMG-Co-A reductase inhibitors are those agents, which have been marketed, most preferred is atorvastatin, pitavastatin or simvastatin, or a pharmaceutically acceptable salt thereof.

HDL-increasing compounds include, but are not limited to, cholesterol ester transfer protein (CETP) inhibitors. Examples of CETP inhibitors include JTT705 disclosed in Example 26 of U.S. Pat. No. 6,426,365 issued Jul. 30, 2002, and pharmaceutically acceptable salts thereof.

Inhibition of interleukin 6 mediated inflammation may be achieved indirectly through regulation of endogenous cholesterol synthesis and isoprenoid depletion or by direct inhibition of the signal transduction pathway utilizing interleukin-6 inhibitor/antibody, interleukin-6 receptor inhibitor/antibody, interleukin-6 antisense oligonucleotide (ASON), gp130 protein inhibitor/antibody, tyrosine kinase inhibitors/antibodies, serine/threonine kinase inhibitors/antibodies, mitogen-activated protein (MAP) kinase inhibitors/antibodies, phosphatidylinositol 3-kinase (PI3K) inhibitors/antibodies, Nuclear factor kappaB (NF-κB) inhibitors/antibodies, IκB kinase (IKK) inhibitors/antibodies, activator protein-1 (AP-1) inhibitors/antibodies, STAT transcription factors inhibitors/antibodies, altered IL-6, partial peptides of IL-6 or IL-6 receptor, or SOCS (suppressors of cytokine signaling) protein, PPAR gamma and/or PPAR beta/delta activators/ligands or a functional fragment thereof.

A suitable antiinflammatory corticosteroid is dexamethasone.

Suitable antiproliferative agents are cladribine, rapamycin, vincristine and taxol.

A suitable inhibitor of extracellular matrix synthesis is halofuginone.

A suitable growth factor or cytokine signal transduction inhibitor is, e.g. the ras inhibitor R115777.

A suitable tyrosine kinase inhibitor is tyrphostin.

Suitable renin inhibitors are described, e.g. in WO 2006/116435. A preferred renin inhibitor is aliskiren, preferably in the form of the hemi-fumarate salt thereof.

MCP-1 antagonists may, e.g. be selected from anti-MCP-1 antibodies, preferably monoclonal or humanized monoclonal antibodies, MCP-1 expression inhibitors, CCR2-antagonists, TNF-alpha inhibitors, VCAM-1 gene expression inhibitors and anti-C5a monoclonal antibodies.

MCP-1 antagonists and compositions containing such inhibitors are described, e.g. in WO02/070509, WO02/081463, WO02/060900, US2006/670364, US2006/677365, WO2006/097624, US2006/316449, WO2004/056727, WO03/053368, WO00/198289, WO00/157226, WO00/046195, WO00/046196, WO00/046199, WO00/046198, WO00/046197, WO99/046991, WO99/007351, WO98/006703, WO97/012615, WO2005/105133, WO03/037376, WO2006/125202, WO2006/085961, WO2004/024921, WO2006/074265.

Suitable MCP-1 antagonists are, for instance, C-243 (Telik Inc.); NOX-E36 (Noxxon Pharma AG); AP-761 (Actimis Pharmaceuticals Inc.); ABN-912, NIBR-177 (Novartis AG); CC-11006 (Celgene Corp.); SSR-150106 (Sanofi-Aventis); MLN-1202 (Millenium Pharmaceuticals Inc.); AGI-1067, AGIX-4207, AGI-1096 (AtherioGenics Inc.); PRS-211095, PRS-211092 (Pharmos Corp.); anti-C5a monoclonal antibodies, e.g. neutrazumab (G2 Therapies Ltd.); AZD-6942 (AstraZeneca plc.); 2-mercaptoimidazoles (Johnson & Johnson); TEI-E00526, TEI-6122 (Deltagen); RS-504393 (Roche Holding AG); SB-282241, SB-380732, ADR-7 (GlaxoSmithKline); anti-MCP-1 monoclonal antibodies (Johnson & Johnson).

Combinations of QC-inhibitors with MCP-1 antagonists may be useful for the treatment of inflammatory diseases in general, including neurodegenerative diseases.

Combinations of QC-inhibitors with MCP-1 antagonists are preferred for the treatment of Alzheimer's disease.

Most preferably the QC inhibitor is combined with one or more compounds selected from the following group:
PF-4360365, m266, bapineuzumab, R-1450, Posiphen, (+)-phenserine, MK-0752, LY-450139, E-2012, (R)-flurbiprofen, AZD-103, AAB-001 (Bapineuzumab), Tramiprosate, EGb-761, TAK-070, Doxofylline, theophylline, cilomilast, tofimilast, roflumilast, tetomilast, tipelukast, ibudilast, HT-0712, MEM-1414, oglemilast, Linezolid, budipine, isocarboxazid, phenelzine, tranylcypromine, indantadol, moclobemide, rasagiline, ladostigil, safinamide, ABT-239, ABT-834, GSK-189254A, Ciproxifan, JNJ-17216498, Fmoc-Ala-Pyrr-CN, Z-Phe-Pro-Benzothiazole, Z-321, ONO-1603, JTP-4819, S-17092, BIBP3226; (R)—N2-(diphenylacetyl)-(R)—N-[1-(4-hydroxyphenyl)ethyl]arginine amide, Cevimeline, sabcomeline, (PD-151832), Donepezil, rivastigmine, (−)-phenserine, ladostigil, galantamine, tacrine, metrifonate, Memantine, topiramate, AVP-923, EN-3231, neramexane, valsartan, benazepril, enalapril, hydrochlorothiazide, amlodipine, diltiazem, isradipine, nicardipine, nifedipine, nimodipine, nisoldipine, nitrendipine, verapamil, amlodipine, acebutolol, atenolol, betaxolol, bisoprolol, carteolol, carvedilol, esmolol, labetalol, metoprolol, nadolol, oxprenolol, penbutolol, pindolol, propranolol, sotalol, timolol, PLAVIX® (clopidogrel bisulfate), PLETAL® (cilostazol), aspirin, ZETIA® (ezetimibe) and KT6-971, statins, atorvastatin, pitavastatin or simvastatin; dexamethasone, cladribine, rapamycin, vincristine, taxol, aliskiren, C-243, ABN-912, SSR-150106, MLN-1202 and betaferon.

In particular, the following combinations are considered:

- a QC inhibitor, preferably a QC inhibitor of formula (I), more preferably a QC inhibitor selected from any one of examples 1-3, 5-15, 17-21, 23-26, 28-30, in combination with Atorvastatin for the treatment and/or prevention of atherosclerosis,
- a QC inhibitor, preferably a QC inhibitor of formula (I), more preferably a QC inhibitor selected from any one of examples 1-3, 5-15, 17-21, 23-26, 28-30, in combination with immunosuppressive agents, preferably rapamycin for the prevention and/or treatment of restenosis,
- a QC inhibitor, preferably a QC inhibitor of formula (I), more preferably a QC inhibitor selected from any one of examples 1-3, 5-15, 17-21, 23-26, 28-30, in combination with immunosuppressive agents, preferably paclitaxel for the prevention and/or treatment of restenosis,
- a QC inhibitor, preferably a QC inhibitor of formula (I), more preferably a QC inhibitor selected from any one of examples 1-3, 5-15, 17-21, 23-26, 28-30, in combination with AChE inhibitors, preferably Donepezil, for the prevention and/or treatment of Alzheimer's disease,
- a QC inhibitor, preferably a QC inhibitor of formula (I), more preferably a QC inhibitor selected from any one of examples 1-3, 5-15, 17-21, 23-26, 28-30, in combination with interferones, preferably Aronex, for the prevention and/or treatment of multiple sclerosis,
- a QC inhibitor, preferably a QC inhibitor of formula (I), more preferably a QC inhibitor selected from any one of examples 1-3, 5-15, 17-21, 23-26, 28-30, in combination with interferones, preferably betaferon, for the prevention and/or treatment of multiple sclerosis,
- a QC inhibitor, preferably a QC inhibitor of formula (I), more preferably a QC inhibitor selected from any one of examples 1-3, 5-15, 17-21, 23-26, 28-30, in combination with interferones, preferably Rebif, for the prevention and/or treatment of multiple sclerosis
- a QC inhibitor, preferably a QC inhibitor of formula (I), more preferably a QC inhibitor selected from any one of examples 1-3, 5-15, 17-21, 23-26, 28-30, in combination with Copaxone, for the prevention and/or treatment of multiple sclerosis,
- a QC inhibitor, preferably a QC inhibitor of formula (I), more preferably a QC inhibitor selected from any one of examples 1-3, 5-15, 17-21, 23-26, 28-30, in combination with dexamethasone, for the prevention and/or treatment of restenosis,
- a QC inhibitor, preferably a QC inhibitor of formula (I), more preferably a QC inhibitor selected from any one of examples 1-3, 5-15, 17-21, 23-26, 28-30, in combination with dexamethasone, for the prevention and/or treatment of atherosclerosis,
- a QC inhibitor, preferably a QC inhibitor of formula (I), more preferably a QC inhibitor selected from any one of examples 1-3, 5-15, 17-21, 23-26, 28-30, in combination with dexamethasone, for the prevention and/or treatment of rheumatoid arthritis,
- a QC inhibitor, preferably a QC inhibitor of formula (I), more preferably a QC inhibitor selected from any one of examples 1-3, 5-15, 17-21, 23-26, 28-30, in combination with HMG-Co-A-reductase inhibitors, for the prevention and/or treatment of restenosis, wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1-3, 5-15, 17-21, 23-26, 28-30, in combination with HMG-Co-A reductase inhibitors, for the prevention and/or treatment of atherosclerosis wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1-3, 5-15, 17-21, 23-26, 28-30, in combination with HMG-Co-A reductase inhibitors, for the prevention and/or treatment of rheumatoid arthritis wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1-3, 5-15, 17-21, 23-26, 28-30, in combination with amyloid-beta antibodies for the prevention and/or treatment of mild cognitive impairment, wherein the amyloid-beta antibody is Acl-24,
- a QC inhibitor, preferably a QC inhibitor of formula (I), more preferably a QC inhibitor selected from any one of examples 1-3, 5-15, 17-21, 23-26, 28-30, in combination with amyloid-beta antibodies for the prevention and/or treatment of Alzheimer's disease, wherein the amyloid-beta antibody is Acl-24,
- a QC inhibitor, preferably a QC inhibitor of formula (I), more preferably a QC inhibitor selected from any one of examples 1-3, 5-15, 17-21, 23-26, 28-30, in combination with amyloid-beta antibodies for the prevention and/or treatment of neurodegeneration in Down Syndrome, wherein the amyloid-beta antibody is Acl-24,
- a QC inhibitor, preferably a QC inhibitor of formula (I), more preferably a QC inhibitor selected from any one of examples 1-3, 5-15, 17-21, 23-26, 28-30, in combination with beta-secretase inhibitors for the prevention and/or treatment of mild cognitive impairment, wherein the beta-secretase inhibitor is selected from WY-25105, GW-840736X and CTS-21166,
- a QC inhibitor, preferably a QC inhibitor of formula (I), more preferably a QC inhibitor selected from any one of examples 1-3, 5-15, 17-21, 23-26, 28-30, in combination with beta-secretase inhibitors for the prevention and/or treatment of Alzheimer's disease, wherein the beta-secretase inhibitor is selected from WY-25105, GW-840736X and CTS-21166,
- a QC inhibitor, preferably a QC inhibitor of formula (I), more preferably a QC inhibitor selected from any one of examples 1-3, 5-15, 17-21, 23-26, 28-30, in combination with beta-secretase inhibitors for the prevention and/or treatment of neurodegeneration in Down Syndrome, wherein the beta-secretase inhibitor is selected from WY-25105, GW-840736X and CTS-21166, a QC inhibitor, preferably a QC inhibitor of formula (I), more preferably a QC inhibitor selected from any one of examples 1-3, 5-15, 17-21, 23-26, 28-30, in combination with gamma-secretase inhibitors for the prevention and/or treatment of mild cognitive impairment, wherein the gamma-secretase inhibitor is selected from LY-450139, LY-411575 and AN-37124, a QC inhibitor, preferably a QC inhibitor of formula (I), more preferably a QC inhibitor selected from any one of examples 1-3, 5-15, 17-21, 23-26, 28-30, in combination with gamma-secretase inhibitors for the prevention and/or treatment of Alzheimer's disease, wherein the gamma-secretase inhibitor is selected from LY-450139, LY-411575 and AN-37124, a QC inhibitor, preferably a QC inhibitor of formula (I), more preferably a QC inhibitor selected from any one of examples 1-3, 5-15, 17-21, 23-26, 28-30, in combination with gamma-secretase inhibitors for the prevention and/or treatment of neurodegeneration in Down Syndrome, wherein the gamma-secretase inhibitor is selected from LY-450139, LY-411575 and AN-37124.

Such a combination therapy is in particular useful for AD, FAD, FDD and neurodegeneration in Down syndrome as well as atherosclerosis, rheumatoid arthritis, restenosis and pancreatitis.

Such combination therapies might result in a better therapeutic effect (less proliferation as well as less inflammation, a stimulus for proliferation) than would occur with either agent alone.

With regard to the specific combination of inhibitors of QC and further compounds it is referred in particular to WO 2004/098625 in this regard, which is incorporated herein by reference.

Pharmaceutical Compositions

To prepare the pharmaceutical compositions of this invention, at least one compound of formula (I) optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, *acacia*, alginate, dextran, sodium carboxymethylcellulose, methylcellulose, polyvinylpyrrolidone or gelatin.

The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as *acacia*, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, *acacia*, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising at least one compound of formula (I), optionally in combination with at least one of the other aforementioned agents and a pharmaceutically acceptable carrier.

The compositions are preferably in a unit dosage form in an amount appropriate for the relevant daily dosage.

Suitable dosages, including especially unit dosages, of the compounds of the present invention include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

EXAMPLES

| Cpd. No. | Structure | Name | Formula | Mol. Weight |
|---|---|---|---|---|
| 1 | 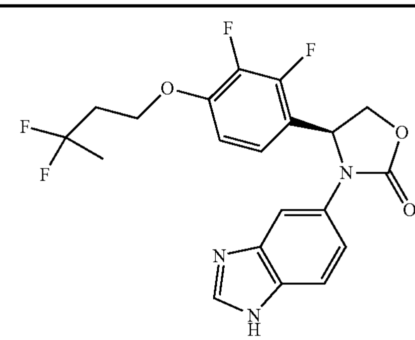 | (S)-3-(1H-benzo[d]imidazol-5-yl)-4-(4-(3,3-difluorobutoxy)-2,3-difluorophenyl)-oxazolidin-2-one | $C_{20}H_{17}F_4N_3O_3$ | 423.36 |

-continued

| Cpd. No. | Structure | Name | Formula | Mol. Weight |
|---|---|---|---|---|
| 2 | 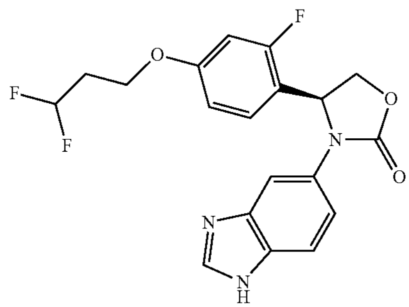 [SMILES: O=C1OC[C@H](c2ccc(OCCC(F)F)cc2F)N1c1ccc2[nH]cnc2c1] | (S)-3-(1H-benzo[d]imidazol-5-yl)-4-(4-(3,3-difluoropropoxy)-2-fluorophenyl)oxazolidin-2-one | $C_{19}H_{16}F_3N_3O_3$ | 391.34 |
| 3 | 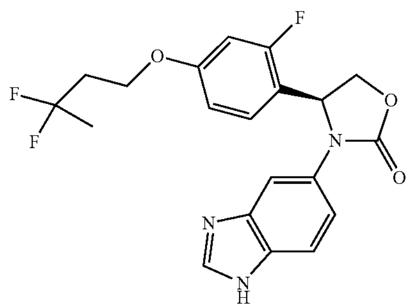 [SMILES: CC(F)(F)CCOc1ccc([C@H]2COC(=O)N2c2ccc3[nH]cnc3c2)c(F)c1] | (S)-3-(1H-benzo[d]imidazol-5-yl)-4-(4-(3,3-difluorobutoxy)-2-fluorophenyl)oxazolidin-2-one | $C_{20}H_{18}F_3N_3O_3$ | 405.37 |
| 4 | 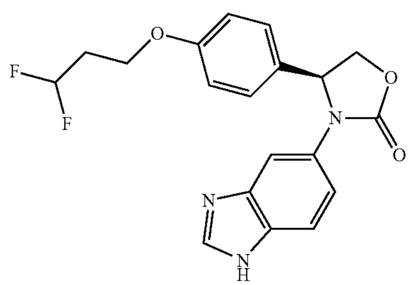 [SMILES: O=C1OC[C@H](c2ccc(OCCC(F)F)cc2)N1c1ccc2[nH]cnc2c1] | (S)-3-(1H-benzo[d]imidazol-5-yl)-4-(4-(3,3-difluoropropoxy)phenyl)oxazolidin-2-one | $C_{19}H_{17}F_2N_3O_3$ | 373.35 |
| 5 | 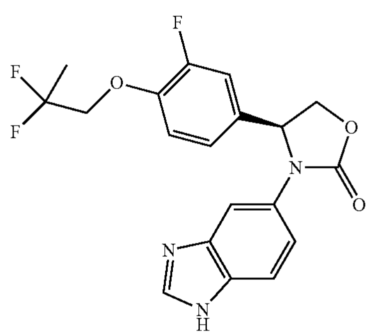 [SMILES: CC(F)(F)COc1ccc([C@H]2COC(=O)N2c2ccc3[nH]cnc3c2)cc1F] | (S)-3-(1H-benzo[d]imidazol-5-yl)-4-(4-(2,2-difluoropropoxy)-3-fluorophenyl)oxazolidin-2-one | $C_{19}H_{16}F_3N_3O_3$ | 391.34 |
| 6 | 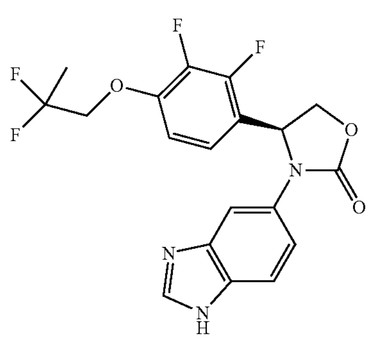 [SMILES: CC(F)(F)COc1ccc([C@H]2COC(=O)N2c2ccc3[nH]cnc3c2)c(F)c1F] | (S)-3-(1H-benzo[d]imidazol-5-yl)-4-(4-(2,2-difluoropropoxy)-2,3-difluorophenyl)oxazolidin-2-one | $C_{19}H_{15}F_4N_3O_3$ | 409.33 |

| Cpd. No. | Structure | Name | Formula | Mol. Weight |
|---|---|---|---|---|
| 7 | 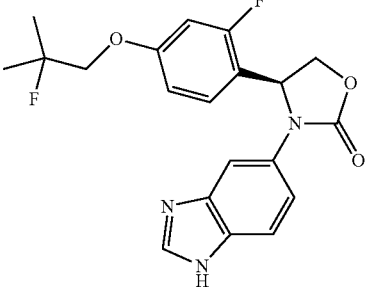 | (S)-3-(1H-benzo[d]imidazol-5-yl)-4-(4-(2,2-difluoropropoxy)-2-fluorophenyl)oxazolidin-2-one | $C_{19}H_{16}F_3N_3O_3$ | 391.34 |
| 8 | 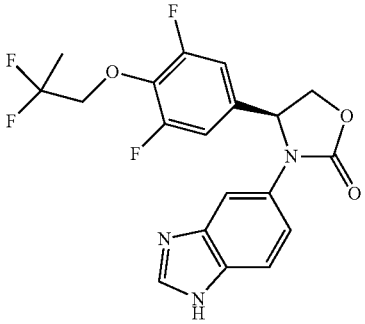 | (S)-3-(1H-benzo[d]imidazol-5-yl)-4-(4-(2,2-difluoropropoxy)-3,5-difluorophenyl)oxazolidin-2-one | $C_{19}H_{15}F_4N_3O_3$ | 409.33 |
| 10 | 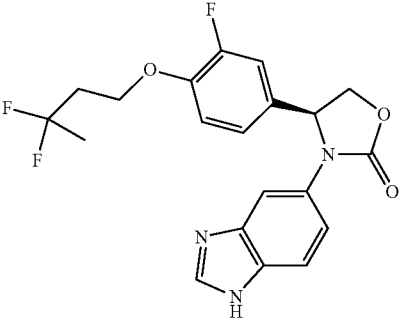 [SMILES: CC(F)(F)CCOc1ccc([C@H]2COC(=O)N2c2ccc3[nH]cnc3c2)cc1F] | (S)-3-(1H-benzo[d]imidazol-5-yl)-4-(4-(3,3-difluorobutoxy)-3-fluorophenyl)oxazolidin-2-one | $C_{20}H_{18}F_3N_3O_3$ | 405.37 |
| 11 | 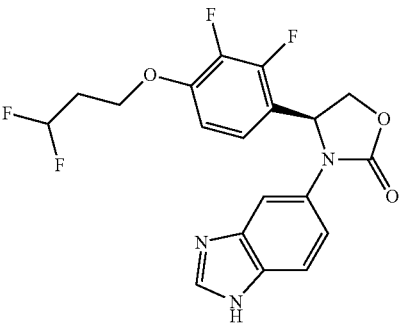 [SMILES: O=C1OC[C@H](c2ccc(OCCC(F)F)c(F)c2F)N1c1ccc2[nH]cnc2c1] | (S)-3-(1H-benzo[d]imidazol-5-yl)-4-(4-(3,3-difluoropropoxy)-2,3-difluorophenyl)oxazolidin-2-one | $C_{19}H_{15}F_4N_3O_3$ | 409.33 |

| Cpd. No. | Structure | Name | Formula | Mol. Weight |
|---|---|---|---|---|
| 12 | 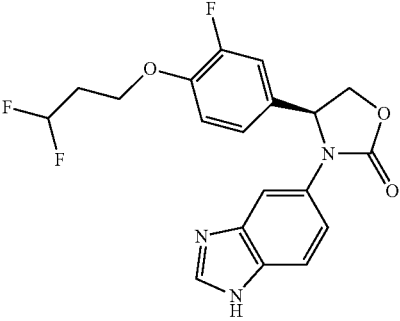 [SMILES: O=C1OC[C@H](c2ccc(OCCC(F)F)c(F)c2)N1c1ccc2[nH]cnc2c1] | (S)-3-(1H-benzo[d]imidazol-5-yl)-4-(4-(3,3-difluoropropoxy)-3-fluorophenyl)oxazolidin-2-one | $C_{19}H_{16}F_3N_3O_3$ | 391.34 |
| 13 | 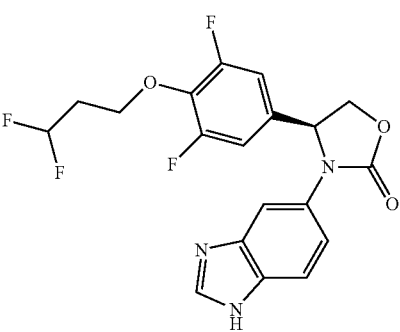 [SMILES: O=C1OC[C@H](c2cc(F)c(OCCC(F)F)c(F)c2)N1c1ccc2[nH]cnc2c1] | S)-3-(1H-benzo[d]imidazol-6-yl)-4-(4-(3,3-difluoropropoxy)-3,5-difluorophenyl)oxazolidin-2-one | $C_{19}H_{15}F_4N_3O_3$ | 409.33 |
| 14 | 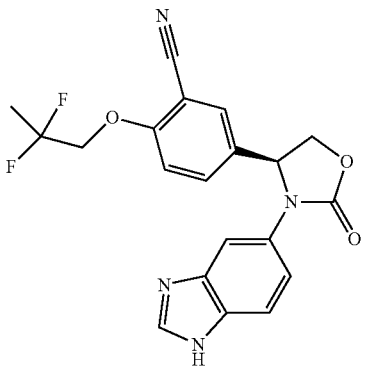 [SMILES: CC(F)(F)COc1ccc([C@H]2COC(=O)N2c2ccc3[nH]cnc3c2)cc1C#N] | (S)-5-(3-(1H-benzo[d]imidazol-5-yl)-2-oxooxazolidin-4-yl)-2-(2,2-difluoropropoxy)benzonitrile | $C_{20}H_{16}F_2N_4O_3$ | 398.36 |
| 15 | 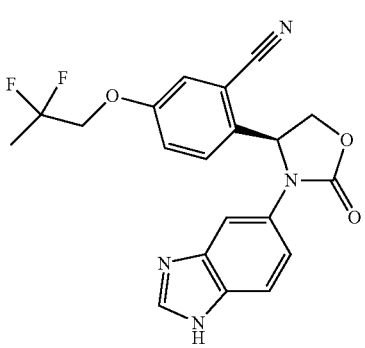 [SMILES: CC(F)(F)COc1ccc([C@H]2COC(=O)N2c2ccc3[nH]cnc3c2)c(C#N)c1] | (S)-2-(3-(1H-benzo[d]imidazol-5-yl)-2-oxooxazolidin-4-yl)-5-(2,2-difluoropropoxy)benzonitrile | $C_{20}H_{16}F_2N_4O_3$ | 398.36 |

-continued

| Cpd. No. | Structure | Name | Formula | Mol. Weight |
|---|---|---|---|---|
| 16 | 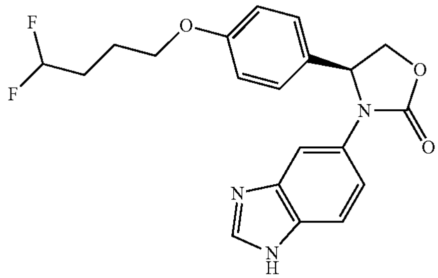 [SMILES: O=C1OC[C@H](c2ccc(OCCCC(F)F)cc2)N1c1ccc2[nH]cnc2c1] | (S)-3-(1H-benzo[d]imidazol-5-yl)-4-(4-(4,4-difluorobutoxy)phenyl)oxazolidin-2-one | $C_{20}H_{19}F_2N_3O_3$ | 387.38 |
| 17 | 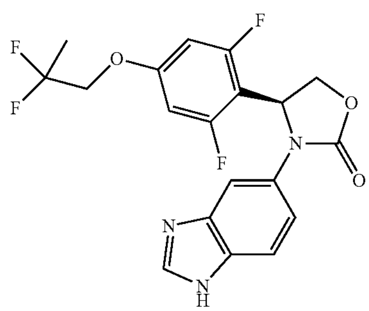 [SMILES: CC(F)(F)COc1cc(F)c([C@H]2COC(=O)N2c2ccc3[nH]cnc3c2)c(F)c1] | (S)-3-(1H-benzo[d]imidazol-5-yl)-4-(4-(2,2-difluoropropoxy)-2,6-difluorophenyl)oxazolidin-2-one | $C_{19}H_{15}F_4N_3O_3$ | 409.33 |
| 18 | 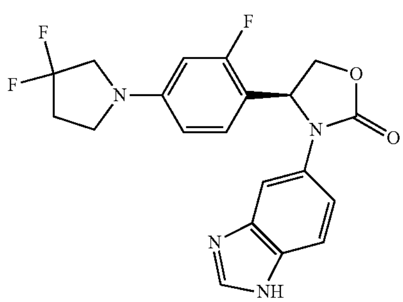 [SMILES: O=C1OC[C@H](c2ccc(N3CCC(F)(F)C3)cc2F)N1c1ccc2[nH]cnc2c1] | (S)-3-(1H-benzo[d]imidazol-5-yl)-4-(4-(3,3-difluoropyrrolidin-1-yl)-2-fluorophenyl)-oxazolidin-2-one | $C_{20}H_{17}F_3N_4O_2$ | 402.37 |
| 19 | 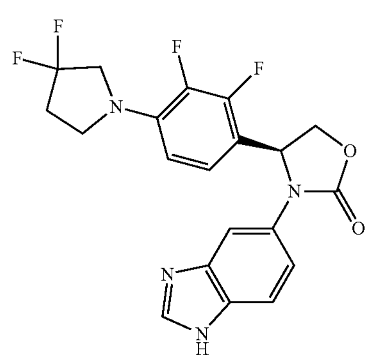 [SMILES: O=C1OC[C@H](c2ccc(N3CCC(F)(F)C3)c(F)c2F)N1c1ccc2[nH]cnc2c1] | (S)-3-(1H-benzo[d]imidazol-5-yl)-4-(4-(3,3-difluoropyrrolidin-1-yl)-2,3-difluorophenyl)-oxazolidin-2-one | $C_{20}H_{16}F_4N_4O_2$ | 420.36 |

-continued

| Cpd. No. | Structure | Name | Formula | Mol. Weight |
|---|---|---|---|---|
| 20 | 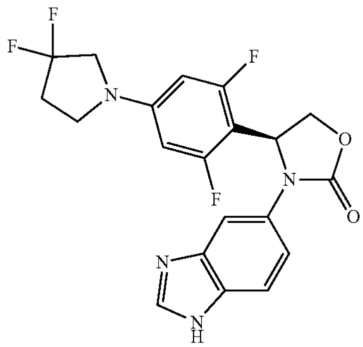 [SMILES: O=C1OC[C@H](c2c(F)cc(N3CCC(F)(F)C3)cc2F)N1c1ccc2[nH]cnc2c1] | (S)-3-(1H-benzo[d]imidazol-5-yl)-4-(4-(3,3-difluoropyrrolidin-1-yl)-2,6-difluorophenyl) oxazolidin-2-one | $C_{20}H_{16}F_4N_4O_2$ | 420.36 |
| 21 | 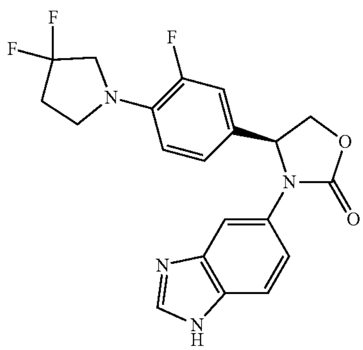 [SMILES: O=C1OC[C@H](c2ccc(N3CCC(F)(F)C3)c(F)c2)N1c1ccc2[nH]cnc2c1] | (S)-3-(1H-benzo[d]imidazol-5-yl)-4-(4-(3,3-difluoropyrrolidin-1-yl)-3-fluorophenyl) oxazolidin-2-one | $C_{20}H_{17}F_3N_4O_2$ | 402.37 |
| 22 | 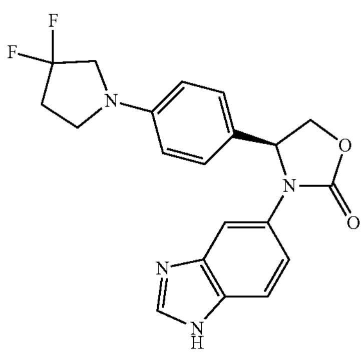 [SMILES: O=C1OC[C@H](c2ccc(N3CCC(F)(F)C3)cc2)N1c1ccc2[nH]cnc2c1] | 3-(1H-benzo[d]imidazol-5-yl)-4-(4-(3,3-difluoropyrrolidin-1-yl)phenyl)oxazolidin-2-one | $C_{20}H_{18}F_2N_4O_2$ | 384.38 |
| 23 | 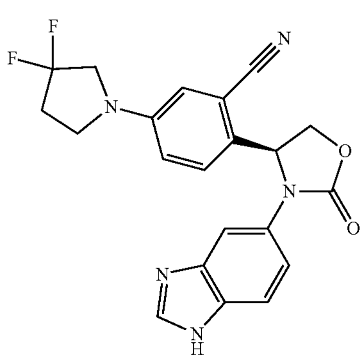 [SMILES: N#Cc1cc(N2CCC(F)(F)C2)ccc1[C@H]1COC(=O)N1c1ccc2[nH]cnc2c1] | (S)-2-(3-(1H-benzo[d]imidazol-5-yl)-2-oxooxazolidin-4-yl)-5-(3,3-difluoropyrrolidin-1-yl)benzonitrile | $C_{21}H_{17}F_2N_5O_2$ | 409.39 |

-continued

| Cpd. No. | Structure | Name | Formula | Mol. Weight |
|---|---|---|---|---|
| 24 | 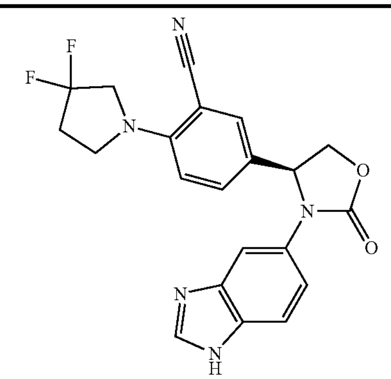 | (S)-5-(3-(1H-benzo[d]imidazol-5-yl)-2-oxooxazolidin-4-yl)-2-(3,3-difluoropyrrolidin-1-yl)benzonitrile | $C_{21}H_{17}F_2N_5O_2$ | 409.39 |
| 25 | 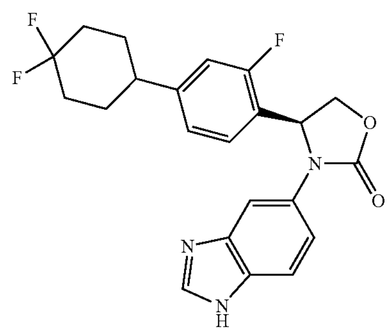 [SMILES: O=C1OC[C@H](c2ccc(C3CCC(F)(F)CC3)cc2F)N1c1ccc2[nH]cnc2c1] | (S)-3-(1H-benzo[d]imidazol-5-yl)-4-(4-(4,4-difluorocyclohexyl)-2-fluorophenyl)oxazolidin-2-one | $C_{22}H_{20}F_3N_3O_2$ | 415.41 |
| 26 | 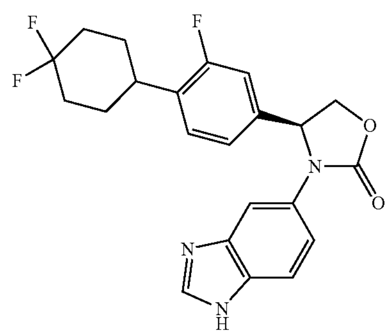 [SMILES: O=C1OC[C@H](c2ccc(C3CCC(F)(F)CC3)c(F)c2)N1c1ccc2[nH]cnc2c1] | (S)-3-(1H-benzo[d]imidazol-5-yl)-4-(4-(4,4-difluorocyclohexyl)-3-fluorophenyl)oxazolidin-2-one | $C_{22}H_{20}F_3N_3O_2$ | 415.41 |
| 27 | 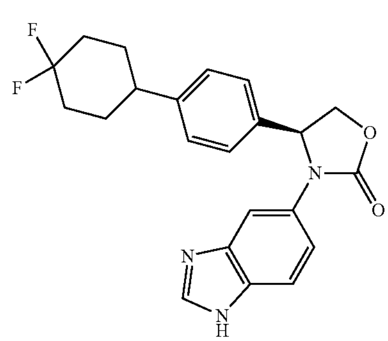 [SMILES: O=C1OC[C@H](c2ccc(C3CCC(F)(F)CC3)cc2)N1c1ccc2[nH]cnc2c1] | (S)-3-(1H-benzo[d]imidazol-5-yl)-4-(4-(4,4-difluorocyclohexyl)phenyl)oxazolidin-2-one | $C_{22}H_{21}F_2N_3O_2$ | 397.42 |

-continued

| Cpd. No. | Structure | Name | Formula | Mol. Weight |
|---|---|---|---|---|
| 28 | 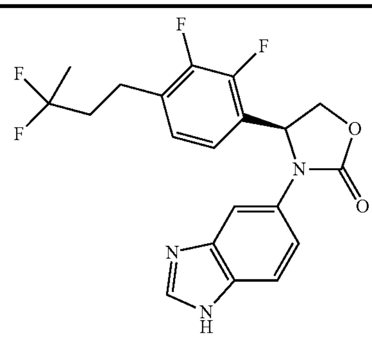 | (S)-3-(1H-benzo[d]imidazol-5-yl)-4-(4-(3,3-difluorobutyl)-2,3-difluorophenyl)oxazolidin-2-one | $C_{20}H_{17}F_4N_3O_2$ | 407.36 |
| 29 | 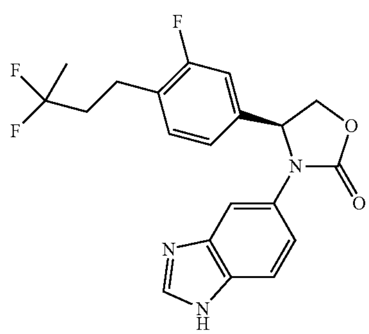 [SMILES: CC(F)(F)CCc1ccc([C@H]2COC(=O)N2c2ccc3[nH]cnc3c2)cc1F] | (S)-3-(1H-benzo[d]imidazol-5-yl)-4-(4-(3,3-difluorobutyl)-3-fluorophenyl)oxazolidin-2-one | $C_{20}H_{18}F_3N_3O_2$ | 389.37 |
| 30 | 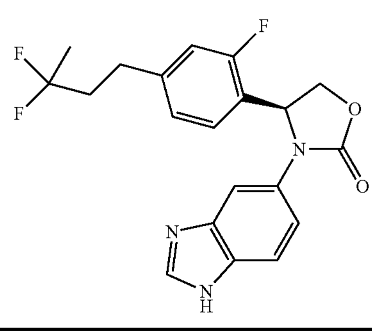 | (S)-3-(1H-benzo[d]imidazol-5-yl)-4-(4-(3,3-difluorobutyl)-2-fluorophenyl)oxazolidin-2-one | $C_{20}H_{18}F_3N_3O_2$ | 389.37 |

The invention further relates to the racemates and R-stereoisomers of the compounds of the present invention:

| | | | | |
|---|---|---|---|---|
| 7a | | (R)-3-(1H-benzo[d]imidazol-5-yl)-4-(4-(2,2-difluoropropoxy)-2-fluorophenyl)oxazolidin-2-one | $C_{19}H_{16}F_3N_3O_3$ | 391.34 |

-continued

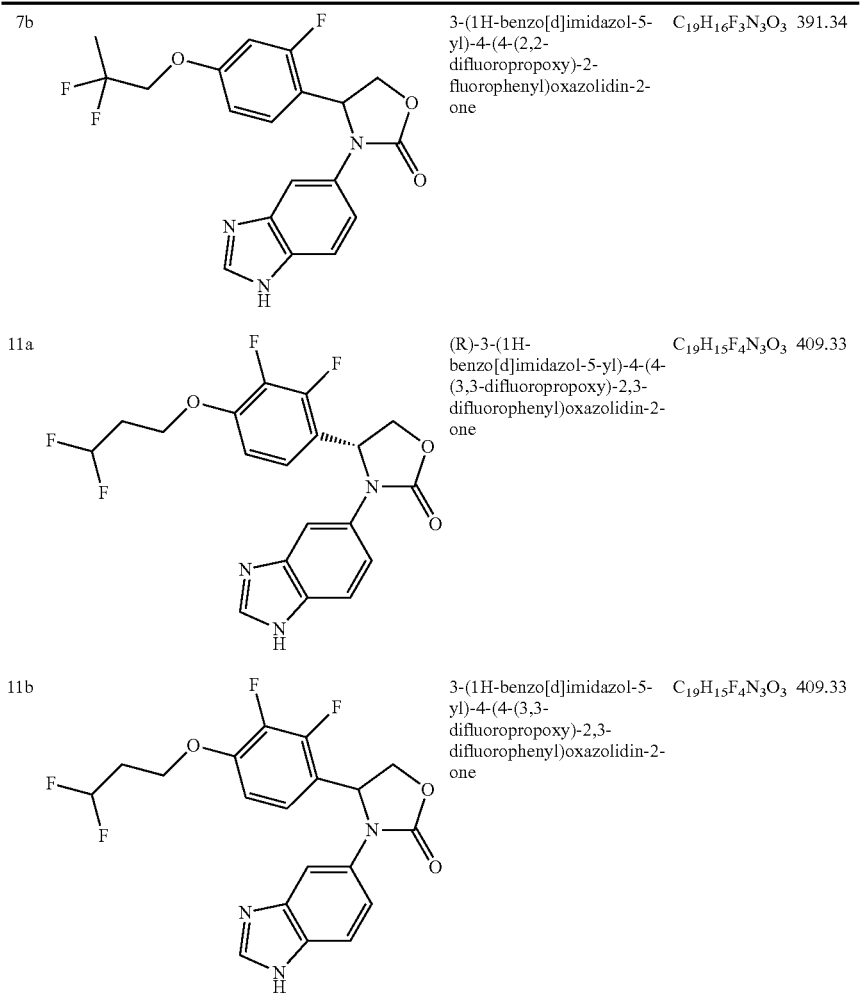

| | | | |
|---|---|---|---|
| 7b | | 3-(1H-benzo[d]imidazol-5-yl)-4-(4-(2,2-difluoropropoxy)-2-fluorophenyl)oxazolidin-2-one | $C_{19}H_{16}F_3N_3O_3$  391.34 |
| 11a | | (R)-3-(1H-benzo[d]imidazol-5-yl)-4-(4-(3,3-difluoropropoxy)-2,3-difluorophenyl)oxazolidin-2-one | $C_{19}H_{15}F_4N_3O_3$  409.33 |
| 11b | | 3-(1H-benzo[d]imidazol-5-yl)-4-(4-(3,3-difluoropropoxy)-2,3-difluorophenyl)oxazolidin-2-one | $C_{19}H_{15}F_4N_3O_3$  409.33 |

General Synthesis Description

Method A

Example 1-3

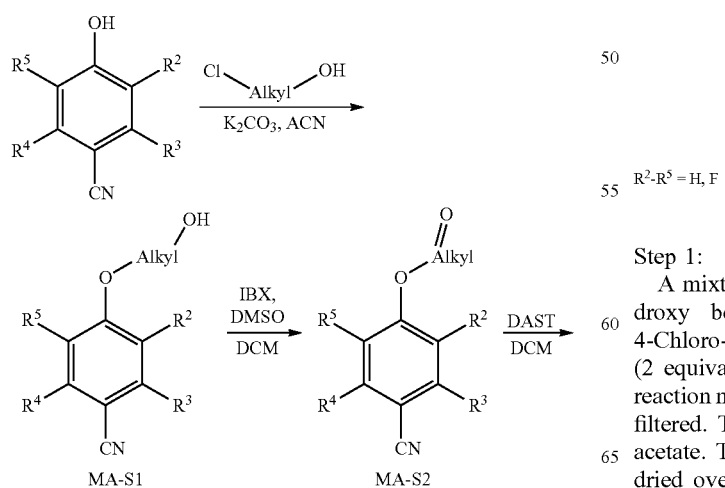

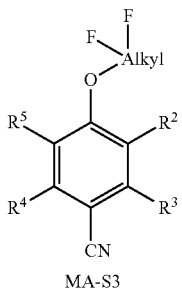

$R^2$-$R^5$ = H, F

Step 1:

A mixture of the corresponding fluoro substituted 4-hydroxy benzonitrile (1 equivalent), the corresponding 4-Chloro-2-butanol (3 equivalents) and potassium carbonate (2 equivalents) in acetonitrile was refluxed for 20 h. The reaction mass was cooled to room temperature and thereafter filtered. The filtrate was partitioned with water and ethyl acetate. The organic layer was washed with water, brine; dried over anhydrous sodium sulfate and concentrated in vacuum to afford the crude intermediates MA-S1.

59

Step 2:

2-Iodoxy benzoic acid (9 equivalents) was added to a solution of MA-S1 (crude, 1 equivalent) in dichloromethane and dimethyl sulfoxide and was stirred for 18 h at room temperature. The reaction mass was filtered and washed with dichloromethane. The combined filtrate and wash layers were washed successively with water, brine; dried over anhydrous sodium sulfate and concentrated in vacuum to resulted in the crude intermediates MA-S2, which were purified by column chromatography.

Step 3:

Diethylamino sulfurtrifluoride (4 equivalents) was added to a solution of MA-S3 (1 equivalent) in dichloromethane at 0° C. The reaction mass was warmed to room temperature and than it was stirred for 35 h. The reaction was quenched into ice water and the organic layer was separated. The aqueous layer was extracted with dichloromethane. The combined organic layer was washed successively with aqueous sodium bicarbonate, water, brine; dried over anhydrous sodium sulfate and concentrated in vacuum to get the crude intermediates MA-S3.

Method B

Example 5-9

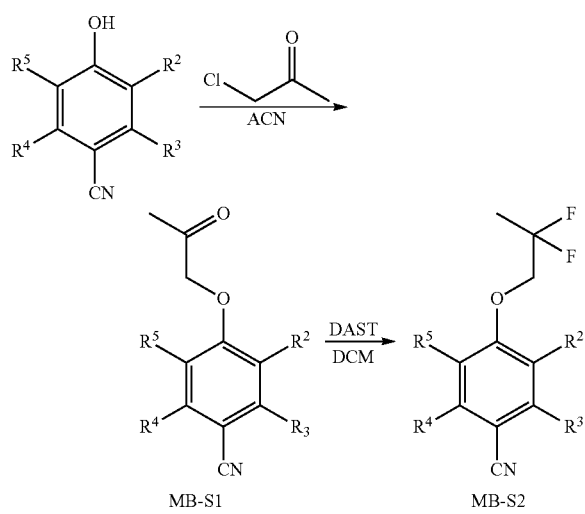

Step 1:

A mixture of the corresponding 4-hydroxy benzonitrile (1 equivalent), chloro acetone (1.5 equivalents) and potassium carbonate (2 equivalents) in acetonitrile was refluxed for 12 h. The reaction mass was cooled to room temperature, filtered and washed with ethyl acetate. The combined filtrate was concentrated in vacuum and the resulting residue was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude intermediate MB-S1.

Step 2:

Diethylamino sulfurtrifluoride (2 equivalents) was added to a solution of MB-S1 (1 equivalent) in dichloromethane at 0° C. and than the mixture was stirred for 2 h at room temperature. The reaction was quenched with ice water and extracted with dichloromethane. The combined organic layer was washed successively with water, brine; dried over anhydrous sodium sulfate and concentrated in vacuum to afford the crude intermediate MB-S2.

60

Method C

Example 1-3, 5-9

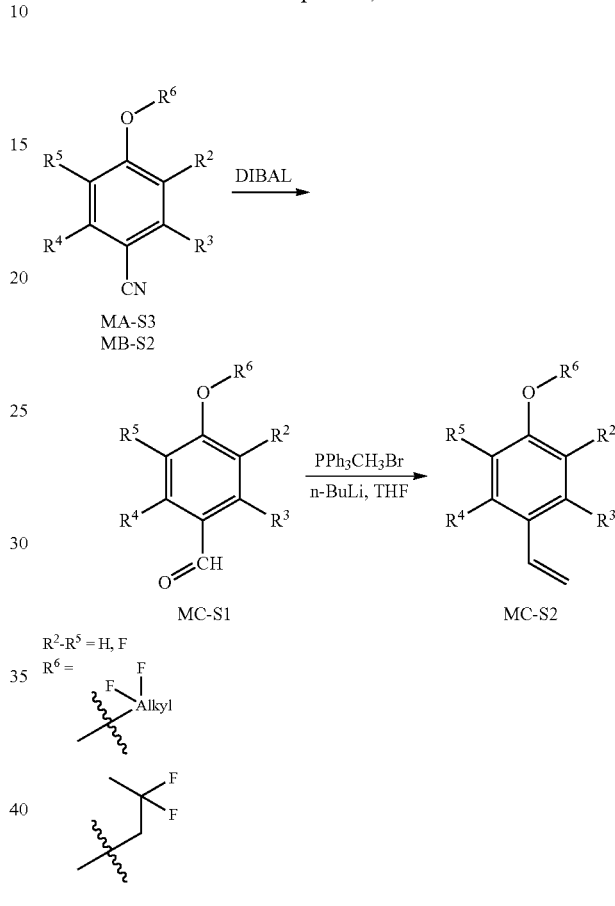

Step 1:

Diisobutylaluminiumhydrid (DIBAL) (1.5 M; 2 equivalents) was added slowly to a solution of the corresponding intermediate MA-S3 or MB-S2 (1 equivalent) in dry and cooled tetrahydrofuran (−30° C.) over 15 min. The reaction mass was warmed to room temperature and stirred for additional 2 h. The reaction was quenched with saturated ammonium chloride solution, filtered and washed with ethyl acetate. The filtrate was washed successively with water brine; dried over anhydrous sodium sulfate and concentrated in vacuum to afford the crude intermediate MC-S1, which was purified by column chromatography over silica gel.

Step 2:

N-Butyl lithium (n-BuLi) in hexane (2.5 M; 2 equivalents) was added to a stirred solution of Triphenyl phosphonium methyl bromide (2 equivalents) in tetrahydrofuran at −50° C. and was further stirred for 30 min at 0-5° C. The reaction mixture was cooled down and a solution of the corresponding intermediate MC-S1 (1 equivalent) in tetrahydrofuran was added drop wise to the reaction at −50° C. The reaction mixture was warmed to room temperature and stirred for additional 1 h. The reaction was quenched with saturated ammonium chloride solution and extracted with ethyl acetate. The combined organic layer was successively washed with water, brine; dried over anhydrous sodium sulfate and concentrated under reduced pressure to get the crude intermediate MC-S2. Purification was done by column chromatography over silica gel.

Method D

Example 10-13

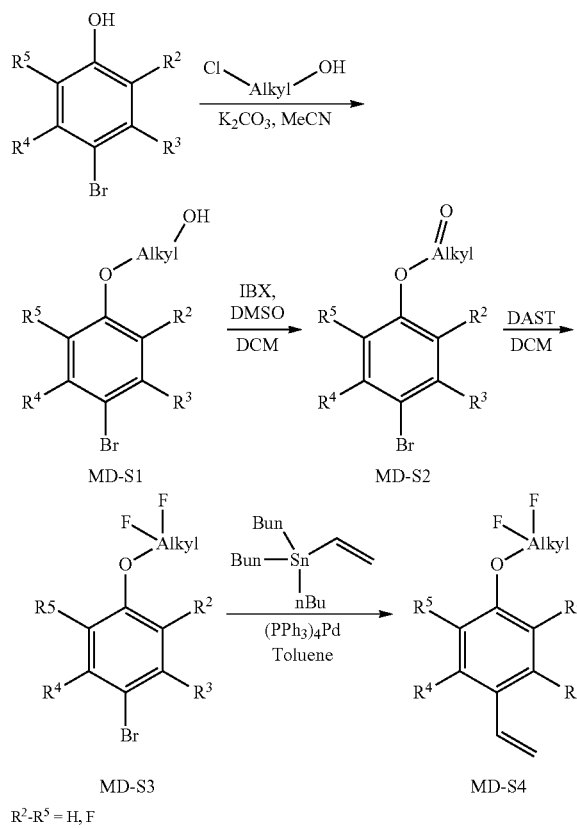

MD-S1

MD-S2

MD-S3

MD-S4

$R^2$-$R^5$ = H, F

Step 1:
A mixture of the corresponding 4-bromo phenol (1 equivalent), the corresponding chloro alkyl alcohol (2 equivalents) and potassium carbonate (3 equivalents) in acetonitrile was refluxed for 24 h. The reaction mass was cooled to room temperature and filtered. The filtrate was partitioned between water and ethyl acetate. The organic layer was washed with water, brine; dried over anhydrous sodium sulfate and concentrated in vacuum to afford the crude intermediate MD-S1, further used for next the step without purification.

Step 2:
2-Iodoxy benzoic acid (3 equivalents) was added to a solution of MD-S1 (1 equivalent) in dichloromethane and dimethylsulfoxide and the mixture stirred for 16 h at room temperature. The reaction mass was filtered and washed with dichloromethane. The combined filtrate and wash portion was washed successively with water, brine; dried over anhydrous sodium sulfate and concentrated in vacuum to afford the crude intermediates. Purification by column chromatography over silica gel afforded the pure compounds MD-S2.

Step 3:
Diethylamino sulfurtrifluoride (4 equivalents) was added to a solution of MD-S2 (1 equivalent) in dichloromethane at 0° C. The reaction was warmed to room temperature and the mixture was stirred for 48 h. The reaction was quenched with ice water and the organic layer was separated. The aqueous layer was extracted with dichloromethane. The combined organic layer was washed successively with water, brine; dried over anhydrous sodium sulfate and concentrated in vacuum to afford the crude intermediate. Purification was done by column chromatography over silica gel to afforded the compound MD-S3.

Step 4:
A solution of MD-S3 (1 equivalent) and tri-n-butyl vinyl tin (1.3 equivalents) in toluene was purged with argon gas for 5 min. Tetrakis-(triphenylphosphine)-palladium (0.2 equivalents) was added and the mixture was continuously purged for another 5 min. The reaction mixture was heated in a sealed tube at 110° C. for 8 h. The mixture was filtered over celite and washed with ethyl acetate. The combined filtrate and washing portion was concentrated in vacuum to afford the crude intermediate. Purification by column chromatography over silica gel afforded finally the pure intermediate MD-S4.

Method E

Example 14

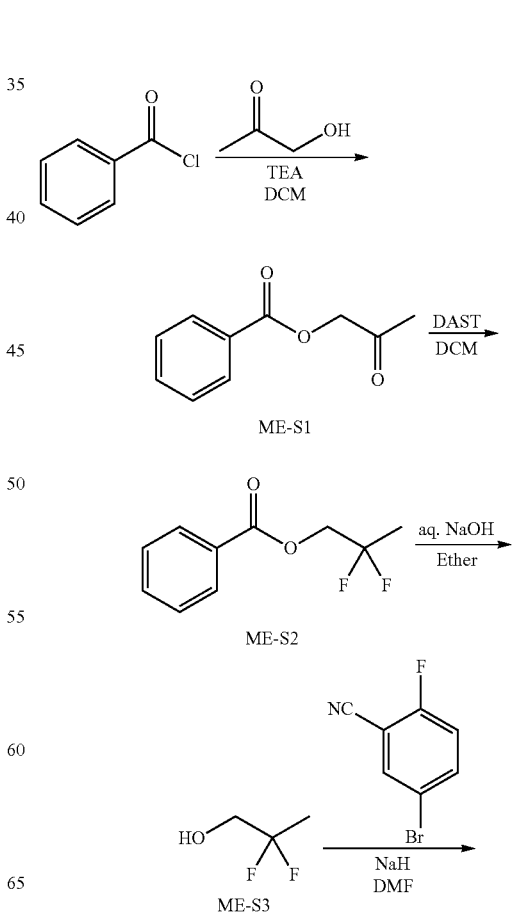

ME-S1

ME-S2

ME-S3

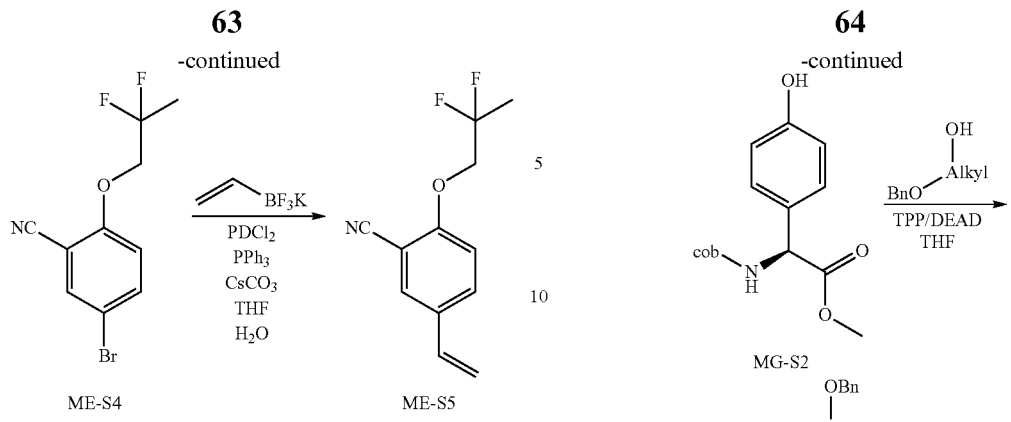

The description is given on Example 14

Method F

Example 15

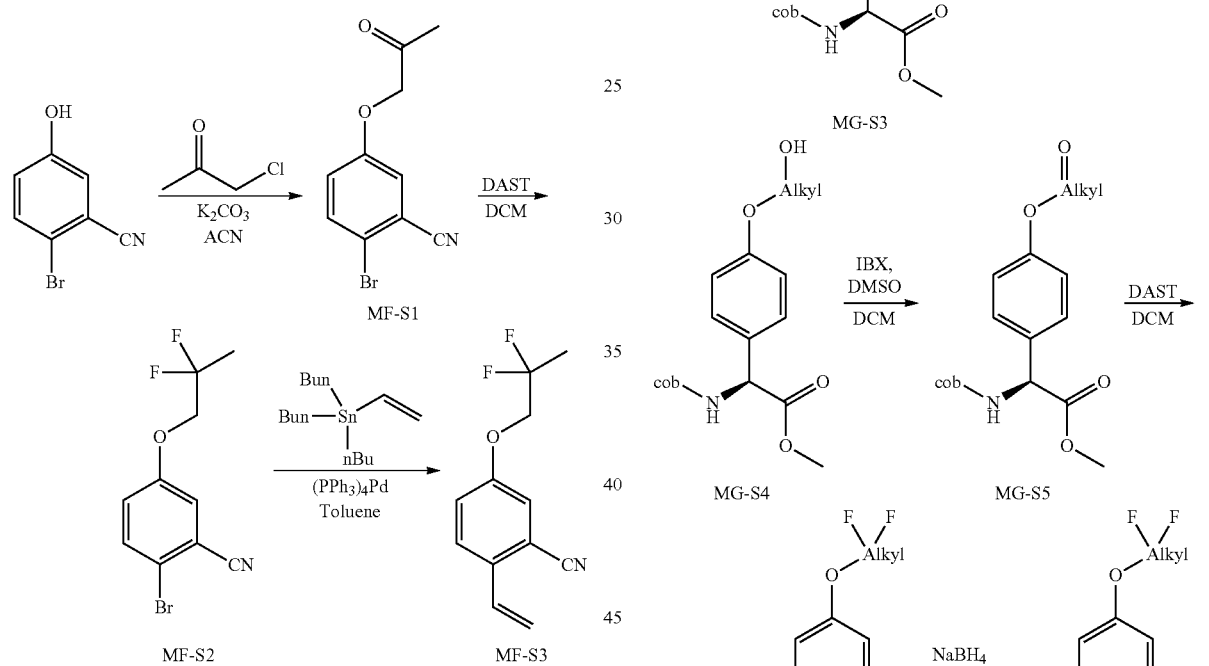

The description is given on Example 15

Method G

Example 4 and 16

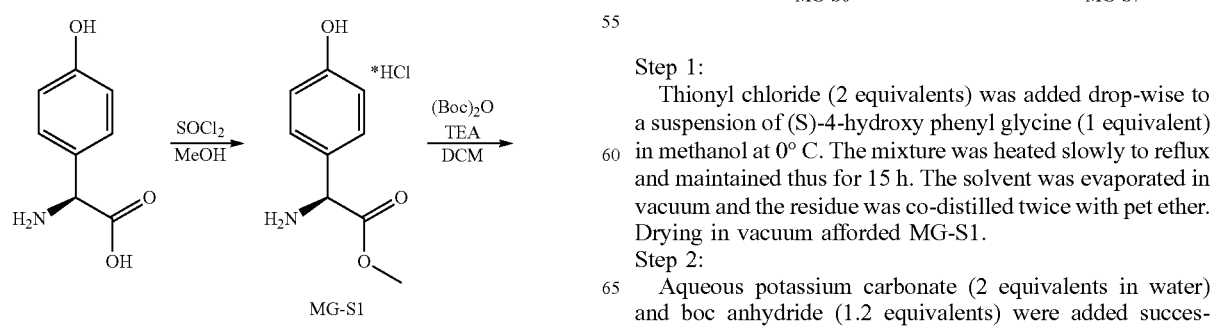

Step 1:
Thionyl chloride (2 equivalents) was added drop-wise to a suspension of (S)-4-hydroxy phenyl glycine (1 equivalent) in methanol at 0° C. The mixture was heated slowly to reflux and maintained thus for 15 h. The solvent was evaporated in vacuum and the residue was co-distilled twice with pet ether. Drying in vacuum afforded MG-S1.

Step 2:
Aqueous potassium carbonate (2 equivalents in water) and boc anhydride (1.2 equivalents) were added successively to a suspension of MG-S1 (1 equivalent) in 1,4- dioxan at 0° C. The reaction mixture was warmed to room temperature and stirred for 2 h. The reaction was quenched into water and extracted with ethyl acetate. The combined organic layer was washed successively with water, brine; dried over anhydrous sodium sulfate and concentrated in vacuum to afford the crude intermediate. The compound was suspended in pet ether, stirred for 30 min, filtered and dried in vacuum to MG-S2.

Step 3:

Triphenyl phosphine (1.5 equivalents) and the corresponding Benzyl-alkyl-alcohol (1.1 equivalents) were added successively to a stirred solution of MG-S2 (1 equivalent) in dry tetrahydrofuran at room temperature. Diethyl-azodicarboxylate (1.5 equivalents) was added drop wise and the reaction mixture was stirred at room temperature for 2 h. The reaction was quenched with water and extracted with ethyl acetate. The combined organic layer was washed with water, brine; dried over anhydrous sodium sulfate and concentrated in vacuum to afford the crude intermediate. Purification by column chromatography over silica gel afforded MG-S3.

Step 4:

A solution of MG-S3 (1 equivalent) in methanol was hydrogenated over Pd/C in a Parr apparatus. The reaction mass was filtered though celite and washed with methanol. The combined filtrate and washing portion was concentrated under reduced pressure to afford MG-S4.

Step 5:

Iodoxy benzoic acid (4 equivalents) was added to a solution of MG-S4 (1 equivalent) in a mixture of dichloromethane and dimethyl sulfoxide, and the solution was stirred for 20 h at room temperature. The reaction mass was filtered and washed with dichloromethane. The combined filtrate and washing portion was washed successively with water, brine; dried over anhydrous sodium sulfate and concentrated in vacuum to afford the crude intermediate. Purification by column chromatography over silica gel afforded MG-S5.

Step 6:

Diethylamino sulfurtrifluoride (2 equivalents) was added to a solution of MG-S5 (1 equivalent) in dichloromethane at 0° C. The reaction mixture was warmed to room temperature and stirred for 3 h. The reaction was quenched with ice water and the organic layer was separated. The aqueous layer was extracted with dichloromethane. The combined organic layer was washed successively with water, brine; dried over anhydrous sodium sulfate and concentrated in vacuum to afford MG-S6.

Step 7:

Sodium borohydride (4 equivalents) was added in two equal lots (over 15 min) to a solution of MG-S6 (1 equivalent) to a mixture of tetrahydrofuran and methanol at room temperature. Due to the exothermic reaction the temperature raised to ~50° C. After completion of the addition the reaction mixture was stirred for 1 h. Ethyl acetate was added and reaction was quenched with saturated ammonium chloride solution. The organic layer was separated and the aqueous layer was extracted with ethyl acetate. The combined organic layer was washed successively with water, brine; dried over anhydrous sodium sulfate and concentrated in vacuum to afford MG-S7, further used without any purification.

Method H

Example 17

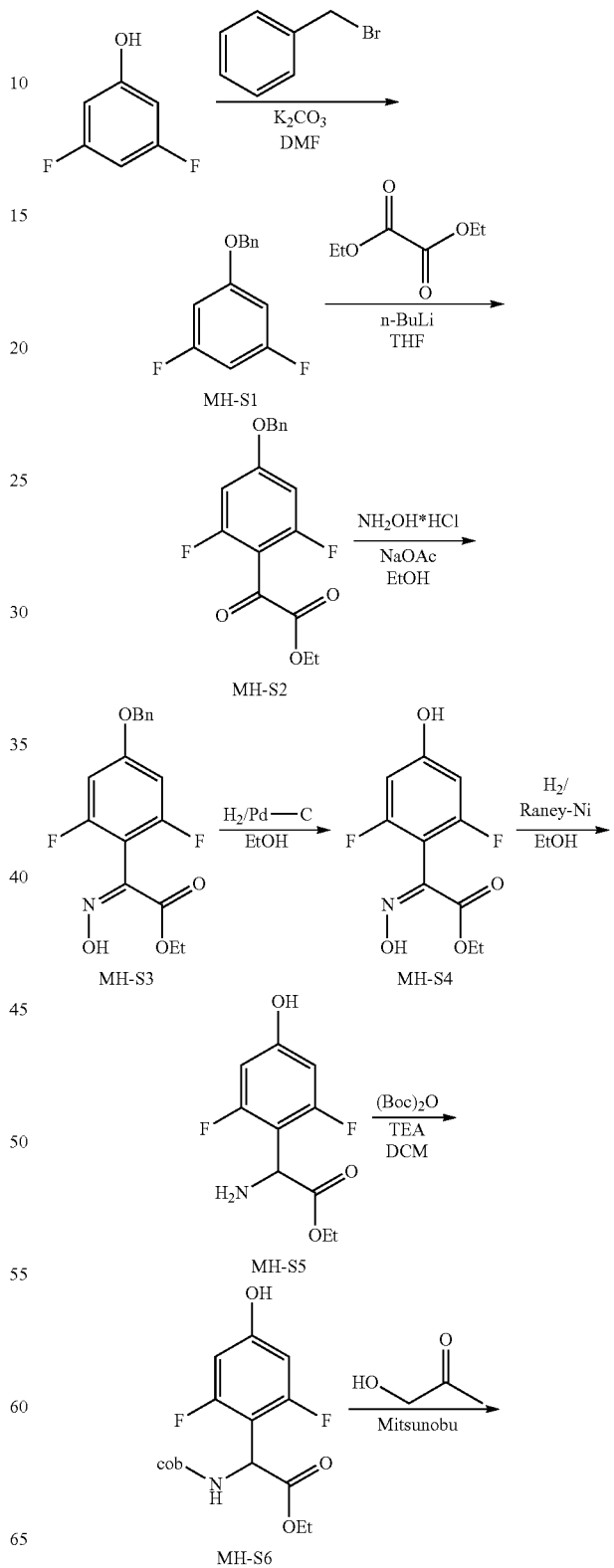

-continued

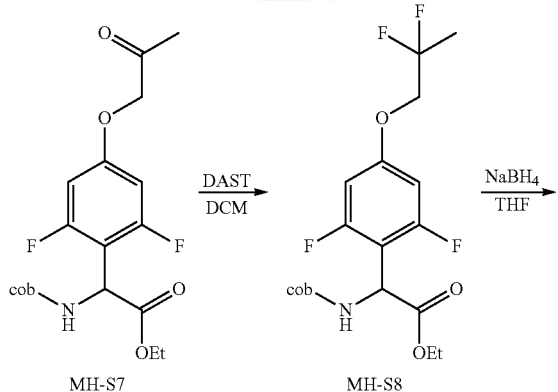

equivalents) in 1-propanol and 0.4 N aqueous sodium hydroxide at 15° C. and stirred for 15 min. A solution of Hydroquinine 1,4-phthalazinediyl diether ((DHQ)₂PHAL, 0.05 equivalents) in 1-propanol was added followed by a solution of the corresponding intermediate MC-S2, MD-S4, ME-S5 or MF-S3 (1 equivalent) in 1-propanol. Finally potassium osmatedihydrate (0.04 equivalents) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediates MJ-S1. Purification was done by column chromatography over silica gel.

Method K

Example 1-17

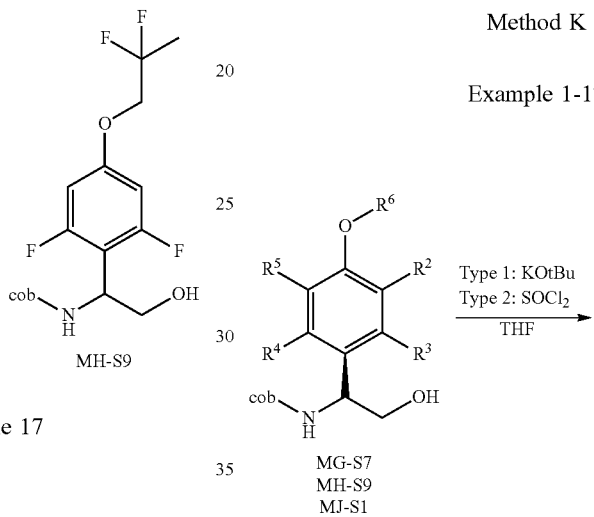

The description is given on Example 17

Method J

Example 1-3, 5-15

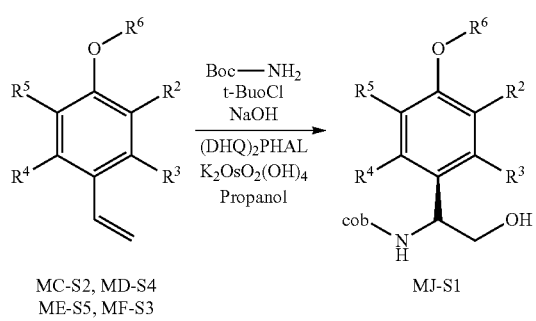

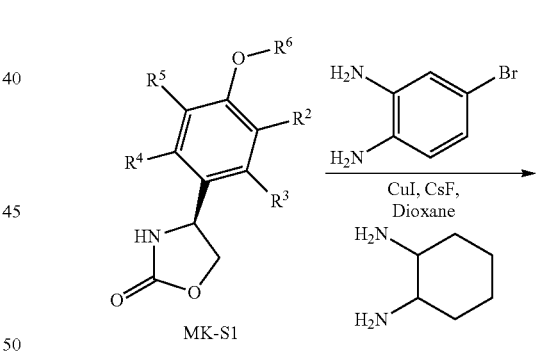

$R^2$-$R^5$ = H, F, CN
$R^6$ =

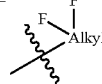

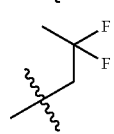

Step 1:
t-Butyl hypochlorite (3 equivalents) was added to a stirred solution of N-t-Butoxycarbonyl-amide (Boc-NH₂) (3

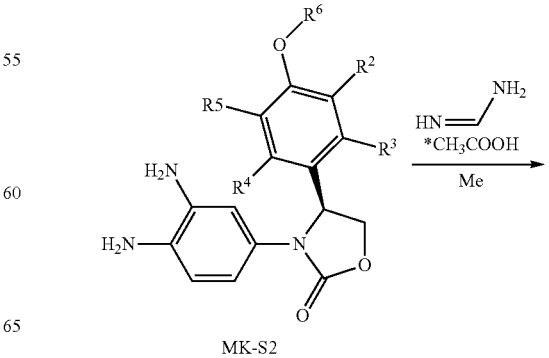

-continued

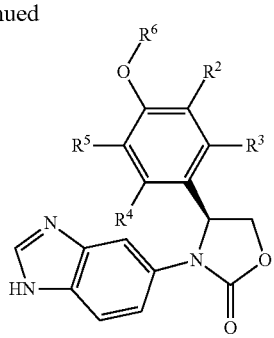

Example 1-17

$R^2-R^5 = H, F, CN$
$R^6 =$

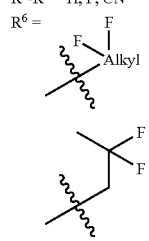

Step 1:
Type 1:
Potassium t-butoxide (3 equivalents) was added to a solution of the corresponding intermediate MG-S7, MH-S9 or MJ-S1 (1 equivalent) in tetrahydrofuran at 0° C. The reaction mass was warmed to room temperature and stirred for 2 h. The reaction was acidified with acetic acid (pH-6) and extracted with ethyl acetate. The separated organic layer was washed successively with water, brine; dried over anhydrous sodium sulfate and concentrated in vacuum afforded the intermediates MK-S1.
Type 2:
Thionylchloride (8 equivalents) was added drop wise to a solution of the corresponding intermediate MG-S7, MH-S9 or MJ-S1 (1 equivalent) in tetrahydrofuran at 0° C. The reaction mixture was warmed to room temperature and stirred for 2 h. The solvent was evaporated under vacuum and the remaining mass was partitioned between saturated sodium bicarbonate solution and ethyl acetate. The separated organic layer was washed successively with water, brine; dried over anhydrous sodium sulfate and concentrated in vacuum to afford MK-S1.
Step 2:
A mixture of the corresponding intermediate MK-S1 (1 equivalent), 1,2-diamino-4-bromobenzene (1 equivalent) and cesium fluoride (2 equivalents) in 1,4-dioxan was purged with argon gas for 10 min. Copper iodide (0.5 equivalents) was added and the reaction mixture was purged for further 10 min. Finally 1,2-diaminocyclohexane (0.05 equivalents) was added and again the reaction mixture was purged for another 10 min. The reaction mass was stirred at 110-115° C. in a sealed tube for 20 h. The reaction was cooled to room temperature, filtered through celite, washed with dioxin and concentrated under reduced pressure to afford the crude intermediates MK-S2. The compound was purified by column chromatography.
Step 3:
Formamidine acetate (3 equivalents) was added to a solution of the corresponding intermediate MK-S2 (1 equivalent) in Acetonitrile and refluxed for 2 h. The reaction mixture was concentrated under reduced pressure and the resulting residue was partitioned between water and ethyl acetate. The organic layer was separated and the aqueous layer was extracted with ethyl acetate. The combined organic layer was washed with water, brine, dried over anhydrous sodium sulfate and concentrated in vacuum to afford crude compound Examples 1-17

The products were either purified by washing with diethyl ether, filtered and dried or purified by preparative HPLC or equivalent methods.

Method L

Example 18-20

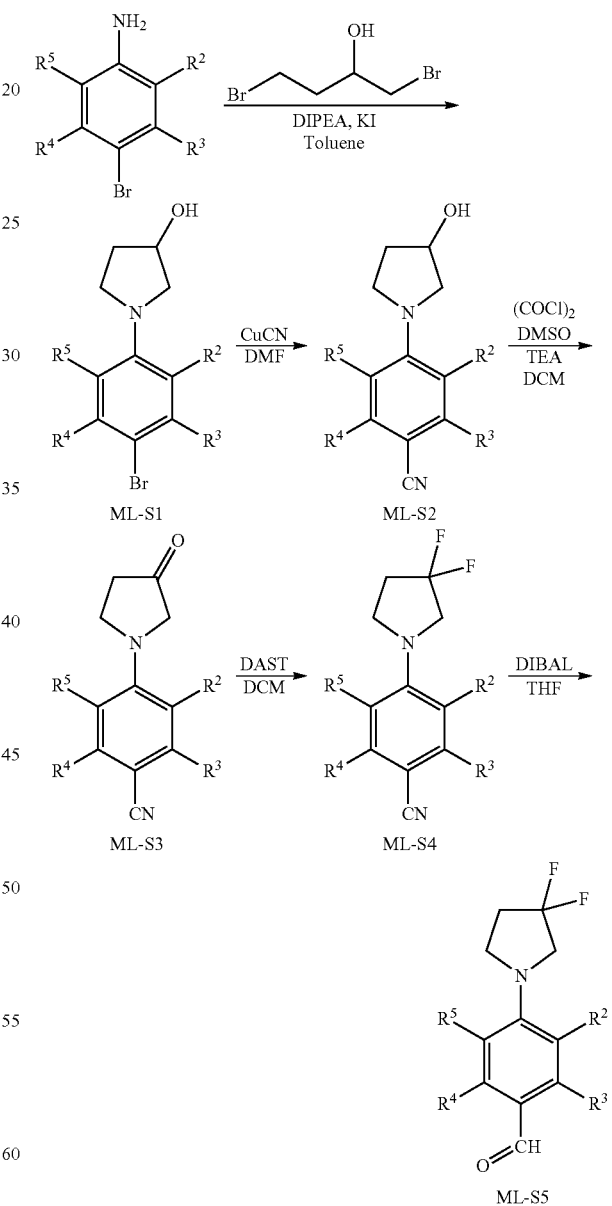

$R^2-R^5 = H, F$

Step 1:
Potassium iodide (2 equivalents), N,N-di-isopropylethylamine (2 equivalents), 1,4-dibromo-2-butanol (2 equivalents) were added successively to the stirred solution of the corresponding 4-bromoaniline (1 equivalent) in toluene. The reaction mass was stirred at 90° C. for 18 h. The reaction mass was filtered and washed with ethyl acetate. The filtrate was washed successively with water, brine; dried over anhydrous sodium sulfate, evaporated in vacuum. Purification by column chromatography over silica gel afforded the intermediate ML-S1.

Step 2:

A solution of ML-S1 (1 equivalent) and cuprous cyanide (1.5 equivalents) in N,N-dimethyl formamide was stirred at 150° C. for 20 h. The reaction mass was evaporated in vacuum, than stirred in an ammonium chloride solution, filtered and washed with dichloromethane. The filtrate was washed with water; dried over anhydrous sodium sulfate and evaporated in vacuum. Purification by column chromatography over silica gel afforded ML-S2.

Step 3:

Oxalyl chloride (2 equivalents) was added to the stirred solution of dimethyl sulfoxide (4 equivalents) in dichloromethane at −78° C. and the mixture was stirred for 1 h. A solution of ML-S2 (1 equivalents) in dichloromethane was added drop wise at −78° C. and the solution was stirred for 1 h at the same temperature. Triethyl amine (5 equivalents) was added and the mixture was warmed to room temperature for 40 min. The reaction mixture was quenched with ice water and extracted with dichloromethane. The separated organic layer was washed with brine; dried over anhydrous sodium sulfate and evaporated in vacuum to afford the crude intermediate ML-S3, further used without any purification.

Step 4:

Diethylamino sulfurtrifluoride (2 equivalents) was added to a solution of ML-S3 (1 equivalent) in dichloromethane at 0° C. and the mixture was stirred for 2 h at ambient temperature. The reaction was quenched with ice water and extracted with dichloromethane. The combined organic layer was washed successively with water, bicarbonate, brine; dried over anhydrous sodium sulfate and concentrated in vacuum to afford the crude intermediate ML-S4, further used without any purification.

Step 5:

Diisobutyl aluminumhydride in toluene (1.5 M, 2 equivalents) was added to a solution of ML-S4 (1 equivalent) in tetrahydrofuran at −70° C. and the mixture slowly warmed to 0° C. The reaction was quenched with saturated ammonium chloride solution, filtered and washed with ethyl acetate. The filtrate was washed with brine; dried over anhydrous sodium sulfate and evaporated in vacuum. Purification by column chromatography over neutral alumina afforded ML-S5.

Method M

Example 21-22

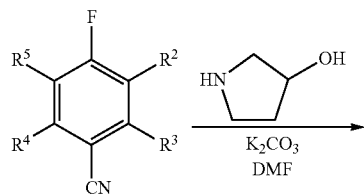

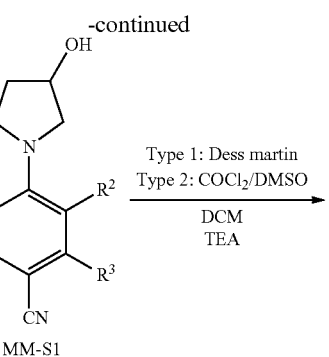

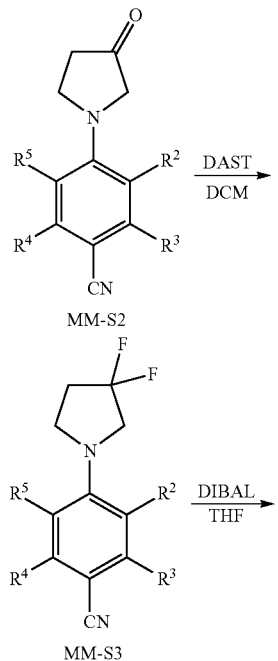

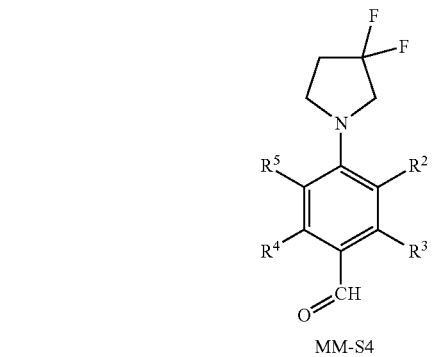

$R^2$-$R^5$ = H, F

Step 1:

(R)-3-Hydroxypyrrolidine (1.5 equivalents) was added to the stirred solution of the corresponding 4-fluorobenzonitrile (1 equivalent) and potassium carbonate (1 equivalent) in dimethyl formamide and the mixture was stirred over night at 80° C. The reaction mass was filtered, washed with ethyl acetate and the filtrate was evaporated in vacuum. The residue was partitioned between water and ethyl acetate. The combined organic layer was washed with water, brine; dried over anhydrous sodium sulfate and concentrated in vacuum to afford the crude intermediate. Purification by column chromatography over neutral alumina afforded MN-S1.

Step 2:

Type 1:

Dess-martin periodinane (2 equivalents) was added to a solution of MM-S1 (1 equivalent) and the mixture was stirred for 15 h. The reaction mass was filtered through celite and washed with dichloromethane. The filtrate was washed with water, brine; dried over anhydrous sodium sulfate and concentrated to afford MM-S2, further used without any purification.

Type 2:

Oxalyl chloride (2 equivalents) was added to a stirred solution of dry dimethylsulfoxide (4 equivalents) in dichloromethane at −78° C. and stirred for 1 h at the same temperature. A solution of MM-S1 (1 equivalent) in dichloromethane was added drop wise at −78° C. and the solution was stirred for 2 h at the same temperature. Triethylamine (5 equivalents) was added and the mixture was stirred for 30 min at room temperature. The reaction was quenched with water and extracted with dichloromethane. The combined organic layer was washed with water, brine; dried over anhydrous sodium sulfate and concentrated in vacuum to afford the crude intermediate. Purification by column chromatography over neutral alumina afforded MM-S2.

Step 3:

Diethylamino sulfurtrifluoride (2.1 equivalents) was added to a solution of MM-S2 (1 equivalent) in dichloromethane at 0° C. The reaction mixture was warmed to room temperature and stirred for 3 h. The reaction was quenched with ice water and the separated organic layer was washed successively with water, brine; dried over anhydrous sodium sulfate and concentrated in vacuum to afford MM-S3, further used without any purification.

Step 4:

Diisobutyl aluminumhydride (DIBAL) in toluene (1 M; 2 equivalents) was slowly added to a stirred solution of MM-S3 (1 equivalent) in tetrahydrofuran at −10° C. The reaction mixture was stirred for 6 h at room temperature. The reaction was quenched with ammonium chloride solution, filtered and the filtrate was extracted in ethyl acetate. The combined organic layer was washed successively with water, brine; dried over anhydrous sodium sulfate and concentrated in vacuum to afford the intermediate MM-S4.

Method N

Example 18-22

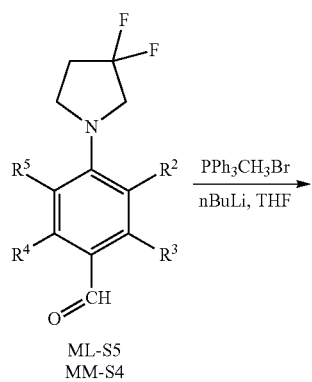

ML-S5
MM-S4

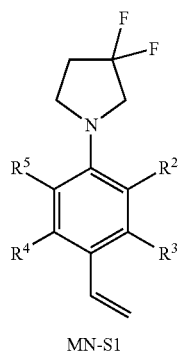

MN-S1

$R^2$-$R^5$ = H, F

Step 1:

n-Butyl lithium in hexane (2.2M; 2 equivalents) was added to a stirred solution of methyl-triphenyl-phosphoniumbromide (2 equivalents) in tetrahydrofuran at −30° C. and the mixture was stirred for 30 min at 0-5° C. A solution of the corresponding intermediates ML-S5 or MM-S4 (1 equivalent) in tetrahydrofuran was added drop wise at −30° C. The temperature was warmed to room temperature and the mixture stirred for 2 h. The reaction was quenched with acetic acid and the pH value was adjusted pH~5. The solution was extracted with ethyl acetate. The combined organic layer was washed successively with water, brine; dried over anhydrous sodium sulfate and concentrated under reduced pressure to afford the crude intermediate. Purification by column chromatography over silica gel afforded MN-S1.

Method O

Example 23

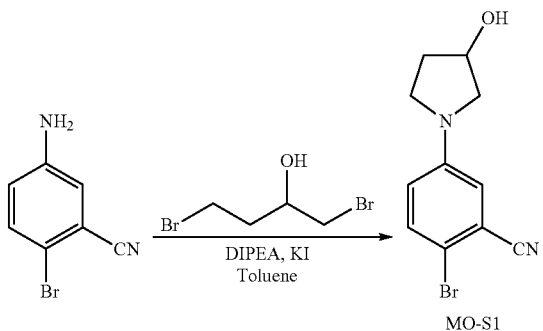

The method description is given at Example 23.

Method P

Example 24

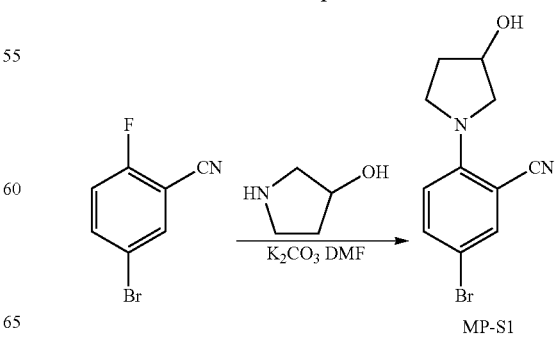

The method description is given at Example 24.

Method Q

Example 23-24

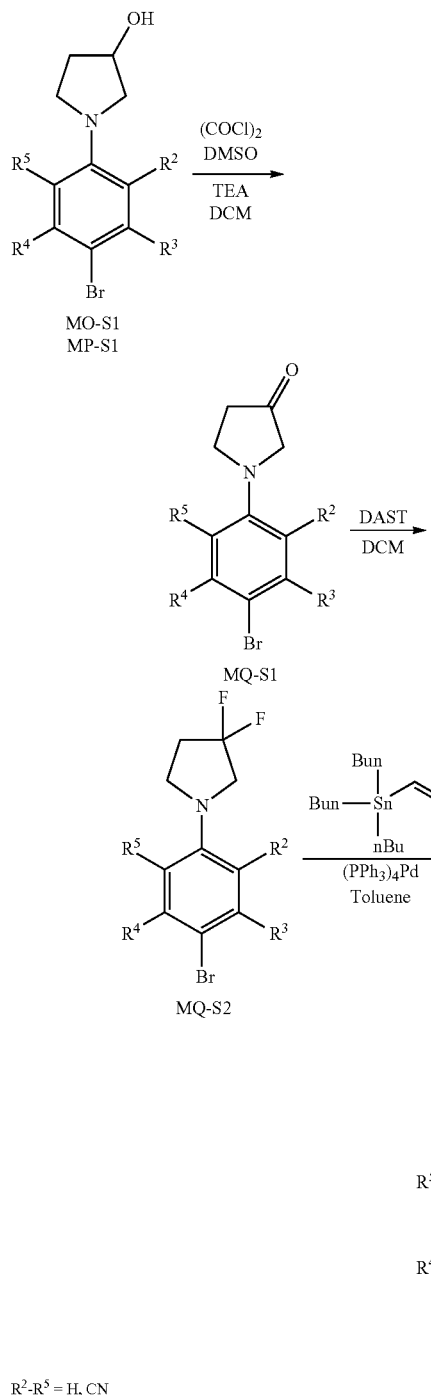

R²-R⁵ = H, CN

Step 1:
Oxalyl chloride (2 equivalents) was added to a solution of dimethylsulfoxide (4 equivalents) in dichloromethane at −78° c. and the mixture was stirred for 30 min. A solution of the corresponding intermediate MO-S1 or MP-S1 (2.45 g, 9.21 mmol) in dichloromethane was slowly added over 10 min and the mixture was stirred for 1 h at −78° C. Triethylamine (5 equivalents) was added and the mixture was stirred at room temperature for 30 min. The reaction was quenched with ice water and extracted with dichloromethane. The combined organic layer was washed successively with water, brine; dried over anhydrous sodium sulfate and concentrated in vacuum to afford MQ-S1, further used without any purification.

Step 2:
Diethylamino sulfurtrifluoride (2 equivalents) was added to a solution of MQ-S1 (1 equivalent) in dichloromethane at 0° C. The reaction mixture was warmed to room temperature and stirred for 1.5 h. The reaction was quenched with ice water and extracted with dichloromethane. The combined organic layer was washed successively with aqueous sodium bicarbonate, water, brine; dried over anhydrous sodium sulfate and concentrated in vacuum to afford the crude intermediate. Purification by column chromatography over silica gel afforded MQ-S2.

Step 3:
A solution of MQ-S2 (1.1 g, 3.85 mmol) and tri-n-butyl vinyl tin (1.3 equivalents) in toluene was purged with argon gas for 5 min. Tetrakis-(triphenylphosphine)-palladium (0.02 equivalents) was added and the mixture was continuously purged for another 5 min. The reaction mixture was heated in a sealed tube at 110° C. for 8 h. The reaction mass was filtered over celite and washed with ethyl acetate. The combined filtrate and washing portion was concentrated in vacuum to afford the crude intermediate. Purification by column chromatography over silica gel afforded MQ-S3.

Method R

Example 18-24

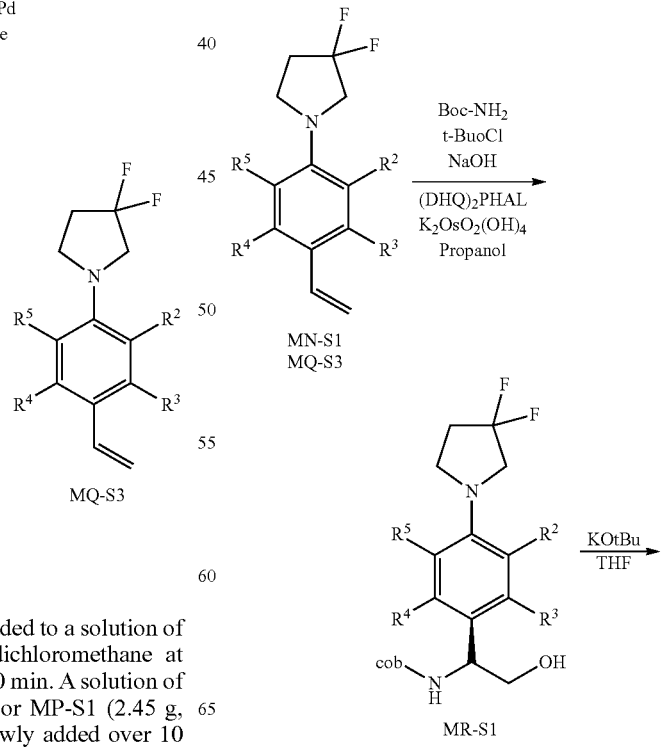

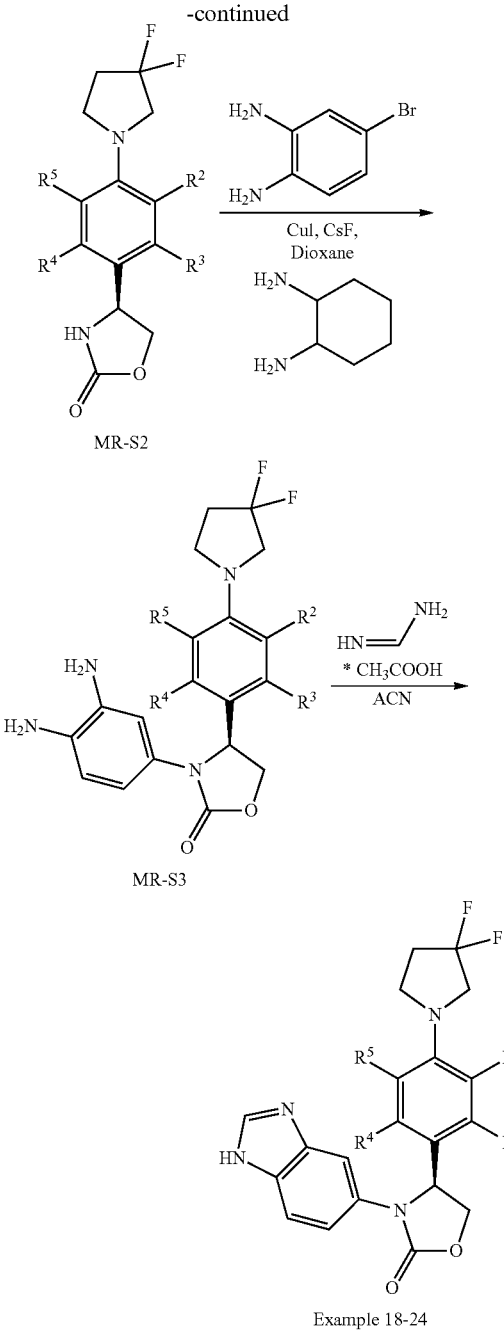

R²-R⁵ = H, F, CN

Step 1:

t-Butyl hypochlorite (3 equivalents) was added to a stirred solution of t-butyl carbamate (3 equivalents) in 1-propanol and 0.4 N aqueous sodium hydroxide at 15° C. and the mixture was stirred for 15 min. A solution of Hydroquinine 1,4-phthalazinediyldiether ((DHQ)₂PHAL, 0.05 equivalents) in 1-propanol was added, followed by a solution of the corresponding intermediate MN-S1 or MQ-S1 (1 equivalent) in 1-propanol. Finally potassium osmatedihydrate (0.04 equivalents) was added and the reaction mixture was stirred for additional 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over silica gel afforded MR-S1.

Step 2:

Potassium-t-butoxide (2 equivalents) was added to a stirred solution of MR-S1 (1 equivalent) in tetrahydrofuranat 0° C. and the mixture was stirred for 1 h at room temperature. The reaction was neutralized with 10% acetic acid and extracted with ethyl acetate. The combined organic layer was washed successively with water, brine; dried over anhydrous sodium sulfate and concentrated under reduced pressure to afford MR-S2, further used without any purification.

Step 3:

A mixture of MR-S2 (1 equivalent), 4-Bromo-1,2-diaminobenzene (1.1 equivalents) and cesium fluoride (2 equivalents) in 1,4-dioxane was purged with argon gas for 10 min in a sealed tube. Copper iodide (0.15 equivalents) and 1,2-diaminocyclohexane (0.15 equivalents) were added and the mixture was continuously purged for another 10 min. The sealed tube was heated for 18 h at 110-115° C. The mixture was filtered through celite, washed with dioxane and the filtrate was concentrated under reduced pressure to give the crude intermediate. Purification by column chromatography over neutral alumina afforded MR-S3.

Step 4:

Formamidine acetate (2 equivalents) was added to a solution of MR-S3 (1 equivalent) in acetonitrile and the mixture was refluxed for 1 h. The solvent was evaporated in vacuum and the resulting residue was partitioned between water and ethyl acetate. The organic layer was separated and the aqueous layer was extracted with ethyl acetate. The combined organic layer was washed with water, brine; dried over anhydrous sodium sulfate and concentrated in vacuum. The crude product was triturated with diethyl ether and dried to afford the Example 18-24.

Method S

Example 25

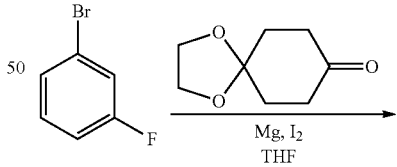

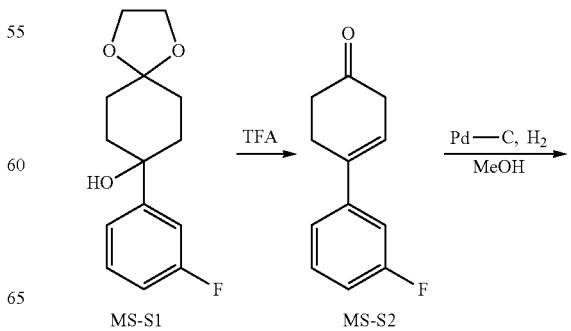

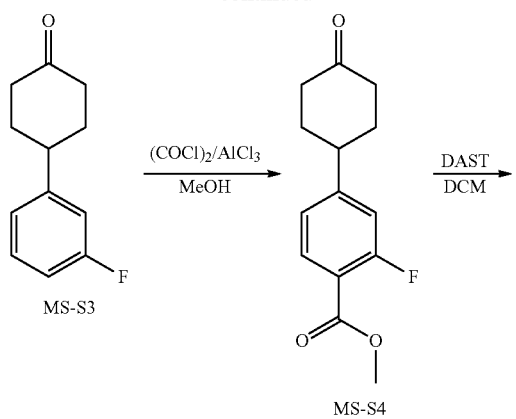
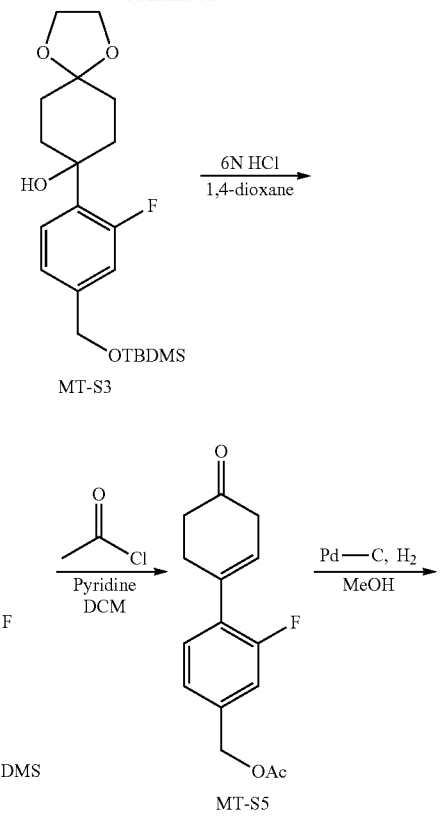
The method description is given at Example 25.
Method T
Example 26
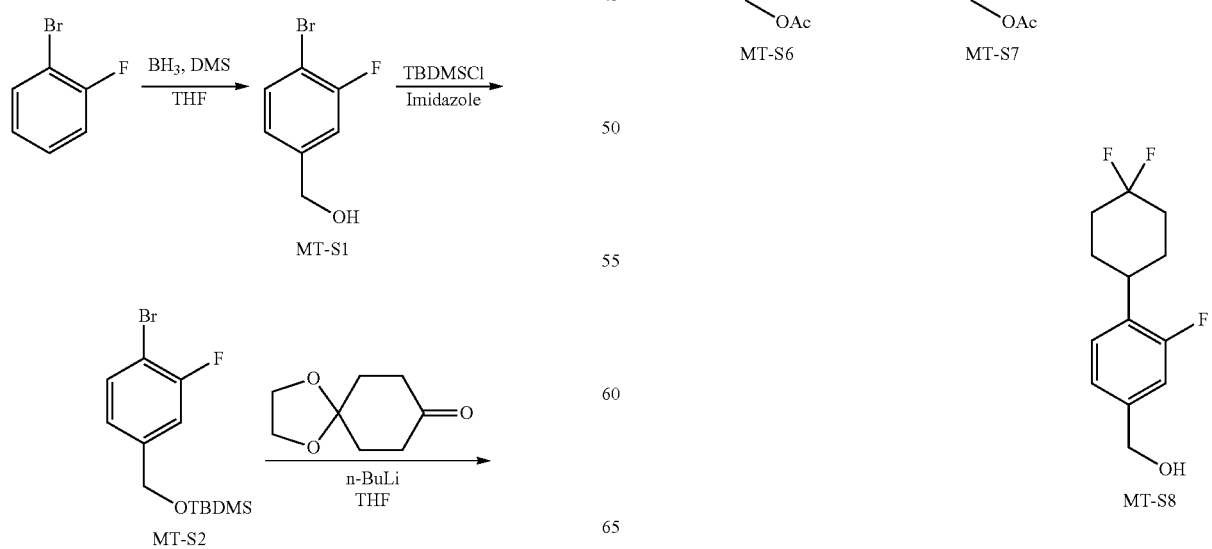
The method description is given at Example 26.

Method U

Example 25-26

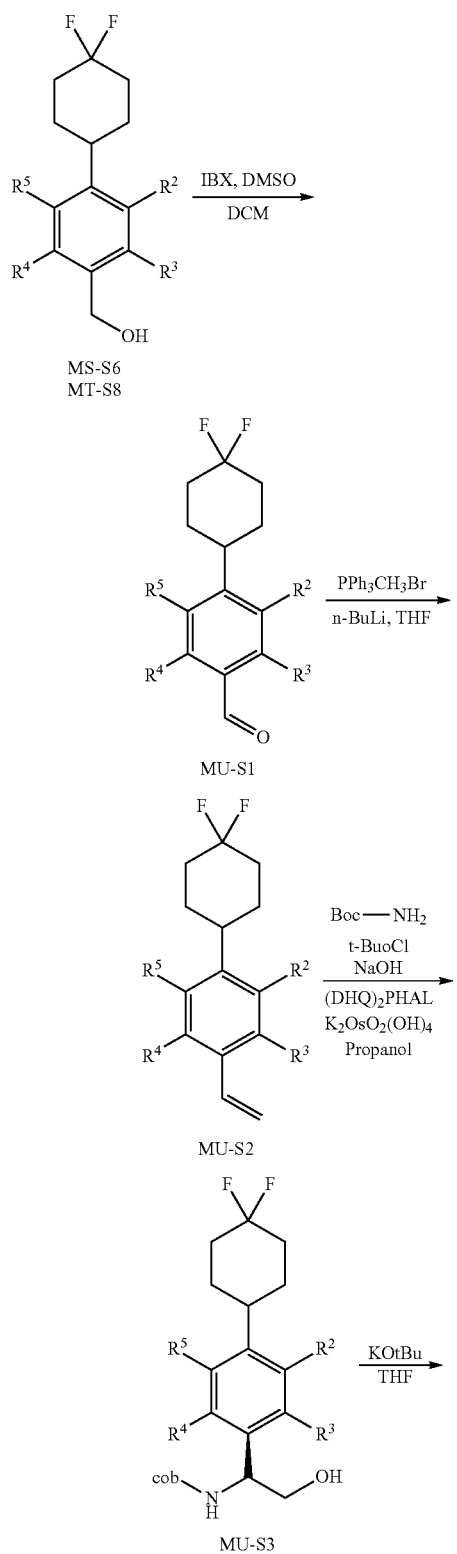

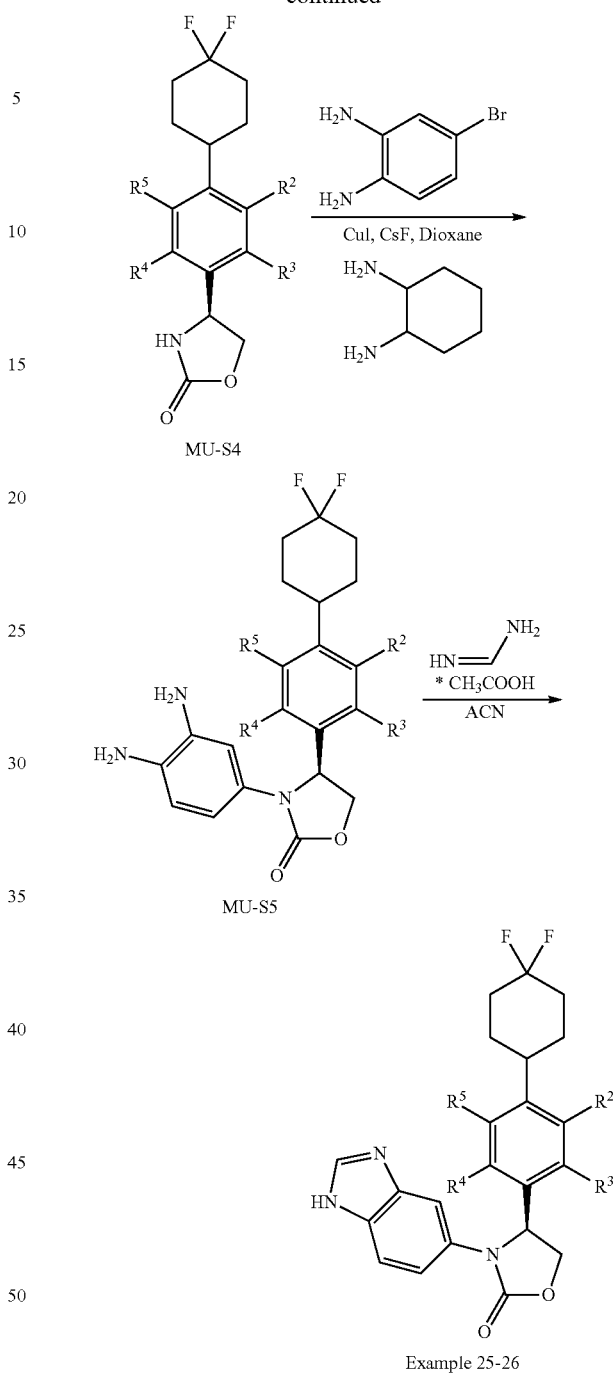

Example 25-26

R²-R⁵ = H, F

Step 1:

2-Iodoxybenzoic acid (3 equivalents) was added to a solution of MS-S6 or MT-S8 (1 equivalent) in dichloromethane:dimethylsulfoxide (3:1) and the mixture was stirred for 8 h at room temperature. The reaction mass was filtered and washed with dichloromethane. The combined filtrate and washing portion was washed successively with water, brine; dried over anhydrous sodium sulfate and concentrated in vacuum to afford the crude intermediate. Purification by column chromatography over silica afforded MU-S1.

Step 2:

N-Butyl lithium (2.2 M; 2 equivalents) was added to a stirred solution of triphenylphosphonium methylbromide (2 equivalents) in tetrahydrofuran at −30° C. and the mixture was stirred for 30 min at 0-5° C. A solution of MU-S1 (1 equivalent) in tetrahydrofuran was added drop wise at −30° C. The temperature was warmed to room temperature and the reaction mixture was stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude intermediate. Purification by column chromatography over silica gel afforded MU-S2.

Step 3:

t-Butylhypochlorite (3.1 equivalents) was added to a stirred solution of t-butyl carbamate (3 equivalents in 1-propanol and 0.4 N aqueous sodium hydroxide at 15° C. and the mixture was stirred for 15 min. A solution of Hydroquinine 1,4-phthalazinediyl diether ((DHQ)$_2$PHAL, 0.05 equivalents) in 1-propanol was added, followed by a solution of MU-S2 (1 equivalent) in 1-propanol. Finally potassium osmatedihydrate (0.4 equivalents) was added and the reaction mixture was stirred for 15 min at room temperature. The reaction was quenched with saturated sodium sulfate solution and extracted with ethyl acetate. The combined organic layer was washed successively with water, brine; dried over anhydrous sodium sulfate and concentrated under reduced pressure to afford the crude intermediate. Purification by column chromatography over silica gel afforded MU-S3.

Step 4:

Potassium-t-butoxide (3 equivalents) was added in 2 portions to a stirred solution of MU-S3 (1 equivalent) in tetrahydrofuran over 15 min at 0° C., and the mixture was stirred for 2 h at room temperature. The reaction was neutralized with 10% acetic acid and extracted with ethyl acetate. The combined organic layer was washed successively with water, brine; dried over anhydrous sodium sulfate and concentrated under reduced pressure to afford MU-S4, further used without any purification.

Step 5:

A mixture of MU-S4 (1 equivalent), 4-Bromo-1,2-diaminobenzene (1 equivalent) and cesium fluoride (2 equivalents) in 1,4-dioxane was purged with argon gas for 30 min. Copper iodide (0.38 equivalents) and 1,2-diaminocyclohexane (0.38 equivalents) were added and the mixture was continuously purged for another 10 min. The reaction was heated in a sealed tube for 16 h at 105-110° C. The reaction mixture was filtered through celite, washed with dioxane and the filtrate was concentrated under reduced pressure to afford the crude intermediate. Purification by column chromatography over neutral alumina afforded MU-S5.

Step 6:

Formamidine acetate (3 equivalents) was added to a solution of MU-S5 (1 equivalent) in acetonitrile and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by column chromatography over neutral afforded the Example 25-26.

Method V

Example 27

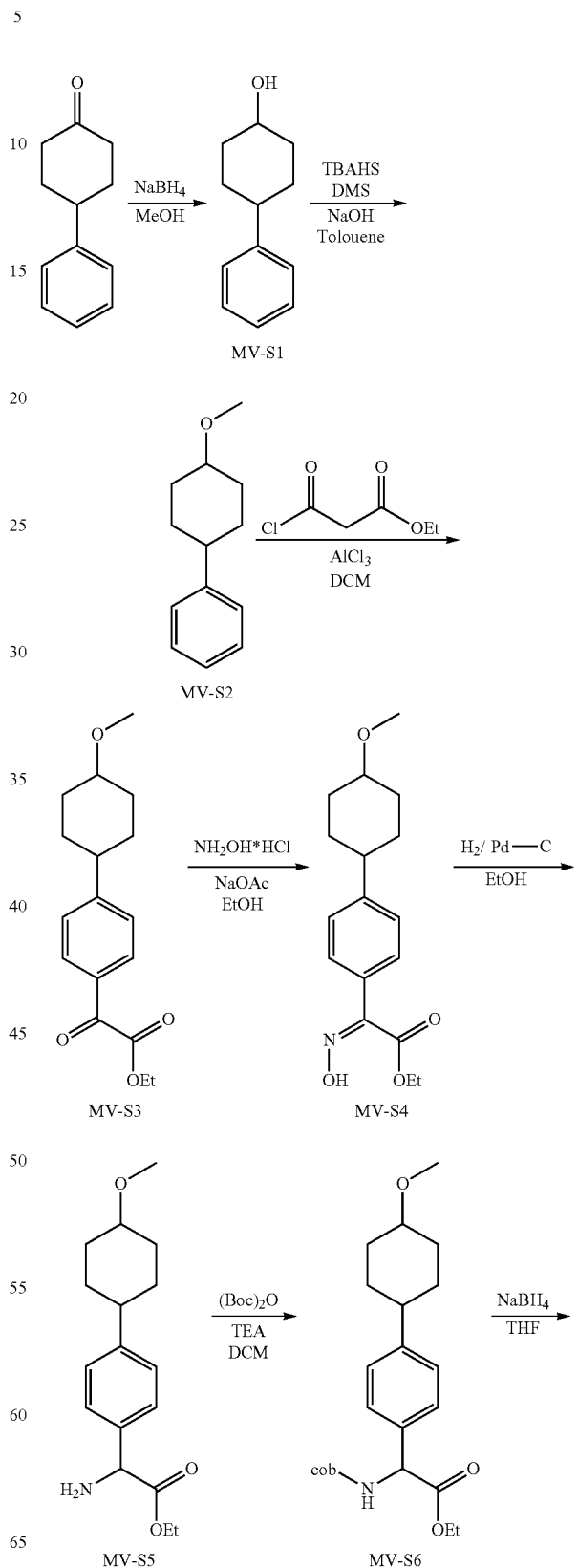

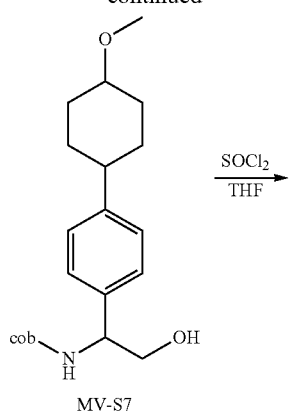
MV-S7
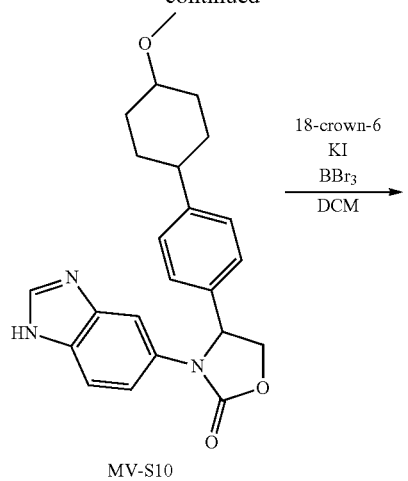
MV-S10
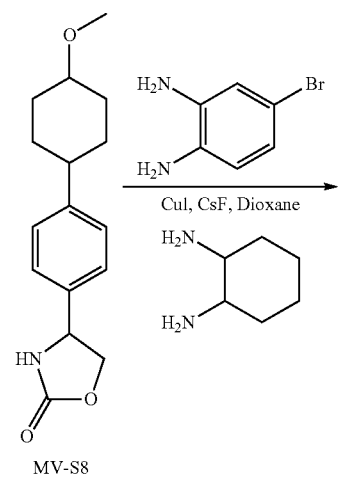
MV-S8
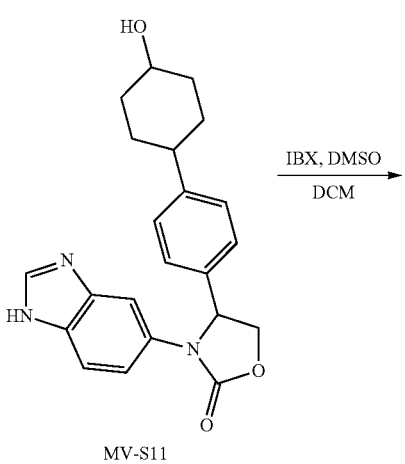
MV-S11
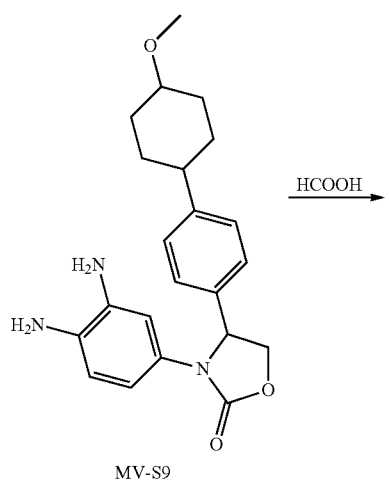
MV-S9
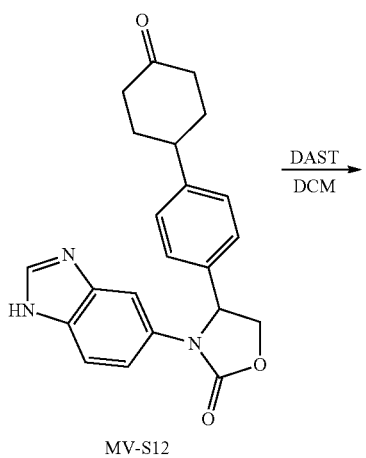
MV-S12

87
-continued
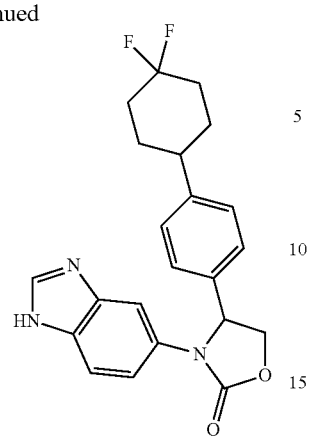
Example 27
The method description is given at Example 27.
Method W
Example 28
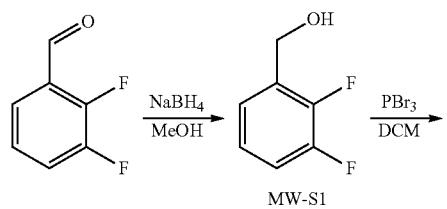
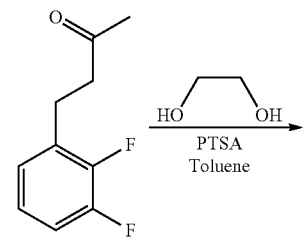
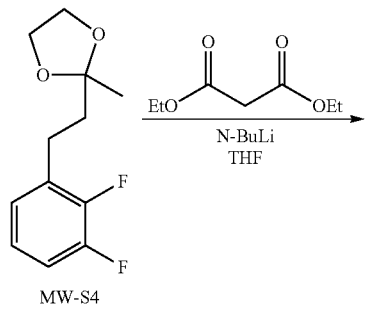
88
-continued
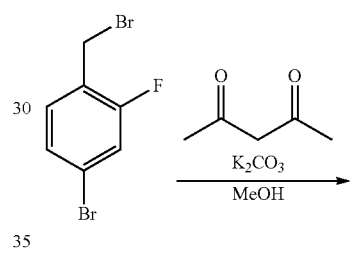
MW-S5
The method description is given at Example 28.
Method X
Example 29
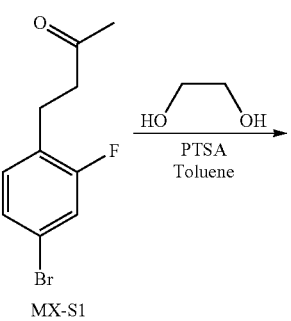
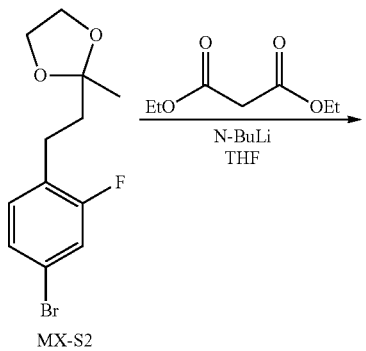

-continued

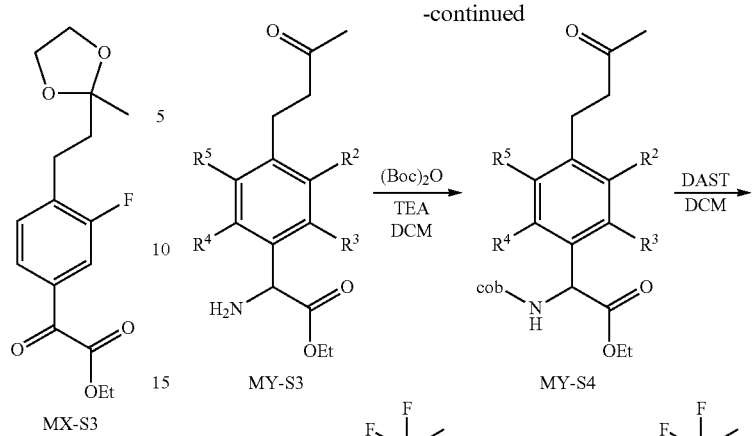

MX-S3

The method description is given at Example 29.

Method Y

Example 28-29

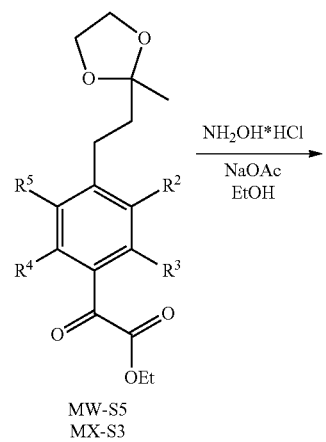

MW-S5
MX-S3

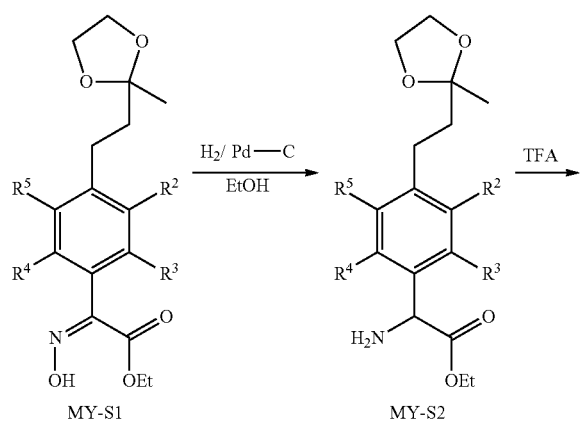

-continued

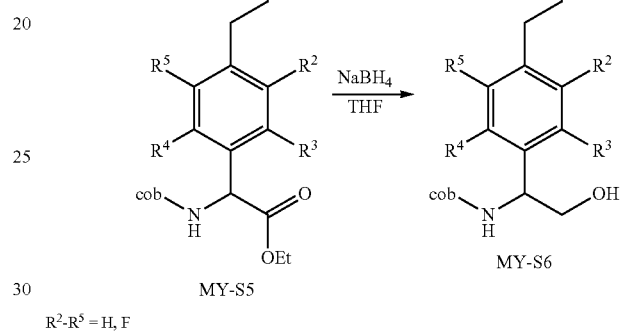

R²-R⁵ = H, F

Step 1:
Sodium acetate (2 equivalents) and hydroxylamine hydrochloride (2 equivalents) were added successively to a solution of the corresponding intermediate MW-S5 or MX-S3 (1 equivalent) in absolute ethanol and the mixture was refluxed for 1 h. The solvent was evaporated in vacuum and the resulting mass was partitioned between water and ethyl acetate. The combined organic layer was washed successively with water, brine; dried over anhydrous sodium sulfate and concentrated in vacuum to afford MY-S1, further used without any purification as.

Step 2:
A solution of MY-S1 (1 equivalent) in absolute ethanol was hydrogenated over 10% Pd—C in a Parr apparatus. The reaction mass was filtered through celite and washed with ethanol. The combined filtrate and washing portion was concentrated under reduced pressure to afford MY-S2, further used without any purification.

Step 3:
A sufficient amount (high excess) of trifluoroacetic acid was added to a solution of MY-S2 (1 equivalent) in dichloromethane at 0° C. and the mixture was stirred for 3 h at room temperature. The solvent was evaporated in vacuum, the remaining mass was dissolved in hydrochlorid acid (6 N) and washed with 40% ethyl acetate in pet ether. The aqueous layer was basified with saturated sodium bicarbonate solution and extracted with dichloromethane. The combined organic layer was washed successively with water, brine; dried over anhydrous sodium sulfate and concentrated in vacuum to afford MY-S3, further used without any purification.

Step 4:
Triethyl amine (3 equivalents) and Di-tertbutyl dicarbonate (1.1 equivalents) were added successively to a solution of MY-S3 (1 equivalent) in dichloromethane and the mixture was stirred for 20 h at room temperature. Water was added and the mixture was extracted with dichloromethane. The combined organic layer was washed successively with water, brine; dried over anhydrous sodium sulfate and concentrated in vacuum to afford the crude intermediate. Purification by column chromatography over silica gel afforded MY-S4.

Step 5:

Diethylamino sulfurtrifluoride (3 equivalents) was added to a solution of MY-S4 (1 equivalent) in dichloromethane at 0° C. and the mixture was stirred for 52 h at room temperature. The reaction was quenched with ice water and extracted with dichloromethane. The combined organic layer was washed successively with water, brine; dried over anhydrous sodium sulfate and concentrated to afford the crude intermediate. Purification by column chromatography over silica gel afforded MY-S5.

Step 6:

Sodium borohydride (2 equivalents) was slowly added to a solution of MY-S5 (1 equivalent) in methanol at room temperature. The reaction mass was stirred for 1 h. Ethyl acetate was added and the reaction was quenched with saturated ammonium chloride solution. The organic layer was separated and the aqueous layer was extracted with ethyl acetate. The combined organic layer was washed successively with water, brine; dried over anhydrous sodium sulfate and concentrated in vacuum to afford MY-S6, further used without any purification.

Method Z

Example 30

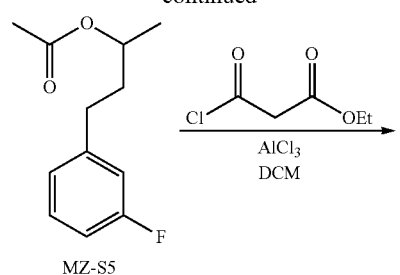

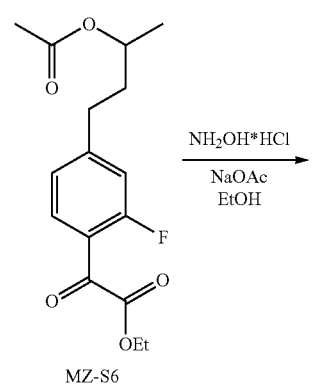

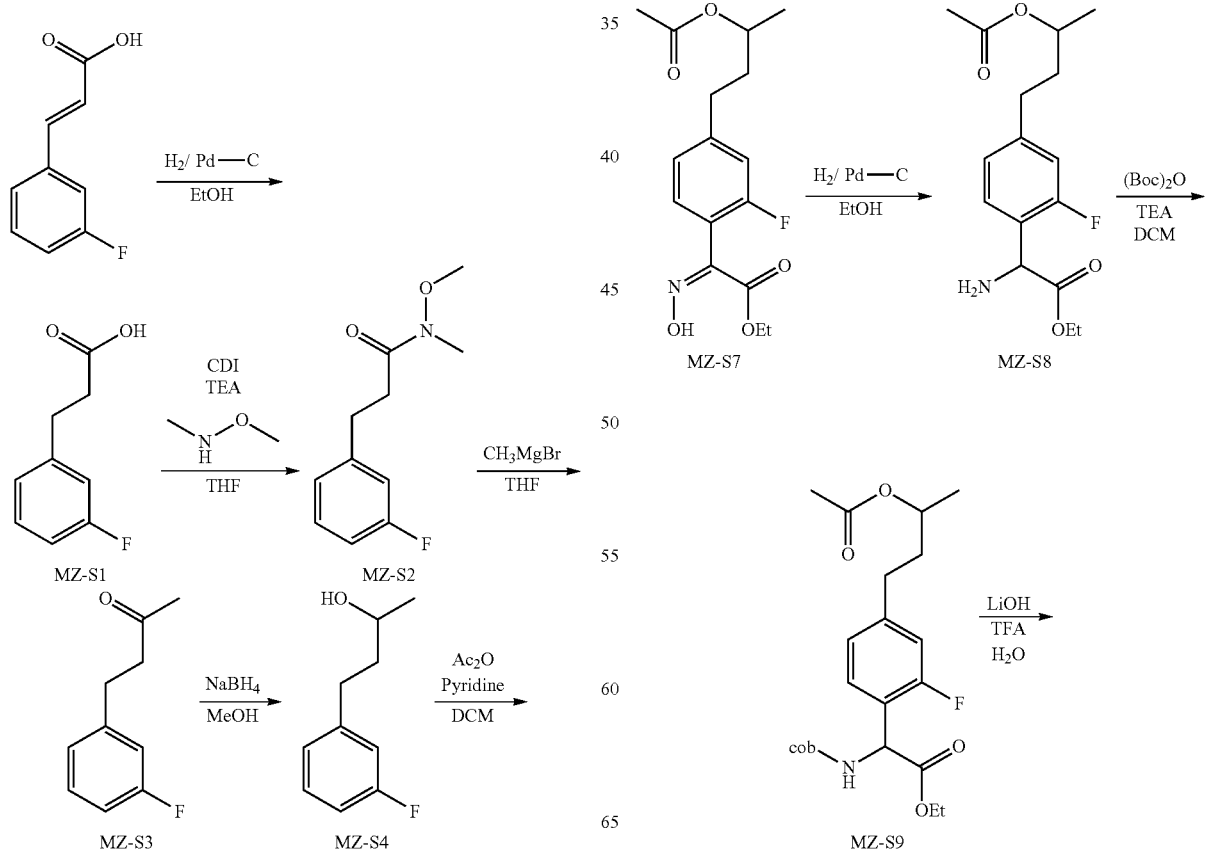

Method AA
Example 28-30
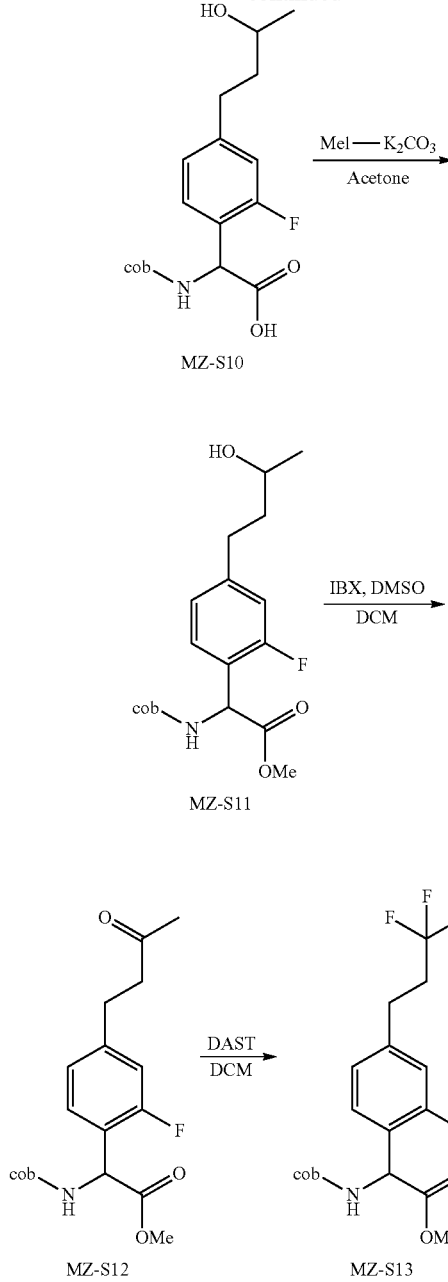
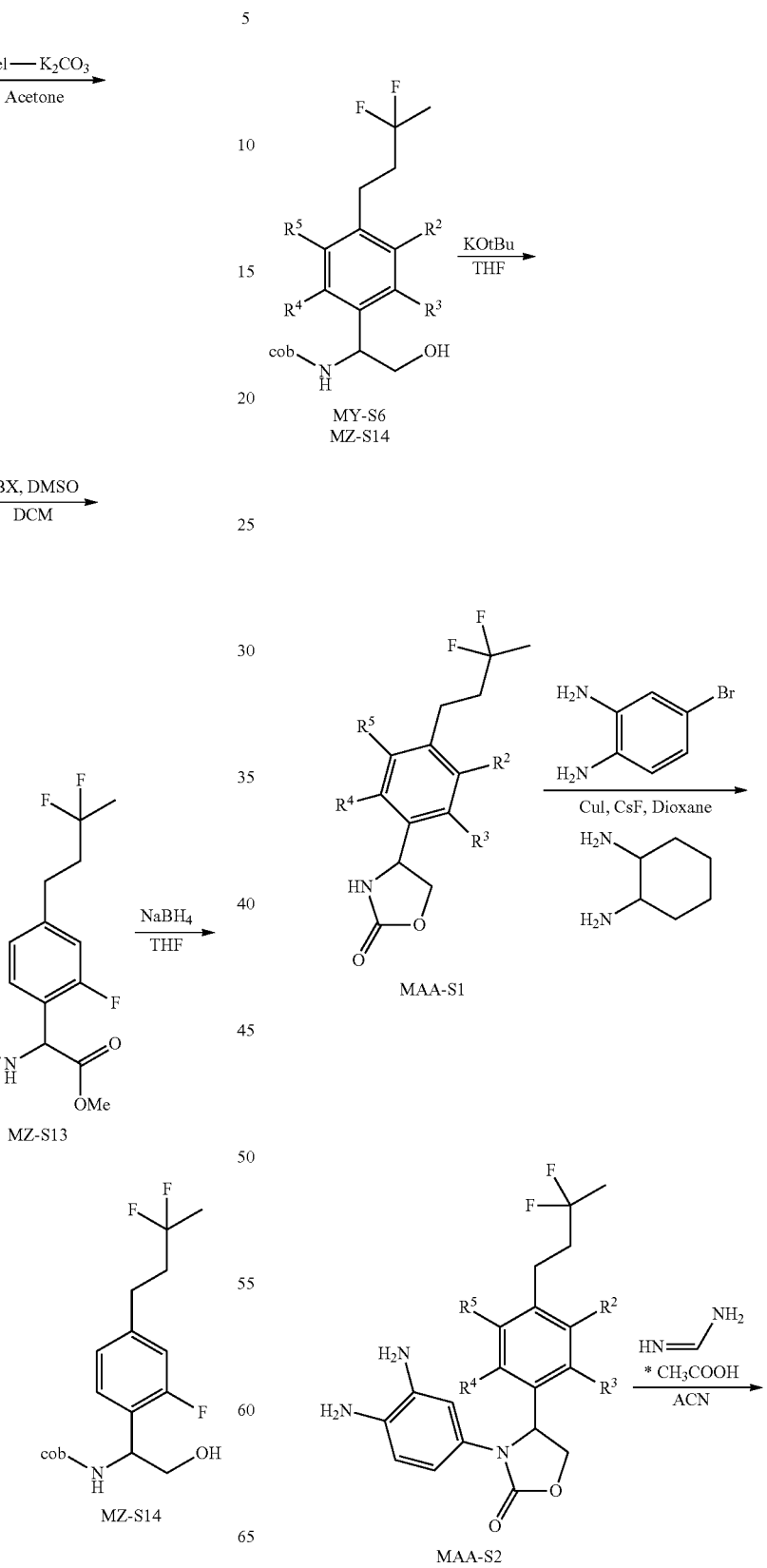
The method description is given at Example 30.

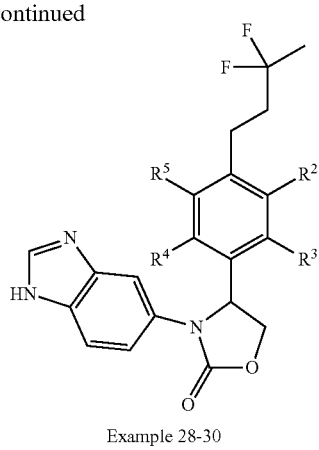

Example 28-30

$R^2-R^5$ = H, F

Step 1:
Potassium t-butoxide (2.5 equivalents) was slowly added to a stirred solution of the corresponding intermediate MY-S6 or MZ-S14 (1 equivalent) in tetrahydrofuran at 0° C. and the mixture was stirred for 3 h at room temperature. The reaction was neutralized with 10% acetic acid and extracted with ethyl acetate. The combined organic layer was washed successively with water, brine; dried over anhydrous sodium sulfate and concentrated under reduced pressure to afford MAA-S1, further used without any purification.

Step 2:
A mixture of MAA-S1 (1 equivalent), 4-Bromo-1,2-diaminobenzene (1 equivalent) and cesium fluoride (2 equivalents) in 1-4dioxane was purged with argon gas for 30 min. Copper iodide (0.2 equivalents) and 1,2-diaminocyclohexane (0.3 equivalents) were added and the mixture was continuously purged for another 10 min. The reaction was heated in a sealed tube for 20 h at 105-110° C. The reaction mixture was filtered through celite, washed with dioxane and the filtrate was concentrated under reduced pressure to give the crude intermediate. Purification by column chromatography over neutral alumina afforded MAA-S2.

Step 3:
Formamidine acetate (3 equivalents) was added to a solution of MAA-S2 (1 equivalent) in acetonitrile and the mixture was refluxed for 1 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product, which was triturated with diethyl ether and dried to afford Example 28-30.

EXAMPLES

Example 1

(S)-3-(1H-benzo[d]imidazol-5-yl)-4-(4-(3,3-difluorobutoxy)-2,3-difluorophenyl)-oxazolidin-2-one Step 1 (MA-S1):
A mixture of 2,3-Di fluoro 4-hydroxy benzonitrile (9.0 g, 58 mmol), 4-Chloro-2-butanol (18.87 g, 174 mmol) and potassium carbonate (16.04 g, 116 mmol)) in Acetonitrile (200 mL) was refluxed for 20 h. The reaction mass was cooled to room temperature, filtered. The filtrate was partitioned with water and ethyl acetate. The organic layer was washed with water, brine; dried over anhydrous sodium sulfate and concentrated in vacuum to afford 18 g (crude) as a yellow liquid.

Step 2 (MA-S2):
2-Iodoxy benzoic acid (89.12 g, 318 mmol) was added to a solution of MA-S1 (7.6 g crude, 36.3 mmol) in dichloromethane (50 mL), dimethyl sulfoxide (50 mL) and stirred for 18 h at room temperature. The reaction mass was filtered and washed with dichloromethane. The combined filtrate and wash solution was again washed successively with water, brine, dried over anhydrous sodium sulfate and concentrated in vacuum to afford the crude MA-S2, which was purified by column chromatography over silica gel (60-120 mesh) using 20% ethyl acetate in pet ether as eluent to afforded 12 g (91%) of 299b as pale yellow solid.

Step (MA-S3):
Diethylamino sulfurtrifluoride (19.7 mL, 142 mmol) was added to a solution of MA-S2 (8 g, 35 mmol) in dichloromethane (160 mL) at 0° C. The reaction mass was warmed to room temperature and stirred for 35 h. The reaction was quenched into ice water and the organic layer was separated. The aqueous layer was extracted with dichloromethane (1×50 mL). The combined organic layer was washed successively with aq sodium bicarbonate, water, brine, dried over anhydrous sodium sulfate and concentrated in vacuum to get crude 9.6 g of MA-S3.

Step 4 (MC-S1):
DIBAL (1.5 M; 52.3 mL, 78 mmol) was added slowly to a solution of MA-S3 (9.6 g, 39 mmol) in dry Tetrahydrofuran (120 mL) at −30° C. over 15 min. The reaction mass was warmed to room temperature and stirred for 2 h. The reaction was quenched with saturated ammonium chloride solution, filtered and washed with ethyl acetate. The filtrate was washed successively with water brine; dried over anhydrous sodium sulfate and concentrated in vacuum to afford the crude MC-S1 which was purified by column chromatography over silica gel (100-200 mesh) using 8-10% ethyl acetate in pet ether as eluent to afforded 5.96 g (98%) of MC-S1 as yellow liquid.

Step 5 (MC-S2):
N-Butyl lithium in hexane (2.5 M; 19.06 mL, 46 mmol) was added to a stirred solution of Triphenyl phosphonium methyl bromide (17.02 g, 46 mmol) in Tetrahydrofuran (100 mL) at −50° C. and was further stirred for 30 min at 0-5° C. A solution of MC-S1 (5.96 g, 23 mmol) in Tetrahydrofuran (50 mL) was added drop wise to the reaction mixture at −50° C. The temperature of the reaction was warmed to room temperature and again stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude MC-S2. Purification by column chromatography over silica gel (60-120 mesh) using 5% ethyl acetate in pet ether as eluent afforded 4.8 g (99%) of MC-S2 as pale yellow liquid.

Step 6 (MJ-S1):
t-Butyl hypochlorite (2.07 mL, 18.21 mmol) was added to a stirred solution of t-butyl carbamate (2.12 g, 18.14 mmol) in 1-propanol (24 mL) and 0.4 N aqueous sodium hydroxide (0.738 g in 46 mL water) at 15° C. and stirred for 15 min. A solution of (DHQ)$_2$PHAL (236 mg, 0.3 mmol) in 1-propanol (24 mL) was added followed by a solution of MC-S2 (1.5 g, 6 mmol) in 1-propanol (24 mL) was added. Finally potassium osmatedihydrate (89 mg, 0.24 mmol) was added and the reaction mixture was stirred for 15 min at room temperature. The reaction was quenched with saturated sodium sulphite solution and extracted with ethyl acetate. The combined organic layer was washed successively with water, brine, dried over anhydrous sodium sulfate and concentrated under reduced pressure to afford crude. Another similar batch was kept and purification of both by column chromatography over silica gel (60-120 mesh) using 18-20% ethyl acetate in pet ether as eluent afforded 2.6 g (56%) of MJ-S1 as yellow solid.

Step 7 (MK-S1):

Potassium t-butoxide (1.7 g, 15.6 mmol) was added to a solution of MJ-S1 (2.0 g, 5.2 mmol) in Tetrahydrofuran (35 mL) at a temperature of 0° C. The reaction mass was warmed to room temperature and stirred for 2 h. The reaction mass was acidified with acetic acid (pH-6) and extracted with ethyl acetate. The separated organic layer was washed successively with water, brine; dried over anhydrous sodium sulfate and concentrated in vacuum afforded 1.15 g of MK-S1 as oil.

Step 8 (MK-S2):

A mixture of MK-S1 (1.15 g, 3.7 mmol), 1,2-diamino-4-bromobenzene (588 mg, 3.7 mmol) and cesium fluoride (1.1 g, 7.5 mmol) in 1,4-dioxan (20 mL) was purged with argon gas for 10 min. To this, copper iodide (355 mg, 1.8 mmol) was added and the reaction mixture continuously purged for another 10 min. Finally 1,2-diaminocyclohexane (21 mg, 0.18 mmol) was added to the reaction and purging continued again for 10 min. The reaction mass was than stirred at 110-115° C. in a sealed tube for 20 h. The reaction mixture was cooled to room temperature, filtered through celite, washed with dioxin and concentrated under reduced pressure to afford the crude intermediate MK-S2. The compound was purified by column chromatography over neutral alumina using 1.5% methanol in chloroform as eluent to afford 890 mg (57%) as brown gummy solid.

Step 9 (Example 1):

Formamidine acetate (680 mg, 6.3 mmol) was added to a solution of MK-S2 (890 mg, 2.1 mmol) in acetonitrile (20 mL) and refluxed for 2 h. The reaction mixture was concentrated under reduced pressure and the resulting residue was partitioned between water and ethyl acetate. The organic layer was separated and the aqueous layer was extracted with ethyl acetate. The combined organic layer was washed with water, brine, dried over anhydrous sodium sulfate and concentrated in vacuum to afford crude. The crude product was purified by washing with diethyl ether, filtered and dried to afford 240 mg (27%) of PQPL-299 as a pale brown solid.

Melting range: 222-223° C.; $^1$H-NMR (400 MHz, DMSO-d6): δ 8.18 (d, 1H); 7.61-7.43 (m, 2H); 7.29-7.17 (m, 2H); 7.00 (t, 1H); 5.92-5.88 (m, 1H); 4.84 (t, 1H); 4.31 (q, 1H); 4.16 (t, 2H); 2.41-2.30 (m, 2H); 1.64 (t, 3H); MS=424.1 (M+1); HPLC~98.03%: Chiral HPLC~99.92%.

Example 2

(S)-3-(1H-benzo[d]imidazol-5-yl)-4-(4-(3,3-difluoropropoxy)-2-fluorophenyl)oxazolidin-2-one Step 1 (MA-S1):

A mixture of 2-Fluoro-4-hydroxy benzonitrile (10.0 g, 72.8 mmol), 3-Chloropropanol (8.4 g, 87.6 mmol) and potassium carbonate (20 g, 146 mmol)) in Acetonitrile (100 mL) was refluxed for 24 h. The reaction mass was cooled to room temperature, filtered. The filtrate was partitioned with water and ethyl acetate. The organic layer was washed with water, brine; dried over anhydrous sodium sulfate and concentrated in vacuum to afford 12 g of MS-S1 as the crude intermediate, further used without purification.

Step 2 (MA-S2):

Dess-martin periodinane (13 g, 30.76 mmol) was added to a solution of MA-S1 (6 g, 30.76 mmol) in dichloromethane (60 mL) and stirred for 3 h at room temperature. The reaction mass was filtered and washed with dichloromethane. The combined filtrate and washings was washed successively with a saturated sodium bicarbonate solution, water, brine; dried over anhydrous sodium sulfate and concentrated in vacuum to afford the crude intermediate. Purification by trituration with pet ether afforded 6 g of MS-S2 as a solid.

Step 3 (MA-S3):

Diethylamino sulfurtrifluoride (17 mL, 124.34 mmol) was added to a solution of MS-S2 (12 g, 62.16 mmol) in dichloromethane (100 mL) at 0° C. The reaction mass was warmed to room temperature and stirred for 3 h. The reaction was quenched into ice water and the organic layer was separated. The aqueous layer was extracted with dichloromethane. The combined organic layer was washed successively with water, brine; dried over anhydrous sodium sulfate and concentrated in vacuum to get 6.2 g of MS-S3 as crude intermediate, further used for the next step without purification.

Step 4 (MC-S1):

DIBAL (1.5 M in THF; 37.2 mL, 55.81 mmol) was added slowly to a solution of MS-S3 (6 g, 27.90 mmol) in dry tetrahydrofuran (100 mL) at −30° C. over 15 min. The reaction mass was warmed to room temperature and stirred for 4 h. The reaction was quenched with saturated ammonium chloride solution, filtered and washed with ethyl acetate. The filtrate was washed successively with water brine; dried over anhydrous sodium sulfate and concentrated in vacuum to afford the crude intermediate, which was purified by column chromatography over silica gel (60-120 mesh) using 10% ethyl acetate in pet ether as eluent to afforded 5 g of MC-S1 as a pale brown liquid.

Step 5 (MC-S2):

N-butyl lithium (2.4 M; 15.3 mL, 36.70 mmol) was added to a stirred solution of Methyl triphenyl phosphonium bromide (13.1 g, 36.70 mmol) in tetrahydrofuran (50 mL) at −30° C. and than the solution stirred for 30 min at 0-5° C. A solution of MC-S1 (4 g, 18.34 mmol) in tetrahydrofuran (30 mL) was added drop wise to the reaction mixture at −30° C. The temperature of the reaction mass was warmed to room temperature and stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) using 5% ethyl acetate in pet ether as eluent afforded 3.4 g of MC-S2 as a pale yellow liquid.

Step 6 (MJ-S1):

t-Butyl hypochlorite (5.38 mL, 47.3 mmol) was added to a stirred solution of t-butylcarbamate (5.52 g, 47.20 mmol) in 1-propanol (32 mL) and 0.4 N aqueous sodium hydroxide (1.98 g in 120 mL water) at 15° C. and stirred for 15 min. A solution of (DHQ)$_2$PHAL (612 mg, 0.78 mmol) in 1-propanol (32 mL) was added, followed by a solution of MC-S2 (3.4 g, 15.60 mmol) in 1-propanol (32 mL). Finally potassium osmate dihydrate (230 mg, 0.62 mmol) was added and the reaction mixture was stirred for another 15 min at room temperature. The reaction was quenched with saturated sodium sulfite solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) using 25% ethyl acetate in pet ether as eluent afforded 1.7 g of MJ-S1 as a brown solid.

Step 7 (MK-S1):

Thionylchloride (2.7 mL, 36.67 mmol) was added drop wise to a solution of MJ-S1 (1.6 g, 4.58 mmol) in tetrahydrofuran (20 mL) at 0° C. The Reaction mass was warmed to room temperature and stirred for 2 h. The reaction mixture was concentrated under reduced pressure and the residue was partitioned between saturated sodium bicarbonate solution and ethyl acetate. The separated organic layer was washed successively with water, brine; dried over anhydrous sodium sulfate and concentrated in vacuum to afford 1.15 g of MK-S1 as a off white solid.

Step 8 (MK-S2):

A mixture of MK-S1 (1.1 g, 4.0 mmol), 1,2-diamino-4-bromobenzene (1.12 g, 6.0 mmol) and cesium fluoride (1.2 g, 8 mmol) in 1,4-dioxan (30 mL) was purged with argon gas for 10 min. To this mixture copper iodide (380 mg, 2 mmol) was added and the solution was further purged for another 10 min. Finally 1,2-diaminocyclohexane (230 mg, 2 mmol) was added and the reaction mixture was continuously purged for another 10 min. The reaction mass was stirred at 110-115° C. in a sealed tube for 18 h. The reaction was cooled to room temperature, filtered through celite pad, washed with dioxin and concentrated under reduced pressure to afford the crude intermediate. The crude compound was purified by column chromatography over neutral alumina using 2% methanol in chloroform as eluent to afford 900 mg of MK-S2 as a brown solid.

Step 9 (Example 2):

Formamidineacetate (740 mg, 7.1 mmol) was added to a solution of MK-S2 (900 mg, 2.36 mmol) in acetonitrile (20 mL) and refluxed for 2 h. The reaction mixture was concentrated under reduced pressure and the resulting residue was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification was done by washing with diethyl ether, filtered and dried to afford 500 mg of Example 2 as a pale brown solid.

Melting range: 199-204° C.; $^1$H-NMR (DMSO-d6): δ 12.2 (s, 1H); 8.17 (s, 1H); 7.57 (d, 1H); 7.49 (d, 1H); 7.34 (t, 1H); 7.22 (d, 1H); 6.84 (dd, 1H); 6.74 (dd, 1H); 6.17 (bt, 1H); 5.85 (q, 1H); 4.83 (t, 1H); 4.24 (q, 1H); 4.07-4.03 (m, 2H); 2.27-2.23 (m, 2H); MS=392.0 (M+1); HPLC~98.63%; Chiral HPLC~99.86%.

Example 3

(S)-3-(1H-benzo[d]imidazol-5-yl)-4-(4-(3,3-difluorobutoxy)-2-fluorophenyl)oxazolidin-2-one Step 1 (MA-S1):

A mixture of 2-Fluoro-4-Hydroxy benzonitrile (10.0 g, 72.99 mmol), 4-Chloro-2-butanol (16 mL, 145.98 mmol) and potassium carbonate (30 g, 218.97 mmol)) in acetonitrile (200 mL) was refluxed for 24 h. The reaction mass was cooled to room temperature and filtered. The filtrate was partitioned with water and ethyl acetate. The organic layer was washed with water, brine; dried over anhydrous sodium sulfate and concentrated in vacuum to afford 18 g of MA-S1 as the crude intermediate, given as a brown liquid.

Step 2 (MA-S2):

2-Iodoxy benzoic acid (80 g, 287.07 mmol) was added to a solution of MA-S1 (15 g, 71.77 mmol) in dichloromethane (100 mL) and dimethyl sulfoxide (100 mL) and stirred for 22 h at room temperature. The reaction mass was filtered and washed with dichloromethane. The combined filtrate and washings was washed successively with water, brine; dried over anhydrous sodium sulfate and concentrated in vacuum to afford the crude intermediate. Purification by trituration with pet ether afforded 13 g of MA-S2 as a off white solid.

Step 3 (MA-S3):

Diethylamino sulfurtrifluoride (21 mL, 154.58 mmol) was added to a solution of MA-S2 (8 g, 38.64 mmol) in dichloromethane (120 mL) at 0° C. The reaction was warmed to room temperature and stirred for 48 h. The reaction was quenched into ice water and the organic layer was separated. The aqueous layer was extracted with dichloromethane (1×200 mL). The combined organic layer was washed successively with water, brine; dried over anhydrous sodium sulfate and concentrated in vacuum to get 7 g of MA-S3 as the crude intermediate, further used for the next step.

Step 4 (MC-S1):

DIBAL (1.5 M; 61 mL, 61 mmol) was added slowly to a solution of MA-S3 (7.0 g, 30.56 mmol) in dry tetrahydrofuran (120 mL) at −30° C. over 15 min. The reaction mass was warmed to room temperature and again stirred for 2 h. The reaction was quenched with saturated ammonium chloride solution, filtered and washed with ethyl acetate. The filtrate was washed successively with water brine; dried over anhydrous sodium sulfate and concentrated in vacuum to afford the crude intermediate, which was purified by column chromatography over silica gel (60-120 mesh) using 5-7% ethyl acetate in pet ether as eluent to afford 6.0 g of MC-S1 as a pale brown liquid.

Step 5 (MC-S2):

N-butyl lithium in hexane (2.5 M; 25 mL, 62.11 mmol) was added to a stirred solution of Triphenyl phosphonium methyl bromide (27 g, 77.58 mmol) in tetrahydrofuran (80 mL) at −30° C. and than the solution was stirred for 30 min at 0-5° C. A solution of MC-S1 (6.0 g, 25.862 mmol) in tetrahydrofuran (40 mL) was added drop wise to the reaction mixture at −30° C. The temperature was warmed to room temperature and the reaction mixture was stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) using 2% ethyl acetate in pet ether as eluent afforded 4.5 g of MC-S2 as a pale yellow liquid.

Step 6 (MJ-S1):

t-Butyl hypochlorite (2.2 mL, 19.56 mmol) was added to a stirred solution of t-butyl carbamate (2.28 g, 19.56 mmol) in 1-propanol (26 mL) and 0.4 N aqueous sodium hydroxide (1.16 g in 73 mL water) at 15° C. and stirred for 15 min. A solution of (DHQ)$_2$PHAL (254 mg, 0.32 mmol) in 1-propanol (26 mL) was added followed by a solution of MC-S2 (1.5 g, 6.5 mmol) in 1-propanol (26 mL). Finally potassium osmatedihydrate (95 mg, 0.26 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) using 18-20% ethyl acetate in pet ether as eluent afforded 600 mg of MJ-S1 as a off-white solid.

Step 7 (MK-S1):

Potassium t-butoxide (920 mg, 8.265 mmol) was added to a solution of MJ-S1 (1.2 g, 3.3 mmol) in tetrahydrofuran (30 mL) at 0° C. The Reaction mass was warmed to room temperature and stirred for 2 h. The reaction mixture was acidified with acetic acid (pH-6) and extracted with ethyl acetate. The separated organic layer was washed successively with water, brine; dried over anhydrous sodium sulfate and concentrated in vacuum afforded 800 mg of MK-S1 as a off white solid.

Step 8 (MK-S2):

A mixture of MK-S1 (800 mg, 2.76 mmol), 1,2-diamino-4-bromobenzene (517 mg, 2.76 mmol) and cesium fluoride (840 mg, 5.53 mmol) in 1,4-dioxan (30 mL) was purged with argon gas for 10 min. Copper iodide (103 mg, 0.544 mmol) was added and the reaction mixture was further purged for another 10 min. Finally 1,2-diaminocyclohexane (350 mg, 0.3 mmol) was added and the reaction mixture was continuously purged for the next 10 min. The reaction mass was than stirred at 110-115° C. in a sealed tube for 18 h. The reaction was cooled to room temperature, filtered through celite, washed with dioxin and concentrated under reduced pressure to afford the crude intermediate. The compound was purified by column chromatography over neutral alumina using 2% methanol in chloroform as eluent to afford 400 mg of MK-S2 as a brown solid.

Step 9 (Example 3):

Formamidine acetate (315 mg, 3.0 mmol) was added to a solution of MK-S2 (400 mg, 1.0 mmol) in acetonitrile (10 mL) and refluxed for 2 h. The reaction mixture was concentrated under reduced pressure and the resulting residue was partitioned between water and ethyl acetate. The organic layer was separated and the aqueous layer was extracted with ethyl acetate. The combined organic layer was washed with water, brine; dried over anhydrous sodium sulfate and concentrated in vacuum to afford crude. The crude product was purified by washing with diethyl ether, filtered and dried to afford 200 mg of Example 3 as a pale brown solid.

Melting range: 199-200° C.; $^1$H-NMR (400 MHz, DMSO-d6): δ 8.17 (d, 1H); 7.58-7.42 (m, 2H); 7.35-7.15 (m, 2H); 6.86-6.81 (m, 1H); 6.75-6.71 (m, 1H); 5.85 (t, 1H); 4.83 (t, 1H); 4.24 (q, 1H); 4.08 (t, 2H); 2.39-2.26 (m, 2H); 1.63 (t, 3H); MS=406.1 (M+1); HPLC~95.71%: Chiral HPLC~99.01%.

Example 4

(S)-3-(1H-benzo[d]imidazol-5-yl)-4-(4-(3,3-difluoropropoxy)phenyl)oxazolidin-2-one Step 1 (MG-S1):

Thionyl chloride (17.5 mL, 0.239 mol) was added to a suspension of (S)-4-hydroxy phenyl glycine (20 g, 0.120 mol) in methanol (100 mL) at 0° C. drop-wise. The mixture was heated slowly to reflux and maintained thus for 15 h. The solvent was evaporated in vacuum and the residue was co-distilled twice with pet ether. Drying in vacuum afforded 25.2 g (96.55%) of MG-S1 as a white solid.

Step 2 (MG-S2):

Aqueous potassium carbonate (31.8 g, 0.230 mol in 100 mL water) and boc anhydride (31.65 mL, 0.138 mol) were added successively to a suspension of MG-S1 (25.0 g, 0.115 mol) in 1,4-dioxan (200 mL) at 0° C. The reaction mixture was warmed to room temperature and stirred for 2 h. The reaction was quenched into water and extracted with ethyl acetate (2×100 mL). The combined organic layer was washed successively with water, brine; dried over anhydrous sodium sulfate and concentrated in vacuum to afford the crude intermediate. The compound was suspended in pet ether, stirred for 30 min, filtered and dried in vacuum to afford 28.9 g (89.43%) of MG-S2 as a white solid.

Step 3 (MG-S3):

Triphenyl phosphine (2.09 g, 8.01 mmol) and 3-Benzyloxy-1-propanol (1.01, 6.40 mmol) were added successively to a stirred solution of MG-S3 (1.5 g, 5.34 mmol) in dry tetrahydrofuran (30 mL) at room temperature. Diethylazo dicarboxylate (50 mL, 0.319 mol) was added drop wise and the reaction mass was stirred at room temperature for 2 h. The reaction was quenched with water and extracted with ethyl acetate. The combined organic layer was washed with water, brine; dried over anhydrous sodium sulfate and concentrated in vacuum to afford the crude intermediate. Purification by column chromatography over silica gel (60-120 mesh) and using 20% ethyl acetate in pet ether as the eluent afforded 1.8 g (78.98%) of MG-S3 as a colorless thick liquid.

Step 4 (MG-S4):

A solution of MG-S3 (1.8 g, 4.21 mmol) in methanol (50 mL) was hydrogenated over Pd/C (10%; 450 mg) at 80 psi for 2 h in a Parr apparatus. The reaction mass was filtered though celite and washed with methanol. The combined filtrate and washing portion was concentrated under reduced pressure to afford 1.3 g (91.10%) of MG-S4 as a off white solid.

Step 5 (MG-S5):

Iodoxy benzoic acid (3.63 g, 12.98 mmol) was added to a solution of MG-S4 (1.1 g, 3.24 mmol) in dichloromethane and dimethyl sulfoxide (30 mL: 1 mL) and the mixture was stirred for 20 h at room temperature. The reaction mass was filtered and washed with dichloromethane. The combined filtrate and washing portion was washed successively with water, brine; dried over anhydrous sodium sulfate and concentrated in vacuum to afford the crude intermediate. Purification by column chromatography over silica gel (60-120 mesh) and using 25% ethyl acetate in pet ether as the eluent afforded 730 mg (66.91%) of MG-S5 as a yellow syrup.

Step 6 (MG-S6):

Diethylamino sulfur trifluoride (0.56 mL, 4.27 mmol) was added to a solution of MG-S5 (720 mg, 2.14 mmol) in dichloromethane (20 mL) at 0° C. The reaction mass was warmed to room temperature and stirred for 2 h. The reaction was quenched with ice water and the organic layer was separated. The aqueous layer was extracted with dichloromethane (1×30 mL). The combined organic layer was washed successively with water, brine; dried over anhydrous sodium sulfate and concentrated in vacuum to afford 700 mg (91.14%) of MG-S6 as a yellow syrup.

Step 7 (MG-S7):

Sodium borohydride (295 mg, 7.80 mmol) was added in two equal lots (over 15 min) to a solution of MG-S6 (700 mg, 1.95 mmol) in mixture of tetrahydrofuran (10 mL) and methanol (4 mL) at room temperature. Due to the exothermic reaction the temperature raised up to ~50° C. After the complete addition, the reaction mass was stirred for 15 h. Ethyl acetate was added and the reaction was quenched with saturated ammonium chloride solution. The organic layer was separated and the aqueous layer was extracted with ethyl acetate. The combined organic layer was washed successively with water, brine; dried over anhydrous sodium sulfate and concentrated in vacuum to afford 600 mg (93.02%) of MG-S7 as a off white solid.

Step 8 (MK-S1):

Thionyl chloride (1.06 mL, 14.50 mmol) was added to a solution of MG-S7 (600 mg, 1.81 mmol) in tetrahydrofuran (20 mL) at 0° C. The reaction mixture was warmed to room temperature and stirred for 4 h. The solvent was evaporated in vacuum and co-distilled twice with toluene to afford the crude intermediate. Purification by column chromatography over neutral alumina and using 1% methanol in chloroform as the eluent afforded 305 mg (65.59%) of MK-S1 as a off white solid.

Step 9 (MK-S2):

A mixture of MK-S1 (300 mg, 1.17 mmol), 1,2-diamino-4-bromobenzene (218 mg, 1.17 mmol), cesium fluoride (356 mg, 2.34 mmol) and copper iodide (34 mg, 0.1755 mmol) in 1,4-dioxan (10 mL) was purged with argon gas for 15 min. 1,2-diaminocyclohexane (20 mg, 0.1755 mmol) was added and the reaction mixture was continuously purged for another 10 min. The reaction mass was stirred at 110-115° C. in a sealed tube for 18 h. The reaction mixture was filtered though celite, washed with dioxan and concentrated under reduced pressure to afford the crude intermediate. Purification by column chromatography over neutral alumina and using 2% methanol in chloroform as the eluent afforded 310 mg (72.99%) of MK-S2 as a brown solid.

Step 10 (Example 4):

Formamidine acetate (258 mg, 2.48 mmol) was added to a solution of MK-S2 (300 mg, 0.83 mmol) in acetonitrile (10 mL) and the mixture was refluxed for 2 h. The reaction mixture was concentrated under reduced pressure and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude intermediate, which was purified by column chromatography over neutral alumina and using 2-3% methanol in chloroform as the eluent to afford 200 mg (64.60%) of Example 14 as a pale brown solid.

Melting range: 198-200° C.; $^1$H-NMR (400 MHz, DMSO-d6): δ 12.41 (s, 1H); 8.16 (s, 1H); 7.57 (d, 1H); 7.47 (bs, 1H); 7.33-7.24 (m, 3H); 6.89 (d, 2H); 6.33-6.03 (m, 1H); 5.69-5.66 (m, 1H); 4.80 (t, 1H); 4.14-4.01 (m, 3H); 2.32-2.18 (m, 2H); MS=374.1 (M+1); HPLC~97.75%; Chiral HPLC~97.87%;

Example 5

(S)-3-(1H-benzo[d]imidazol-5-yl)-4-(4-(2,2-difluoropropoxy)-3-fluorophenyl)oxazolidin-2-one Step 1 (MB-S1):

A mixture of 3-fluoro-4-hydroxy benzonitrile (4.0 g, 29.17 mmol), chloro acetone (3.5 mL, 43.76 mmol) and potassium carbonate (8.06 g, 58.3 mmol)) in acetonitrile (50 mL) was refluxed for 2 h. The reaction was cooled to room temperature, filtered and washed with ethyl acetate. The combined filtrate was concentrated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford 5.0 g (89.3%) of the crude intermediate MB-S1 as a brown solid.

Step 2 (MB-S2):

Diethylamino sulfurtrifluoride (7.1 mL, 51.8 mmol) was added to a solution of MB-S1 (5.0 g, 25.9 mmol) in dichloromethane (50 mL) at 0° C. and the mixture was stirred for 2 h at room temperature. The reaction was quenched with ice water and extracted with dichloromethane. The combined organic layer was washed successively with water, brine; dried over anhydrous sodium sulfate and concentrated in vacuum to afford 5.1 g (91.7%) of the crude intermediate MB-S2 as a brown liquid.

Step 3 (MC-S1):

DIBAL in toluene (1.5 M; 23.25 mL, 34.88 mmol) was added slowly to a solution of MB-S2 (5.0 g, 23.25 mmol) in dry tetrahydrofuran (70 mL) at −30° C. over 15 min. The reaction mass was warmed to room temperature and the solution was stirred for 2 h. The reaction was quenched with saturated ammonium chloride solution, filtered and washed with ethyl acetate. The filtrate was washed successively with water brine; dried over anhydrous sodium sulfate and concentrated in vacuum to afford the crude intermediate, which was purified by column chromatography over silica gel (60-120 mesh) using 9-10% ethyl acetate in pet ether as eluent to afford 3.8 g (75.09%) of MC-S1 as a pale yellow liquid.

Step 4 (MC-S2):

N-butyl lithium in hexane (2.5 M; 112.8 mL, 32.11 mmol) was added to a stirred solution of Triphenyl phosphonium methyl bromide (11.46 g, 32.11 mmol) in tetrahydrofuran (40 mL) at −30° C. and the solution was stirred for 30 min at 0-5° C. A solution of MC-S1 (3.5 g, 16.05 mmol) in tetrahydrofuran (20 mL) was added drop wise to the reaction mixture at −30° C. The temperature was warmed to room temperature and the reaction mixture was stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 2% ethyl acetate in pet ether as the eluent afforded 2.5 g (72.25%) of MC-S2 as a pale yellow liquid.

Step 5 (MJ-S1):

t-Butyl hypochlorite (3.96 mL, 34.83 mmol) was added to a stirred solution of t-butyl carbamate (4.06 g, 34.72 mmol) in 1-propanol (57.8 mL) and 0.4 N aqueous sodium hydroxide (1.41 g in 88 mL water) at 15° C. and the mixture was stirred for 15 min. A solution of (DHQ)$_2$PHAL (450 mg, 0.578 mmol) in 1-propanol (57.8 mL) was added, followed by a solution of MC-S2 (2.5 g, 11.57 mmol) in 1-propanol (57.8 mL). Finally potassium osmatedihydrate (170 mg, 0.462 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over neutral alumina and using 20-22% ethyl acetate in pet ether as the eluent afforded 900 mg of MJ-S1 as a white solid.

Step 6 (MK-S1):

To a stirred solution of potassium-t-butoxide (866 mg, 7.73 mmol) in tetrahydrofuran (10 mL) was added a solution of MJ-S1 (900 mg, 2.57 mmol) in tetrahydrofuran (10 mL) at 0° C. and the mixture was stirred for 3 h at room temperature. The reaction was neutralized with 10% acetic acid and extracted with ethyl acetate. The combined organic layer was washed successively with water, brine; dried over anhydrous sodium sulfate and concentrated under reduced pressure to afford the crude intermediate, which was triturated with pet ether and dried to afford 670 mg of MK-S1 as a yellow solid.

Step 7 (MK-S2):

A mixture of MK-S1 (650 mg, 2.36 mmol), 4-bromo-1,2-diamino benzene (236 mg, 2.36 mmol) and cesium fluoride (718 mg, 4.72 mmol) in 1,4-dioxane (20 mL) was purged with argon gas for 15 min. Copper iodide (67.36 mg, 0.354 mmol) and 1,2-diaminocyclohexane (40.4 mg, 0.354 mmol) were added and purging continued for another 10 min. The reaction mixture was heated in a sealed tube for 20 h at 110-115° C. The reaction mixture was filtered through celite, washed with dioxane and the filtrate was concentrated under reduced pressure to give the crude intermediate. Purification by column chromatography over neutral alumina and using 2-3% methanol in chloroform as the eluent afforded 450 mg of MK-S2 as a brown solid.

Step 8 (Example 5):

Formamidine acetate (328 mg, 3.15 mmol) was added to a solution of MK-S2 (400 mg, 1.05 mmol) in acetonitrile (15 mL) and the solution was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product, which was purified by washing with diethyl ether, filtered and dried to afforded 220 mg (53.65%) of Example 5 as a pale brown solid.

Melting range: 224-227° C.; $^1$H-NMR (400 MHz, DMSO-d6): δ 8.17 (s, 1H); 7.59 (s, 1H); 7.50 (bs, 1H); 7.16 (t, 3H); 5.70 (t, 1H); 4.80 (t, 1H); 4.29 (t, 2H); 4.15 (t, 1H); 1.67 (t, 3H); MS=392.1 (M+1); HPLC~97.00%: Chiral HPLC~97.20%.

Example 6

(S)-3-(1H-benzo[d]imidazol-5-yl)-4-(4-(2,2-difluoropropoxy)-2,3-difluorophenyl)oxazolidin-2-one Step 1 (MB-S1):

A mixture of 2,3-difluoro-4-hydroxy benzonitrile (4.5 g, 29.01 mmol), chloro acetone (3.5 mL, 43.52 mmol) and potassium carbonate (8.02 g, 58.02 mmol) in acetonitrile (100 mL) was refluxed for 2 h. The reaction was cooled to room temperature, filtered and washed with ethyl acetate. The combined filtrate was concentrated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford 5.6 g (91.8%) of the crude intermediate MB-S1 as a brown solid.

Step 2 (MB-S2):

Diethylamino sulfurtrifluoride (7.3 mL, 53.08 mmol) was added to a solution of MB-S1 (5.6 g, 26.54 mmol) in dichloromethane (60 mL) at 0° C. and the mixture was stirred for 2 h at room temperature. The reaction was quenched with ice water and extracted with dichloromethane. The combined organic layer was washed successively with water, brine; dried over anhydrous sodium sulfate and concentrated in vacuum to afford 5.6 g (90.77%) of the crude intermediate MB-S2 as a brown liquid.

Step 3 (MC-S1):

DIBAL in THF (1 M; 48 mL, 48 mmol) was added slowly to a solution of MB-S2 (5.6 g, 24.03 mmol) in dry tetrahydrofuran (100 mL) at −30° C. over 15 min. The reaction mixture was warmed to room temperature and further stirred for 2 h. The reaction was quenched with saturated ammonium chloride solution, filtered and washed with ethyl acetate. The filtrate was washed successively with water brine; dried over anhydrous sodium sulfate and concentrated in vacuum to afford the crude intermediate. Purification by column chromatography over silica gel (60-120 mesh) using 10-12% ethyl acetate in pet ether as eluent afforded 4.6 g (81.13%) of MC-S1 as a pale yellow liquid.

Step 4 (MC-S2):

n-Butyl lithium in hexane (2.1 M; 18.56 mL, 38.98 mmol) was added to a stirred solution of Triphenyl phosphonium methyl bromide (13.92 g, 38.98 mmol) in tetrahydrofuran (100 mL) at −30° C. and the solution was stirred for 30 min at 0-5° C. A solution of MC-S1 (4.6 g, 19.49 mmol) in tetrahydrofuran (40 mL) was added drop wise at −30° C. The temperature was warmed to room temperature and the mixture was stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) using 2% ethyl acetate in pet ether as eluent afforded 2.5 g (54.82%) of MC-S2 as a pale yellow liquid.

Step 5 (MJ-S1):

t-Butyl hypochlorite (3.65 mL, 32.14 mmol) was added to a stirred solution of t-butyl carbamate (3.75 g, 32.05 mmol) in 1-propanol (42.5 mL) and 0.4 N aqueous sodium hydroxide (1.302 g in 81 mL water) at 15° C. and stirred for 15 min. A solution of (DHQ)$_2$PHAL (416 mg, 0.534 mmol) in 1-propanol (42.5 mL) was added, followed by a solution of MC-S2 (2.5 g, 10.68 mmol) in 1-propanol (42.5 mL). Finally potassium osmatedihydrate (157 mg, 0.427 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over neutral alumina and using 22-25% ethyl acetate in pet ether as eluent afforded 600 mg of MJ-S1 as a white solid.

Step 6 (MK-S1):

Potassium-t-butoxide (550 mg, 4.90 mmol) was added to a stirred solution of MJ-S1 (600 mg, 1.63 mmol) in tetrahydrofuran (20 mL) at 0° C. and the mixture was stirred for 3 h at room temperature. The reaction was neutralized with 10% acetic acid and extracted with ethyl acetate. The combined organic layer was washed successively with water, brine; dried over anhydrous sodium sulfate and concentrated under reduced pressure to afford the crude intermediate, which was triturated with pet ether and dried to afford 370 mg of MK-S1 as a yellow solid.

Step 7 (MK-S2):

A mixture of MK-S1 (370 mg, 1.26 mmol), 4-Bromo-1,2-diamino benzene (236 mg, 1.26 mmol) and cesium fluoride (383 mg, 2.52 mmol) in 1,4-dioxane (15 mL) was purged with argon gas for 30 min. Copper iodide (36 mg, 0.19 mmol) and 1,2-diaminocyclohexane (22 mg, 0.19 mmol) were added and purging continued for another 10 min. The reaction mixture was heated in a sealed tube for 18 h at 110-115° C. The resulting mass was filtered through celite, washed with dioxane and the filtrate was concentrated under reduced pressure to give the crude intermediate. Purification by column chromatography over neutral alumina and using 2-3% methanol in chloroform as the eluent afforded 310 mg of MK-S2 as a brown semi solid.

Step 8 (Example 6):

Formamidine acetate (260 mg, 2.48 mmol) was added to a solution of MK-S2 (300 mg, 0.83 mmol) in acetonitrile (15 mL) and the mixture was refluxed for 2 h. The solvent was evaporated in vacuum and the resulting residue was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by column chromatography over neutral alumina and using 2.5-3% methanol in dichloromethane as the eluent afforded 120 mg (38.71%) of Example 6 as a pale brown solid.

Melting range: 235-237° C.; $^1$H-NMR (400 MHz, DMSO-d6): δ 8.18 (d, 1H); 7.61-7.43 (m, 2H); 7.30-7.17 (m, 2H); 7.03 (t, 1H); 5.94-5.89 (m, 1H); 4.88 (t, 1H); 4.37-4.30 (m, 3H); 1.67 (t, 3H); MS=410.1 (M+1); HPLC~96.30%: Chiral HPLC~98.75%.

Example 7

(S)-3-(1H-benzo[d]imidazol-5-yl)-4-(4-(2,2-difluoropropoxy)-2-fluorophenyl)oxazolidin-2-one Step 1 (MB-S1):

A mixture of 2-fluoro-4-hydroxy benzonitrile (1 g, 7.29 mmol), chloro acetone (0.88 mL, 10.94 mmol) and potassium carbonate (2.0 g, 14.58 mmol) in acetonitrile (10 mL) was refluxed for 12 h. The reaction was cooled to room temperature, filtered and washed with ethyl acetate. The combined filtrate was concentrated in vacuum and the resulting residue was partitioned between water and ethyl acetate. The organic layer was separated and the aqueous layer was extracted with ethyl acetate. The combined organic layer was washed with water, brine; dried over anhydrous sodium sulfate and concentrated in vacuum to afford 1.25 g (85.8%) of the crude intermediate MB-S1 as a brown solid, further used for the next step.

Step 2 (MB-S2):

Diethylamino sulfurtrifluoride (1.36 mL, 10.36 mmol) was added to a solution of MB-S1 (1.0 g, 5.18 mmol) in dichloromethane (10 mL) at 0° C. and the mixture was stirred for 2 h at room temperature. The reaction was quenched with ice water and extracted with dichloromethane. The combined organic layer was washed successively with water, brine; dried over anhydrous sodium sulfate and concentrated in vacuum to afford 1.0 g (86.2%) of the crude intermediate MB-S2 as a brown liquid.

Step 3 (MC-S1):

DIBAL in THF (1 M; 9.3 mL, 9.3 mmol) was added slowly to a solution of MB-S2 (1.0 g, 4.65 mmol) in dry tetrahydrofuran (10 mL) at −30° C. over 5 min. The reaction mixture was warmed to room temperature and stirred for 2 h. The reaction was quenched with saturated ammonium chloride solution, filtered and washed with ethyl acetate (3×25 mL). The filtrate was washed successively with water brine; dried over anhydrous sodium sulfate and concentrated in vacuum to afford the crude intermediate. Purification by column chromatography over silica gel (60-120 mesh) using 10% ethyl acetate in pet ether as eluent afforded 520 mg (51.4%) of MC-S1 as a color less liquid.

Step 4 (MC-S2):

n-Butyl Lithium in hexane (2.5 M; 7.3 mL, 18.34 mmol) was added to a stirred solution of Triphenyl phosphonium methyl bromide (6.5 g, 18.34 mmol) in tetrahydrofuran (20 mL) at −50° C. and the solution was further stirred for 30 min at 0-5° C. A solution of MC-S1 (2.0 g, 9.17 mmol) in tetrahydrofuran (10 mL) was added drop wise to the reaction mixture at −30° C. The temperature of the reaction mass was warmed to room temperature and stirred for additional 1 h. The reaction was quenched with saturated ammonium chloride solution and extracted with ethyl acetate (3×25 mL). The combined organic layer was washed successively with water, brine; dried over anhydrous sodium sulfate and concentrated under reduced pressure to afford the crude intermediate. Purification by column chromatography over silica gel (60-120 mesh) using 1% ethyl acetate in pet ether as eluent afforded 1.2 g (60.6%) of MC-S2 as a color less liquid.

Step 5 (MJ-S1):

t-Butyl hypochlorite (2.5 mL, 22.27 mmol) was added to a stirred solution of t-butyl carbamate (2.59 g, 22.20 mmol) in 1-propanol (29 mL) and 0.4 N aqueous sodium hydroxide (900 mg in 55 mL water) at 15° C. and stirred for 15 min. A solution of (DHQ)$_2$PHAL (288 mg, 0.37 mmol) in 1-propanol (29 mL) was added, followed by a solution of MC-S2 (1.6 g, 7.4 mmol) in 1-propanol (29 mL). Finally potassium osmatedihydrate (108 mg, 0.296 mmol) was added and the reaction mixture was again stirred for 15 min at room temperature. The reaction was quenched with saturated sodium sulphite solution and extracted with ethyl acetate (3×25 mL). The combined organic layer was washed successively with water, brine; dried over anhydrous sodium sulfate and concentrated under reduced pressure to afford the crude intermediate. Purification by column chromatography over 60-120 silica mesh using 22-25% ethyl acetate in pet ether as eluent afforded 1.0 g (40%) of MJ-S1 as a white solid.

Step 6 (MK-S1):

Potassium-t-butoxide (640 mg, 5.73 mmol) was added to a stirred solution of MJ-S1 (1.0 g, 2.86 mmol) in tetrahydrofuran (15 mL) at 0° C. and the mixture was stirred for 3 h at room temperature. The reaction was neutralized with 10% acetic acid and extracted with ethyl acetate (3×25 mL). The combined organic layer was washed successively with water, brine; dried over anhydrous sodium sulfate and concentrated under reduced pressure to afford the crude intermediate, which was triturated with pet ether and dried to afford 600 mg (76.9%) of MKS1 as a color less liquid.

Step 7 (MK-S2):

A mixture of MK-S1 (600 mg, 2.18 mmol), 4-Bromo-1, 2-diamino benzene (407 mg, 2.18 mmol) and cesium fluoride (662 mg, 4.36 mmol) in 1,4-dioxane (15 mL) was purged with argon gas for 10 min. Copper iodide (62 mg, 0.327 mmol) and 1,2-diaminocyclohexane (37 mg, 0.327 mmol) were added and purging continued for another 10 min. The reaction mixture was heated in a sealed tube for 18 h at 110-115° C. The reaction mixture was filtered through celite, washed with dioxane and the filtrate was concentrated under reduced pressure to give the crude intermediate. Purification by column chromatography over neutral alumina by using 2-3% methanol in chloroform as the eluent afforded 350 mg (42.1%) of MK-S2 as a brown color solid.

Step 8 (Example 7):

Formamidine acetate (300 mg, 2.89 mmol) was added to a solution of MK-S2 (350 mg, 0.964 mmol) in acetonitrile (10 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product, which was triturated with di-ethyl ether and dried to afford 190 mg (53%) of Example 5 as a off white color solid.

Melting range: 205-209° C.; $^1$H-NMR (400 MHz, DMSO-d6): δ 8.16 (s, 1H); 7.57 (d, 1H); 7.48 (d, 1H); 7.36 (t, 1H); 7.20 (q, 1H); 6.90 (dd, 1H); 6.80 (dd, 1H); 5.83 (q, 1H); 4.84 (t, 1H); 4.27-4.20 (m, 3H); 1.66 (t, 3H); MS=392.1 (M+1); HPLC~98.40%: Chiral HPLC~98.43%.

Example 8

(S)-3-(1H-benzo[d]imidazol-5-yl)-4-(4-(2,2-difluoropropoxy)-3,5-difluorophenyl)oxazolidin-2-one Step 1 (MB-S1):

A mixture of 3,5-difluoro-4-hydroxy benzonitrile (4.3 g, 27.77 mmol), chloro acetone (3.3 mL, 41.66 mmol) and potassium carbonate (7.6 g, 55.55 mmol) in acetonitrile (40 mL) was refluxed for 2 h. The reaction mass was cooled to room temperature, filtered and washed with ethyl acetate. The combined filtrate was concentrated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford 3.8 g (65.5%) of MB-S1 as a brown liquid, further used for the next step.

Step 2 (MB-S2):

Diethylamino sulfurtrifluoride (5.0 mL, 37.91 mmol) was added to a solution of MB-S1 (4.0 g, 18.95 mmol) in dichloromethane (40 mL) at 0° C. and the mixture was stirred for 4 h at room temperature. The reaction was quenched with ice water and extracted with dichloromethane. The combined organic layer was washed successively with water, brine; dried over anhydrous sodium sulfate and concentrated in vacuum to afford 5.0 g of the crude intermediate MB-S2 as a brown liquid, further used for the next step.

Step 3 (MC-S1):

DIBAL in toluene (1.5 M; 29 mL, 42.91 mmol) was added slowly to a solution of MB-S2 (5.0 g, 21.45 mmol) in dry tetrahydrofuran (100 mL) at −30° C. over 15 min. The mixture was warmed to room temperature and the solution was stirred for 2 h. The reaction was quenched with saturated ammonium chloride solution, filtered and washed with ethyl acetate. The filtrate was washed successively with water brine; dried over anhydrous sodium sulfate and concentrated in vacuum to afford the crude intermediate. Purification by column chromatography over silica gel (60-120 mesh) and using 4-8% ethyl acetate in pet ether as the eluent afforded 3.0 g (60%) of MC-S1 as an oil.

Step 4 (MC-S2):

n-Butyl lithium in hexane (2.5 M; 10.2 mL, 25.42 mmol) was added to a stirred solution of Triphenyl phosphonium methyl bromide (9.0 g, 25.42 mmol) in tetrahydrofuran (30 mL) at −30° C. and the mixture was stirred for 30 min at 0-5° C. A solution of MC-S1 (3.0 g, 12.78 mmol) in tetrahydrofuran (40 mL) was added drop wise to the mixture at −30° C. The temperature was warmed to room temperature and the solution was stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 2% ethyl acetate in pet ether as the eluent afforded 2.0 g (64.4%) of MC-S2 as an oil.

Step 5 (MJ-S1):

t-Butyl hypochlorite (2.92 mL, 35.72 mmol) was added to a stirred solution of t-butyl carbamate (3.98 g, 25.64 mmol) in 1-propanol (34 mL) and 0.4 N aqueous sodium hydroxide (65 mL) at 15° C. and the mixture was stirred for 15 min. A solution of (DHQ)$_2$PHAL (332 mg, 0.43 mmol) in 1-propanol (34 mL) was added, followed by a solution of MC-S2 (2.0 g, 8.54 mmol) in 1-propanol (34 mL). Finally potassium osmatedihydrate (125 mg, 0.4272 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over neutral alumina and using 22-25% ethyl acetate in pet ether as the eluent afforded 1.3 g (40%) of MJ-S1 as a white solid.

Step 6 (MK-S1):

Potassium-t-butoxide (764 mg, 6.824 mmol) was added to a stirred solution of MJ-S1 (1.3 g, 3.412 mmol) in tetrahydrofuran (20 mL) at 0° C. and the mixture was stirred for 3 h at room temperature. The reaction was neutralized with 10% acetic acid and extracted with ethyl acetate. The combined organic layer was washed successively with water, brine; dried over anhydrous sodium sulfate and concentrated under reduced pressure to afford the crude intermediate, which was triturated with pet ether and dried to afford 800 mg (76%) of MK-S1 as a yellow gummy solid.

Step 7 (MK-S2):

A mixture of MK-S1 (760 mg, 2.59 mmol), 4-bromo-1, 2-diamino benzene (485 mg, 2.59 mmol) and cesium fluoride (789 mg, 5.19 mmol) in 1,4-dioxane (60 mL) was purged with argon gas for 30 min. Copper iodide (98.7 mg, 0.51 mmol) and 1,2-diaminocyclohexane (50 mg, 0.51 mmol) were added and purging continued for another 10 min. The reaction mixture was heated in a sealed tube for 18 h at 110-115° C. The reaction mixture was filtered through celite, washed with dioxane and the filtrate was concentrated under reduced pressure to give the crude intermediate. Purification by column chromatography over neutral alumina and using 2-3% methanol in chloroform as the eluent afforded 500 mg (53%) of MK-S2 as a yellowish brown solid.

Step 8 (Example 8):

Formamidine acetate (391 mg, 3.75 mmol) was added to a solution of MK-S2 (500 mg, 1.25 mmol) in acetonitrile (50 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product, which was triturated with di-ethyl ether and dried to afford 300 mg (58.5%) of Example 8 as a yellow solid.

Melting range: 205-207° C.; $^1$H-NMR (400 MHz, DMSO-d6): δ 12.50 (bs, 1H); 8.18 (s, 1H); 7.63 (s, 1H); 7.51 (d, 1H); 7.28 (m, 3H); 5.75 (t, 1H); 4.81 (t, 1H); 4.31 (t, 2H);

4.15 (q, 1H); 1.66 (t, 3H); MS=410.1 (M+1); HPLC~98.42%; Chiral HPLC~95.03%.

Example 10

(S)-3-(1H-benzo[d]imidazol-5-yl)-4-(4-(3,3-difluorobutoxy)-3-fluorophenyl)oxazolidin-2-one Step 1 (MD-S1):
A mixture of 4-bromo-2-fluoro phenol (8.0 g, 41.8 mmol), 4-chloro-2-butanol (9.0 g, 83.7 mmol) and potassium carbonate (17.3 g, 125.6 mmol) in acetonitrile (100 mL) was refluxed for 24 h. The reaction mass was cooled to room temperature and filtered. The filtrate was partitioned with water and ethyl acetate. The organic layer was washed with water, brine; dried over anhydrous sodium sulfate and concentrated in vacuum to afford 8.0 g of MD-S1 as the crude intermediate MD-S1, further used for the next step without purification.

Step 2 (MD-S2):
2-Iodoxy benzoic acid (25.5 g, 91.25 mmol) was added to a solution of MD-S1 (8.0 g, 30.4 mmol) in dichloromethane (100 mL) and dimethylsulfoxide (50 mL) and the mixture was stirred for 16 h at room temperature. The reaction mass was filtered and washed with dichloromethane. The combined filtrate and washing portion was washed successively with water, brine; dried over anhydrous sodium sulfate and concentrated in vacuum to afford the crude intermediate. Purification by column chromatography over silica gel (60-120 mesh) and using 7-8% ethyl acetate in pet ether as the eluent afforded 5.0 g (63% in two steps) of MD-S2 as a pale brown liquid.

Step 3 (MD-S3):
Diethylamino sulfurtrifluoride (10.7 mL, 76.6 mmol) was added to a solution of MD-S2 (5.0 g, 19.1 mmol) in dichloromethane (100 mL) at 0° C. The reaction mixture was warmed to room temperature and stirred for 48 h. The reaction was quenched with ice water and the organic layer was separated. The aqueous phase was extracted with dichloromethane. The combined organic layer was washed successively with water, brine; dried over anhydrous sodium sulfate and concentrated in vacuum to afford the crude intermediate. Purification was done by column chromatography over silica gel (60-120 mesh) and using 2% ethyl acetate in pet ether as the eluent to afford 4.0 g (74%) of MD-S3 as a brown liquid.

Step 4 (MD-S4):
A solution of MD-S3 (4.0 g, 14.1 mmol) and tri-n-butyl vinyl tin (5.18 mL, 17.6 mmol) in toluene (60 mL) was purged with argon gas for 5 min. Tetrakis-(triphenylphosphine)-palladium (326 mg, 0.28 mmol) was added and the mixture was continuously purged for another 5 min. The reaction mass was heated in a sealed tube at 110° C. for 8 h. The reaction mixture was filtered over celite and washed with ethyl acetate. The combined filtrate and washing portion was concentrated in vacuum to afford the crude intermediate. Purification by column chromatography over silica gel (60-120 mesh) and using pet ether as the eluent afforded 3.0 g (92%) of MD-S4 as a colorless liquid.

Step 5 (MJ-S1):
t-Butylhypochlorite (4.46 mL, 39.2 mmol) was added to a stirred solution of t-butylcarbamate (4.5 g, 39.1 mmol) in 1-propanol (52 mL) and 0.4 N aqueous sodium hydroxide (1.6 g in 100 mL water) at 15° C. and the mixture was stirred for 15 min. A solution of (DHQ)$_2$PHAL (500 mg, 0.6 mmol) in 1-propanol (52 mL) was added, followed by a solution of MD-S4 (3.0 g, 13.0 mmol) in 1-propanol (52 mL). Finally potassium osmatedihydrate (240 mg, 0.6 mmol) was added and the reaction mixture was stirred for 15 min at room temperature. The reaction was quenched with saturated sodium sulfate solution and extracted with ethyl acetate. The combined organic layer was washed successively with water, brine; dried over anhydrous sodium sulfate and concentrated under reduced pressure to afford the crude compound. Purification by column chromatography over silica gel (60-120 mesh) and using 18-20% ethyl acetate in pet ether as the eluent afforded 1.2 g (25%) of the intermediate MJ-S1 as a brown solid.

Step 6 (MK-S1):
Potassium t-butoxide (550 mg, 4.9 mmol) was added portion wise to a solution of MJ-S1 (1.2 g, 3.3 mmol) in tetrahydrofuran (60 mL) at 0° C. The reaction was warmed to room temperature and the mixture was stirred for 2 h. The reaction was acidified with acetic acid (pH-6) and extracted with ethyl acetate. The separated organic layer was washed successively with water, brine; dried over anhydrous sodium sulfate and concentrated in vacuum afforded 700 mg (73%) of MK-S1 as a off white solid, further used without any purification.

Step 7 (MK-S2):
A mixture of MK-S1 (700 g, 2.4 mmol), 1,2-diamino-4-bromobenzene (380 mg, 2.4 mmol) and cesium fluoride (718 g, 4.8 mmol) in 1,4-dioxan (30 mL) was purged with argon gas for 10 min. Copper iodide (69 mg, 0.36 mmol) was added and the reaction mixture was continuously purged for another 10 min. Finally 1,2-diaminocyclohexane (41 mg, 0.36 mmol) was added and again the reaction was purged for 10 min. The reaction mass was stirred at 110-115° C. in a sealed tube for 18 h. The reaction mixture was cooled to room temperature, filtered through celite, washed with dioxin and concentrated under reduced pressure to afford the crude compound. Purification was done by column chromatography over neutral alumina using 2% methanol in chloroform as eluent to afford 500 mg (51%) of MK-S2 as a brown solid.

Step 8 (Example 10):
Formamidine acetate (394 mg, 3.7 mmol) was added to a solution of MK-S2 (500 mg, 1.2 mmol) in acetonitrile (20 mL) and the mixture was refluxed for 2 h. The solution was concentrated under reduced pressure and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification was done by washing with diethyl ether, filtered and dried to afford 350 mg (68%) of Example 10 as a pale brown solid.

Melting range: 206.7-213.7° C.; $^1$H-NMR (400 MHz, DMSO-d6): δ 12.2 (d, 1H); 8.17 (d, 1H); 7.58 (d, 1H); 7.53 (dd, 1H); 7.34 (t, 2H); 7.29-7.11 (m, 3H); 5.69 (t, 1H); 4.80 (t, 1H); 4.17-4.11 (m, 3H); 2.40-2.29 (m, 2H); 1.64 (t, 3H); MS=406.0 (M+1); HPLC~97.19%: Chiral HPLC~99.62%.

Example 11

(S)-3-(1H-benzo[d]imidazol-5-yl)-4-(4-(3,3-difluoropropoxy)-2,3-difluorophenyl)oxazolidin-2-one Step 1 (MD-S1):
A mixture of 4-Bromo-2,3-difluorophenol (2 g, 9.57 mmol), 3-chloro-1-propanol (1.0 mL, 11.48 mmol) and potassium carbonate (2.64 g, 19.14 mmol) in acetonitrile (20 mL) was stirred at 80° C. for 40 h. The reaction mass was filtered and washed with ethyl acetate. The combined filtrate and washing portion was concentrated in vacuum to afford 2.5 g of MD-S1 (98.42%) as a off white solid.

Step 2 (MD-S2):

Dess-martin periodinane (4.47 g, 10.30 mmol) was added to a solution of MD-S1 (2.5 g, 9.36 mmol) in dichloromethane (40 mL) at 0° C. and the mixture was stirred at room temperature for 1 h. The solvent was evaporated in vacuum and the resulting mass was suspended in diethyl ether, and the reaction mixture was stirred for 15 min and thereafter filtered. The filtrate was washed successively with water, brine; dried over anhydrous sodium sulfate and concentrated in vacuum to afford 2.4 g (96.42%) of MD-S2 as a colorless syrup.

Step 3 (MD-S3):

Diethylamino sulfurtrifluoride (2.36 mL, 9.02 mmol) was added to a solution of MD-S2 (2.4 g, 9.02 mmol) in dichloromethane (30 mL) at 0° C. and the mixture was stirred at room temperature for 3 h. The reaction was quenched with ice water and extracted with dichloromethane. The combined organic layer was washed successively with water, brine; dried over anhydrous sodium sulfate and concentrated in vacuum to afford the crude intermediate. Purification by column chromatography over silica gel (60-120 mesh) and using 5% ethyl acetate in pet ether as the eluent afforded 1.5 g (57.96%) of MD-S3 as a colorless syrup.

Step 4 (MD-S4):

A solution of MD-S3 (1.5 g, 5.23 mmol) and tri-n-butyl vinyl tin (1.92 mL, 6.53 mmol) in toluene (50 mL) was purged with argon gas for 5 min. Tetrakis-(tri phenyl phosphine)-palladium (121 mg, 0.1 mmol) was added and purged continuously for another 5 min. The reaction mass was heated in a sealed tube at 110° C. for 8 h. The reaction mass was filtered over celite and washed with ethyl acetate. The combined filtrate and washing portion was concentrated in vacuum to afford the crude intermediate. Purification by column chromatography over silica gel (60-120 mesh) and using 2% ethyl acetate in pet ether as the eluent afforded 1.2 g (98.36%) of MD-S4 as a colorless liquid.

Step 5 (MJ-S1):

t-Butyl hypochlorite (1.76 mL, 15.44 mmol) was added to a stirred solution of t-butylcarbamate (1.8 g, 15.38 mmol) in 1-propanol (20.5 mL) and 0.4 N aqueous sodium hydroxide (626 mg in 39 mL water) at 10° C.-15° C. and the mixture was stirred for 15 min. A solution of (DHQ)$_2$PHAL (200 mg, 0.26 mmol) in 1-propanol (20.5 mL) was added, followed by a solution of MD-S4 (1.2 g, 5.13 mmol) in 1-propanol (20.5 mL). Finally potassium osmatedihydrate (75 mg, 0.20 mmol) was added and the reaction mixture was stirred for 15 min at room temperature. The reaction was quenched with saturated sodium sulfite solution and extracted with ethyl acetate. The combined organic layer was washed successively with water, brine; dried over anhydrous sodium sulfate and concentrated under reduced pressure to afford the crude intermediate. Purification by column chromatography over silica gel (100-200 mesh) and using 25-30% ethyl acetate in pet ether as the eluent afforded 710 mg (37.76%) of MJ-S1 as a white solid.

Step 6 (MK-S1):

Thionylchloride (1.1 mL, 15.26 mmol) was added to a solution of MJ-S1 (700 mg, 1.91 mmol) in tetrahydrofuran (20 mL) at 0° C. The Reaction was warmed to room temperature and the solution was stirred for 3 h. The solvent were evaporated in vacuum and the resulting mass was partitioned between ice cold saturated sodium bicarbonate solution and ethyl acetate. The organic layer was separated and the aqueous layer was extracted with ethyl acetate. The combined organic layer was washed successively with water, brine; dried over anhydrous sodium sulfate and concentrated in vacuum to afford the crude intermediate, which was triturated with pet ether and dried to afford 480 mg (85.87%) of MK-S1 as a off white solid.

Step 7 (MK-S2):

A mixture of MK-S1 (480 mg, 1.64 mmol), 4-bromo-1,2-diaminobenzene (370 mg, 1.96 mmol) and cesium fluoride (500 mg, 3.28 mmol) in 1,4-dioxane (20 mL) was purged with argon gas for 15 min. Copper iodide (47 mg, 0.24 mmol) and 1,2-diaminocyclohexane (27 mg, 0.24 mmol) were added and the mixture was continuously purged for another 10 min. The reaction mixture was stirred in a sealed tube for 20 h at 110-115° C. The resulting mass was filtered through celite, washed with dioxane and the filtrate was concentrated under reduced pressure to give the crude intermediate. Purification by column chromatography over neutral alumina using 1-2% methanol and dichloromethane as the eluent afforded 480 mg (73.40%) of MK-S2 as a brown solid.

Step 8 (Example 11):

Formamidineacetate (375 mg, 3.61 mmol) was added to a solution of MK-S2 (480 mg, 1.20 mmol) in acetonitrile (10 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the rude intermediate. Purification by triturating with 8:2 (diethyl ether: ethyl acetate) afforded 350 mg of Example 11 as a pale brown solid.

Melting range: 222-225.5° C.; $^1$H-NMR (400 MHz, DMSO-d6): δ 12.22 (s, 1H); 8.18 (s, 1H); 7.60 (s, 1H); 7.49 (bs, 1H); 7.29-7.19 (m, 2H); 6.99 (t, 1H); 6.26 (bt, 1H); 5.88 (t, 1H); 4.87 (t, 1H); 4.33 (q, 1H); 4.16 (t, 2H); 2.29-2.16 (m, 2H); MS=410.0 (M+1); HPLC~99.78%: Chiral HPLC~99.82%.

Example 12

(S)-3-(1H-benzo[d]imidazol-5-yl)-4-(4-(3,3-difluoropropoxy)-3-fluorophenyl)oxazolidin-2-one Step 1 (MD-S1):

A mixture of 4-Bromo-2-fluorophenol (5.0 g, 26.17 mmol), 3-chloro-1-propanol (2.8 g, 31.41 mmol), and potassium carbonate (7.23 g, 52.34 mmol) in acetonitrile (50 mL) was heated at 85° C. for 12 h. The solvent was evaporated in vacuum and the resulting mass was partitioned between water and ethyl acetate. The combined organic layer was washed successively with water, brine; dried over anhydrous sodium sulfate and concentrated in vacuum to afford 6.0 g of the crude intermediate MD-S1 as a color less liquid, further used without purification.

Step 2 (MD-S2):

Dess-martin periodinane (11.50 g, 26.50 mmol) was added to a solution of MD-S1 (6.0 g, 24.09 mmol) in dichloromethane (60 mL) at 0° C. and the mixture was stirred at room temperature for 1 h. The reaction mixture was filtered through celite, washed with dichloromethane and the solvent was evaporated under reduced pressure to afford 4.5 g of the crude intermediate as a colorless oil.

Step 3 (MD-S3):

Diethylamino sulfurtrifluoride (6.1570 g, 36.43 mmol) was added to a solution of MD-S2 (4.5 g, 18.21 mmol) in dichloromethane (40 mL) at 0° C. and the mixture was stirred for 3 h at room temperature. The reaction was quenched with ice water and extracted with dichloromethane. The combined organic layer was washed successively with water, brine; dried over anhydrous sodium sulfate and concentrated to afford the crude intermediate. Purification by column chromatography over silica gel (60-120 mesh) and using 10% ethyl acetate in pet ether as the eluent afforded 3.3 g of MD-S3 as a colorless oil.

Step 4 (MD-S4):

A solution of MD-S3 (2.8 g 10.48 mmol) and tri-n-butyl vinyl tin (3.84 mL, 13.10 mmol) in toluene (30 mL) was purged with argon gas for 5 min. Tetrakis-(tri phenyl phosphine)-palladium (242 mg, 0.1 mmol) was added and the mixture was continuously purged for another 5 min. The reaction mass was heated in a sealed tube at 110° C. for 8 h. The reaction mass was filtered over celite and washed with ethyl acetate. The combined filtrate and washing portion was concentrated in vacuum to afford the crude intermediate. Purification by column chromatography over silica gel (60-120 mesh) and using 2% ethyl acetate in pet ether as the eluent afforded 1.2 g (98.36%) of MD-S4 as a colorless liquid.

Step 5 (MJ-S1):

t-Butyl hypochlorite (2.14 mL, 18.81 mmol) was added to a stirred solution of t-butylcarbamate (2.193 g, 18.75 mmol) in 1-propanol (25 mL) and 0.4 N aqueous sodium hydroxide (48 ml) at 15° C. and the mixture was stirred for 15 min. A solution of (DHQ)$_2$PHAL (235 mg, 0.312 mmol) in 1-propanol (25 mL) was added, followed by a solution of MD-S4 (1.35 g, 6.25 mmol) in 1-propanol (25 mL). Finally potassium osmatedihydrate (92 mg, 0.25 mmol) was added and the reaction mixture was stirred for 30 min at room temperature. The reaction was quenched with saturated sodium sulfite solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 17% ethyl acetate in pet ether as the eluent afforded 1.1 g of MJ-S1 as a off-white solid.

Step 6 (MK-S1):

Thionylchloride (0.84 mL, 11.44 mmol) was added drop wise to a solution of MJ-S1 (1.0 g, 2.873 mmol) in tetrahydrofuran (25 mL) at 0° C. The reaction mixture was warmed to room temperature and stirred for 3 h. The solvent was evaporated and the remaining mass was diluted with water. Saturated sodium hydrogen carbonate solution was added (50 mL) and the mixture was extracted with chloroform (2×100 mL). The combined organic layers were dried over anhydrous sodium sulfate and concentrated in vacuum to give 900 mg of MK-S1 as a off white solid, further used without purification.

Step 7 (MK-S2):

A mixture of MK-S1 (900 mg, 3.2727 mmol), 1,2-diamino-4-bromobenzene (1.22 g, 6.5454 mmol) and cesium fluoride (995 mg, 6.5454 mmol) in 1,4-dioxan (10 mL) was purged with argon gas for 20 min. Copper iodide (93 mg, 0.490 mmol) and 1,2-diaminocyclohexane (55 mg, 0.490 mmol) was added and the mixture was continuously purged for another 10 min. The reaction mass was stirred at 110° C. in a sealed tube for 18 h. The resulting mixture was filtered through celite pad, washed with dioxane and concentrated under reduced pressure to afford the crude intermediate. The compound was purified by column chromatography over neutral alumina and using 2% methanol in chloroform as the eluent to afford 600 mg of MK-S2 as a brown solid.

Step 8 (Example 12):

Formamidine acetate (515 mg, 4.958 mmol) was added to a solution of MK-S2 (600 mg, 1.652 mmol) in acetonitrile (20 mL) and the mixture was refluxed for 3 h. The reaction mixture was concentrated under reduced pressure and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. The crude compound was washed successively with 2% methanol in diethyl ether and filtered to afford 300 mg of Example 12 as a off white solid.

Melting range: 198.5-201.7° C.; $^1$H-NMR (400 MHz, DMSO-d6): δ 12.2 (d, 1H); 8.16 (s, 1H); 7.58-7.09 (m, 5H); 6.17 (bt, 1H); 5.68 (t, 1H); 4.80 (t, 1H); 4.14 (q, 3H); 2.50-2.21 (m, 2H); MS=392.0 (M+1); HPLC~99.52%: Chiral HPLC~98.71%.

Example 13

S)-3-(1H-benzo[d]imidazol-6-yl)-4-(4-(3,3-difluoropropoxy)-3,5-difluorophenyl)oxazolidin-2-one Step (MD-S1):

A mixture of 4-bromo-1,6-difluorophenol (8 g, 38.10 mmol), 3-chloro-1-propanol (4.82 mL, 57.14 mmol) and potassium carbonate (10.53 g, 76.2 mmol) in dimethyl formamide (70 mL) was heated at 80° C. for 6 h. The reaction mass was filtered and washed with diethyl ether. Water was added to the filtrate and extracted with diethyl ether. The combined organic layer was washed successively with water, brine; dried over anhydrous sodium sulfate and concentrated in vacuum to afford 8 g of the crude intermediate MD-S1 as a brown liquid, further used without any purification.

Step 2 (MD-S2):

Dess-martin periodinane (12.95 g, 29.85 mmol) was added to a solution of MD-S1 (8 g, 29.85 mmol) in dichloromethane (80 mL) at 0° C. and the mixture was stirred at room temperature for 15 min. The solvent was evaporated in vacuum and the resulting mass was suspended in diethyl ether, stirred for 15 min and filtered. The filtrate was washed successively with water, brine; dried over anhydrous sodium sulfate and concentrated in vacuum to afford the crude intermediate. Purification by column chromatography over silica gel (60-120 mesh) and using 5% ethyl acetate in pet ether as the eluent afforded 5 g (62.97%) of MD-S2 as a pale yellow liquid.

Step 3 (MD-S3):

Diethylamino sulfur trifluoride (4.92 mL, 37.60 mmol) was added to a solution of MD-S2 (5 g, 18.80 mmol) in dichloromethane (100 mL) at 0° C. and the mixture was stirred at room temperature for 20 h. The reaction was quenched with ice water and extracted with dichloromethane. The combined organic layer was washed successively with water, brine; dried over anhydrous sodium sulfate and concentrated in vacuum to afford the crude intermediate. Purification by column chromatography over silica gel (60-120 mesh) and using 3% ethyl acetate in pet ether as the eluent afforded 3.3 g (61.17%) of MD-S3 as a pale yellow liquid.

Step 4 (MD-S4):

A solution of MD-S3 (1.5 g, 5.23 mmol) and tri-n-butylvinyl tin (1.92 mL, 6.53 mmol) in toluene (60 mL) was purged with argon gas for 5 min. Tetrakis-(tri phenyl phosphine)-palladium (121 mg, 0.1 mmol) was added and the mixture was continuously purged for another 5 min. The reaction mass was heated in a sealed tube at 110° C. for 8 h. The reaction mass was filtered over celite and washed with ethyl acetate. The combined filtrate and washing portion was concentrated in vacuum to afford the crude intermediate. Purification by column chromatography over silica gel (60-120 mesh) and using pet ether as the eluent afforded 1.2 g (98.36%) of MD-S4 as a colorless liquid.

Step 5 (MJ-S1):

t-Butylhypochlorite (1.9 mL, 16.70 mmol) was added to a stirred solution of t-butyl carbamate (1.95 g, 16.67 mmol) in 1-propanol (22 mL) and 0.4 N aqueous sodium hydroxide (677 mg in 42 mL water) at 10° C.-15° C. and the mixtures was stirred for 15 min. A solution of $(DHQ)_2PHAL$ (216 mg, 0.28 mmol) in 1-propanol (22 mL) was added followed by a solution of MD-S4 (1.3 g, 5.55 mmol) in 1-propanol (22 mL). Finally potassium osmatedihydrate (82 mg, 0.22 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over silica gel (100-200 mesh) and using 18-22% ethyl acetate in pet ether as the eluent afforded 700 mg (34.38%) of MJ-S1 as a white solid.

Step 6 (MK-S1):

Thionyl chloride (1.03 mL, 14.17 mmol) was added to a solution of MJ-S1 (650 mg, 1.77 mmol) in tetrahydrofuran (30 mL) at 0° C. The reaction was warmed to room temperature and stirred for 2 h. The solvent were evaporated in vacuum and the resulting mass was partitioned between saturated sodium bicarbonate solution and ethyl acetate. The organic layer was separated and the aqueous layer was extracted with ethyl acetate. The combined organic layer was washed successively with water, brine; dried over anhydrous sodium sulfate and concentrated in vacuum to afford the crude intermediate, which was triturated with pet ether and dried to afford 400 mg (77.22%) of MK-S1 as a pale yellow solid.

Step 7 (MK-S2):

A mixture of MK-S1 (400 mg, 1.36 mmol), 4-bromo-1, 2-diaminobenzene (306 mg, 1.64 mmol) and cesium fluoride (413 mg, 2.72 mmol) in 1,4-dioxane (20 mL) was purged with argon gas for 15 min. Copper iodide (39 mg, 0.20 mmol) and 1,2-diaminocyclohexane (23 mg, 0.20 mmol) were added and the mixture was continuously purged for another 10 min. The reaction mixture was heated in a sealed tube for 20 h at 110-115° C. The mixture was filtered through celite, washed with dioxane and the filtrate was concentrated under reduced pressure to give the crude intermediate. Purification by column chromatography over neutral alumina and using 1-1.5% methanol in dichloromethane as the eluent afforded 400 mg (73.80%) of MK-S2 as a brown gummy liquid.

Step 8 (Example 13):

Formamidine acetate (312 mg, 3.00 mmol) was added to a solution of MK-S2 (400 mg, 1.00 mmol) in acetonitrile (10 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by triturating with 8:2 (diethyl ether: ethyl acetate) afforded 310 mg of Example 13 as a pale brown solid.

Melting range: 207-209.4° C.; $^1$H-NMR (400 MHz, DMSO-d6): δ 8.19 (s, 1H); 7.63 (d, 1H); 7.50 (d, 1H); 7.29-7.24 (m, 3H); 6.37-5.99 (m, 1H); 5.76 (t, 1H); 4.81 (t, 1H); 4.18-4.13 (m, 3H); 2.29-2.16 (m, 2H); MS=410.0 (M+1); HPLC~99.11%: Chiral HPLC~99.96%.

Example 14

(S)-5-(3-(1H-benzo[d]imidazol-5-yl)-2-oxooxazolidin-4-yl)-2-(2,2-difluoropropoxy)benzonitrile Step 1 (ME-S1):

Triethylamine (18.5 mL, 135 mmol) was added to a solution of hydroxyacetone (5.0 g, 67.49 mmol) in dichloromethane (80 mL) at 0° C. Benzoyl chloride (7.84 mL, 67.49 mmol) was added drop wise over 15 min and DMAP (200 mg) was added. The reaction mass was warmed to room temperature and stirred for 1 h. The reaction was quenched with water and extracted with dichloromethane. The combined organic layer was washed successively with water, brine; dried over anhydrous sodium sulfate and concentrated in vacuum to afford the crude intermediate. Purification by column chromatography over silica gel (60-120 mesh) and using 8% ethyl acetate in pet ether as the eluent afforded 8 g of ME-S1 as a colorless liquid.

Step 2 (ME-S2):

Diethylamino sulfurtrifluoride (5.9 mL, 44.94 mmol) was added to a solution of ME-S1 (4.0 g, 22.47 mmol) in dichloromethane (40 mL) at 0° C. and the solution was stirred at room temperature for 18 h. The reaction was quenched with ice water and the mixture was extracted with dichloromethane. The combined organic layer was washed successively with water, brine; dried over anhydrous sodium sulfate and concentrated in vacuum to afford 4.0 g of ME-S2 as a brown liquid.

Step 3 (ME-S3):

A solution of ME-S2 (4 g, 20.0 mmol) in diethyl ether (80 mL) was heated at 60° C. for 4 h. The reaction mass was cooled to room temperature and extracted with diethyl ether. The combined organic layer was washed successively with water, brine; dried over anhydrous sodium sulfate and concentrated under mild reduced pressure at room temperature to afford 4 g of ether containing ME-S3.

Step 4 (ME-S4):

A solution of crude ME-S3 (3.8 g, 39.58 mmol) in Dimethyl formamide (5 mL) was added to a suspension of sodium hydride (60%; 1.3 g, 32.5 mmol) in dry dimethyl formamide (20 mL) at 0° C. and the mixture was stirred at room temperature for 1 h. The reaction mass was again cooled to 0° C. and a solution of 5-bromo-2-fluoro benzonitrile (2.36 g, 11.8 mmol) in dimethyl formamide (5 mL) was added. The reaction mass was warmed to room temperature and stirred for 30 min, quenched with saturated ammonium chloride solution and extracted with diethyl ether. The combined organic layer was washed successively with water, brine; dried over anhydrous sodium sulfate and concentrated in vacuum to afford the crude intermediate. Purification by column chromatography over silica gel (60-120 mesh) and using 8% ethyl acetate in pet ether as the eluent afforded 2.5 g (69.4%) of ME-S4 as a yellow gummy liquid.

Step 5 (ME-S5):

A mixture of ME-S4 (1 g, 3.62 mmol), potassium vinyl trifluoroborate (490 mg, 3.62 mmol), triphenyl phosphine (57 mg, 0.22 mmol) and cesium carbonate (3.56 g, 10.86 mmol) in tetrahydrofuran (40 mL) and water (4 mL) was purged with argon gas for 5 min. Palladium chloride (13 mg, 0.07 mmol) was added and the mixture was continuously purged for another 5 min. The reaction was heated in a sealed tube for 18 h. The reaction mass was filtered over celite and washed with ethyl acetate. Water was added, the organic layer was separated and the aqueous layer was extracted with ethyl acetate. The combined organic layer was washed successively with water, brine; dried over anhydrous sodium sulfate and concentrated in vacuum to afford the crude intermediate. Purification by column chromatography over silica gel (60-120 mesh) and using 4-5% ethyl acetate in pet ether as the eluent afforded 600 mg (74.35%) of ME-S5 as a pale yellow liquid.

Step 6 (MJ-S1):

t-Butyl hypo chlorite (0.92 mL, 8.09 mmol) was added to a stirred solution of t-butyl carbamate (945 mg, 8.07 mmol) in 1-propanol (11 mL) and 0.4 N aqueous sodium hydroxide (330 mg in 16.5 mL water) at 10-15° C. and stirred the mixture was for 15 min. A solution of (DHQ)$_2$PHAL (105 mg, 0.13 mmol) in 1-propanol (11 mL) was added, followed by a solution of ME-S5 (600 mg, 2.69 mmol) in 1-propanol (11 mL). Finally potassium osmate dihydrate (40 mg, 0.11 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 32% ethyl acetate in pet ether as the eluent afforded 480 mg (50.16%) of MJ-S1 as a white solid.

Step 7 (MK-S1):

Potassium-t-butoxide (450 mg, 4.04 mmol) was added to a stirred solution of MJ-S1 (480 mg, 1.35 mmol) in tetrahydrofuran (10 mL) at 0° C. and the mixture was stirred for 2 h at room temperature. The reaction was neutralized with 10% acetic acid and the mass was extracted with ethyl acetate. The combined organic layer was washed successively with water, brine; dried over anhydrous sodium sulfate and concentrated under reduced pressure to afford the crude intermediate, which was triturated with pet ether and dried to afford 350 mg of MK-S1 as a off white solid.

Step 8 (MK-S2):

A mixture of MK-S1 (340 mg, 1.20 mmol), 4-bromo-1, 2-diaminobenzene (2 mg, 1.20 mmol) and cesium fluoride (3 mg, 2.40 mmol) in 1,4-dioxane (15 mL) was purged with argon gas for 15 min. Copper iodide (34 mg, 0.18 mmol) and 1,2-diaminocyclohexane (21 mg, 0.18 mmol) were added and the mixture was continuously purged for another 10 min. The reaction mixture was heated in a sealed tube for 18 h at 110-115° C. The reaction mass was filtered through celite, washed with dioxane and the filtrate was concentrated under reduced pressure to give the crude intermediate. Purification by column chromatography over neutral alumina and using 3% methanol in dichloromethane as the eluent afforded 300 mg (64.3%) of MK-S2 as a brown solid.

Step 9 (Example 14):

Formamidine acetate (300 mg, 0.75 mmol) was added to a solution of MK-S2 (300 mg, 0.75 mmol) in acetonitrile (5 mL) and the mixture was refluxed for 1 h. The solvent was evaporated in vacuum and the resulting residue was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by preparative TLC using 4.5% methanol in dichloromethane as the eluent afforded 110 mg of Example 14 with a purity of ~91.87% measured by LCMS. Further purification using preparative HPLC was done under consideration of the following conditions:

Column: Sun fire C-18 (250*30 mm*10μ); mobile Phase: A: acetonitrile; B: 10 mM ammonium acetate (50:50); flow rate: 38 ml/min; diluent: ACN+MeOH+mobile phase; Method: Gradient; Column Temp ° C.: Ambient The fractions were evaporated in vacuum and the resulting residue was partitioned between water and dichloromethane. The organic layer was separated and the aqueous layer was extracted with dichloromethane. The combined organic layer was washed with water, brine; dried over anhydrous sodium sulfate and concentrated in vacuum to afford 80 mg (28%) of Example 14 as a white solid.

Melting range: 155.6-158° C.; $^1$H-NMR (400 MHz, DMSO-d6): δ 8.17 (d, 1H); 7.89 (s, 1H); 7.76-7.70 (m, 1H); 7.59 (d, 1H); 7.54-7.42 (m, 1H); 7.23-7.15 (m, 2H); 4.82 (t, 1H); 4.41 (t, 2H); 4.17 (t, 1H); 1.70 (t, 3H); MS=399.0 (M+1); HPLC~99.72%; Chiral HPLC~97.92%.

Example 15

(S)-2-(3-(1H-benzo[d]imidazol-5-yl)-2-oxooxazolidin-4-yl)-5-(2,2-difluoropropoxy)benzonitrile Step 1 (MF-S1):

A mixture of 2-bromo-5-hydroxybenzonitrile (12 g, 60.61 mmol), chloroacetone (5.85 mL, 72.73 mmol) and potassium carbonate (16.75 g, 121 mmol)) in acetonitrile (100 mL) was refluxed for 2 h. The reaction mass was cooled to room temperature, filtered and washed with ethyl acetate. The combined filtrate was concentrated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude intermediate. Purification by column chromatography over silica gel (60-120 mesh) and using 15-20% ethyl acetate in pet ether as the eluent afforded 6.75 g (43.86%) of MF-S1 as a off white solid.

Step 2 (MF-S2):

Diethylamino sulfurtrifluoride (6.9 mL, 52.75 mmol) was added to a solution of MF-S1 (6.7 g, 26.38 mmol) in dichloromethane (80 mL) at 0° C. and the mixture was stirred at room temperature for 2 h. The reaction was quenched with ice water and extracted with dichloromethane. The combined organic layer was washed successively with water, brine; dried over anhydrous sodium sulfate and concentrated in vacuum to afford the crude intermediate. Purification by column chromatography over silica gel (60-120 mesh) and using 6% ethyl acetate in pet ether as the eluent afforded 4 g (54.94%) of MF-S2 as a white solid.

Step 3 (MF-S3):

A solution of MF-S2 (1.5 g, 5.43 mmol) and tri-n-butyl vinyl tin (2 mL, 6.79 mmol) in toluene (50 mL) was purged with argon gas for 5 min. Tetrakis-(triphenylphosphine)-palladium (125 mg, 0.11 mmol) was added and the mixture was continuously purged for another 5 min. The reaction mass was heated in a sealed tube at 110° C. for 8 h. The reaction mass was filtered over celite, washed with ethyl acetate and the filtrate was concentrated in vacuum to afford the crude intermediate. Purification by column chromatography over silica gel (60-120 mesh) and using 3% ethyl acetate in pet ether as the eluent afforded 1.2 g (99.17%) of MF-S3 as a colorless liquid.

Step 4 (MJ-S1):

t-Butyl hypo chlorite (1.84 mL, 16.19 mmol) was added to a stirred solution of t-butyl carbamate (1.89 g, 16.14 mmol) in 1-propanol (21.5 mL) and 0.4 N aqueous sodium hydroxide (656 mg in 41 mL water) at 10-15° C. and the mixture was stirred for 15 min. A solution of (DHQ)$_2$PHAL (210 mg, 0.27 mmol) in 1-propanol (21.5 mL) was added, followed by a solution of MF-S3 (1.2 g, 5.38 mmol) in 1-propanol (21.5 mL). Finally potassium osmate dihydrate (80 mg, 0.21 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over silica gel (100-200 mesh) and using 25% ethyl acetate in pet ether as the eluent afforded 900 mg (47.12%) of MJ-S1 as a white solid.

Step 5 (MK-S1):

Thionyl chloride (1.3 mL, 17.98 mmol) was added to a solution of MJ-S1 (800 mg, 2.25 mmol) in tetrahydrofuran (20 mL) at 0° C. The reaction mass was warmed to room temperature and stirred for 5 h. The solvent was evaporated in vacuum and the resulting mass was partitioned between saturated sodium bicarbonate solution and ethyl acetate. The organic layer was separated and the aqueous layer was extracted with ethyl acetate. The combined organic layer was washed successively with water, brine; dried over anhydrous sodium sulfate and concentrated in vacuum to afford the crude intermediate, which was triturated with pet ether and dried to afford 450 mg (70.98%) of MK-S1 as a off white solid.

Step 6 (MK-S2):

A mixture of MK-S1 (500 mg, 1.77 mmol), 4-bromo-1,2-diaminobenzene (400 mg, 2.13 mmol) and cesium fluoride (540 mg, 3.54 mmol) in 1,4-dioxane (20 mL) was purged with argon gas for 15 min. Copper iodide (50 mg, 0.26 mmol) and 1,2-diaminocyclohexane (30 mg, 0.26 mmol) were added and the mixture was continuously purged for another 10 min. The reaction mixture was heated in a sealed tube for 20 h at 110-115° C. The reaction mixture was filtered through celite, washed with dioxane and the filtrate was concentrated under reduced pressure to give the crude intermediate. Purification by column chromatography over neutral alumina and using 1% methanol in dichloromethane as the eluent afforded 500 mg (72.89%) of MK-S2 as a pale brown solid.

Step 7 (Example 15):

Formamidine acetate (536 mg, 5.15 mmol) was added to a solution of MK-S2 (500 mg, 1.29 mmol) in acetonitrile (10 mL) and the mixture was refluxed for 1.5 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by triturating with 8:2 (diethyl ether: dichloromethane) afforded 300 mg (58.48%) of Example 15 as a brown solid.

Melting range: 137.9-140.0° C.; $^1$H-NMR (400 MHz, DMSO-d6): δ 8.18 (s, 1H); 7.64-7.58 (m, 2H); 7.49 (d, 2H); 7.33-7.20 (m, 32); 5.95 (t, 1H); 4.92 (t, 1H); 4.31 (t, 3H); 1.67 (t, 3H); MS=399.0 (M+1); HPLC~98.91%; Chiral HPLC~98.62%.

Example 16

(S)-3-(1H-benzo[d]imidazol-5-yl)-4-(4-(4,4-difluorobutoxy)phenyl)oxazolidin-2-one Step 1 (MG-S1):

Thionyl chloride (17.5 mL, 0.239 mol) was added to a suspension of (S)-4-hydroxy phenyl glycine (20 g, 0.120 mol) in methanol (100 mL) at 0° C. drop-wise. The mixture was heated slowly to reflux and maintained thus for 15 h. The solvent was evaporated in vacuum and the residue was co-distilled twice with pet ether. Drying in vacuum afforded 25.2 g (96.55%) of MG-S1 as a white solid.

Step 2 (MG-S2):

Aqueous potassium carbonate (31.8 g, 0.230 mol in 100 mL water) and boc anhydride (31.65 mL, 0.138 mol) were added successively to a suspension of MG-S1 (25.0 g, 0.115 mol) in 1,4-dioxan (200 mL) at 0° C. The reaction mixture was warmed to room temperature and stirred for 2 h. The reaction was quenched into water and extracted with ethyl acetate (2×100 mL). The combined organic layer was washed successively with water, brine; dried over anhydrous sodium sulfate and concentrated in vacuum to afford the crude intermediate. The compound was suspended in pet ether, stirred for 30 min, filtered and dried in vacuum to afford 28.9 g (89.43%) of MG-S2 as a white solid.

Step 3 (MG-S3):

Triphenyl phosphine (1.39 g, 5.33 mmol) and 4-benzyloxy-1-butanol (0.70 g, 3.91 mmol) were added successively to a stirred solution of MG-S2 (1.0 g, 3.55 mmol) in dry tetrahydrofuran (30 mL) at room temperature. Diethylazodicarboxylate (950 mg, 5.3 mmol) was added drop wise and the reaction mixture was stirred at room temperature for 2 h. The reaction was quenched with water and extracted with ethyl acetate. The combined organic layer was washed with water, brine; dried over anhydrous sodium sulfate and concentrated in vacuum to afford the crude intermediate. Purification by column chromatography over silica gel (60-120 mesh) and using 6% ethyl acetate in pet ether as the eluent afforded 1.1 g (70.06%) of MG-S3 as a colorless thick liquid.

Step 4 (MG-S4):

A solution of MG-S3 (1.1 g, 2.481 mmol) in methanol (50 mL) was hydrogenated over Pd/C (10%; 150 mg) at 80 psi for 2 h in a Parr apparatus. The reaction mass was filtered though celite and washed with methanol. The combined filtrate and washing portion was concentrated under reduced pressure to afford 800 mg (91.32%) of MG-S4 as a off white solid.

Step 5 (MG-S5):

Iodoxy benzoic acid (2.535 g, 9.053 mmol) was added to a solution of MG-S4 (800 mg, 2.264 mmol) in dichloromethane (20 mL) and dimethyl sulfoxide (3 mL) and the mixture was stirred for 20 h at room temperature. The reaction mass was filtered and washed with dichloromethane. The combined filtrate and washing portion was washed successively with water, brine; dried over anhydrous sodium sulfate and concentrated in vacuum to afford the crude intermediate. Purification by column chromatography over silica gel (60-120 mesh) and using 20% ethyl acetate in pet ether as the eluent afforded 780 mg (98.11%) of MG-S5 as a yellow syrup.

Step 6 (MG-S6):

Diethylamino sulfurtrifluoride (0.58 mL, 4.44 mmol) was added to a solution of MG-S5 (780 mg, 2.22 mmol) in dichloromethane (20 mL) at 0° C. The reaction mixture was warmed to room temperature and stirred for 3 h. The reaction was quenched with ice water and the organic layer was separated. The aqueous layer was extracted with dichloromethane (1×30 mL). The combined organic layer was washed successively with water, brine; dried over anhydrous sodium sulfate and concentrated in vacuum to afford 600 mg (72.90%) of MG-S6 as a yellow syrup.

Step 7 (MG-S7):

Sodium borohydride (243 mg, 6.42 mmol) was added in two equal lots (over 15 min) to a solution of MG-S6 (600 mg, 1.60 mmol) in mixture of tetrahydrofuran (10 mL) and methanol (4 mL) at room temperature. Due to the exothermic reaction the temperature raised ~50° C. After completion of addition the reaction mixture was stirred for 1 h. Ethyl acetate was added and reaction was quenched with saturated ammonium chloride solution. The organic layer was separated and the aqueous layer was extracted with ethyl acetate. The combined organic layer was washed successively with water, brine; dried over anhydrous sodium sulfate and concentrated in vacuum to afforded 400 mg (72.20%) of MG-S7 as a off white solid, further used without any purification.

Step 8 (MK-S1):

Potassium t-butoxide (390 mg, 3.478 mmol) was added to a solution of MG-S7 (400 mg, 1.159 mmol) in tetrahydrofuran (20 mL) at 0° C. The reaction mixture was warmed to room temperature and stirred for 2 h. The reaction mass was acidified (pH-6). Ethyl acetate was added, the organic layer was separated and the aqueous layer was extracted with ethyl acetate. The combined organic layer was washed successively with water, brine; dried over anhydrous sodium sulfate and volatiles were evaporated in vacuum, co distilled twice with toluene to afford the crude intermediate. Purification by column chromatography over neutral alumina and using 1% methanol in chloroform as the eluent afforded 250 mg (79.61%) of MK-S1 as a off white solid.

Step 9 (MK-S2):

A mixture of MK-S1 (250 mg, 0.92 mmol), 1,2-diamino-4-bromobenzene (175 mg, 0.92 mmol), cesium fluoride (152 mg, 1.845 mmol) and copper iodide (30 mg, 0.138 mmol) in 1,4-dioxan (10 mL) was purged with argon gas for 15 min. 1,2-diaminocyclohexane (20 mg, 0.17 mmol) was added and the mixture was continuously purged continued for another 10 min. The reaction mixture was stirred at 110-115° C. in a sealed tube for 18 h. The reaction mass was filtered through celite, washed with dioxan and concentrated under reduced pressure to afford the crude intermediate. Purification by column chromatography over neutral alumina and using 2% methanol in chloroform as the eluent afforded 200 mg (57.47%) of MK-S2 as a brown solid.

Step 10 (Example 16):

Formamidine acetate (206 mg, 1.98 mmol) was added to a solution of MK-S2 (200 mg, 0.66 mmol) in acetonitrile (10 mL) and the mixture was refluxed for 2 h. The reaction mixture was concentrated under reduced pressure and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product, which was purified by preparative HPLC using the following conditions:

Column: X Bridge C18 (30×250 mm) 5µ; mobile phase: 0.01 M ammonium acetate (Aq): $CH_3CN$; flow rate: 35 ml/min; used diluents: ACN+MeOH+THF The corresponding fractions were concentrated in vacuum and partitioned between water and chloroform. The separated organic layer was washed with brine solution, dried over anhydrous sodium sulphate and concentrated in vacuum to afford 55 mg of Example 16 as a solid.

Melting range: 187-191° C.; $^1$H-NMR (400 MHz, DMSO-d6): δ 12.42 (s, 1H); 8.16 (s, 1H); 7.56 (s, 1H); 7.46 (bs, 1H); 7.31 (d, 2H); 7.23 (bs, 1H); 6.87 (d, 2H); 6.27-5.97 (m, 2H); 5.67 (t, 1H); 4.80 (t, 1H); 4.13 (q, 1H); 3.92 (t, 2H); 1.95-1.72 (m, 4H); MS=386.0 (M+1); HPLC~96.46%; Chiral HPLC~92.72%.

Example 17

(S)-3-(1H-benzo[d]imidazol-5-yl)-4-(4-(2,2-difluoropropoxy)-2,6-difluorophenyl)oxazolidin-2-one Step 1 (MH-S1):

Benzyl bromide (10.11 mL, 84.61 mmol) was added to the stirred solution of 3,5-difluorophenol (10 g, 76.92 mmol) and potassium carbonate (21.22 g, 153.84 mmol) in N,N-dimethylformamide (100 mL). The reaction mixture was heated to 85° C. and stirred for 12 h. The reaction mixture was filtered washed with diethylether. The filtrate was washed with water, brine; dried over anhydrous sodium sulfate. The organic layer was concentrated under reduced pressure to afford 12.6 g (74.55%) of MH-S1 as a yellow liquid.

Step 2 (MH-S2):

N-Butyl lithium (2.4 M; 18.9 mL, 45.45 mmol) was added to a solution of MH-S1 (10.0 g, 45.46 mmol) in dry tetrahydrofuran (70 mL) at −78° C. and the mixture was stirred for 1 h at the same temperature. The mixture was added to a solution of diethyl oxalate (9.17 ml, 90.90 mmol) in tetrahydrofuran (30 mL) at −78° C. over 15 min. The reaction mass was warmed to room temperature and stirred for 15 minutes. The reaction was quenched with saturated ammonium chloride solution and extracted with ethyl acetate. The combined organic layer was washed successively with water, brine; dried over anhydrous sodium sulfate and concentrated in vacuum to afford the crude intermediate. Purification by column chromatography over silica (60-120 mesh) and using 4% ethyl acetate in pet ether as the eluent afforded 7.3 g (50.34%) of MH-S2 as a yellow liquid.

Step 3 (MH-S3):

Sodium acetate (3.74 g, 45.62 mmol) and hydroxylamine hydrochloride (3.16 g, 45.62 mmol) were added successively to a solution of MH-S2 (7.3 g, 22.81 mmol) in absolute ethanol (70 mL) and the mixture was refluxed for 2 h. The solvent was evaporated in vacuum and the resulting mass was partitioned between water and ethyl acetate. The combined organic layer was washed successively with water, brine; dried over anhydrous sodium sulfate and concentrated in vacuum to afford 7.6 g (99.47%) of the crude intermediate MH-S3 as a yellow liquid, further used without any purification.

Step 4 (MH-S4):

A solution of MH-S3 (7.6 g, 22.68 mmol) in absolute ethanol (150 mL) was used for the hydrogenation using 10% Pd—C in a Parr apparatus (80 psi) for 12 h. The reaction mass was filtered through celite and washed with ethanol.

The combined filtrate and washing portion was concentrated under reduced pressure to afford 5.2 g (94.03%) of the crude intermediate MH-S4 as a pale brown syrup, further used without any purification.

Step 5 (MH-S5):

MH-S4 (5.2 g, 2.12 mmol) in ethanol (70 mL) was hydrogenated over Raney-Nickel (5.0 g) in a Parr operator. The reaction mixture was stirred for 48 h at 80 psi. The mixture was filtered through celite and washed with ethanol. The filterate was concentrated under reduced pressure to afford 4.8 g (97.95%) of MH-S5 as the crude intermediate, further used without any purification.

Step 6 (MH-S6):

Triethylamine (5.8 mL, 41.54 mmol) and di-tert-butyl bicarbonate (4.7 mL, 20.77 mmol) were added successively to a solution of MH-S5 (4.8 g, 20.77 mmol) in dichloromethane (50 mL) and the mixture was stirred for 20 h at room temperature. The reaction was quenched with water and extracted with dichloromethane. The combined organic layer was washed successively with water, brine; dried over anhydrous sodium sulfate and concentrated in vacuum to afford the crude intermediate. Purification by column chromatography over silica gel (60-120 mesh) and using 30% Ethyl acetate in pet ether as the eluent afforded 2.8 g (40.75%) of MH-S6 as a gummy solid.

Step 7 (MH-S7):

A mixture of MH-S6 (2.8 g, 8.45 mmol), chloroacetone (0.84 mL, 10.15 mmol) and potassium carbonate (2.3 g, 16.91 mmol) in acetonitrile (30 mL) was refluxed for 5 h. The reaction mass was cooled to room temperature, filtered and washed with ethyl acetate. The combined filtrate was concentrated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuo to afford 2.4 g (70.79%) of MH-S7 as a gummy solid.

Step 8 (MH-S8):

Diethylamino sulfurtrifluoride (1.6 mL, 11.97 mmol) was added to a solution of MH-S7 (2.4 g, 5.98 mmol) in dichloromethane (30 mL) at 0° C. and the mixture was stirred for 2 h at room temperature. The reaction was quenched with ice water and extracted with dichloromethane. The combined organic layer was washed successively with saturated sodium bicarbonate solution, water, brine; dried over anhydrous sodium sulfate and concentrated in vacuum to afford the crude intermediate. Purification by column chromatography over silica gel (60-120 mesh) and using 15% ethyl acetate in pet ether as the eluent afforded 1.7 g (69.67%) of MH-S8 as a gummy solid.

Step 9 (MH-S9):

MH-S8 (1.5 g, 3.66 mmol) in tetrahydrofuran (15 mL) was added to the stirred solution of lithium-aluminum hydride (420 mg, 10.98 mmol) in tetrahydrofuran (10 mL) at 0° C. The reaction mixture was warmed to room temperature, quenched with saturated sodium sulfate solution, filtered and washed with ethyl acetate solution. The aqueous and organic layers were separated and the organic layer was washed with water, brine; dried over anhydrous sodium sulfate and concentrated under reduced pressure to afford the crude intermediate. Purification by column chromatography over silica gel (60-120 mesh) and using 20% ethyl acetate in pet ether as the eluent afforded 800 mg (59.70%) of MH-S9 as a gummy solid.

Step 10 (MK-S1):

Thionyl chloride (0.8 mL, 10.21 mmol) was added drop wise to a stirred solution of MH-S9 (750 mg, 2.04 mmol) in tetrahydrofuran (15 mL) at 0° C. The reaction mixture was warmed to room temperature and stirred for 5 h. The solvent was evaporated under reduced pressure. The resulting mass was basified with saturated sodium bicarbonate solution and extracted with ethyl acetate. The organic layer was washed with water, brine; dried over anhydrous sodium sulfate and concentrated under reduced pressure to afford the crude intermediate. Washing with pet ether and afterwards drying the remaining mass did purification, which afforded 450 mg (75.25%) of MK-S1.

Step 11 (MK-S2):

A mixture of MK-S1 (450 mg, 1.53 mmol), 4-Bromo-1,2-diaminobenzene (430 mg, 2.30 mmol) and cesium fluoride (465 mg, 3.06 mmol) in 1,4-dioxane (20 mL) was purged with argon gas for 30 min. Copper iodide (44 mg, 0.23 mmol) and 1,2-diaminocyclohexane (26 mg, 0.23 mmol) were added and the mixture was continuously purged for another 10 min. The reaction mixture was heated in a sealed tube for 16 h at 105-110° C. The reaction mixture was filtered through celite, washed with dioxane and the filtrate was concentrated under reduced pressure to give the crude intermediate. Purification by column chromatography over neutral alumina and using 1.5-2% methanol in dichloromethane as the eluent afforded 450 mg (73.52%) of MK-S2 as a brown solid.

Step 12 (Example 17):

Formamidine acetate (352 mg, 3.38 mmol) was added to a solution of MK-S2 (450 mg, 1.12 mmol) in acetonitrile (10 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layers were washed with water, brine; dried over anhydrous sodium sulfate and concentrated in vacuum to afford the crude product. Purification by column chromatography over neutral alumina and using 2-2.5% methanol in dichloromethane as the eluent afforded 360 mg of Example 17, which was triturated with n-pentane and thereafter dried to afford 310 mg of Example 17 as a light yellow solid.

Melting range: 122.2-126.8° C.; $^1$H-NMR (400 MHz, DMSO-d6): δ 8.18 (s, 1H); 7.54 (s, 2H); 7.18 (s, 1H); 6.80 (d, 2H); 6.00 (q, 1H); 4.84 (t, 1H); 4.38 (t, 1H); 4.25 (t, 2H); 1.65 (t, 3H); MS=410.1 (M+1); HPLC~99.19%; Chiral HPLC~99.21%.

Example 18

(S)-3-(1H-benzo[d]imidazol-5-yl)-4-(4-(3,3-difluoropyrrolidin-1-yl)-2-fluorophenyl)-oxazolidin-2-one Step 1 (ML-S1):

Potassium iodide (5.24 g, 31.57 mmol), N,N-di-isopropylethylamine (4.08 g, 31.57 mmol) and 1,4-dibromo-2-butanol (7.32 g, 31.57 mmol) were added successively to the stirred solution of 4-bromo-3-fluoroaniline (3 g, 15.78 mmol) in toluene (25 mL). The reaction mixture was stirred at 90° C. for 18 h. The reaction mass was filtered and washed with ethyl acetate. The filtrate was washed successively with water, brine; dried over anhydrous sodium sulfate and evaporated in vacuum. Purified by column chromatography over silica gel and using 20% ethyl acetate in pet ether as the eluent afforded 2 g (48.8%) of ML-S1 as a brown solid.

Step 2 (ML-S2):

A solution of ML-S1 (2 g, 7.69 mmol) and cuprous cyanide (1.03 g, 11.44 mmol) in N,N-dimethyl formamide (20 mL) was heated at 150° C. for 20 h. The reaction mass was evaporated in vacuum, thereafter stirred in ammonium chloride solution, filtered and washed with dichloromethane. The filtrate was washed with water; dried over anhydrous sodium sulfate and evaporated in vacuum. Purification by column chromatography over silica gel and using 30% ethyl acetate in pet ether as the eluent afforded 950 mg (60.1%) of ML-S2 as a yellow solid.

Step 3 (ML-S3):

Oxalyl chloride (1.18 g, 9.29 mmol) was added to the stirred solution of Dimethylsulfoxide (1.44 g, 18.43 mmol) in dichloromethane (15 mL) at −78° C. and the mixture stirred for 1 h. A solution of ML-S2 (950 mg, 4.61 mmol) in dichloromethane (20 mL) was added drop wise at −78° C. and the reaction mixture was stirred for 1 h at the same temperature. Triethyl amine (2.32 g, 22.97 mmol) was added and the mixture was warmed to room temperature in the next 40 min. The reaction was quenched with ice water and extracted with dichloromethane. The separated organic layer was washed with brine; dried over anhydrous sodium sulfate and was evaporated in vacuum to afford 900 mg (95.74%) of ML-S3 as a yellow solid.

Step 4 (ML-S4):

Diethylamino sulfurtrifluoride (1.42 g, 8.82 mmol) was added to a solution of ML-S3 (900 mg, 4.41 mmol) in dichloromethane (10 mL) at 0° C. and the mixture was stirred for 2 h at ambient temperature. The reaction was quenched with ice water and extracted with dichloromethane. The combined organic layer was washed successively with water, bicarbonate, brine; dried over anhydrous sodium sulfate and concentrated in vacuum to afford 900 mg of the crude intermediate ML-S4 as a brown liquid.

Step 5 (ML-S5):

Diisobutyl aluminumhydride in toluene (1.5 M, 5.3 mL, 7.96 mmol) was added to a solution of ML-S4 (900 mg, 3.98 mmol) in tetrahydrofuran (10 mL) at −70° C. and the mixture was slowly warmed to 0° C. Afterwards the reaction was quenched with saturated ammonium chloride solution, filtered and washed with ethyl acetate. The filtrate was washed with brine; dried over anhydrous sodium sulfate and the solvent was evaporated in vacuum. Purification by column chromatography over neutral alumina and using 15% ethyl acetate in pet ether as the eluent afforded 580 mg (63.6%) of ML-S5 as pale yellow solid.

Step 6 (MN-S1):

n-Butyl lithium in hexane (2.2 M; 2.3 mL, 5.06 mmol) was added to a stirred solution of methyl-triphenylphosphoniumbromide (1.8 g, 5.06 mmol) in tetrahydrofuran (10 mL) at −30° C. and the mixture was stirred for 30 min at 0-5° C. A solution of ML-S5 (580 mg, 2.53 mmol) in tetrahydrofuran (10 mL) was added drop wise at −30° C. The temperature was warmed to room temperature and the reaction mixture was stirred for 2 h. The reaction was quenched with acetic acid and the pH-Value was adjusted to pH-5. The solution was extracted with ethyl acetate (3×25 mL). The combined organic layer was washed successively with water, brine; dried over anhydrous sodium sulfate and concentrated under reduced pressure to afford the crude intermediate. Purification by column chromatography over silica gel (60-120 mesh) and using 1% ethyl acetate in pet ether as the eluent afforded 330 mg (57.5%) of MN-S1 as a pale yellow liquid.

Step 7 (MR-S1):

t-Butyl hypochlorite (0.49 mL, 4.37 mmol) was added to a stirred solution of t-butyl carbamate (510 mg, 4.35 mmol) in 1-propanol (5.8 mL) and 0.4 N aqueous sodium hydroxide (11.08 mL) at 15° C. and the mixture was further stirred for 15 min. A solution of (DHQ)$_2$PHAL (56.62 mg, 0.07 mmol) in 1-propanol (5.8 mL) was added, followed by a solution of MN-S1 (330 mg, 1.45 mmol) in 1-propanol (5.8 mL). Finally potassium osmatedihydrate (21.4 mg, 0.058 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 15% ethyl acetate in pet ether as the eluent afforded 280 mg (53.53%) of MR-S1 as a white solid.

Step 8 (MR-S2):

Potassium-t-butoxide (186.6 mg, 1.67 mmol) was added to a stirred solution of MR-S1 (280 mg, 0.83 mmol) in tetrahydrofuran (10 mL) at 0° C. and the mixture was stirred for 1 h at room temperature. The reaction mixture was neutralized with 10% acetic acid and extracted with ethyl acetate. The combined organic layer was washed successively with water, brine; dried over anhydrous sodium sulfate and concentrated under reduced pressure to afford 180 mg (81%) of the intermediate MR-S2 as a pale yellow solid.

Step 9 (MR-S3):

A mixture of MR-S1 (180 mg, 0.63 mmol), 4-Bromo-1,2-diaminobenzene (117.7 mg, 0.67 mmol) and cesium fluoride (191 mg, 1.26 mmol) in 1,4-dioxane (10 mL) was purged with argon gas for 10 min in a sealed tube. Copper iodide (18 mg, 0.09 mmol) and 1,2-diaminocyclohexane (10.8 mg, 0.09 mmol) were added and the mixture was continuously purged for another 10 min. The sealed tube was heated for 18 h at 110-115° C. The reaction mixture was filtered through celite, washed with dioxane and the filtrate was concentrated under reduced pressure to give the crude intermediate. Purification by column chromatography over neutral alumina and using 2-3% methanol in chloroform as the eluent afforded 150 mg (60.97%) of MR-S3 as a brown color solid.

Step 10 (Example 18):

Formamidine acetate (107 mg, 0.765 mmol) was added to a solution of MR-S3 (150 mg, 0.38 mmol) in acetonitrile (5 mL) and the mixture was refluxed for 1 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum. The crude product was triturated with diethyl ether and dried to afford 80 mg (52.3%) of Example 18 as a solid.

Melting range: 273-278° C.; $^1$H-NMR (400 MHz, DMSO-d6): δ 8.16 (d, 1H); 7.54-7.28 (m, 2H); 7.27-7.14 (m, 2H); 6.39-6.31 (m, 2H); 5.79 (t, 1H); 4.81 (t, 1H); 4.21 (q, 1H); 3.16 (t, 2H); 3.39 (t, 2H); 2.51-2.27 (merged with DMSO, 2H); MS=403.1 (M+1); HPLC~98.19%; Chiral HPLC~99.44%.

Example 19

(S)-3-(1H-benzo[d]imidazol-5-yl)-4-(4-(3,3-difluoropyrrolidin-1-yl)-2,3-difluorophenyl)-oxazolidin-2-one Step 1 (ML-S1):

Diisopropyl ethylamine (1.6 mL, 9.6 mmol) and potassium iodide (1.5 g, 9.6 mmol) was added to a solution of 4-bromo-2,3-difluoroaniline (1.0 g, 4.80 mmol) in toluene (15 mL) and the mixture was stirred for 10 min at room temperature. 1,4-dibromo-2-butanol (1.1 mL, 9.6 mmol) was added and the reaction mixture was stirred at 90° C. for 24 h. The reaction mass was filtered and washed with ethyl acetate. The filtrate was washed successively with water, brine; dried over anhydrous sodium sulfate and evaporated in vacuum. Purification by column chromatography over silica gel (60-120 mesh) and using 15% ethyl acetate in pet ether as the eluent afforded 500 mg (38.46%) of ML-S1 as a light brown color solid.

Step 2 (ML-S2):

Cuprous cyanide (962 mg, 10.75 mmol) was added to a solution of ML-S1 (2.5 g, 8.96 mmol) in dimethyl formamide (20 mL) and the mixture was stirred at 155° C.-160° C. for 12 h. The reaction mass was cooled to room temperature, filtered and the solvent was evaporated under reduced pressure. The resulting mass was dissolved in ethyl acetate (100 mL) and washed with water and brine. The organic layer was dried over with anhydrous sodium sulfate and concentrated under reduced pressure to give the crude intermediate. Purification by column chromatography over silica gel (60-120 mesh) and using 25% ethyl acetate in pet ether as the eluent afforded 1.0 g (50%) of ML-S2 as a pale brown color solid.

Step 3 (ML-S3):

Oxalyl chloride (0.92 mL, 10.66 mmol) was added to a stirred solution of dry dimethyl sulfoxide (1.52 mL, 21.30 mmol) in dichloromethane (10 mL) at −78° C. and the mixture was stirred for 1 h at the same temperature. A solution of ML-S2 (1.2 g, 5.33 mmol) in dichloromethane (5 mL) was added drop wise at −78° C. and the mixture was stirred for 1 h at the same temperature. Triethyl amine (3.5 mL, 26.65 mmol) was added and the mixture was further stirred for 30 min at room temperature. The reaction was quenched with water and extracted with dichloromethane. The combined organic layer was washed with water, brine; dried over anhydrous sodium sulfate and concentrated in vacuum to afford the crude intermediate. Purification by column chromatography over neutral alumina and using ethyl acetate in pet ether as the eluent afforded 750 mg (63%) of ML-S3 as a solid.

Step 4 (ML-S4):

Diethylamino sulfurtrifluoride (0.82 mL, 6.27 mmol) was added to a solution of ML-S3 (700 mg, 3.13 mmol) in dichloromethane (10 mL) at 0° C. and the mixture was stirred for 2 h at room temperature. The reaction was quenched with ice water and extracted with dichloromethane. The combined organic layer was washed successively with water, brine and saturated sodium hydrogencarbonate; dried over anhydrous sodium sulfate and concentrated in vacuum to afford 700 mg (92%) of ML-S4 as a brown liquid.

Step 5 (ML-S5):

DIBAL in toluene (1.5 M; 3.8 mL, 5.71 mmol) was added slowly over 5 min to a solution of ML-S4 (700 mg, 2.85 mmol) in dry tetrahydrofuran (10 mL) at −30° C. The reaction mass was warmed to room temperature and stirred for 2 h. The reaction was quenched with saturated ammonium chloride solution, filtered and washed with ethyl acetate (3×25 mL). The filtrate was washed successively with water brine; dried over anhydrous sodium sulfate and concentrated in vacuum to afford the crude intermediate. Purification by column chromatography over neutral alumina and using 20% ethyl acetate in pet ether as the eluent afforded 370 mg (52.4%) of ML-S5 as a color less liquid.

Step 6 (MN-S1):

N-Butyl lithium in hexane (2.2 M; 1.35 mL, 2.99 mmol) was added to a stirred solution of triphenylphosphonium methylbromide (1.07 g, 2.99 mmol) in tetrahydrofuran (10 mL) at −50° C. and the mixture was stirred for 30 min at 0-5° C. A solution of ML-S5 (370 mg, 1.49 mmol) in tetrahydrofuran (10 mL) was added drop wise at −30° C. The temperature was warmed to room temperature and the mixture was stirred for 1 h. The reaction was quenched with saturated ammonium chloride solution and extracted with ethyl acetate (3×25 mL). The combined organic layer was washed successively with water, brine; dried over anhydrous sodium sulfate and concentrated under reduced pressure to afford the crude intermediate. Purification by column chromatography over silica gel (60-120 mesh) and using 5% ethyl acetate in pet ether as the eluent afforded 250 mg (68.11%) of MN-S1 as a color less liquid.

Step 7 (MR-S1):

t-Butyl hypochlorite (0.34 mL, 3.07 mmol) was added to a stirred solution of t-butyl carbamate (358 mg, 3.06 mmol) in 1-propanol (4 mL) and 0.4 N aqueous sodium hydroxide (124 mg in 7.7 mL water) at 15° C. and the mixture was stirred for 15 min. A solution of (DHQ)$_2$PHAL (39 mg, 0.051 mmol) in 1-propanol (4 mL) was added, followed by a solution of MN-S1 (250 mg, 1.02 mmol) in 1-propanol (4 mL). Finally potassium osmatedihydrate (15 mg, 0.04 mmol) was added and the reaction mixture was stirred for 15 min at room temperature. The reaction was quenched with saturated sodium sulphite solution and extracted with ethyl acetate (3×25 mL). The combined organic layer was washed successively with water, brine; dried over anhydrous sodium sulfate and concentrated under reduced pressure to afford the crude intermediate. Purification by column chromatography over silica gel (60-120 mesh) and using 22-25% ethyl acetate in pet ether as the eluent afforded 250 mg (64.9%) of MR-S1 as a white solid.

Step 8 (MR-S2):

Potassium-t-butoxide (148 mg, 1.32 mmol) was added to a stirred solution of MR-S1 (250 mg, 0.66 mmol) in tetrahydrofuran (10 mL) at 0° C. and the mixture was stirred for 1 h at room temperature. The reaction was neutralized with 10% acetic acid and extracted with ethyl acetate (3×25 mL). The combined organic layer was washed successively with water, brine; dried over anhydrous sodium sulfate and concentrated under reduced pressure to afford 175 mg (87%) of MR-S2 as a yellow color solid.

Step 9 (MR-S3):

A mixture of MR-S2 (175 mg, 0.575 mmol), 4-Bromo-1,2-diaminobenzene (107 mg, 0.575 mmol) and cesium fluoride (174 mg, 1.15 mmol) in 1,4-dioxane (10 mL) was purged with argon gas for 10 min. Copper iodide (16 mg, 0.086 mmol) and 1,2-diaminocyclohexane (10 mg, 0.086 mmol) were added and the mixture was continuously purged for another 10 min. The reaction was heated in a sealed tube for 24 h at 110-115° C. The reaction mixture was filtered through celite, washed with dioxane and the filtrate was concentrated under reduced pressure to give the crude intermediate. Purification by column chromatography over neutral alumina and using 1.5% methanol in chloroform as the eluent afforded 190 mg (80.5%) of MR-S3 as a brown color solid.

Step 10 (Example 19):

Formamidine acetate (145 mg, 1.39 mmol) was added to a solution of MR-S3 (190 mg, 0.464 mmol) in acetonitrile (10 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product, which was triturated with diethylether and dried to afford 130 mg (67%) of Example 19 as a off pale brown color solid.

Melting range: 236-244° C.; $^1$H-NMR (400 MHz, DMSO-d6): δ 8.17 (d, 1H); 7.58-7.43 (m, 2H); 7.29-7.16 (m, 1H); 7.10-7.03 (m, 1H); 6.52 (t, 1H); 5.85 (q, 1H); 4.83 (t, 1H); 4.27 (q, 1H); 3.73 (t, 2H); 3.50 (t, 2H); 2.51-2.36 (merged with DMSO, 2H); MS=421.1 (M+1); HPLC~98.86%; Chiral HPLC~99.94%.

Example 20

(S)-3-(1H-benzo[d]imidazol-5-yl)-4-(4-(3,3-difluoropyrrolidin-1-yl)-2,6-difluorophenyl) oxazolidin-2-one Step 1 (ML-S1):

Potassium iodide (4.7 g, 28.8 mmol), N,N-diisopropylethylamine (3.7 g, 28.8 mmol) and 1,4-dibromo-2-butanol (6.6 g, 28.8 mmol) were added successively to the stirred solution of 4-bromo-2,6-difluoroaniline (3 g, 14.4 mmol) in toluene (30 mL) and the mixture was stirred at 90° C. for 18 h. The reaction mass was filtered, washed with ethyl acetate and the filtrate was washed successively with water, brine; dried over anhydrous sodium sulfate and evaporated in vacuum to give crude the compound intermediate. Purification by column chromatography over silica gel and using 20% ethyl acetate in pet ether as the eluent afforded 2 g (49.9%) of ML-S1 as a brown solid.

Step 2 (ML-S2):

A solution of ML-S1 (2 g, 7.19 mmol) and cuprous cyanide (1.28 g, 14.3 mmol) in N,N-dimethyl formamide (20 mL) was heated at 150° C. for 20 h. The reaction mass was evaporated in vacuum and the residue was stirred in ammonium chloride solution, filtered and washed with dichloromethane. The filtrate was washed with water; dried over anhydrous sodium sulfate and evaporated in vacuum to give the crude intermediate. Purification by column chromatography over silica gel and using 30% ethyl acetate in pet ether as the eluent afforded 950 mg (57%) of ML-S2 as a yellow solid.

Step 3 (ML-S3):

Oxalyl chloride (2.7 mL, 31.2 mmol) was added to a stirred solution of dimethyl sulfoxide (4.4 mL, 62.5 mmol) in dichloromethane (15 mL) at −78° C. and the mixture was stirred for 1 h at −78° C. A solution of ML-S2 (3.5 mg, 15.6 mmol) in dichloromethane (50 mL) was slowly added and the mixture was stirred for 1 h at the same temperature. Triethyl amine (10.8 mL, 78.0 mmol) was added and the reaction was slowly warmed to room temperature and thereafter it was stirred for 1 h. The mixture was partitioned between water and dichloromethane. The separated organic layer was washed brine; dried over anhydrous sodium sulfate and evaporated in vacuum to afford 2.0 g (57.8%) ML-S3 as a yellow solid.

Step 4 (ML-S4):

Diethylamino sulfurtrifluoride (3.8 g, 22.5 mmol) was added to a solution of ML-S3 (2.0 g, 9.0 mmol) in dichloromethane (30 mL) at 0° C. and the mixture was stirred for 2 h at ambient temperature. The reaction was quenched with ice water and extracted with dichloromethane. The combined organic layer was washed successively with water, bicarbonate, brine; dried over anhydrous sodium sulfate and concentrated in vacuum to afford 1.8 g (81.8%) of ML-S4 as a brown liquid, further used without any purification.

Step 5 (ML-S5):

Diisobutyl aluminumhydride (1.5 M, 7.3 mL, 11.0 mmol) was added to a solution of ML-S4 (1.8 g, 7.3 mmol) in Tetrahydrofuran (20 mL) at −20° C. and the mixture was slowly warmed to 0° C. The reaction was quenched with saturated ammonium chloride solution, filtered and washed with ethyl acetate. The filtrate was washed with brine; dried over anhydrous sodium sulfate and evaporated in vacuum to afford the crude intermediate. Purification by column chromatography over silica gel (60-120 mesh) and using 12% ethyl acetate in pet ether as the eluent afforded 1.0 g (55.0%) of ML-S5 as a pale yellow solid.

Step 6 (MN-S1):

n-Butyllithium in hexane (2.2 M; 3.6 mL, 8.0 mmol) was added to a stirred solution of methyl triphenylphosphoniumbromide (2.8 g, 8.0 mmol) in tetrahydrofuran (20 mL) at −30° C. and the mixture was stirred for 30 min at 0-5° C. A solution of ML-S5 (1.0 g, 4.0 mmol) in tetrahydrofuran (10 mL) was added drop wise at −30° C. The reaction mass was slowly warmed to room temperature and stirred for 2 h at this temperature. The reaction was quenched with acetic acid and the pH-Value was adjusted to pH-5. The mass was filtered and washed with ethyl acetate. The filtrate was washed successively with water, brine; dried over anhydrous sodium sulfate and concentrated under reduced pressure to afford the crude intermediate. Purification by column chromatography over silica gel (60-120 mesh) and using 1% ethyl acetate in pet ether as the eluent afforded 800 mg (82%) of MN-S1 as an off white solid.

Step 7 (MR-S1):

t-Butylhypochlorite (1.11 mL, 9.8 mmol) was added to a stirred solution of t-butyl carbamate (1.14 g, 9.78 mmol) in 1-propanol (13 mL) and 0.4 N aqueous sodium hydroxide (25 mL) at 15° C. and the mixture was stirred for 15 min. A solution of (DHQ)$_2$PHAL (127 mg, 0.05 mmol) in 1-propanol (13 mL) was added, followed by a solution of MN-S1 (800 mg, 3.26 mmol) in 1-propanol (13 mL). Finally potassium osmatedihydrate (48 mg, 0.04 mmol) was added and the reaction mixture was stirred for 15 min at room temperature. The reaction was quenched with saturated sodium sulfate solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 18% ethyl acetate in pet ether as the eluent afforded 700 mg (57%) of MR-S1 as an off white solid.

Step 8 (MR-S2):

Potassium-t-butoxide (620 mg, 5.5 mmol) was added to a stirred solution of MR-S1 (700 mg, 1.8 mmol) in tetrahydrofuran (20 mL) at 0° C. and the mixture was stirred for 1 h at room temperature. The reaction was neutralized with 10% acetic acid and extracted with ethyl acetate. The combined organic layer was washed successively with water, brine; dried over anhydrous sodium sulfate and concentrated under reduced pressure to get the crude intermediate. Purification by column chromatography over silica gel (100-200 mesh) and using 24-26% ethyl acetate in pet ether as the eluent afforded 90 mg (16%) of MR-S2 as an off white solid.

Step 9 (MR-S3):

A mixture of MR-S2 (90 mg, 0.29 mmol), 4-Bromo-1,2-diaminobenzene (50 mg, 0.29 mmol) and cesium fluoride (87 mg, 0.59 mmol) in 1,4-dioxane (5 mL) was purged with argon gas for 10 min in a sealed tube. Copper iodide (7.44 mg, 0.04 mmol) and 1,2-diaminocyclohexane (4.6 mg, 0.04 mmol) were added and the mixture was continuously purged for another 10 min. The sealed tube was heated for 18 h at 110-115° C. The reaction mixture was filtered through celite, washed with dioxane and the filtrate was concentrated under reduced pressure to give the crude intermediate. Purification by column chromatography over neutral alumina and using 2-3% methanol in chloroform as the eluent afforded 100 mg (82%) of MR-S3 as a brown solid.

Step 10 (Example 20):

Formamidine acetate (76 mg, 0.72 mmol) was added to a stirred solution of MR-S3 (100 mg, 0.24 mmol) in acetonitrile (5 mL) and the mixture was refluxed for 1 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification was done by preparative HPLC using the following conditions:

Column: Packed C-18 (250*25 mm*10µ); mobile phase: A: acetonitrile; B: 10 mM ammonium acetate (50:50); flow rate: 25 ml/min; used diluents: ACN+MeOH+mobile phase; method: gradient; column temp ° C.: ambient The resulting fractions were evaporated in vacuum and the resulting mass was partitioned between water and dichloromethane. The organic layer was separated and the aqueous layer was extracted with dichloromethane. The combined organic layer was washed with water, brine; dried over anhydrous sodium sulfate and concentrated in vacuum to afford 50 mg of Example 20 as a brown solid.

$^1$H-NMR (400 MHz, DMSO-d6): δ 8.19 (s, 1H); 7.50 (d, 2H); 7.19 (d, 1H); 6.24 (d, 2H); 5.96-5.91 (m, 1H); 4.83 (t, 1H); 4.31 (q, 1H); 3.62 (t, 2H); 3.39 (t, 2H); 2.50-2.40 (merged with DMSO, 2H); MS=421.0 (M+1); HPLC~99.08%; Chiral HPLC~84.18%.

Example 21

(S)-3-(1H-benzo[d]imidazol-5-yl)-4-(4-(3,3-difluoropyrrolidin-1-yl)-3-fluorophenyl) oxazolidin-2-one Step 1 (MM-S1):

Potassium carbonate (22 g, 79.13 mmol) was added to a solution of 3-hydroxypyrrolidone hydrochloride (9.6 g, 79.12 mmol) in dimethylformamide (60 mL) and the mixture was stirred for 15 min. 3,4-difluorobenzonitrile (10 g, 71.94 mmol) was added and the mixture was stirred at 90° C. for 9 h. The reaction was cooled to room temperature and than quenched with ice water. The resulting mass was filtered and washed with water, pet ether and dried in vacuum to afford 10 g (67.5%) of MM-S1 as an off white solid.

Step 2 (MM-S2):

Dess-martin periodinane (41.2 g, 97.08 mmol) was added to a solution of MM-S1 (10 g, 48.5 mmol) and the mixture was stirred for 15 h. The reaction mass was filtered through celite and washed with dichloromethane. The filtrate was washed with water, brine; dried over anhydrous sodium sulfate and concentrated to afford 3.2 g (32%) of MM-S2 as an off white solid.

Step 3 (MM-S3):

Diethylamino sulfurtrifluoride (3.85 mL, 29.41 mmol) was added to a solution of MM-S2 (3.0 g, 14.70 mmol) in dichloromethane (30 mL) at 0° C. and the mixture was stirred for 4 h at room temperature. The reaction was quenched with ice water and extracted with dichloromethane. The combined organic layer was washed successively with water, bicarbonate, brine; dried over anhydrous sodium sulfate and concentrated in vacuum to afford 2.8 g (84.3%) of MM-S3 as a brown liquid.

Step 4 (MM-S4):

DIBAL in toluene (16.5 ml, 24.77 mmol) was added to a solution of MM-S3 (2.8 g, 12.38 mmol) in tetrahydrofuran (30 mL) at −70° C. and the mixture was slowly warmed to 0° C. The reaction was quenched with saturated ammonium chloride and extracted with ethyl acetate. The salts were filtered and the remaining mass was washed with ethyl acetate. The organic layer was separated from the filtrate and washed with brine; dried over anhydrous sodium sulfate and concentrated under reduced pressure to afford the crude intermediate. Purification by column chromatography over neutral alumina and using 5% ethyl acetate in pet ether as the eluent afforded 1.5 g (53%) of MM-S4 as a pale yellow solid.

Step 5 (MN-S1):

n-Butyllithium in hexane (2.5M; 5.24 mL, 13.10 mmol) was added to a stirred solution of triphenylphosphonium methylbromide (4.67 g, 13.10 mmol) in tetrahydrofuran (40 mL) at −30° C. and the mixture was stirred for 30 min at 0-5° C. A solution of MM-S4 (1.5 g, 6.55 mmol) in tetrahydrofuran (10 mL) was added drop wise at −30° C. The temperature was warmed to room temperature and the mixture was stirred for 1 h. The reaction was quenched with acetic acid and the pH-value was adjusted to pH-5. The mixture was extracted with ethyl acetate (3×25 mL). The combined organic layer was washed successively with water, brine; dried over anhydrous sodium sulfate and concentrated under reduced pressure to afford the crude intermediate. Purification by column chromatography over silica gel (60-120 mesh) and using 1% ethyl acetate in pet ether as the eluent afforded 1.2 g (81%) of MN-S1 as a pale yellow solid.

Step 6 (MR-S1):

t-Butyl hypochlorite (0.98 mL, 8.59 mmol) was added to a stirred solution of t-butyl carbamate (1 g, 2.86 mmol) in 1-propanol (11.5 mL) and 0.4 N aqueous sodium hydroxide (349 mg in 22 mL water) at 15° C. and the mixture was stirred for 15 min. A solution of DHQ$_2$PHAL (111 mg, 0.143 mmol) in 1-propanol (11.5 mL) was added, followed by a solution of MN-S1 (650 mg, 2.86 mmol) in 1-propanol (11.5 mL). Finally potassium osmatedihydrate (42 mg, 0.114 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 20% ethyl acetate in pet ether as the eluent afforded 400 mg (38.8%) of MR-S1 as a white solid.

Step 7 (MR-S2):

Potassium-t-butoxide (497 mg, 4.44 mmol) was added to a stirred solution of MR-S1 (800 mg, 2.22 mmol) in tetrahydrofuran (10 mL) at 0° C. and the mixture was stirred for 1 h at room temperature. The reaction was neutralized with 10% acetic acid and extracted with ethyl acetate. The combined organic layer was washed successively with water, brine; dried over anhydrous sodium sulfate and concentrated under reduced pressure to afford 490 mg (76.5%) of MR-S2 as a pale yellow solid.

Step 8 (MR-S3):

A mixture of MR-S2 (490 mg, 1.70 mmol), 4-Bromo-1, 2-diaminobenzene (318 mg, 1.70 mmol) and cesium fluoride (517 mg, 3.40 mmol) in 1,4-dioxane (10 mL) was purged with argon gas for 10 min in a sealed tube. Copper iodide (48 mg, 0.255 mmol) and 1,2-diaminocyclohexane (29 mg, 0.255 mmol) were added and the mixture was continuously purged for another 10 min. The sealed tube was heated for 18 h at 110-115° C. The reaction mixture was filtered through celite, washed with dioxane and the filtrate was concentrated under reduced pressure to give the crude intermediate. Purification by column chromatography over neutral alumina and using 2-3% methanol in chloroform as the eluent afforded 220 mg (31.2%) of MR-S3 as a brown color solid.

Step 9 (Example 21):

Formamidine acetate (110 mg, 100.12 mmol) was added to a solution of MR-S3 (200 mg, 50.6 mmol) in acetonitrile (5 mL) and the mixture was refluxed for 1 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product, which was triturated with di-ethyl ether and dried to afford 125 mg of Example 21 as a light brown solid.

Melting range: 265-269° C.; $^1$H-NMR (400 MHz, DMSO-d6): δ 8.17 (s, 1H); 7.58 (d, 1H); 7.48 (d, 1H); 7.25-7.18 (m, 2H); 7.09 (d, 1H); 6.72 (t, 1H); 5.65 (q, 1H); 4.78 (t, 1H); 4.13 (q, 1H); 3.66 (t, 2H); 3.45 (t, 2H); 2.50-2.35 (m, 2H); MS=403.1 (M+1); HPLC~96.84%; Chiral HPLC~99.40%.

Example 22

3-(1H-benzo[d]imidazol-5-yl)-4-(4-(3,3-difluoropyrrolidin-1-yl)phenyl)oxazolidin-2-one Step 1 (MM-S1):

(R)-3-Hydroxy pyrrolidine (1.6 g, 18.30 mmol) was added to the stirred solution of 4-fluorobenzonitrile (1.5 g, 12.19 mmol) and potassium carbonate (1.68 g, 12.19 mmol) in dimethylformamide (20 mL) and the mixture was stirred over night at 80° C. The reaction mass was filtered, washed with ethyl acetate and the filtrate was evaporated in vacuum. The mass was partitioned between water and ethyl acetate. The combined organic layer was washed with water, brine; dried over anhydrous sodium sulfate and concentrated in vacuum to afford the crude intermediate. Purification by column chromatography over neutral alumina and using ethyl acetate in pet ether as the eluent afforded 1.9 g of MM-S1 as a solid.

Step 2 (MM-S2):

Oxalylchloride (1.18 mL, 13.90 mmol) was added to a stirred solution of dry dimethylsulfoxide (1.87 mL, 27.80 mmol) in dichloromethane (20 mL) at −78° C. and the mixture was stirred for 1 h at the same temperature. A solution of MM-S1 (1.1 g, 6.95 mmol) in dichloromethane was added drop wise at −78° C. and the mixture was further stirred for 2 h at the same temperature. Triethylamine (4.83 mL, 34.75 mmol) was added and the mixture was stirred for 30 min at room temperature. The reaction was quenched with water and extracted with dichloromethane. The combined organic layer was washed with water, brine; dried over anhydrous sodium sulfate and concentrated in vacuum to afford the crude intermediate. Purification by column chromatography over neutral alumina and using ethyl acetate in pet ether as the eluent afforded 930 mg of MM-S2 as a solid.

Step 3 (MM-S3):

Diethylamino sulfurtrifluoride (1.95 mL, 13.44 mmol) was added to a solution of MM-S2 (930 mg, 6.4 mmol) in dichloromethane (20 mL) at 0° C. The reaction mixture was warmed to room temperature and stirred for 3 h. The reaction was quenched with ice water and the separated organic layer was washed successively with water, brine; dried over anhydrous sodium sulfate and concentrated in vacuum to afford 900 mg of MM-S3 as a solid.

Step 4 (MM-S4):

Diisobutyl aluminumhydride in toluene (1 M; 12.5 mL, 12.50 mmol) was slowly added to a stirred solution of MN-S4 (1.3 g, 6.25 mmol) in tetrahydrofuran at −10° C. The reaction mass was stirred for 6 h at room temperature. The reaction was quenched with ammonium chloride solution, filtered and the filtrate was extracted in ethyl acetate. The combined organic layer was washed successively with water, brine; dried over anhydrous sodium sulfate and concentrated in vacuum to afford 900 mg of MN-S4 as a yellow liquid.

Step 5 (MN-S1):

n-Butyl lithium in hexane (2 M; 1.4 mL, 2.8 mmol) was added to a stirred solution of Triphenylphosphonium methylbromide (1 g, 2.82 mmol) in tetrahydrofuran (20 mL) at 0° C. and the solution stirred for 1 h. A solution of MN-S4 (300 mg, 1.42 mmol) in tetrahydrofuran (10 mL) was added drop wise at −10° C. and the solution was stirred for 3 h. The reaction was quenched with saturated ammonium chloride solution and extracted with dichloromethane. The organic layer was washed with brine; dried over anhydrous sodium sulfate and concentrated under reduced pressure to give the crude intermediate. Purification by column chromatography over neutral alumina and using 5% ethyl acetate in pet ether as the eluent afforded 150 mg of MN-S1 as a yellow liquid.

Step 6 (MR-S1):

tert-Butylhypochloride (1.24 mL, 11.56 mmol) was added to a stirred solution of t-butyl carbamate (1.33 g, 11.41 mmol) in 1-propanol (25 mL) and 0.4 N aqueous sodium hydroxide (326 mg in 24 mL water) at 0° C. and the mixture was stirred for 15 min. A solution of (DHQ)$_2$PHAL (140 mg, 0.0189 mmol) in 1-propanol (25 mL) was added, followed by MN-S1 (6 mg, 3.79 mmol) in 1-propanol (25 mL). Finally potassium osmatedihydrate (5.5 mg, 0.0151 mmol) were added and the reaction mixture was stirred for 30 min at room temperature. The reaction was quenched with saturated sodium sulphite solution and extracted with ethyl acetate. The combined organic layer was washed with water, brine; dried over anhydrous sodium sulfate and concentrated under reduced pressure to afford the crude intermediate. Purification by column chromatography over neutral alumina and using as 40% ethyl acetate in pet ether as the eluent afforded 500 mg of MR-S1 as a white solid.

Step 7 (MR-S2):

Potassium-t-butoxide (327 mg, 2.92 mmol) was added to a stirred solution of MR-S1 (500 mg, 1.46 mmol) in tetrahydrofuran (50 mL) at 0° C. and the mixture was stirred for 8 h at room temperature. The reaction mixture was concentrated under reduced pressure and the resulting mass was extracted with dichloromethane. The combined organic layer was washed with water, brine; dried over anhydrous sodium sulfate and evaporated to afford the crude intermediate. Purification by column over neutral alumina and using 30% ethyl acetate in pet ether as the eluent afforded 200 mg of MR-S2 as a yellow solid.

Step 8 (MR-S3):

A mixture of MR-S2 (200 mg, 0.543 mmol), 4-bromo-1, 2-diaminobenzene (108 mg, 0.597 mmol), cesium fluoride (165 mg, 1.08 mmol) and copper iodide (51 mg, 0.271 mmol) in 1,4-dioxane (10 mL) was purged with argon gas for 30 min. 1,2-diaminocyclohexane (9.2 mg, 0.08 mmol)

was added and the mixture was continuously purged for another 10 min. The reaction was stirred for 36 hours at 110-115° C. in a sealed tube. The reaction mixture was filtered through celite, washed with dioxane and concentrated under reduced pressure to afford the crude intermediate. Purification by column chromatography over neutral alumina and using 1% methanol in chloroform as the eluent afforded 80 mg of MR-S3 as a brown solid.

Step 9 (Example 22):

MR-S3 (80 mg, 0.213 mmol) was stirred in formic acid (5 mL) for 2 h at 80-90° C. The reaction mixture was diluted with water and extracted with ethyl acetate. The organic layer was washed successively with saturated bicarbonate solution, brine; the combined organic layers were concentrated under reduced pressure to afford the crude product. Purification by preparative TLC and using 4% methanol in chloroform as the eluent afforded 30 mg of Example 22 as a yellow solid.

Melting range: 245-250° C.; $^1$H-NMR (400 MHz, DMSO-d6): δ 12.40 (d, 1H); 8.13 (d, 1H); 7.52-7.13 (m, 5H); 6.51 (t, 2H); 5.57 (t, 1H); 4.76 (t, 1H); 4.09 (t, 1H); 3.61-3.33 (merged with DMSO moisture, 4H); 2.48-2.40 (merged with DMSO, 2H); MS=383.0 (M−1); HPLC~92.07%.

Example 23

(S)-2-(3-(1H-benzo[d]imidazol-5-yl)-2-oxooxazolidin-4-yl)-5-(3,3-difluoropyrrolidin-1-yl)benzonitrile Step 1 (MO-S1):

Potassium iodide (5.22 g, 31.47 mmol), N,N-Diisopropyl ethylamine (5.4 mL, 31.47 mmol) and 1,4-dibromo-2-butanol (3.7 mL, 31.47 mmol) were added successively to a stirred solution of 5-Amino-2-bromobenzonitril (3.1 g, 15.74 mmol) in toluene (50 mL). The reaction mixture was stirred at 90° C. for 20 h. The reaction mass was filtered, washed with ethyl acetate and the filtrate was washed successively with water, brine; dried over anhydrous sodium sulfate and evaporated in vacuum to afford the crude intermediate. Purification by column chromatography over silica gel (60-120 mesh) and using 24-25% ethyl acetate in pet ether as the eluent afforded 2.45 g (58.47%) of MO-S1 as a brown solid.

Step 2 (MQ-S1):

Oxalyl chloride (1.61 mL, 18.42 mmol) was added to a solution of dimethylsulfoxide (2.62 mL, 36.84 mmol) in dichloromethane (50 mL) at −78° C. and the solution was stirred for 30 min. A solution of MO-S1 (2.45 g, 9.21 mmol) in dichloromethane (20 mL) was slowly added over 10 min and the mixture was stirred for 1 h at the −78° C. Triethylamine (6.42 mL, 46.05 mmol) was added and the mixture was stirred at room temperature for 30 min. The reaction was quenched with ice water and extracted with dichloromethane. The combined organic layer was washed successively with water, brine; dried over anhydrous sodium sulfate and concentrated in vacuum to afford 2.4 g (98.76%) of MQ-S1 as a brown solid.

Step 3 (MQ-S2):

Diethylamino sulfurtrifluoride (2.2 mL, 16.67 mmol) was added to a solution of MQ-S1 (2.4 g, 8.33 mmol) in dichloromethane (50 mL) at 0° C. The reaction mixture was warmed to room temperature and stirred for 1.5 h. The reaction was quenched ice water and extracted with dichloromethane. The combined organic layer was washed successively with aqueous sodium bicarbonate, water, brine; dried over anhydrous sodium sulfate and concentrated in vacuum to afford the crude intermediate. Purification by column chromatography over silica gel (60-120 mesh) and using 3% ethyl acetate in pet ether as the eluent afforded 1.8 g (75.63%) of MQ-S2 as an off white solid.

Step 4 (MQ-S3):

A solution of MQ-S2 (1.1 g, 3.85 mmol) and tri-n-butylvinyl tin (1.4 mL, 4.81 mmol) in toluene (60 mL) was purged with argon gas for 5 min. tetrakis-(tri-phenyl-phosphine)-palladium (89 mg, 0.08 mmol) was added and the mixture was continuously purged for another 5 min. The reaction mass was heated in a sealed tube at 110° C. for 8 h. The reaction mass was filtered over celite and washed with ethyl acetate. The combined filtrate and washing portion was concentrated in vacuum to afford the crude intermediate. Purification by column chromatography over silica gel (60-120 mesh) and using 2% ethyl acetate in pet ether as the eluent afforded 900 mg (100%) of MQ-S3 as a colorless syrup.

Step 5 (MR-S1):

t-Butylhypochlorite (1.32 mL, 11.59 mmol) was added to a stirred solution of t-butyl carbamate (1.35 g, 11.54 mmol) in 1-propanol (15.4 mL) and 0.4 N aqueous sodium hydroxide (470 mg in 29.4 mL water) at 10-15° C. and the mixture was stirred for 15 min. A solution of (DHQ)$_2$PHAL (150 mg, 0.19 mmol) in 1-propanol (15.4 mL) was added, followed by a solution of MQ-S3 (900 mg, 3.85 mmol) in 1-propanol (15.4 mL). Finally potassium osmatedihydrate (57 mg, 0.15 mmol) was added and the reaction mixture was stirred for 15 min at room temperature. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Purification by column chromatography over silica gel (100-200 mesh) and using 25-26% ethyl acetate in pet ether as the eluent afforded 510 mg (36.1%) of MR-S1 as a white solid.

Step 6 (MR-S2):

Thionyl chloride (0.8 mL, 10.90 mmol) was added to a solution of MR-S1 (500 mg, 1.36 mmol) in tetrahydrofuran (20 mL) at 0° C. The reaction mixture was warmed to room temperature and stirred for 4 h. The solvent was evaporated in vacuum and the resulting mass was partitioned between saturated sodium bicarbonate solution and ethyl acetate. The organic layer was separated and the aqueous layer was extracted with ethyl acetate. The combined organic layer was washed successively with water, brine; dried over anhydrous sodium sulfate and concentrated in vacuum to afford the crude intermediate, which was triturated with pet ether and dried to afford 390 mg (97.99%) of MR-S2 as a pale yellow solid.

Step 7 (MR-S3):

A mixture of MR-S2 (390 mg, 1.33 mmol), 4-Bromo-1,2-diaminobenzene (300 mg, 1.60 mmol) and cesium fluoride (404 mg, 2.66 mmol) in 1,4-dioxane (15 mL) was purged with argon gas for 15 min. Copper iodide (38 mg, 0.20 mmol) and 1,2-diaminocyclohexane (23 mg, 0.20 mmol) were added and the mixture was continuously purged for another 10 min. The reaction mixture was heated in a sealed tube for 18 h at 110-115° C. The reaction mass was filtered through celite, washed with dichloromethane and the filtrate was concentrated under reduced pressure to afford the crude intermediate. Purification by column chromatography over neutral alumina and using 1-2% methanol in dichloromethane as the eluent afforded 360 mg (67.84%) of MR-S3 as a pale brown solid.

Step 8 (Example 23):

Formamidine acetate (365 mg, 3.51 mmol) was added to a solution of MR-S3 (350 mg, 0.88 mmol) in acetonitrile (10 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by triturating with diethyl ether:dichloromethane:ethyl acetate (8:1:1) afforded 200 mg (55.40%) of Example 23 as a brown solid.

Melting range: 156.2-159.8° C.; $^1$H-NMR (400 MHz, DMSO-d6): δ 7.97 (s, 1H); 7.65 (s, 1H); 7.55 (d, 1H); 7.35 (d, 1H); 7.26 (merged with CDCl$_3$, 1H); 6.65 (d, 2H); 5.81 (t, 1H); 4.91 (t, 1H); 4.26 (q, 1H); 3.60 (t, 2H); 3.48 (t, 2H); 2.53-2.43 (m, 2H); MS=410.0 (M+1); HPLC~97.77%; Chiral HPLC~98.59%.

Example 24

(S)-5-(3-(1H-benzo[d]imidazol-5-yl)-2-oxooxazolidin-4-yl)-2-(3,3-difluoropyrrolidin-1-yl)benzonitrile Step 1 (MP-S1):

Potassium carbonate (2.07 g, 15 mmol) was added to a solution of 3-hydroxypyrrolidine hydrochloride (0.617 g, 5 mmol) in dimethylformamide (20 mL), followed by 2-flouro-5-bromo-benzonitrile (1 g, 5 mmol) and the mixture was stirred in a sealed tube at 90° C. for 20 h. The reaction mass was cooled to room temperature and the solvent was evaporated under vacuum. The remaining mass was dissolved in ethyl acetate, washed with water, brine; dried over anhydrous sodium sulfate and concentrated in vacuum to afford 1.3 g of MP-S1 as a gummy red liquid.

Step 2 (MQ-S1):

Dry dimethylsulfoxide (1.39 mL, 20 mmol) was added drop wise to a stirred solution of oxalylchloride (0.84 mL, 10 mol) in dichloromethane (30 m L) at −78° C. and the mixture was stirred for 20 min at the same temperature. A solution of MP-S1 (1.31 g, 4.9 mmol) in dichloromethane (20 mL) was added and the reaction mixture was stirred for 1 h at −78° C. Triethylamine (3.25 mL, 25 mmol) was added and the mixture was stirred for 15 min at −78° C., than warmed to room temperature and further stirred for 45 min. The reaction was quenched with ice water and the organic layer was separated. The aqueous layer was extracted with dichloromethane and the combined organic layer was washed successively with water, brine; dried over anhydrous sodium sulfate and concentrated in vacuum to afford 1.34 g of MQ-S2 as an orange solid.

Step 3 (MQ-S2):

Diethylamino sulfurtrifluoride (1.24 mL, 4.6 mmol) was added to a solution of MQ-S1 (8 g, 35 mmol) in dichloromethane (23 mL) at 0° C. The reaction mass was warmed to room temperature and stirred for 90 min. The reaction was quenched with ice water and the organic layer was separated. The aqueous layer was extracted with dichloromethane. The combined organic layer was washed successively with aqueous sodium bicarbonate, water, brine; dried over anhydrous sodium sulfate and concentrated in vacuum to afford the crude intermediate. Purification by column chromatography over silica gel (100-200 mesh) and using 0-5% ethyl acetate in pet ether as the eluent afforded 960 mg of MQ-S2 as a white solid.

Step 4 (MQ-S3):

A mixture of MQ-S2 (0.84 g, 2.9 mmol), tri-n-butylvinyl tin (1.1 mL, 3.62 mmol) in toluene was purged for 5 min using argon gas. Tetrakis(triphenylphosphine) palladium (0.067 g, 0.02 mmol) was added and the mixture was continuously purged 5 min. Thereafter the mixture was refluxed for 8 h. The reaction mixture was filtered over celite bed, washed with ethyl acetate and concentrated under reduced pressure to afford the crude intermediate. Purification by column chromatography over silica gel (60-120 mesh) and using 0-2% ethyl acetate in pet ether as the eluent afforded 700 mg of MQ-S3 as a colorless liquid.

Step 5 (MR-S1):

t-Butylhypochlorite (1.023 mL, 8.99 mmol) was added to a stirred solution of t-butyl carbamate (1.049 g, 8.97 mmol) in 1-propanol (12 mL) and 0.4 N aqueous sodium hydroxide (0.364 g in 22.8 mL water) at 15° C. and the mixture was stirred for 15 min. A solution of (DHQ)$_2$PHAL (116 mg, 0.14 mmol) in 1-propanol (12 mL) was added and the mixture was stirred for 5 min. A solution of MQ-S3 (0.7 g, 2.99 mmol) in 1-propanol (12 mL) was added and the mixture was stirred for 5 min. Finally potassium osmatedihydrate (44 mg, 0.11 mmol) was added and the reaction mixture was stirred for 5 min at 15° C., warmed to room temperature and further stirred for 5 min. The reaction was quenched with saturated sodium sulphite solution and extracted with ethyl acetate. The combined organic layer was washed successively with water, brine; dried over anhydrous sodium sulfate and concentrated under reduced pressure to afford the crude intermediate. Another similar batch was kept and Purification of both batches by column chromatography over silica gel (60-120 mesh) and using 0-28% ethyl acetate in pet ether as the eluent afforded 380 mg of MR-S1 as a yellow liquid.

Step 6 (MR-S2):

A solution of MR-S1 (0.4 g, 1.08 mmol) in tetrahydrofuran (10 mL) was added to a solution of potassium t-butoxide (0.4 g, 1.08 mmol) in tetrahydrofuran (10 mL) at 0° C. The reaction mixture was warmed to room temperature and stirred for 2 h. The reaction was acidified with acetic acid and the pH-value was adjusted to pH-6. The mixture was extracted with ethyl acetate and the separated organic layer was washed successively with water, brine; dried over anhydrous sodium sulfate and concentrated in vacuum to afford 346 mg of MR-S2 as a brown gummy solid.

Step 7 (MR-S3):

A mixture of MR-S2 (0.406 g, 1.38 mmol), 1,2-diamino-4-bromobenzene (261 mg, 1.38 mmol) and cesium fluoride (0.409 g, 2.7 mmol) in 1,4-dioxan (25 mL) was purged with argon gas for 10 min. Copper iodide (131 mg, 0.69 mmol) was added and the reaction mixture was continuously purged for another 10 min. Finally 1,2-diaminocyclohexane (0.02 ml, 0.17 mmol) was added and the mixture was further purged for 10 min. The reaction mass was stirred at 110-115° C. in a sealed tube for 14 h. The reaction mixture was cooled to room temperature, filtered though celite, washed with 10% methanol in dichloromethane and concentrated under reduced pressure to afford the crude intermediate. Purification by column chromatography over neutral alumina and using 0-1.6% methanol in chloroform as the eluent afforded 269 mg of MR-S3 as a brown gummy solid.

Step 8 (Example 24):

Formamidine acetate (350 mg, 3 mmol) was added to a solution of MR-S3 (269 mg, 0.67 mmol) in acetonitrile (15 mL) and the mixture was refluxed for 30 min. The reaction mixture was concentrated under reduced pressure and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification was done by preparative HPLC using the following conditions:

Column: Packed C-18 (250*25 mm*10μ); mobile phase: A: acetonitrile; B: 10 mM ammonium acetate (50:50); flow rate: 25 mL/min; used diluent: ACN+MeOH+mobile phase; method: gradient.

The corresponding fractions were evaporated in vacuum and the resulting mass was partitioned between water and dichloromethane. The organic layer was separated and the aqueous layer was extracted with dichloromethane. The combined organic layer was washed with water, brine; dried over anhydrous sodium sulfate and concentrated in vacuum to afford 69 mg of Example 24 as a brown solid.

$^1$H-NMR (400 MHz, DMSO-d6): δ 8.17 (s, 1H); 7.64-7.47 (m, 4H); 7.24 (d, 1H); 6.79 (d, 1H); 5.68 (t, 1H); 4.78 (t, 1H); 4.14 (t, 1H); 3.90 (t, 2H); 3.70 (t, 2H); 2.50-2.43 (merged with DMSO, 2H); MS=410.0 (M+1); HPLC~98.07%; Chiral HPLC~94.81%.

Example 25

(S)-3-(1H-benzo[d]imidazol-5-yl)-4-(4-(4,4-difluorocyclohexyl)-2-fluorophenyl)oxazolidin-2-one Step 1 (MS-S1):
3-Fluoro-1-bromobenzene (1 mL, 11.6 mmol) was added to a mixture of magnesium (1.2 g, 48.0 mmol) and a small amount (tip of a spatula) of iodine in dry tetrahydrofuran (20 mL) under organ atmosphere. After the color changed from bluish to colorless the remaining 3-fluoro-1-bromobenzene (3.3 mL, 38.4 mmol) was added and the mixture was stirred for 2 h at 50° C. 1,4-cyclohexane monoethyleneketal (7.2 g, 50 mmol) was added and the mixture was stirred at room temperature for 1 h. The reaction was quenched with saturated ammonium chloride, extracted with ethyl acetate and the separated organic layer was washed successively with water, brine; dried over anhydrous sodium sulfate and concentrated in vacuum to afford the crude intermediate. Purification by column chromatography over silica gel (60-120 mesh) and using 15% ethyl acetate in pet ether as the eluent afforded 4.0 g (50%) of MS-S1 as a white solid.

Step 2 (MS-S2):
A mixture of MS-S1 (4.0 g, 15.8 mmol) and trifluoro acetic acid (40 mL) was stirred at 80° C. for 1 h. The mixture was evaporated in vacuum, afterwards basified with saturated sodium bicarbonate and extracted with ethyl acetate. The combined organic layer was washed successively with water, brine; dried over anhydrous sodium sulfate and concentrated in vacuum to afford 4 g of the intermediate MS-S2 as a yellow liquid, further used without any purification.

Step 3 (MS-S3):
A solution of MS-S2 (4 g, 21.0 mmol) in absolute ethanol (100 mL) was hydrogenated over 10% Pd—C in a Parr apparatus (70 psi) for 5 h. The reaction mass was filtered through celite and washed with ethanol. The combined filtrate and washing portion was concentrated under reduced pressure to afford the crude intermediate. Purification by column chromatography over silica gel (60-120 mesh) and using 7% ethyl acetate in pet ether as the eluent afforded 2.7 g (66%) of MS-S3 as a colorless liquid.

Step 4 (MS-S4):
Oxalyl chloride (7.1 g, 56.2 mmol) and aluminum chloride (7.5 g. 56.2 mmol) were successively added to a solution of MS-S3 (2.7 g, 14.0 mmol) in dichloromethane (60 mL) at −30° C. and the mixture was stirred for 2 h at room temperature. Methanol (20 mL) was added at −30° C. and the reaction mixture was warmed to room temperature and stirred for 12 h at this temperature. The reaction was quenched with ice water, basified with saturated sodium bicarbonate and extracted with dichloromethane. The separated organic layer was washed successively with water, brine; dried over anhydrous sodium sulfate and concentrated in vacuum to afford the crude product. Purification by column chromatography over silica gel (60-120 mesh) and using 15% ethyl acetate in pet ether as the eluent afforded 4.0 g (50%) of MS-S4 as an off white solid.

Step 5 (MS-S5):
Diethylamino sulfurtrifluoride (3.35 mL, 24.1 mmol) was added to a solution of MS-S4 (2.0 g, 8.0 mmol) in dichloromethane (30 mL) at 0° C. and the mixture was stirred for 2 h at room temperature. The reaction was quenched with ice water and extracted with dichloromethane. The combined organic layer was washed successively with water, brine; dried over anhydrous sodium sulfate and concentrated in vacuum to afford 2 g, (91%) of MS-S5 as a colorless oil, further used without any purification.

Step 6 (MS-S6):
A solution of MS-S5 (2 g, 7.3 mmol) in tetrahydrofuran (20 mL) was added to a suspension of lithium-aluminum hydride in hexane (279 mg, 7.3 mmol) at 0° C. and the mixture was stirred for 1 h at room temperature. The reaction was quenched with saturated sodium sulfate solution and filtered. The filtrate was partitioned between water and ethyl acetate. The separated organic layer was washed successively with water, brine; dried over anhydrous sodium sulfate and concentrated in vacuum to afforded 2 g of MS-S6 as a colorless liquid, further used without any purification.

Step 7 (MU-S1):
2-Iodoxybenzoic acid (6.8 g, 24.5 mmol) was added to a solution of MS-S6 (2 g, 8.1 mmol) in dichloromethane (30 mL) and dimethylsulfoxide (10 mL) and the mixture was stirred for 8 h at room temperature. The reaction mass was filtered and washed with dichloromethane. The combined filtrate and washing portion was washed successively with water, brine; dried over anhydrous sodium sulfate and concentrated in vacuum to afford the crude intermediate. Purification by column chromatography over silica gel (60-120 mesh) and using 2% ethyl acetate in pet ether as the eluent afforded 1.0 g (50%) of MU-S1 as a pale yellow liquid.

Step 8 (MU-S2):
N-Butyl lithium (2.2 M; 3.7 mL, 8.2 mmol) was added to a stirred solution of triphenylphosphonium methylbromide (2.95 g, 8.2 mmol) in tetrahydrofuran (10 mL) at −30° C. and the mixture was stirred for 30 min at 0-5° C. A solution of MU-S1 (1.0 g, 4.1 mmol) in tetrahydrofuran (10 mL) was added drop wise at −30° C. The temperature was warmed to room temperature and the reaction mixture was stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 1% ethyl acetate in pet ether as the eluent afforded 800 mg (80%) of MU-S2 as a pale yellow liquid.

Step 9 (MU-S3):

t-Butylhypochlorite (1.14 mL, 10.0 mmol) was added to a stirred solution of t-butyl carbamate (1.17 g, 9.8 mmol) in 1-propanol (13.2 mL) and 0.4 N aqueous sodium hydroxide (406 mg in 25.4 mL water) at 15° C. and the mixture was stirred for 15 min. A solution of (DHQ)$_2$PHAL (128 mg, 0.16 mmol) in 1-propanol (13.2 mL) was added followed by a solution of MU-S2 (800 mg, 3.2 mmol) in 1-propanol (13.2 mL. Finally potassium osmatedihydrate (49 mg, 0.12 mmol) was added and the reaction mixture was stirred for 15 min at room temperature. The reaction was quenched with saturated sodium sulfate solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 18-20% ethyl acetate in pet ether as the eluent afforded 500 mg (40%) of MU-S3 as a white solid.

Step 10 (MU-S4):

Potassium-t-butoxide (450 mg, 4.0 mmol) was added in 2 portions to a stirred solution of MU-S3 (500 mg, 1.3 mmol) in tetrahydrofuran (20 mL) at 0° C. over 15 min and the mixture was stirred for 2 h at room temperature. The reaction was neutralized with 10% acetic acid and extracted with ethyl acetate. The combined organic layer was washed successively with water, brine; dried over anhydrous sodium sulfate and concentrated under reduced pressure to afforded 300 mg (75%) of MU-S4 as a brown solid.

Step 11 (MU-S5):

A mixture of MU-S4 (300 mg, 1.0 mmol), 4-Bromo-1,2-diaminobenzene (157 mg, 1.0 mmol) and cesium fluoride (297 mg, 2.0 mmol) in 1,4-dioxane (40 mL) was purged with argon gas for 30 min. Copper iodide (28 mg, 0.38 mmol) and 1,2-diaminocyclohexane (17 mg, 0.38 mmol) were added and the mixture was continuously purged for another 10 min. The reaction was heated in a sealed tube for 16 h at 105-110° C. The reaction mixture was filtered through celite, washed with dioxane and the filtrate was concentrated under reduced pressure to afford the crude intermediate. Purification by column chromatography over neutral alumina and using 1.5-2% methanol in dichloromethane as the eluent afforded 200 mg (49%) of MU-S5 as a brown solid.

Step 12 (Example 25):

Formamidine acetate (150 mg, 1.48 mmol) was added to a solution of MU-S5 (200 mg, 0.49 mmol) in acetonitrile (20 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by column chromatography over neutral alumina and using 2-2.5% methanol in dichloromethane as the eluent to afforded 100 mg (49%) of Example 25 as an off white solid.

Melting range: 251.9-253.7° C.; $^1$H-NMR (400 MHz, DMSO-d6): δ 12.45 (s, 1H); 8.17 (s, 1H); 7.62 (d, 1H); 7.48 (d, 1H); 7.37-7.25 (m, 2H); 7.11-7.03 (m, 2H); 5.91 (q, 1H); 4.84 (t, 1H); 4.24 (q, 1H); 2.61 (t, 1H); 2.04-1.77 (m, 6H); 1.63-1.54 (m, 2H); MS=416.08 (M+1); HPLC~96.71%.

Example 26

(S)-3-(1H-benzo[d]imidazol-5-yl)-4-(4-(4,4-difluorocyclohexyl)-3-fluorophenyl)oxazolidin-2-one Step 1 (MT-S1):

Boranmethyl sulfide in ether (5.0 M; 38.3 mL, 191.8 mmol) was added to a solution of 4-bromo-3-fluorobenzoic acid (21.0 g, 95.9 mmol) in dry tetrahydrofuran (250 mL) at 0° C. and the reaction mixture was stirred at room temperature for 6 h. The reaction was quenched with saturated sodium hydrogen carbonate solution, extracted with ethyl acetate, and the combined organic layers were washed with water, brine; dried over anhydrous sodium sulfate and filtered. The solvent was evaporated under vacuum to afford 18 g (91.6%) of MT-S1 as a colorless liquid, further used without any purification.

Step 2 (MT-S2):

tert-Butylmethylsilyl chloride (16.5 g, 105.3 mmol) and imidazole (11.95 g, 175.6 mmol) was added to a solution of MT-S1 (18 g, 87.8 mmol) in dimethylformamide (200 mL) at −10° C. and the reaction mixture was stirred at room temperature for 48 h. The reaction was quenched with saturated ammonium chloride solution, extracted with ethyl acetate and the combined organic layer was washed with water, brine; dried over anhydrous sodium sulfate, filtered and the solvent was evaporated under vacuum to afford the crude intermediate. Purification by column chromatography over silica gel (60-120 mesh) and using 2-5% ethyl acetate in pet ether as the eluent afforded 20 g (71.4%) of MT-S2 as a colorless liquid.

Step 3 (MT-S3):

N-Butyl lithium in hexane (2.2 M; 56.6 mL, 125.4 mmol) was added was to a solution of MT-S2 (20 g, 62.7 mmol) in dry tetrahydrofuran (200 mL) at −78° C. and the mixture was stirred for 30 min. A solution of 1,4-cyclohexane monoethyleneketal (9.8 g, 62.7 mmol) in dry tetrahydrofuran (50 mL) at −78° C. was added and the temperature was warmed to 0° C. The reaction was quenched with saturated ammonium chloride solution, extracted with ethyl acetate and the combined organic layer was were washed with water, brine; dried over anhydrous sodium sulfate, filtered and the solvent was evaporated under vacuum to afford 18 g of the crude intermediate MT-S3 as a yellow oily liquid, further used without any purification.

Step 4 (MT-S4):

A mixture of MT-S3 (15.0 g, 37.87 mmol), 6N HCl (100 mL) in 1,4-dioxane (100 mL) was stirred at 80° C. for 3 h. The reaction was cooled to room temperature and the solvent was evaporated under vacuum. The remaining mass was diluted with water, extracted with ethyl acetate and the combined organic layer was washed with water, brine; dried over anhydrous sodium sulfate, filtered and the solvent was evaporated under vacuum to afford the crude intermediate. Purification by column chromatography over silica gel (100-200 mesh) and using 27% ethyl acetate in pet ether as the eluent afforded 4 g of MT-S4 as a yellow oily liquid.

Step 5 (MT-S5):

To a solution of MT-S4 (4.0 g, 18.18 mmol) in dichloromethane (40 mL) pyridine (7.32 mL, 90.9 mmol) was added at 0° C. and the mixture was stirred for 10 min. Acetyl chloride (1.93 mL, 27.27 mmol) was added and the reaction mixture was stirred for 2 h at room temperature. The reaction was cooled to 0° C. and then quenched with 2 N hydrochloric acid. The organic layer was separated, washed with water, brine; dried over anhydrous sodium sulfate, filtered and the solvent was evaporated under vacuum to afford the crude intermediate. Purification by column chromatography over silica gel (100-200 mesh) and using 15% ethyl acetate in pet ether as the eluent afforded 2 g (42%) of MT-S5 as a yellow oily liquid.

Step 6 (MT-S6):

A solution of MT-S5 (2 g, 7.63 mmol) in absolute ethanol (40 mL) was hydrogenated over 10% Pd—C) in a Parr apparatus (40 psi) for 3 h. The reaction mass was filtered through celite and washed with ethanol. The combined filtrates were concentrated under reduced pressure to afford the crude intermediate. Purification by column chromatography over silica gel (100-200 mesh) and using 15% ethyl acetate in pet ether as the eluent afforded 1.7 g of MT-S6 (84.5%) as an off-white solid.

Step 7 (MT-S7):

Diethylamino sulfurtrifluoride (2.65 mL, 19.3 mmol) was added to a solution of MT-S6 (1.7 g, 6.4 mmol) in dichloromethane (30 mL) at 0° C. and the mixture was stirred for 2 h at room temperature. The reaction was quenched with ice water and extracted with dichloromethane. The combined organic layer was successively washed with water, brine; dried over anhydrous sodium sulfate and concentrated in vacuum to afford the crude intermediate. Purification by column chromatography over silica gel (60-120 mesh) and using 4% ethyl acetate in pet ether as the eluent afforded 1.5 g (81%) of MT-S7 as a brown oily liquid.

Step 8 (MT-S8):

Lithiumhydroxide monohydride (758.5 mg, 15.73 mmol) was added to a solution of MT-S7 (1.5 g, 5.24 mmol) in tetrahydrofuran:water (1 mL:1.20 mL) at room temperature and the mixture was stirred for 5 h. The organic solvent was evaporated under vacuum. The resulting aqueous layer was cooled to 0° C. and acidified with 1 N hydrochloric acid and extracted with dichloromethane. The combined organic layer was washed successively with water, brine; dried over anhydrous sodium sulfate and concentrated in vacuum to afford 1.2 g (93%) of MT-S8 as a yellow color liquid, further used without any purification.

Step 9 (MU-S1):

2-Iodoxy benzoic acid (4.13 mg, 14.75 mmol) was added to a solution of MT-S8 (1.2 g, 4.9 mmol) in dichloromethane (30 mL) and dimethylsulfoxide (4 mL) and the mixture was stirred for 5 h at room temperature. The reaction mass was filtered and washed with dichloromethane. The combined filtrates were washed successively with water, brine; dried over anhydrous sodium sulfate and concentrated in vacuum to afford the crude intermediate. Purification by column chromatography over silica gel (60-120 mesh) and using 5% ethyl acetate in pet ether as the eluent afforded 900 mg (75.6%) of MU-S1 as a yellow solid.

Step 10 (MU-S2):

N-Butyllithium (2.2 M; 3.4 mL, 7.44 mmol) was added to a stirred solution of Triphenylphosphonium methylbromide (2.65 g, 7.44 mmol) in tetrahydrofuran (10 mL) at −60° C. and the mixture was stirred for 30 min at 0-5° C. A solution of MU-S1 (900 mg, 3.72 mmol) in tetrahydrofuran (10 mL) was added drop wise at −30° C. The temperature mass was warmed to room temperature and the reaction mixture was stirred for 1 h. The reaction was quenched with saturated ammonium chloride solution and extracted with ethyl acetate. The combined organic layer was washed successively with water, brine; dried over anhydrous sodium sulfate and concentrated under reduced pressure to afford the crude intermediate. Purification by column chromatography over silica gel (60-120 mesh) and using 2% ethyl acetate in pet ether as the eluent afforded 680 mg (75.7%) of MU-S2 as a pale yellow liquid.

Step 11 (MU-S3):

t-Butylhypochlorite (97 mL, 8.52 mmol) was added to a stirred solution of t-butyl carbamate (994.5 mg, 8.5 mmol) in 1-propanol (11.2 mL) and 0.4 N aqueous sodium hydroxide (345.7 mg in 21.3 mL water, 8.64 mmol) at 10-15° C. and the mixture was stirred for 15 min. A solution of (DHQ)$_2$PHAL (110.03 mg, 0.14 mmol) in 1-propanol (11.2 mL) was added, followed by a solution of MU-S2 (680 mg, 2.8 mmol) in 1-propanol (11.2 mL). Finally potassium osmatedihydrate (41.7 mg, 0.11 mmol) was added and the reaction mixture was stirred for 15 min at room temperature. The reaction was quenched with saturated sodium sulfite solution and extracted with ethyl acetate. The combined organic layer was washed successively with water, brine; dried over anhydrous sodium sulfate and concentrated under reduced pressure to afford the crude intermediate. Purification by column chromatography over silica gel (100-200 mesh) and using 16-20% ethyl acetate in pet ether as the eluent afforded 500 mg (47.6%) of MU-S3 as an off-white solid.

Step 12 (MU-S4):

Potassium t-butoxide (450 mg, 4.02 mmol) was slowly added in 2 lots over 15 min to a stirred solution of MU-S3 (500 mg, 1.34 mmol) in tetrahydrofuran (20 mL) at 0° C. and the solution was stirred for 3 h at room temperature. The reaction mixture was neutralized with 10% acetic acid and extracted with ethyl acetate. The combined organic layer was washed successively with water, brine; dried over anhydrous sodium sulfate and concentrated under reduced pressure to afford 300 mg (75%) of MU-S4 as a yellow solid, further used without any purification.

Step 13 (MU-S5):

A mixture of MU-S4 (300 mg, 1.0 mmol), 4-Bromo-1,2-diaminobenzene (187 mg, 1.0 mmol) and cesium fluoride (305 mg, 2.0 mmol) in 1,4-dioxane (40 mL) was purged with argon gas for 30 min. Copper iodide (28.6 mg, 0.15 mmol) and 1,2-diaminocyclohexane (17 mg, 0.15 mmol) were added and the mixture was continuously purged for another 10 min. The reaction was heated in a sealed tube for 24 h at 105-110° C. The reaction mixture was filtered through celite, washed with dioxane and the filtrate was concentrated under reduced pressure to afford the crude intermediate. Purification by column chromatography over neutral alumina and using 1.3-2% methanol in chloroform as the eluent afforded 200 mg (49%) of MU-S5 as a brown solid.

Step 14 (Example 26):

Formamidine acetate (154.07 mg, 1.48 mol) was added to a solution of MU-S5 (200 mg, 0.49 mmol) in acetonitrile (20 mL) and the mixture was refluxed for 2 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by washing with ether and evaporation of the solvent under vacuum afforded 130 mg (63%) of Example 26 as an off white solid.

Melting range: 270-273.5° C.; $^1$H-NMR (400 MHz, DMSO-d6): δ 8.17 (s, 1H); 7.61 (d, 1H); 7.56-7.43 (m, 1H); 7.36-7.21 (m, 3H); 5.75 (q, 1H); 4.80 (t, 1H); 4.15 (q, 1H); 2.89 (t, 1H); 2.04-1.60 (m, 8H); MS=416.2 (M+1); HPLC~99.16%: Chiral HPLC~99.60%.

Example 27

(S)-3-(1H-benzo[d]imidazol-5-yl)-4-(4-(4,4-difluorocyclohexyl)phenyl)oxazolidin-2-one Step 1 (MV-S1):

Sodium borohydride (0.54 g, 14.36 mmol) was added to a solution of 4-phenylcyclohexanone (5.0 g, 28.73 mmol) in ethanol (50 mL) at room temperature and the solution was stirred for 30 min. The organic solvent was evaporated, ammonium chloride solution was added and the mixture was extracted with dichloromethane. The combined organic layer was washed successively with water, brine; dried over anhydrous sodium sulfate and the solvent was evaporated to afford 5.0 g of MV-S1 as white color solid, further used without any purification.

Step 2 (MV-S2):

Tetrabutylammoniumhydrogen sulfate (1.42 g, 4.21 mmol) and dimethylsulfate (14.15 g, 112.35 mmol) were added to a solution of MV-S1 (5.0 g, 28.08 mmol) in aqueous sodium hydroxide (50%):toluene (1:1; 100 mL) and the mixture was stirred at 80° C. for 48 h. The reaction mixture was diluted with water, acidified by hydrochlorid acid (10%) and extracted with ethyl acetate. The combined organic layer was washed with water, brine; dried over anhydrous sodium sulfate and the solvent was evaporated to afford the crude intermediate. Purification by column chromatography over silica gel (60-120 mesh) and using 2-4% ethyl acetate in pet ether as the eluent afforded 4.0 g of MV-S3 as a colorless oil.

Step 3 (MV-S3):

Ethylchloro oxalate (7.16 mL, 63.15 mmol) and aluminium chloride (8.42 g, 63.15 mmol) were added to a solution of MV-S2 (2.0 g, 13.33 mmol) in dichloromethane (60 mL) at −20° C. The mixture was stirred for 1 h, warmed to room temperature and further stirred for 2 h. The reaction was quenched with saturated sodium hydrogen carbonate solution at 0° C., filtered and washed with excess of ethyl acetate (200 mL). The organic layer was separated, washed with water, brine; dried over anhydrous sodium sulfate and evaporated under reduced pressure to afford 3.0 g MV-S3 as a brown color liquid, further used without any purification.

Step 4 (MV-S4):

Hydroxylamine hydrochloride (1.44 g, 20.68 mmol) and sodium acetate (1.69 g, 20.68 mmol) were added to a solution of MV-S3 (2.5 g, 10 mmol) in ethanol (30 mL) and the mixture was stirred at 80° C. for 2 h. The reaction mixture was cooled to room temperature and filtered. The filtrate was evaporated to afford the crude intermediate. The mass was suspended in water and extracted with dichloromethane. The combined organic layer was dried over anhydrous sodium sulfate and evaporated to afford 3.1 g of MV-S4 as a colorless liquid, further used without any purification.

Step 5 (MV-S5):

MV-S4 (3.1 g, 10.16 mmol) in absolute ethanol was hydrogenated over 10% Pd—C (0.62 g, 20%) in a Parr apparatus (80 Psi) at room temperature 12 h. The reaction mixture was filtered through celite and the solvent was evaporated to afford 3.0 g of MV-S5 as a colorless liquid, further used without any purification.

Step 6 (MV-S6):

Boc anhydride (2.23 g, 10.3 mmol) was added to a solution of MV-S5 (3.0 g, 10.30 mmol) and Triethylamine (1.6 mL, 12.37 mmol) in dichloromethane (30 mL), and the mixture was stirred for 12 h at room temperature. The reaction mixture was washed with water (30 mL) and extracted with dichloromethane (3×50 mL). The combined organic layer was washed with brine (20 mL); dried over anhydrous sodium sulfate and the solvent was evaporated to afford 2.9 g of the MV-S6 as a brown oil, further used without any purification.

Step 7 (MV-S7):

Sodium borohydride (0.82 g, 21.48 mmol) was added to a solution of MV-S6 (2.1 g, 5.37 mmol) in ethanol (30 mL) at room temperature and the mixture was stirred at 50° C. for 3 h. The solvent was evaporated under reduced pressure and saturated ammonium chlorid solution (25 mL) was added. The mixture was diluted with water and extracted with dichloromethane. The combined organic layer was washed with brine; the solvent was evaporated afford 1.5 g of MV-S7 as a gummy mass, further used without any purification.

Step 8 (MV-S8):

Thionyl chloride (2.5 mL, 34.38 mmol) was added to a solution of MV-S7 (1.5 g, 4.29 mmol) in tetrahydrofuran (20 mL) at 0° C. The reaction mixture was warmed to room temperature and further stirred for 12 h. The solvent was evaporated and saturated sodium hydrogen carbonate solution (10 mL) was added. The mixture was extracted with chloroform (3×25 mL) and the combined organic layer was dried over anhydrous sodium sulfate and concentrated in vacuum to afford 1.0 g of MV-S8 as an off white solid, further used without any purification.

Step 9 (MV-S9):

A mixture of MV-S8 (1 g, 3.63 mmol), 1,2-diamino4-bromobenzene (0.74 g, 3.99 mmol), cesium fluoride (1.1 g, 7.26 mmol) and copper iodide (0.1 g, 0.54 mmol) in 1,4-dioxane (15 mL) was purged with argon gas for 15 min. 1,2-diaminocyclohexane (61 mg, 0.22 mmol) was added and the reaction mixture was continuously purged for another 15 min. The reaction mixture was stirred in a sealed tube for 24 h at 120° C. The reaction mixture was filtered through celite, washed with dioxane and the solvent was evaporated under reduced pressure. Purification by column chromatography over neutral alumina and using 3% methanol in chloroform as the eluent afforded 1 g of MV-S9 as a pale brown solid.

Step 10 (MV-S10):

A solution of MV-S9 (1.1 g, 2.62 mmol) in formic acid (10 mL) was stirred for 1 h at 90° C. The reaction mixture was concentrated under reduced pressure and the resulting mass was basified with saturated sodium bicarbonate solution and extracted with chloroform. The combined organic layer was washed with water, brine; dried over anhydrous sodium sulfate and evaporated under reduced pressure to afford the crude intermediate. The mass was triturated with n-pentane and dried to afford 1 g of MV-S10.

Step 11 (MV-S11):

A solution of 18-crown-6-ether (4.46 g, 16.87 mmol) saturated with potassium iodide in dry dichloromethane (30 mL) was added to a solution of MV-S10 (1.1 g, 2.81 mmol) in dichloromethane (10 mL). The mixture was cooled to −30° C., boron tribromide (0.8 mL, 8.43 mmol) was added and the mixture was stirred at room temperature for 3 h. the reaction was quenched sodium bicarbonate solution, diluted with water and extracted with dichloromethane. The combined organic layer was washed with water, brine; dried over anhydrous sodium sulfate and evaporated to afford the crude intermediate. Purification over neutral alumina and using 3-4% methanol in chloroform as the eluent afforded 450 mg of MV-S11.

Step 12 (MV-S12):

A solution of MV-S11 (0.4 g, 1.06 mmol) in dichloromethane (20 mL) was added to a suspension of 2-Iodoxybenzoic acid (0.89 g, 3.18 mmol) in dimethylsulfoxide (7 mL) and the mixture was stirred at room temperature for 12 h. The reaction mixture was filtered, washed with saturated sodium bicarbonate solution, water, brine; dried over anhydrous sodium sulphate and evaporated the solvent under reduced pressure to afford 300 mg of MV-S12 as an off white solid. Purification by preparative TLC and using 4% methanol in chloroform as the eluent afforded 50 mg of MV-S12 as an off white solid.

Step 13 (Example 27):

Diethylaminosulfur triflouride (0.25 g, 0.31 mL, 1.6 mmol) was added to a solution of MV-S12 (0.15 g, 0.4 mmol) in dichloromethane (5 mL) at 0° C. and the mixture was refluxed for 48 hours. The reaction mixture was quenched with ice, basified with saturated bicarbonate solution and extracted with dichloromethane. The combined organic layer was washed with water, brine; dried over anhydrous sodium sulfate and evaporated afford 140 mg of the crude compound as a brown solid. Purification was done by preparative HPLC using the following conditions:

Column: Zodiacsil 220×50 mm 10μ, mobile phase: 0.01% ammonium carbonate in methanol T/% B: 0/50, 3/50, 20/90; flow rate: 20 mL/min, UV: 210 nm, used diluents: methanol, acetonitril.

The corresponding fractions were concentrated under reduced pressure and partitioned between water and chloroform. The separated organic layer was washed with brine; dried over anhydrous sodium sulfate and concentrated under reduced pressure afford 20 mg of Example 27 as a pale brown solid.

$^1$H-NMR (400 MHz, CDCl$_3$): δ 7.98 (s, 1H), 7.70 (s, 1H), 7.52 (s, 1H), 7.21-7.1 (Merged with CDCl$_3$, 4H), 5.45-5.41 (q, 1H), 4.81 (t, 1H), 4.25-4.22 (q, 1H), 2.53 (d, 1H), 2.17-2.02 (m, 2H), 1.86-1.25 (m, 7H): MS=398.1 (M+1); HPLC~98.36%.

Example 28

(S)-3-(1H-benzo[d]imidazol-5-yl)-4-(4-(3,3-difluorobutyl)-2,3-difluorophenyl)oxazolidin-2-one Step 1 (MW-S1):
Sodium borohydride (5.3 g, 140.84 mmol) was slowly added in 3 equal portions (over 25 min) to a solution of 2,3-difluorobenzaldehyde (20 g, 140.84 mmol) in methanol (200 mL) at 0° C. Due to the exothermic reaction the temperature raised up to ~50° C. The reaction mixture was stirred for 1 h and the solvent was evaporated under reduced pressure. Ethyl acetate and thereafter saturated ammonium chloride solution was added. The organic layer was separated and the aqueous layer was extracted with ethyl acetate. The combined organic layer was washed successively with water, brine; dried over anhydrous sodium sulfate and concentrated in vacuum to afford 20 g of MW-S1 as a colorless liquid, further used without any purification.

Step 2 (MW-S2):
Phosphorous tribromide (6.7 ml, 69.44 mmol) was added drop wise over 15 min to a solution of MW-S1 (20 g, 138.88 mmol) in diethylether (250 mL) at −10° C. The reaction mixture was stirred for 1 h. The reaction was quenched with saturated sodium hydrogen carbonate solution. The organic layer was separated and the aqueous layer was extracted with diethylether. The combined organic layer was washed successively with water, brine; dried over anhydrous sodium sulfate and concentrated in vacuum to afford 20 g of MW-S2 as a light brown liquid, further used without any purification.

Step 3 (MW-S3):
A mixture of MW-S3 (20 g, 96.618 mmol), 2,4-pentadione (9.6 mL, 96.618 mmol) and potassium carbonate (13.32 g, 96.618 mmol) in methanol (150 mL) was refluxed for 20 h. The solvent was filtered and evaporated in vacuum and the resulting mass was partitioned between water and ethyl acetate. The organic layer was separated and the aqueous layer was extracted with ethyl acetate. The combined organic layer was washed successively with water, brine; dried over anhydrous sodium sulfate and concentrated in vacuum to afford the crude intermediate. Purification by column chromatography over silica gel (60-120 mesh) and using 8-9% ethyl acetate in pet ether as the eluent afforded 14 g of MW-S3 as a pale yellow liquid.

Step 4 (MW-S4):
A solution of MW-S3 (14 g, 76.086 mmol), ethylene glycol (11.8 mL, 190.21 mmol) and p-toluenesulfonic acid (2.1 g, 11.413 mmol) in toluene (200 mL) was refluxed under Dean-Stark conditions for 3 h. The solvent was evaporated in vacuum and the resulting mass was partitioned between water and ethyl acetate. The organic layer was separated and the aqueous layer was extracted with ethyl acetate. The combined organic layer was washed successively with water, brine; dried over anhydrous sodium sulfate and concentrated in vacuum to afford the crude intermediate. Purification by column chromatography over silica gel (60-120 mesh) and using 6-8% ethyl acetate in pet ether as the eluent afforded 14.0 g (86.75%) of MW-S4 as a pale yellow liquid.

Step 5 (MW-S5):
n-Butyllithium in hexane (2.5 M; 20.9 mL, 52.16 mmol) was added to a solution of MW-S4 (10.0 g, 43.47 mmol) in dry tetrahydrofuran (80 mL) at −78° C. and the mixture was stirred for 1 h at the same temperature. The mass was slowly added to a solution of diethyl oxalate (9.53 g, 65.21 mmol) in tetrahydrofuran (60 mL) at −78° C. over 15 min. The reaction mixture was stirred for 1 h, thereby the temperature raised to −60° C. The reaction was quenched with saturated ammonium chloride solution and extracted with ethyl acetate. The combined organic layer was washed successively with water, brine; dried over anhydrous sodium sulfate and concentrated in vacuum to afford 14 g of MW-S5 as a yellow syrup, further used without any purification.

Step 6 (MY-S1):
Sodium acetate (7.97 g, 84.84 mmol) and hydroxylamine hydrochloride (5.85 g, 84.85 mmol) were added successively to a solution of MW-S5 (14 g, 42.42 mmol) in absolute ethanol (120 mL) and the mixture was refluxed for 1 h. The solvent was evaporated in vacuum and the resulting mass was partitioned between water and ethyl acetate. The combined organic layer was washed successively with water, brine; dried over anhydrous sodium sulfate and concentrated in vacuum to afford 14 g of MY-S1 as a yellow syrup.

Step 7 (MY-S2):
A solution of MY-S1 (14 g, 40.57 mmol) in absolute ethanol (200 mL) was hydrogenated over 10% Pd—C in a Parr apparatus (80 psi) for 20 h. The reaction mass was filtered through celite and washed with ethanol. The combined filtrate and washing portion was concentrated under reduced pressure to afford 14.0 g of MY-S2 as a pale brown syrup.

Step 8 (MY-S3):
Trifluoroacetic acid (150 mL) was added to a solution of MY-S2 (12.0 g, 36.25 mmol) in dichloromethane (50 mL) at 0° C. and the mixture was stirred for 3 h at room temperature. The solvent was evaporated in vacuum, the remaining mass was dissolved in hydrochlorid acid (6 N) and washed with 40% ethyl acetate in pet ether. The aqueous layer was basified with saturated sodium bicarbonate solution and extracted with dichloromethane. The combined organic layer was washed successively with water, brine; dried over anhydrous sodium sulfate and concentrated in vacuum to afford 6.01 g of MY-S3 as a yellow liquid.

Step 9 (MY-S4):
Triethyl amine (8.9 mL, 63.15 mmol) and Di-tert-butyl dicarbonate (5 mL, 23.15 mmol) were added successively to a solution of MY-S3 (6.0 g, 21.052 mmol) in dichloromethane (100 mL) and the mixture was stirred for 20 h at room temperature. Water was added and extracted with dichloromethane. The combined organic layer was washed successively with water, brine; dried over anhydrous sodium sulfate and concentrated in vacuum to afford the crude intermediate. Purification by column chromatography over silica gel (60-120 mesh) and using 20% ethyl acetate in pet ether as the eluent afforded 3.5 g of MY-S4 as a yellow gummy liquid.

Step 10 (MY-S5):

Diethylamino sulfurtrifluoride (1.6 mL, 11.75 mmol) was added to a solution of MY-S4 (1.50 g, 3.896 mmol) in dichloromethane (30 mL) at 0° C. and the mixture was stirred for 52 h at room temperature. The reaction was quenched with ice water and extracted with dichloromethane. The combined organic layer was washed successively with water, brine; dried over anhydrous sodium sulfate and concentrated to afford the crude intermediate. Purification by column chromatography over silica gel (60-120 mesh) and using 10% ethyl acetate in pet ether as the eluent afforded 800 mg of MY-S5 as a colorless oil.

Step 11 (MY-S6):

Sodium borohydride (150 mg, 3.93 mmol) was slowly added in 3 equal lots (over 15 min) to a solution of MY-S5 (800 mg, 1.965 mmol) in methanol (10 mL) at room temperature. Due to the exothermic reaction the temperature raised to ~50° C. The reaction mass was stirred for 1 h. Ethyl acetate was added and the reaction was quenched with saturated ammonium chloride solution. The organic layer was separated and the aqueous layer was extracted with ethyl acetate. The combined organic layer was washed successively with water, brine; dried over anhydrous sodium sulfate and concentrated in vacuum to afford 700 mg of MY-S6 as a white solid.

Step 12 (MAA-S1):

Potassium t-butoxide (540 mg, 4.807 mmol) was added in 4 lots to a stirred solution of MY-S6 (700 mg, 1.92 mmol) in tetrahydrofuran (25 mL) at 0° C. over 15 min and the mixture was stirred for 3 h at room temperature. The reaction was neutralized with 10% acetic acid and extracted with ethyl acetate. The combined organic layer was washed successively with water, brine; dried over anhydrous sodium sulfate and concentrated under reduced pressure to afford 400 mg of MAA-S1 as a white solid.

Step 13 (MAA-S2):

A mixture of MAA-S1 (400 mg, 1.38 mmol), 4-Bromo-1,2-diaminobenzene (257 mg, 1.38 mmol) and cesium fluoride (417 mg, 2.75 mmol) in 1-4dioxane (20 mL) was purged with argon gas for 30 min. Copper iodide (52 mg, 0.27 mmol) and 1,2-diaminocyclohexane (45 mg, 0.38 mmol) were added and the mixture was continuously purged for another 10 min. The reaction was heated in a sealed tube for 20 h at 105-110° C. The reaction mixture was filtered through celite, washed with dioxane and the filtrate was concentrated under reduced pressure to give the crude intermediate. Purification by column chromatography over neutral alumina and using 1.5-2% methanol in dichloromethane as the eluent afforded 250 mg of MAA-S2 as a brown solid.

Step 14 (Example 28):

Formamidine acetate (196 mg, 1.88 mmol) was added to a solution of MAA-S2 (250 mg, 0.63 mmol) in acetonitrile (20 mL) and the mixture was refluxed for 1 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product, which was triturated with diethyl ether and dried to afford 150 mg of Example 28 as an off white solid.

Melting range: 191.8-196.3° C.; $^1$H-NMR (400 MHz, DMSO-d6): δ 12.45 (s, 1H); 8.19 (s, 1H); 7.62 (d, 1H); 7.57-7.44 (m, 1H); 7.33-7.09 (m, 3H); 5.91 (q, 1H); 4.86 (t, 1H); 4.30 (q, 1H); 2.71 (t, 2H); 2.18-2.05 (m, 2H); 1.59 (t, 3H); MS=408.1 (M+1); HPLC~97.51%.

Example 29

(S)-3-(1H-benzo[d]imidazol-5-yl)-4-(4-(3,3-difluorobutyl)-3-fluorophenyl)oxazolidin-2-one Step 1 (MX-S1):

A mixture of 4-Bromo-2-Fluorobenzyl bromide (20 g, 74.65 mmol), 2,4-Pentadione (7.68 mL, 74.65 mmol) and potassium carbonate (10.32 g, 74.65 mmol) in methanol (200 mL) was refluxed for 16 h. The solvent was evaporated in vacuum and the resulting mass was partitioned between water and ethyl acetate. The organic layer was separated and the aqueous layer was extracted with ethyl acetate. The combined organic layer was washed successively with water, brine; dried over anhydrous sodium sulfate and concentrated in vacuum to afford the crude intermediate. Purification by column chromatography over silica gel (60-120 mesh) and using 8-9% ethyl acetate in pet ether as the eluent afforded 12 g (65.50%) of MX-S1 as a pale yellow liquid.

Step 2 (MX-S2):

A solution of MX-S1 (10.75 g, 43.88 mmol), ethylene glycol (6.1 mL, 109.69 mmol) and p-toluenesulfonic acid (1.25 g, 6.55 mmol) in toluene (100 mL) was refluxed under Dean-Stark conditions for 3 h. The solvent was evaporated in vacuum and the resulting residue was partitioned between water and ethyl acetate. The organic layer was separated and the aqueous layer was extracted with ethyl acetate. The combined organic layer was washed successively with water, brine; dried over anhydrous sodium sulfate and concentrated in vacuum to afford the crude intermediate. Purification by column chromatography over silica gel (60-120 mesh) and using 6-8% ethyl acetate in pet ether as the eluent afforded 11.0 g (86.75%) of MX-S2 as a pale yellow liquid.

Step 3 (MX-S3):

n-Butyllithium in hexane (2.2 M; 9.44 mL, 20.76 mmol) was added to a solution of MX-S2 (6.0 g, 20.76 mmol) in dry tetrahydrofuran (120 mL) at −78° C. and the mixture was stirred for 1 h at the same temperature. The mixture was added to a solution of diethyl oxalate (5.53 g, 37.37 mmol) in tetrahydrofuran (120 mL) at −78° C. over 15 min. The reaction mass was stirred for 1 h, whereas the temperature raised to −60° C. The reaction was quenched with saturated ammonium chloride solution and extracted with ethyl acetate. The combined organic layer was washed successively with water, brine; dried over anhydrous sodium sulfate and concentrated in vacuum to afford 6.5 g of MX-S3 as a yellow syrup, further used without any purification.

Step 4 (MY-S1):

Sodium acetate (3.44 g, 41.93 mmol) and hydroxylamine hydrochloride (2.91 g, 41.93 mmol) were added successively to a solution of MX-S3 (6.5 g, 20.97 mmol) in absolute ethanol (65 mL) and the mixture was refluxed for 1 h. The solvent was evaporated in vacuum and the resulting residue was partitioned between water and ethyl acetate. The combined organic layer was washed successively with water, brine; dried over anhydrous sodium sulfate and concentrated in vacuum to afford 6.5 g of MY-S1 as a yellow syrup.

Step 5 (MY-S2):

A solution of MY-S1 (6.5 g, 20.0 mmol) in absolute ethanol (150 mL) was hydrogenated over 10% Pd—C in a Parr apparatus (80 psi) for 20 h. The reaction mass was filtered through celite and washed with ethanol. The combined filtrate and washing portion was concentrated under reduced pressure to afford 6.0 g MY-S2 as a pale brown syrup.

Step 6 (MY-S3):

Trifluoroacetic acid (50 mL) was added to a solution of MY-S2 (5.0 g, 16.08 mmol) in dichloromethane (50 mL) at 0° C. and the mixture was stirred for 30 min at room temperature. The solvent was evaporated in vacuum, and the remaining mass was dissolved in hydrochloric acid (6 N) and washed with 50% ethyl acetate in pet ether. The aqueous layer basified with saturated sodium bicarbonate solution and extracted with dichloromethane. The combined organic layer was washed successively with water, brine; dried over anhydrous sodium sulfate and concentrated in vacuum to afford 2.01 g (42.93%) of MY-S3 as a yellow liquid.

Step 7 (MY-S4):

Triethyl amine (2.09 mL, 14.95 mmol) and Di-tert-butyl dicarbonate (2.06 mL, 8.99 mmol) were added successively to a solution of MY-S3 (2.0 g, 7.49 mmol) in dichloromethane (50 mL) and the mixture was stirred for 20 h at room temperature. Water was added and the mixture was extracted with dichloromethane. The combined organic layer was washed successively with water, brine; dried over anhydrous sodium sulfate and concentrated in vacuum to afford the crude intermediate. Purification by column chromatography over silica gel (60-120 mesh) and using 20% ethyl acetate in pet ether as the eluent afforded 2.0 g (72.73%) of MY-S4 as a yellow gummy liquid.

Step 8 (MY-S5):

Diethylamino sulfurtrifluoride (2.14 mL, 16.35 mmol) was added to a solution of MY-S4 (2.0 g, 5.45 mmol) in dichloromethane (30 mL) at 0° C. and the mixture was stirred for 2 h at room temperature. The reaction was quenched with ice water and extracted with dichloromethane. The combined organic layer was washed successively with water, brine; dried over anhydrous sodium sulfate and concentrated in vacuum to afford 1.4 g (66.04%) of MY-S5 as a colorless oil.

Step 9 (MY-S6):

Sodium borohydride (680 mg, 18.00 mmol) was slowly added in 3 equal lots (over 15 min) to a solution of MY-S5 (1.4 g, 3.60 mmol) in methanol (30 mL) at room temperature. Due to the exothermic reaction the temperature raised to ~50° C. The reaction mixture was stirred for 1 h. Ethyl acetate was added and the reaction was quenched with saturated ammonium chloride solution. The organic layer was separated and the aqueous layer was extracted with ethyl acetate. The combined organic layer was washed successively with water, brine; dried over anhydrous sodium sulfate and concentrated in vacuum to afford 1.1 g (88%) of MY-S6 as a white solid.

Step 10 (MAA-S1):

Potassium t-butoxide (1.06 g, 9.51 mmol) was slowly added in 4 lots (over 15 min) to a stirred solution of MY-S6 (1.1 g, 3.17 mmol) in tetrahydrofuran (40 mL) at 0° C. and the mixture was stirred for 2 h at room temperature. The reaction mixture was neutralized with 10% acetic acid and extracted with ethyl acetate. The combined organic layer was washed successively with water, brine; dried over anhydrous sodium sulfate and concentrated under reduced pressure to afford the crude intermediate. Purification by column chromatography over neutral alumina and using 1% methanol in dichloromethane as the eluent afforded 700 mg (80.92%) of MAA-S1 as a white solid.

Step 11 (MAA-S2):

A mixture of MAA-S1 (700 mg, 2.56 mmol), 4-Bromo-1,2-diaminobenzene (480 mg, 2.56 mmol) and cesium fluoride (780 mg, 5.12 mmol) in 1,4-dioxane (40 mL) was purged with argon gas for 30 min. Copper iodide (75 mg, 0.38 mmol) and 1,2-diaminocyclohexane (45 mg, 0.38 mmol) were added and the mixture was continuously purged for another 10 min. The reaction was heated in a sealed tube for 16 h at 105-110° C. The reaction mixture was filtered through celite, washed with dioxane and the filtrate was concentrated under reduced pressure to afford the crude intermediate. Purification by column chromatography over neutral alumina and using 1.5-2% methanol in dichloromethane as the eluent afforded 600 mg (61.85%) of MAA-S2 as a brown solid.

Step 12 (Example 29):

Formamidine acetate (495 mg, 1.58 mmol) was added to a solution of MAA-S2 (600 mg, 1.58 mmol) in acetonitrile (20 mL) and the mixture was refluxed for 1 h. The solvent was evaporated in vacuum and the resulting mass was partitioned between water and ethyl acetate. The organic layer was separated and the aqueous layer was extracted with ethyl acetate. The combined organic layer was washed with water, brine; dried over anhydrous sodium sulfate and concentrated in vacuum to afford the crude product. Purification by column chromatography over neutral alumina and using 2-2.5% methanol in dichloromethane as the eluent afforded 370 mg of the product which was triturated with diethyl ether and dried to afford 350 mg (56.91%) of Example 29 as an off white solid.

Melting range: 163.9-170.2° C.; $^1$H-NMR (400 MHz, DMSO-d6): δ 12.47 (s, 1H); 8.17 (s, 1H); 7.61 (d, 1H); 7.48 (s, 1H); 7.32-7.16 (m, 4H); 5.74 (q, 1H); 4.82 (t, 1H); 4.14 (q, 1H); 2.67 (t, 2H); 2.11-2.05 (m, 2H); 1.59 (t, 3H); MS=390.1.1 (M+1); HPLC~98.50%.

Example 30

(S)-3-(1H-benzo[d]imidazol-5-yl)-4-(4-(3,3-difluorobutyl)-2-fluorophenyl)oxazolidin-2-one Step 1 (MZ-S1):

3-fluorocinammic acid (20 g, 121.9 mmol) was hydrogenated with 10% Pd—C(2 g) in ethanol under hydrogen pressure (70 psi) for 2 h. The reaction mass was filtered through celite and washed with ethanol. The filtrate was concentrated under reduced pressure to afford 19.5 g (97%) of MZ-S1 as an off white solid, further used without any purification.

Step 2 (MZ-S2):

N,N-Carbonyl di-imidazole (22.83 g, 14.09 mmol) and triethylamine (16 mL, 11.7 mmol) was added to a solution of MZ-S1 (19.5 g, 11.7 mmol) in tetrahydrofuran (150 ml) and the mixture was refluxed for 1 h. The reaction was cooled to room temperature and a suspension of N,O-dimethylhydroxylamine hydrochloride (13.8 g, 14.09 mmol) and triethylamine (16 mL, 11.7 mmol) in tetrahydrofuran (100 mL) was added. The reaction mixture was stirred for 1 h at room temperature. Water was added and the mixture was extracted with ethyl acetate. The combined organic layer was washed with water, brine; dried over anhydrous sodium sulfate and concentrated under vacuum to afford 27 g of MZ-S2, further used without any purification.

Step 3 (MZ-S3):

A solution of methyl-magnesium bromide (64.5 mL, 142.10 mmol) was added to a solution of MZ-S2 (27 g, 129.18 mmol) in diethyl ether (160 mL) at 0° C. and the mixture was stirred for 4 h at room temperature. The reaction was quenched with ammonium chloride solution and extracted with ethyl acetate. The combined organic layer was washed with water, brine; dried over anhydrous sodium sulfate and concentrated under vacuum to afford the crude intermediate. Purification by column chromatography over silica gel (60-120 mesh) and using 10% ethyl acetate in pet ether as the eluent afforded 10.2 g of MZ-S3.

Step 4 (MZ-S4):

Sodium borohydride (8 g, 48.19 mmol) was added to solution of MZ-S3 (8 g, 48.19 mmol) in methanol (80 mL). The reaction mixture was stirred for 1 hour. The solvent was evaporated under reduced pressure and the remaining mass was separated between water and ethyl acetate. The combined organic layer was washed successively with water, brine; dried over anhydrous sodium sulfate to afford 8 g of MZ-S4 as a solid, further used without any purification.

Step 5 (MZ-S5):

Pyridine (7.4 g, 94.04 mmol) was added to a solution of MZ-S4 (7.9 g, 47.02 mmol) in dichloromethane (100 mL) at 0° C. and the mixture was stirred for 10 min. Acetyl chloride (4.4 g, 56.42 mmol) was added and the mixture was further stirred at room temperature for 1 h. Water was added and the mixture was extracted with dichloromethane. The combined organic layer was washed successively with water, brine; dried over anhydrous sodium sulfate and concentrated under reduced pressure to afford 8.3 g (84.6%) of MZ-S5 as a solid, further used without any purification.

Step 6 (MZ-S6):

Ethyloxalyl chloride (17.3 mL, 152.3 mmol) was added to a solution of MZ-S5 (8 g, 38.09 mmol) in dichloromethane (120 mL) at −20° C. Aluminum chloride (20.32 g, 152.3 mmol) was added portion wise at the same temperature and the mixture was stirred for 1 h at −20° C. The reaction was slowly warmed to room temperature and was further stirred for 5 h. The reaction was quenched with saturated bicarbonate solution and extracted with dichloromethane. The mixture was filtered and the separated organic layer was washed with water, brine; dried over anhydrous sodium sulfate and concentrated under reduced pressure to afford the crude intermediate. Purification by column chromatography over silica gel (60-120 mesh) and using 5% ethyl acetate in pet ether as the eluent afforded 3.7 g (32%) of MZ-S6 as a solid.

Step 7 (MZ-S7):

A mixture of MZ-S6 (3.5 g, 11.62 mmol), sodium acetate (1.90 g, 23.25 mmol) and hydroxylamine hydrochloride (1.61 g, 23.25 mmol) in ethanol (25 mL) was refluxed for 2 h. The reaction mass was filtered and the filtrate was directly taken for the next step without isolation.

Step 8 (MZ-S8):

MZ-S7 (3.5 g, 11.11 mmol) in absolute ethanol (50 mL) was hydrogenated with 10% Pd—C (150 mg) in a Parr apparatus (80 psi) for 15 h. The mixture was filtered through celite washed with ethanol. The filtrate w as concentrated under reduced pressure to afford 3 g of MZ-S8, further used without any purification.

Step 9 (MZ-S9):

Triethylamine (2.7 mL, 20.06 mmol) and di-tert-butyl dicarbonate (2.6 mL, 12.04 mmol) was added successively to a solution of MZ-S9 (3 g, 10.03 mmol) in dichloromethane (25 mL) at room temperature and the mixture was stirred for 1 h. The reaction was quenched with water and extracted with dichloromethane. The combined organic layer was washed successively with water, brine; dried over anhydrous sodium sulfate and concentrated in vacuum to afford the crude intermediate. Purification by column chromatography over silica gel (60-120 mesh) and using 5% ethyl acetate in pet ether as the eluent afforded 2.8 g of MZ-S9 as an oily liquid.

Step 10 (MZ-S10):

To the stirred solution of MZ-S9 (2.8 g, 6.81 mmol) in tetrahydrofuran (10 mL) and water (20 mL) water, lithium hydroxide (1.1 g, 27.25 mmol) was added and the mixture was stirred for 3 h at room temperature. The reaction mixture was concentrated under reduced pressure. Water (5 mL) was added and the mixture was neutralized with acetic acid an extracted with ethyl acetate. The combined organic layer was dried over anhydrous sodium sulfate and concentrated under reduced pressure to afford 2.2 g of MZ-S10, further used without any purification.

Step 11 (MZ-S11):

Methyl iodide (1.83 g, 12.90 mmol) was added to a solution of MZ-S10 (2.2 g, 6.45 mmol) and potassium carbonate (1.07 g, 7.74 mmol) in acetone (20 mL) and the mixture was stirred for 3 h at room temperature. The solvent was evaporated under reduced pressure and ethyl acetate was added. The organic layer was filtered, washed successively with water, brine; dried over anhydrous sodium sulfate and concentrated under reduced pressure to afford 2 g of MZ-S11 as a solid, further used without any purification.

Step 12 (MZ-S12):

Iodoxybenzoic acid (6.3 g, 22.53 mmol) was added to a solution of MZ-S11 (2 g, 5.63 mmol) in dichloromethane (20 mL) and dimethylsulfoxide (5 mL) and the mixture was stirred for 60 h at room temperature. The reaction mass was filtered and washed with dichloromethane. The combined filtrate and washing portion was washed successively with water, brine; dried over anhydrous sodium sulfate and concentrated in vacuum to afford the crude intermediate. Purification by column chromatography over silica gel and using 20% ethyl acetate in pet ether as the eluent afforded 1.8 g of MZ-S12 as an oily liquid.

Step 13 (MZ-S13):

Diethylamino sulfurtrifluoride (1.9 mL, 14.52 mmol) was added to a solution of MZ-S12 (1.7 g, 4.84 mmol) in dichloromethane (10 mL) at 0° C. The reaction was warmed to room temperature and stirred for 72 h. The reaction was quenched with ice water and the organic layer was separated. The aqueous layer was extracted with dichloromethane. The combined organic layer was washed successively with water, saturated solution of sodium bicarbonate, brine; dried over anhydrous sodium sulfate and evaporated in vacuum to afford the crude intermediate. Purification by column chromatography over silica gel (60-120 mesh) and using 10% ethyl acetate in pet ether as the eluent afforded 800 mg of MZ-S13 as a brown liquid.

Step 14 (MZ-S14):

Sodium borohydride (122 mg, 3.21 mmol) was added to solution of MZ-S13 (800 mg, 2.14 mmol) in methanol (50 mL). The mixture was stirred for 1 h. The solvent was evaporated under reduced pressure and ethyl acetate was added. The organic layer was washed successively with water, brine; dried over anhydrous sodium sulfate to afford 720 mg of MZ-S14 as white solid, further used without any purification.

Step 16 (MAA-S1):

A solution of MZ-S14 (720 mg, 2.08 mmol) in tetrahydrofuran (80 mL) was added to suspension of potassium t-butoxide (467 mg, 4.17 mmol) in tetrahydrofuran (2 mL) at 0° C. and the mixture was stirred for 2 h at room temperature. The reaction mixture was concentrated under reduced pressure, dichloromethane was added and the mixture was acidified with acetic acid to adjust the pH-value to pH-6. The mixture was washed with dichloromethane and the combined organic layer was washed with water, brine; dried over anhydrous sodium sulfate and evaporated to afford the crude intermediate. Purification by column chromatography over neutral alumina and using 1% methanol in dichloromethane as the eluent afforded 420 mg of MAA-S1 as a solid.

Step 17 (MAA-S2):

A mixture of MAA-S1 (420 mg, 1.61 mol), 4-bromo-1,2-diaminobenzene (302 mg, 1.61 mmol), cesium fluoride (491 mg, 3.23 mmol) and copper iodide (46 mg, 0.24 mmol) in 1,4-dioxane (20 mL) was purged with argon gas for 15 min in a sealed tube. 1,2-diaminocyclohexane (52.5 mg, 0.44 mmol) was added and the mixture was continuously purged for another 10 min. The reaction was heated for 20 h at 110-115° C. The reaction mixture was filtered, washed with dioxane and concentrated under reduced pressure to afford the crude intermediate. Purification by column chromatography over neutral alumina and using 2% methanol in chloroform as the eluent afforded 300 mg of MAA-S2 as a brown solid.

Step 18 (Example 30):

A mixture of MAA-S2 (300 mg, 0.817 mmol), formamidine acetate (170 mg, 1.634 mmol) in acetonitril (10 mL) was stirred for 2 h at 80-90° C. The reaction mixture was evaporated, water was added the mixture was extracted with ethyl acetate. The combined organic layer was washed successively with water, brine; dried over anhydrous sodium sulfate and evaporated under reduced pressure to afford the crude product. Diethylether (10 mL) and methanol (2 mL) was added and the mixture was stirred for 10 min. The mixture was filtered and the remaining solid was dried to afford 135 mg of Example 30 as a brown solid.

Melting range: 151.2-155.5° C.; $^1$H-NMR (400 MHz, DMSO-d6): δ 12.45 (s, 1H); 8.17 (s, 1H); 7.60 (d, 1H); 7.48 (bs, 1H); 7.34 (t, 1H); 7.25 (bs, 1H); 7.11 (d, 1H); 7.03 (d, 1H); 5.91 (q, 1H); 4.85 (t, 1H); 4.25 (q, 1H); 2.68-2.64 (m, 2H); 2.17-2.05 (m, 2H); 1.58 (t, 3H); MS=390.2 (M+1); HPLC~99.41%.

Activity Screening

Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, Hørsholm, Denmark) in 0.2 M Tris/HCl, pH 8.0 containing 20 mM EDTA and an appropriately diluted aliquot of QC in a final volume of 250 µl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 µmol pGlu-βNA from H-Gln-βNA per minute under the described conditions.

In a second fluorometric assay, QC was activity determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 J Neurosci Methods 30, 23-28) utilizing glutamate dehydrogenase as auxiliary enzyme. Samples consisted of the respective QC substrate, 0.3 mM NADH, 14 mM α-Ketoglutaric acid and 30 U/ml glutamate dehydrogenase in a final volume of 250 µl. Reactions were started by addition of QC and persued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except of the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software. The inhibitor assay was performed at two different pH levels, pH 6.0 and pH 8.0: The respective pH value in the assay solution was adjusted using conventional methods.

Pharmacokinetic Parameters

Methods

Three mice (strain CD-1) were administered orally 30 mg/kg of each test compound dissolved in 0.8% Methocel. Samples were taken at the time points 10 min, 0.5, 1, 2, 4 and 8 hr after test compound administration for plasma and brain collection.

Blood Collection

The mice were anesthetized with Isoflurane. Approximate 200 µL of each blood sample were collected via cardiac puncture for terminal bleeding into K2EDTA tubes. Blood samples were put on ice and centrifuged at 2000 g for 5 min to obtain plasma sample within 15 minutes. CSF collection: The animals were euthanized with pure $CO_2$ inhalation. A mid line incision was made on the neck. The muscle under the skin was cut to expose the cisterna magna. The cisterna magna was penetrated with the sharp end of a capillary and CSF was collected via capillarity.

Brain Collection

After CSF collection, a perfusion with 7× total mouse blood volume (approximate 15 ml) of ice-cold PBS (pH 7.4) was conducted via cardiac puncture before brain collection. A mid-line incision was made in the animal scalp. The brain was removed and rinsed with cold saline. Brain was placed into a screw-top tube and weighed. Brain samples were homogenized for 2 min with 3 volumes (v/w) of PBS (pH 7.4) and then analyzed with LC-MS/MS. The brain concentration was corrected with a dilution factor of 4 as following:

Brain concentration=brain homogenate conc.×4, assuming 1 g wet brain tissue equals to 1 ml.

Plasma, brain and CSF samples were stored at approximately −80° C. until analysis.

Sample Preparation

For plasma samples: An aliquot of 20 μl sample was added with 200μ IS (Diclofenac, 200 ng/mL) in ACN, the mixture was vortexed for 2 min and centrifuged at 12.000 rpm for 5 min. 1 μl supernatant was injected for LC-MS/MS analysis.

For diluted plasma samples: An aliquot of 4 μl sample was added with 16 μl blank plasma, mixed well, added with 200 μl IS (Diclofenac, 200 ng/ml) in ACN.

For Brain samples: Brain tissue was homogenized for 2 min with 3 volumes (v/w) of PBS. An aliquot of 20 μl sample was added with 200 μl IS (Diclofenac, 200 ng/ml) in ACN, the mixture was vortexed for 2 min and centrifuged at 12000 rpm for 5 min. 1 μl supernatant was injected for LC-MS/MS analysis.

For CSF samples: The CSF sample was added with corresponding 20 fold volume of IS (Diclofenac, 200 ng/ml) in ACN, the mixture was vortexed for 2 min. 3 μl supernatant was injected for LC-MS/MS analysis.

Tmax, T1/2, AUC and log BB values were calculated using conventional methods.

Results

Analytical Methods

HPLC

Method [A]: The analytical HPLC-system consisted of a Merck-Hitachi device (model LaChrom®) utilizing a LUNA® RP 18 (5 μm), analytical column (length: 125 mm, diameter: 4 mm), and a diode array detector (DAD) with $\lambda$=214 nm as the reporting wavelength. The compounds were analyzed using a gradient at a flow rate of 1 mL/min; whereby eluent (A) was acetonitrile, eluent (B) was water, both containing 0.1% (v/v) trifluoro acetic acid applying the following gradient: 0 min-5 min→5% (A), 5 min-17 min→5-15% (A), 15 min-27 min→15-95% (A) 27 min-30 min→95% (A), Method [B]: 0 min-15 min→5-60% (A), 15 min-20 min→60-95% (A), 20 min-23 min→95% (A), Method [C]: 0 min-20 min→5-60% (A), 20 min-25 min→60-95% (A). 25 min-30 min→95% (A).

Method [B]: The analytical HPLC-system consisted of a Agilent MSD 1100 utilizing a Waters SunFire RP 18 (2.5 μm), analytical column (length: 50 mm, diameter: 2.1 mm), and a diode array detector (DAD) with $\lambda$=254 nm as the reporting wavelength. The compounds were analyzed using a gradient at a flow rate of 0.6 mL/min; whereby eluent (A) was acetonitrile, eluent (B) was water and eluent (C) 2% formic acid in acetonitrile applying the following gradient:

| Cpd. No. | Ki hQC pH 6 [nM] | Ki hQC pH 8 [nM] | Organ | Tmax [HH:Min:Sec] | T½ [HH:Min:Sec] | AUC BRAIN | logBB |
|---|---|---|---|---|---|---|---|
| 1 | 2.905 | 3.5805 | Brain | 02:15:46 | 01:34:06 | 158.11 | −0.9363 |
|  |  |  | CSF | 02:01:54 | 01:24:30 |  |  |
| 2 | 8.5 | 6.5399 | Brain | 00:54:20 | 01:30:57 | 73.024 | −1.1517 |
|  |  |  | CSF | 00:40:08 | 00:45:23 |  |  |
| 3 | 5.0304 | 5.0169 | CSF | 01:02:04 | 02:00:00 | 185.66 | −1.0428 |
|  |  |  | Brain | 01:38:26 | 01:47:16 |  |  |
| 4 | 12.58 | 17.823 |  |  |  |  |  |
| 5 | 21.266 | 19.192 | Brain | 02:18:42 | 01:36:08 | 139.15 | −1.0928 |
|  |  |  | CSF | 01:23:23 | 02:32:11 |  |  |
| 6 | 6.207 | 6.7076 | Brain | 01:59:24 | 03:33:37 | 195.11 | −1.0431 |
|  |  |  | CSF | 01:36:49 | 03:19:45 |  |  |
| 7 | 9.8306 | 10.871 | CSF | 00:57:56 | 03:38:34 | 209.76 | −0.9439 |
|  |  |  | Brain | 01:29:37 | 03:03:49 |  |  |
| 8 | 25.952 | 30.934 | Brain | 01:55:19 | 01:58:50 | 107.12 | −0.9993 |
|  |  |  | CSF | 01:05:21 | 02:20:02 |  |  |
| 10 | 8.9503 | 8.9859 | Brain | 02:01:10 | 02:04:04 | 116.73 | −1.1234 |
|  |  |  | CSF | 01:37:26 | 02:26:52 |  |  |
| 11 | 3.3447 | 5.54 | CSF | 00:48:12 | 02:24:52 | 164.34 | −0.9451 |
|  |  |  | Brain | 01:47:27 | 02:27:02 |  |  |
| 12 | 13.1 | 15.4 | Brain | 01:31:05 | 02:24:32 | 87.749 | −1.1821 |
|  |  |  | CSF | 01:28:36 | 02:28:03 |  |  |
| 13 | 13.094 | 24.503 |  |  |  |  |  |
| 14 | 22.516 | 31.563 |  |  |  |  |  |
| 15 | 22.689 | 36.412 |  |  |  |  |  |
| 16 | 15.955 | 22.111 |  |  |  |  |  |
| 17 | 6.6648 | 8.29 |  |  |  |  |  |
| 18 | 2.6882 | 2.9232 | CSF | 00:30:27 | 01:02:22 | 39.888 | −1.2913 |
|  |  |  | Brain | 00:59:37 | 02:53:43 |  |  |
| 19 | 2.4869 | 2.5297 | CSF | 01:35:58 | 02:38:15 | 33.255 | −1.2208 |
|  |  |  | Brain | 02:04:21 | 01:26:12 |  |  |
| 20 | 4.5258 | 5.2928 |  |  |  |  |  |
| 21 | 10.39 | 16.668 | Brain | 02:32:52 | 01:45:57 | 41.783 | −1.208 |
|  |  |  | CSF | 01:31:27 | 05:11:55 |  |  |
| 22 | 20.445 | 15.111 |  |  |  |  |  |
| 23 | 5.1497 | 7.8928 |  |  |  |  |  |
| 24 | 11.421 | 15.542 |  |  |  |  |  |
| 25 | 9.2351 | 11.285 |  |  |  |  |  |
| 26 | 13.56 | 14.325 |  |  |  |  |  |
| 27 | 15.4 | 44.3 |  |  |  |  |  |
| 28 | 23.8 | 14.9 |  |  |  |  |  |
| 29 | 29.7 | 29.136 |  |  |  |  |  |
| 30 | 12.033 | 12.217 |  |  |  |  |  |

| Time min | % Solvent B | % Solvent C |
|---|---|---|
| 0 | 90 | 5 |
| 2.5 | 10 | 5 |
| 4 | 10 | 5 |
| 4.5 | 90 | 5 |
| 6 | 90 | 5 |

The purities of all reported compounds were determined by the percentage of the peak area at 214 nm.

Mass-Spectrometry, NMR-Spectroscopy:

ESI-Mass spectra were obtained with a SCIEX API 365 spectrometer (Perkin Elmer) utilizing the positive ionization mode.

The $^1$H NMR-Spectra (500 MHz) were recorded at a BRUKER AC 500. The solvent was DMSO-D6, unless otherwise specified. Chemical shifts are expressed as parts per million (ppm) downfiled from tetramethylsilan. Splitting patterns have been designated as follows: s (singulet), d (doublet), dd (doublet of doublet), t (triplet), m (multiplet) and br (broad signal).

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals are recorded and filtered using LeCroy 9350M digital storage oscilloscope linked to a personal computer. Samples (5 µl were mixed with equal volumes of the matrix solution. For matrix solution DHAP/DAHC was used, prepared by solving 30 mg 2',6'-dihydroxyacetophenone (Aldrich) and 44 mg diammonium hydrogen citrate (Fluka) in 1 ml acetonitrile/0.1% TFA in water (1/1, v/v). A small volume (≈1 µl of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of Glu$^1$-cyclization, Aβ-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ(3-21)a] concentrations, and 0.2 U QC is added all 24 hours. In case of Aβ(3-21)a, the assays contained 1% DMSO. At different times, samples are removed from the assay tube, peptides extracted using ZipTips (Millipore) according to the manufacturer's recommendations, mixed with matrix solution (1:1 v/v) and subsequently the mass spectra recorded. Negative controls either contain no QC or heat deactivated enzyme. For the inhibitor studies the sample composition was the same as described above, with exception of the inhibitory compound added (5 mM or 2 mM of a test compound of the invention).

Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and embodiments of groups recited above.

Abbreviations
ACN acetonitrile
CDI N,N-carbonyl di-imidazole
(DHQ)$_2$PHAL hydroquinine 1,4-phthalazinediyldiether
DAD diode array detector
DAST diethylamino sulfurtrifluoride
DEAD diethyl-azodicarboxylate
DCM dichlormethane
DEA diethylamine
DHAP/DAHC dihydroxyacetone phosphate/dihydro-5-aza-cytidine
DIBAL diisobutlyaluminiumhydride
DIPEA N, N-di-isopropylethylamine
DMS dimethylsulfate
DMSO dimethylsulfoxide
EDTA ethylenediamine-N,N,N',N'-tetraacetic acid
EtOH ethanole
HPLC high performance liquid chromatography
IBX 2-iodoxy benzoic acid
KOtBu potassium t-butoxide
LD-TOF laser-desorption time-of-flight mass spectrometry
MeI methyl iodide
MS mass spectrometry
NaOAc sodium acetate
n-BuLi n-butyl lithium
NMR nuclear magnetic resonance
PTSA p-toluenesulfonic acid
PPh$_3$ triphenyl phosphine
(PPh$_3$)$_4$Pd tetrakis-(triphenylphosphine)-palladium
PPh$_3$CH$_3$Br triphenyl phosphonium methyl bromide
TBDMSCl tert-butylmethylsilyl chloride
t-BuoCl t-butyl hypochlorite
TEA triethylamine
TBAHS tetrabutylammoniumhydrogen sulfate
TFA trifluoroacetic acid
THF tetrahydrofuran
TLC thin layer chromatography
TPP triphenylphosphine

The invention claimed is:

1. A compound of formula (I),

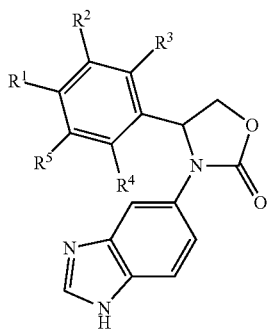

or a pharmaceutically acceptable salt, solvate or polymorph thereof, including all tautomers and stereoisomers thereof, wherein $R^1$ represents alkyl, —O-alkyl, heterocyclyl, or cycloalkyl;

$R^2$ and $R^3$ independently represent hydrogen, halogen, or CN;

$R^4$ and $R^5$ independently represent hydrogen or halogen;

wherein at least one of $R^2$, $R^3$, $R^4$, and $R^5$ is halogen or CN; and wherein the above alkyl, —O-alkyl, heterocyclyl, or cycloalkyl groups are substituted by one or more halogen.

2. The compound according to claim 1 wherein:

$R^1$ represents alkyl, —O-alkyl, heterocyclyl, or cycloalkyl;

$R^2$ and $R^3$ independently represent hydrogen, fluorine, or CN;

$R^4$ and $R^5$ independently represent hydrogen or fluorine;

wherein at least one of $R^2$, $R^3$, $R^4$, and $R^5$ is fluorine or CN; and wherein the above alkyl, —O-alkyl, heterocyclyl, or cycloalkyl groups are substituted by one or more fluorine.

3. The compound according to claim 1, wherein $R^1$ is selected from the group consisting of:

—O—$C_{2-6}$alkyl substituted by one or more halogen; and
—O—$C_{3-4}$alkyl substituted by one or more halogen.

4. The compound according to claim 1, wherein $R^1$ is selected from the group consisting of:

—O—$C_{2-6}$alkyl substituted by one or more fluorine; and
—O—$C_{3-4}$alkyl substituted by one or more fluorine.

5. The compound according to claim 1, wherein $R^1$ is selected from the group consisting of:

difluoropropoxy;
difluorobutoxy;
difluoropyrrolidinyl;
difluorocyclohexyl; and
difluorobutyl.

6. The compound according to claim 1, wherein $R^1$ is selected from the group consisting of:

pyrrolidinyl substituted by one or more halogen;
cyclohexyl substituted by one or more halogen;
—$C_{2-6}$alkyl substituted by one or more halogen; and
—$C_{3-4}$alkyl substituted by one or more halogen.

7. The compound according to claim 1, wherein $R^1$ is selected from the group consisting of:

3,3-difluoropyrrolidin-1-yl;
4,4-difluorocyclohexyl;
2,2-difluoropropoxy;
3, 3-difluoropropoxy;
3,3-difluorobutoxy; and
3,3-difluorobutyl.

8. The compound to claim 1, wherein $R^1$ is selected from the group consisting of:

cyclohexyl substituted by one or more fluorine;
—$C_{2-6}$alkyl substituted by one or more fluorine; and
—$C_{3-4}$alkyl substituted by one or more fluorine.

9. The compound according to claim 1, wherein $R^2$ and $R^5$ are halogen and $R^3$ and $R^4$ are hydrogen;
$R^2$ is halogen and $R^3$, $R^4$, and $R^5$ are hydrogen;
$R^3$ and $R^4$ are halogen, and $R^2$ and $R^5$ are hydrogen;
$R^3$ is halogen, and $R^2$, $R^4$, and $R^5$ are hydrogen;
$R^2$ and $R^3$ are halogen, and $R^4$ and $R^5$ are hydrogen;
$R^2$ is CN and $R^3$, $R^4$, and $R^5$ are hydrogen; or
$R^3$ is CN and $R^2$, $R^4$, and $R^5$ are hydrogen.

10. The compound according to claim 1 or a pharmaceutically acceptable salt, solvate, or polymorph thereof, including all tautomers and stereoisomers, wherein the compound is selected from the group consisting of:

(S)-3-(1H-benzo[d]imidazol-5-yl)-4-(4-(3,3-difluorobutoxy)-2,3-difluorophenyl)-oxazolidin-2-one;

(S)-3-(1H-benzo[d]imidazol-5-yl)-4-(4-(3,3-difluoropropoxy)-2-fluorophenyl)oxazolidin-2-one;
(S)-3-(1H-benzo[d]imidazol-5-yl)-4-(4-(3,3-difluorobutoxy)-2-fluorophenyl)oxazolidin-2-one;
(S)-3-(1H-benzo[d]imidazol-5-yl)-4-(4-(2,2-difluoropropoxy)-3-fluorophenyl)oxazolidin-2-one;
(S)-3-(1H-benzo[d]imidazol-5-yl)-4-(4-(2,2-difluoropropoxy)-2,3-difluorophenyl)oxazolidin-2-one;
(S)-3-(1H-benzo[d]imidazol-5-yl)-4-(4-(2,2-difluoropropoxy)-2-fluorophenyl)oxazolidin-2-one;
(S)-3-(1H-benzo[d]imidazol-5-yl)-4-(4-(2,2-difluoropropoxy)-3,5-difluorophenyl)oxazolidin-2-one;
(S)-3-(1H-benzo[d]imidazol-5-yl)-4-(4-(3,3-difluorobutoxy)-3-fluorophenyl)oxazolidin-2-one;
(S)-3-(1H-benzo[d]imidazol-5-yl)-4-(4-(3,3-difluoropropoxy)-2,3-difluorophenyl)oxazolidin-2-one;
(S)-3-(1H-benzo[d]imidazol-5-yl)-4-(4-(3,3-difluoropropoxy)-3-fluorophenyl)oxazolidin-2-one;
(S)-3-(1H-benzo[d]imidazol-6-yl)-4-(4-(3,3-difluoropropoxy)-3,5-difluorophenyl)oxazolidin-2-one;
(S)-5-(3-(1H-benzo[d]imidazol-5-yl)-2-oxooxazolidin-4-yl)-2-(2,2-difluoropropoxy) benzonitrile;
(S)-2-(3-(1H-benzo[d]imidazol-5-yl)-2-oxooxazolidin-4-yl)-5-(2,2-difluoropropoxy) benzonitrile;
(S)-3-(1H-benzo[d]imidazol-5-yl)-4-(4-(2,2-difluoropropoxy)-2,6-difluorophenyl)oxazolidin-2-one;
(S)-3-(1H-benzo[d]imidazol-5-yl)-4-(4-(3,3-difluoropyrrolidin-1-yl)-2-fluorophenyl)-oxazolidin-2-one;
(S)-3-(1H-benzo[d]imidazol-5-yl)-4-(4-(3,3-difluoropyrrolidin-1-yl)-2,3-difluorophenyl)-oxazolidin-2-one;
(S)-3-(1H-benzo[d]imidazol-5-yl)-4-(4-(3,3-difluoropyrrolidin-1-yl)-2,6-difluorophenyl) oxazolidin-2-one;
(S)-3-(1H-benzo[d]imidazol-5-yl)-4-(4-(3,3-difluoropyrrolidin-1-yl)-3-fluorophenyl) oxazolidin-2-one;
(S)-2-(3-(1H-benzo[d]imidazol-5-yl)-2-oxooxazolidin-4-yl)-5-(3,3-difluoropyrrolidin-1-yl)benzonitrile;
(S)-5-(3-(1H-benzo[d]imidazol-5-yl)-2-oxooxazolidin-4-yl)-2-(3,3-difluoropyrrolidin-1-yl)benzonitrile;
(S)-3-(1H-benzo[d]imidazol-5-yl)-4-(4-(4,4-difluorocyclohexyl)-2-fluorophenyl)oxazolidin-2-one;
(S)-3-(1H-benzo[d]imidazol-5-yl)-4-(4-(4,4-difluorocyclohexyl)-3-fluorophenyl)oxazolidin-2-one;
(S)-3-(1H-benzo[d]imidazol-5-yl)-4-(4-(3,3-difluorobutyl)-2,3-difluorophenyl)oxazolidin-2-one;
(S)-3-(1H-benzo[d]imidazol-5-yl)-4-(4-(3,3-difluorobutyl)-3-fluorophenyl)oxazolidin-2-one; and
(S)-3-(1H-benzo[d]imidazol-5-yl)-4-(4-(3,3-difluorobutyl)-2-fluorophenyl)oxazolidin-2-one.

11. The compound according to claim 1 or a pharmaceutically acceptable salt, solvate, or polymorph thereof, including all tautomers and stereoisomers, wherein the compound is (S)-3-(1H-benzo[d]imidazol-5-yl)-4-(4-(2,2-difluoropropoxy)-2-fluorophenyl)oxazolidin-2-one.

12. The compound according to claim 1 or a pharmaceutically acceptable salt, solvate, or polymorph thereof, including all tautomers and stereoisomers, wherein the compound is (S)-3-(1H-benzo[d]imidazol-5-yl)-4-(4-(3,3-difluoropropoxy)-2, 3-difluorophenyl)oxazolidin-2-one.

13. A method of treatment of a disease associated with glutaminyl cyclase, which comprises administering to a subject an effective amount of a compound according to claim 1.

14. A pharmaceutical composition comprising a compound according to claim 1 in combination with one or more therapeutically acceptable diluents or carriers.

15. The pharmaceutical composition of claim 14, which comprises additionally at least one compound, selected from the group consisting of neuroprotectants, antiparkinsonian drugs, amyloid protein deposition inhibitors, beta amyloid synthesis inhibitors, antidepressants, anxiolytic drugs, antipsychotic drugs, and anti-multiple sclerosis drugs.

16. The pharmaceutical composition of claim 14, which comprises additionally at least one compound, selected from the group consisting of PEP-inhibitors, LiCl, inhibitors of inhibitors of DP IV or DP IV-like enzymes, acetylcholinesterase (ACE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors, interferon-tau (trophoblastin), and SAIK-MS.

17. The method according to claim 13, wherein the disease is selected from the group consisting of Kennedy's disease, duodenal cancer with or without *Helicobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, Guillain-Barré syndrome, and chronic inflammatory demyelinizing polyradiculoneuropathy.

18. The method according to claim 13, wherein the disease selected from the group consisting of mild cognitive impairment, Alzheimer's disease, Familial British Dementia, Familial Danish Dementia, neurodegeneration in Down Syndrome, and Huntington's disease.

19. The method according to claim 13, wherein the disease selected from the group consisting of rheumatoid arthritis, atherosclerosis, pancreatitis, and restenosis.

20. A process for the preparation of a compound of formula (I) according to claim 1, which comprises:
(a) preparing a compound of formula (I) from a compound of formula (II):

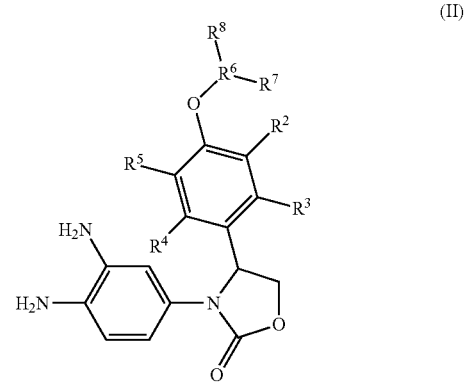

by reacting a compound of formula (II) with formamidine acetate in the presence of a suitable solvent, wherein
R², R³, R⁴, and R⁵ and are as defined above for compounds of formula (I); R⁶ is alkyl and R⁷ and R⁸ are halogen; or
(b) preparing a compound of formula (I) from a compound of formula (III):

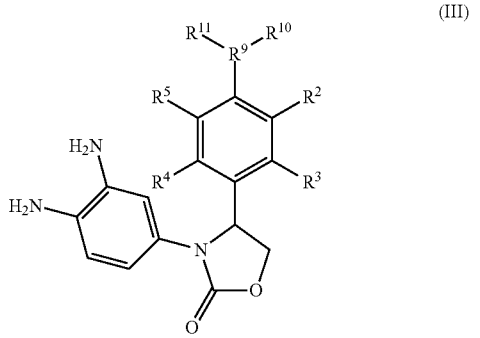

by reacting a compound of formula (III) with formamidine acetate in the presence of a suitable solvent,
wherein
R², R³, R⁴, and R⁵ are as defined above for compounds of formula (I) and R⁹ is cycloalkyl or heterocyclyl and R¹⁰ and R¹¹ are halogen; or
(c) preparing a compound of formula (I) from a compound of formula (IV):

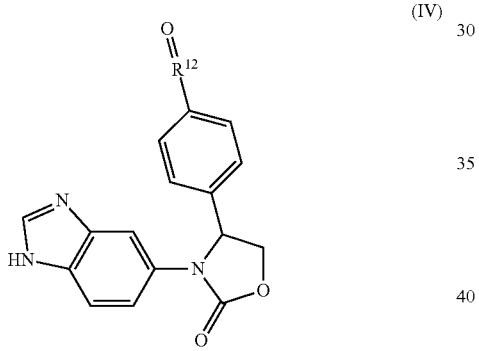

by reacting a compound of formula (IV) with diethylaminosulfur trifluoride employed in the presence of a suitable solvent;
wherein R¹² is cycloalkyl; or (d) preparing a compound of formula (I) from a compound of formula (V):

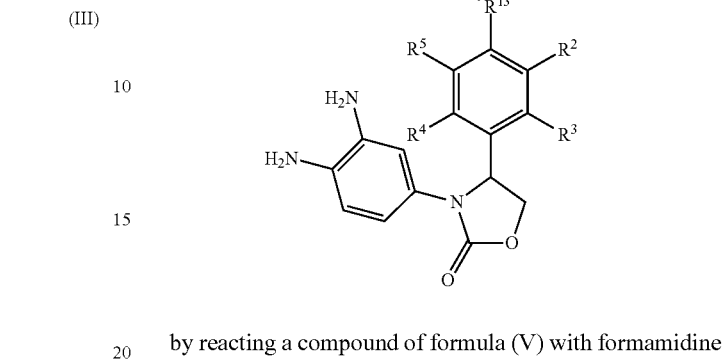

by reacting a compound of formula (V) with formamidine acetate in the presence a suitable solvent;
wherein
R¹, R², and R⁴ are as defined above for compounds of formula (I), R¹³ is alkyl and R¹⁴ and R¹⁵ are halogen.

21. The compound according to claim 1, wherein
R¹ is selected from the group consisting of:
  pyrrolidinyl substituted by one or more fluorine;
  cyclohexyl substituted by one or more fluorine; and
  $C_{2-6}$alkyl substituted by one or more fluorine;
R² is fluorine;
R³ is fluorine
R⁴ is fluorine; or
R⁵ fluorine.

22. The process according to claim 20, wherein
R⁷ is fluorine;
R⁸ is fluorine;
R¹⁰ is fluorine;
R¹¹ is fluorine;
R¹⁴ is fluorine;
R¹⁵ is fluorine;
the solvent is acetonitrile or dichloromethane; or
the agent is diethylaminosulfur trifluoride.

* * * * *

SEQUENCE LISTING

<160> NUMBER OF SEQ ID NOS: 20

<210> SEQ ID NO 1
<211> LENGTH: 42
<212> TYPE: PRT
<213> ORGANISM: Homo sapiens

```
<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 40
<212> TYPE: PRT
<213> ORGANISM: Homo sapiens

<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 4
<211> LENGTH: 38
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 5
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 5

Gln Gly Pro Trp Leu Glu Glu Glu Glu Ala Tyr Gly Trp Met Asp
1               5                   10                  15

Phe
```

```
<210> SEQ ID NO 6
<211> LENGTH: 13
<212> TYPE: PRT
<213> ORGANISM: Homo sapiens

<400> SEQUENCE: 6

Gln Leu Tyr Glu Asn Lys Pro Arg Arg Pro Tyr Ile Leu
1               5                   10

<210> SEQ ID NO 7
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 7

Gln His Trp Ser Tyr Gly Leu Arg Pro Gly
1               5                   10

<210> SEQ ID NO 8
<211> LENGTH: 97
<212> TYPE: PRT
<213> ORGANISM: Homo sapiens

<400> SEQUENCE: 8

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
            20                  25                  30

Lys Ala Leu Asn Cys His Leu Pro Ala Ile Ile Phe Val Thr Lys Arg
        35                  40                  45

Asn Arg Glu Val Cys Thr Asn Pro Asn Asp Asp Trp Val Gln Glu Tyr
    50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

<210> SEQ ID NO 9
<211> LENGTH: 76
<212> TYPE: PRT
<213> ORGANISM: Homo sapiens

<400> SEQUENCE: 9

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75
```

```
<210> SEQ ID NO 10
<211> LENGTH: 76
<212> TYPE: PRT
<213> ORGANISM: Homo sapiens

<400> SEQUENCE: 10

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 11
<211> LENGTH: 68
<212> TYPE: PRT
<213> ORGANISM: Homo sapiens

<400> SEQUENCE: 11

Gln Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln
            20                  25                  30

Cys Pro Lys Pro Gly Val Ile Leu Leu Thr Lys Arg Gly Arg Gln Ile
        35                  40                  45

Cys Ala Asp Pro Asn Lys Lys Trp Val Gln Lys Tyr Ile Ser Asp Leu
50                  55                  60

Lys Leu Asn Ala
65

<210> SEQ ID NO 12
<211> LENGTH: 373
<212> TYPE: PRT
<213> ORGANISM: Homo sapiens

<400> SEQUENCE: 12

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30

Ser Cys Gly Lys Arg Ala Ile Ile Leu Glu Thr Arg Gln His Arg Leu
        35                  40                  45

Phe Cys Ala Asp Pro Lys Glu Gln Trp Val Lys Asp Ala Met Gln His
50                  55                  60

Leu Asp Arg Gln Ala Ala Ala Leu Thr Arg Asn Gly Gly Thr Phe Glu
65                  70                  75                  80

Lys Gln Ile Gly Glu Val Lys Pro Arg Thr Thr Pro Ala Ala Gly Gly
            85                  90                  95

Met Asp Glu Ser Val Val Leu Glu Pro Glu Ala Thr Gly Glu Ser Ser
                100                 105                 110

Ser Leu Glu Pro Thr Pro Ser Ser Gln Glu Ala Gln Arg Ala Leu Gly
            115                 120                 125
```

-continued

Thr Ser Pro Glu Leu Pro Thr Gly Val Thr Gly Ser Ser Gly Thr Arg
130                 135                 140

Leu Pro Pro Thr Pro Lys Ala Gln Asp Gly Gly Pro Val Gly Thr Glu
145                 150                 155                 160

Leu Phe Arg Val Pro Val Ser Thr Ala Ala Thr Trp Gln Ser Ser
            165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Gly Gln Arg Val Trp
210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Pro Val Ser Ser Glu Gly Thr
                260                 265                 270

Pro Ser Arg Glu Pro Val Ala Ser Gly Ser Trp Thr Pro Lys Ala Glu
        275                 280                 285

Glu Pro Ile His Ala Thr Met Asp Pro Gln Arg Leu Gly Val Leu Ile
290                 295                 300

Thr Pro Val Pro Asp Ala Gln Ala Ala Thr Arg Arg Gln Ala Val Gly
305                 310                 315                 320

Leu Leu Ala Phe Leu Gly Leu Leu Phe Cys Leu Gly Val Ala Met Phe
                325                 330                 335

Thr Tyr Gln Ser Leu Gln Gly Cys Pro Arg Lys Met Ala Gly Glu Met
                340                 345                 350

Ala Glu Gly Leu Arg Tyr Ile Pro Arg Ser Cys Gly Ser Asn Ser Tyr
            355                 360                 365

Val Leu Val Pro Val
    370

<210> SEQ ID NO 13
<211> LENGTH: 76
<212> TYPE: PRT
<213> ORGANISM: Homo sapiens

<400> SEQUENCE: 13

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
                20                  25                  30

Ser Ser His Cys Pro Arg Glu Ala Val Ile Phe Lys Thr Lys Leu Asp
            35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 14
<211> LENGTH: 33
<212> TYPE: PRT
<213> ORGANISM: Homo sapiens

```
<400> SEQUENCE: 14

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
                20                  25                  30

Leu

<210> SEQ ID NO 15
<211> LENGTH: 11
<212> TYPE: PRT
<213> ORGANISM: Homo sapiens

<400> SEQUENCE: 15

Arg Pro Lys Pro Gln Gln Phe Phe Gly Leu Met
1               5                   10

<210> SEQ ID NO 16
<211> LENGTH: 32
<212> TYPE: PRT
<213> ORGANISM: Artificial sequence
<220> FEATURE:
<223> OTHER INFORMATION: Synthetic peptide

<400> SEQUENCE: 16

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
                20                  25                  30

<210> SEQ ID NO 17
<211> LENGTH: 30
<212> TYPE: PRT
<213> ORGANISM: Artificial sequence
<220> FEATURE:
<223> OTHER INFORMATION: Synthetic peptide

<400> SEQUENCE: 17

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
                20                  25                  30

<210> SEQ ID NO 18
<211> LENGTH: 34
<212> TYPE: PRT
<213> ORGANISM: Artificial sequence
<220> FEATURE:
<223> OTHER INFORMATION: Synthetic peptide

<400> SEQUENCE: 18

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
                20                  25                  30

Glu Asn

<210> SEQ ID NO 19
<211> LENGTH: 34
<212> TYPE: PRT
<213> ORGANISM: Artificial sequence
<220> FEATURE:
<223> OTHER INFORMATION: Synthetic peptide
```

```
<400> SEQUENCE: 19

Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
            20                  25                  30

His Tyr

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Gln Tyr Asn Ala Asp
1               5
```